(12) United States Patent
Dejima

(10) Patent No.: US 11,717,320 B2
(45) Date of Patent: Aug. 8, 2023

(54) METHOD OF OPERATING SURGICAL SYSTEM

(71) Applicant: FUJIFILM Corporation, Tokyo (JP)

(72) Inventor: Takumi Dejima, Waltham, MA (US)

(73) Assignee: FUJIFILM Corporation, Tokyo (JP)

(*) Notice: Subject to any disclaimer, the term of this patent is extended or adjusted under 35 U.S.C. 154(b) by 239 days.

(21) Appl. No.: 16/942,787

(22) Filed: Jul. 30, 2020

(65) Prior Publication Data

US 2020/0352595 A1   Nov. 12, 2020

Related U.S. Application Data

(63) Continuation of application No. 16/802,520, filed on Feb. 26, 2020, which is a continuation of application No. PCT/JP2017/039123, filed on Oct. 30, 2017.
(Continued)

(51) Int. Cl.
*A61B 17/34* (2006.01)
*A61B 1/00* (2006.01)
(Continued)

(52) U.S. Cl.
CPC ...... *A61B 17/3421* (2013.01); *A61B 1/00091* (2013.01); *A61B 1/00094* (2013.01);
(Continued)

(58) Field of Classification Search
CPC ............ A61B 17/3421; A61B 17/3423; A61B 17/00234; A61B 17/3496; A61B 17/3468;
(Continued)

(56) References Cited

U.S. PATENT DOCUMENTS 3,013,656 A    12/1961   Murphy, Jr.
3,485,352 A    12/1969   Pilger
(Continued)

FOREIGN PATENT DOCUMENTS

WO    2015147153    10/2015
WO    2015147154    10/2015
(Continued)

OTHER PUBLICATIONS

"International Search Report (Form PCT/ISA/210)" of PCT/JP2017/039123, dated Jan. 9, 2018, with English translation thereof, pp. 1-5.
(Continued)

*Primary Examiner* — Jessica Weiss
(74) *Attorney, Agent, or Firm* — JCIPRNET

(57) ABSTRACT

A method of operating a surgical system including an endoscope, a treatment tool, an overtube, and a sheathing tube. The method includes the following steps: removing the treatment tool from the sheathing tube inserted into a body cavity through a body wall in a state where the sheathing tube is covering an outer circumference of the overtube into which an insertion part of the endoscope and an insertion part of the treatment tool are inserted, while keeping a state where the sheathing tube is covering the outer circumference of the overtube; removing the endoscope from the overtube while keeping a state where the sheathing tube is covering the outer circumference of the overtube; and removing the sheathing tube from the body wall while keeping a state where the sheathing tube is covering the outer circumference of the overtube.

7 Claims, 103 Drawing Sheets

Related U.S. Application Data

(60) Provisional application No. 62/552,398, filed on Aug. 31, 2017.

(51) Int. Cl.
*A61B 1/313* (2006.01)
*A61B 17/02* (2006.01)
*A61B 17/00* (2006.01)

(52) U.S. Cl.
CPC ........ *A61B 1/00144* (2013.01); *A61B 1/3132* (2013.01); *A61B 17/00234* (2013.01); *A61B 2017/00238* (2013.01); *A61B 2017/00296* (2013.01); *A61B 2017/00477* (2013.01); *A61B 2017/347* (2013.01); *A61B 2017/3409* (2013.01)

(58) Field of Classification Search
CPC ........... A61B 2017/00238; A61B 2017/00296; A61B 2017/00477; A61B 2017/3409; A61B 2017/347; A61B 2017/3445; A61B 1/00091; A61B 1/00094; A61B 1/00144; A61B 1/3132; A61B 1/00135
USPC ....................................................... 604/264
See application file for complete search history.

(56) References Cited

U.S. PATENT DOCUMENTS

| | | | |
|---|---|---|---|
| 4,226,328 A | 10/1980 | Beddow | |
| 5,144,942 A | 9/1992 | Decarie et al. | |
| 5,318,543 A | 6/1994 | Ross et al. | |
| 5,353,929 A | 10/1994 | Foster | |
| 5,554,097 A | 9/1996 | Guy | |
| 6,358,197 B1 | 3/2002 | Silverman et al. | |
| D471,640 S | 3/2003 | McMichael et al. | |
| 7,694,821 B1 | 4/2010 | Asfora | |
| 8,584,849 B2 | 11/2013 | McCaffrey | |
| 10,434,259 B2 | 10/2019 | Dejima et al. | |
| 2003/0149443 A1* | 8/2003 | Gaskill, III | A61B 17/3421 606/190 |
| 2012/0310147 A1 | 12/2012 | Poll et al. | |
| 2016/0331402 A1* | 11/2016 | Wada | A61B 1/0014 |
| 2017/0007109 A1 | 1/2017 | Dejima et al. | |
| 2017/0020629 A1* | 1/2017 | Mikkaichi | A61B 90/39 |
| 2017/0172389 A1* | 6/2017 | Fujisaki | A61B 1/00172 |
| 2018/0008129 A1* | 1/2018 | Kuwae | A61B 1/3132 |
| 2018/0296242 A1 | 10/2018 | Kuwae et al. | |
| 2019/0350619 A1* | 11/2019 | Fujii | A61B 17/3423 |
| 2020/0187759 A1* | 6/2020 | Yamada | A61B 1/00126 |

FOREIGN PATENT DOCUMENTS

| | | | | |
|---|---|---|---|---|
| WO | 2016152625 | | 9/2016 | |
| WO | 2017119402 | | 7/2017 | |
| WO | WO-2018143082 | A1 * | 8/2018 | ............... A61B 1/00 |

OTHER PUBLICATIONS

"Written Opinion of the International Searching Authority (Form PCT/ISA/237)" of PCT/JP2017/039123, dated Jan. 9, 2018, with English translation thereof, pp. 1-12.

"Search Report of Europe Counterpart Application", dated Jul. 6, 2020, pp. 1-7.

Office Action of Japan Counterpart Application, with English translation thereof, dated Feb. 26, 2021, pp. 1-8.

"Office Action of Europe Counterpart Application", dated Jun. 30, 2022, p. 1-p. 4.

"Office Action of Japan Counterpart Application" with English translation thereof, dated Sep. 15, 2021, p. 1-p. 8.

"Notice of Allowance of U.S. Appl. No. 16/802,520", dated Apr. 14, 2023, pp. 1-10.

* cited by examiner

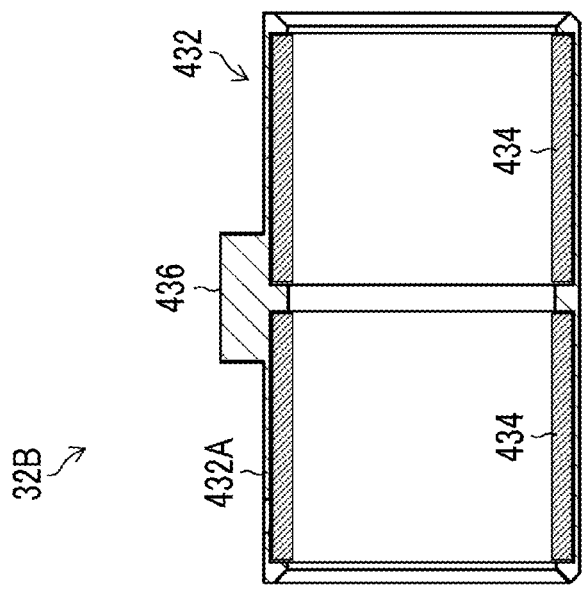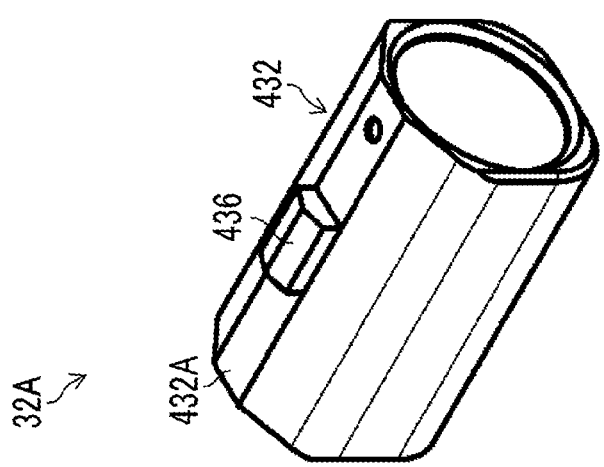
FIG. 32

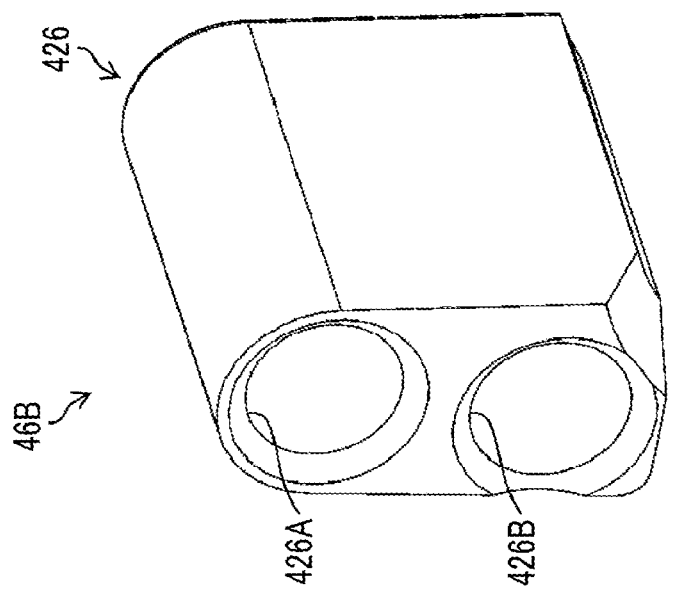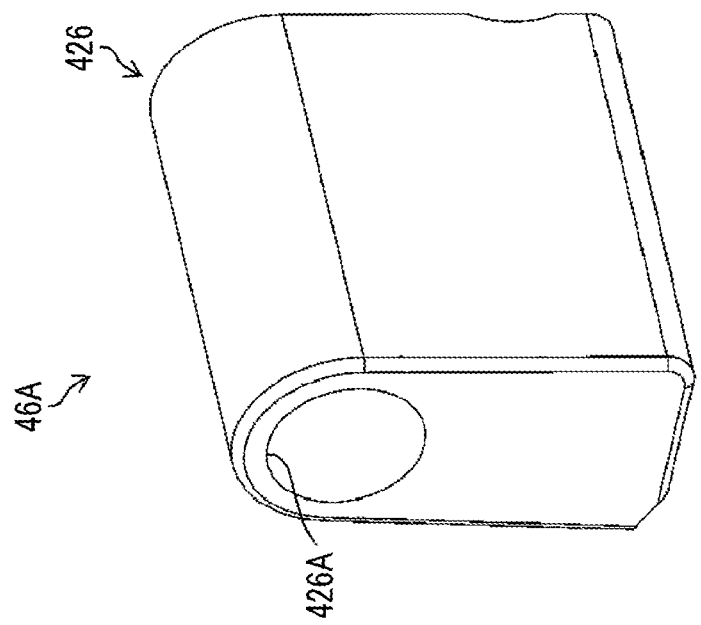
FIG. 46

METHOD OF OPERATING SURGICAL SYSTEM

CROSS-REFERENCE TO RELATED APPLICATIONS

This is a continuation application of and claims the priority benefit of a prior application Ser. No. 16/802,520 filed on Feb. 26, 2020. The prior application Ser. No. 16/802,520 is a Continuation of PCT International Application No. PCT/JP2017/039123 filed on Oct. 30, 2017 claiming priority under 35 U.S.C § 119(a) to U.S. Provisional Application No. 62/552,398 filed on Aug. 31, 2017. Each of the above applications is hereby expressly incorporated by reference, in their entirety, into the present application.

BACKGROUND OF THE INVENTION

1. Field of the Invention

The present invention relates to a surgical system for inserting a medical instrument into a body cavity.

2. Description of the Related Art

In recent years, since invasion to a patient is small compared to surgery in which a laparotomy, a thoracotomy, or the like is performed, endoscopic surgery using endoscopes (hard endoscopes), such as a laparoscope and the like, is widely performed. In the endoscopic surgery, a plurality of holes are formed in a patient's body wall, an endoscope is inserted into a body cavity from one hole of the plurality of holes, and a treatment tool is inserted into the body cavity from another hole. Then, treatment of living body tissue is performed with the treatment tool while observing the living body tissue within the body cavity with the endoscope.

In the endoscopic surgery, by using an overtube (also referred to as a trocar) having a plurality of insertion passages into which an insertion part of an endoscope and an insertion part of a treatment tool are respectively inserted, the insertion part of the endoscope and the insertion part of the treatment tool are inserted into the body cavity as in WO2016/152625A and WO2015/147153A. The overtube is inserted into the body cavity from a hole formed in a body wall. The formation of the hole in the body wall and the insertion of the overtube into the hole are performed by the overtube puncturing the body wall. In this case, an inner needle (also referred to as an obturator) is inserted into the overtube, and a sheathing tube (also referred to as an outer sheath) is sheathed to the overtube. In addition, in order to keep an observation window provided in a distal end surface of the insertion part of the endoscope clean, a syringe that ejects a cleaning liquid is connected to the overtube via a tube.

SUMMARY OF THE INVENTION

In general, each of instruments used in endoscopic surgery, including an overtube, a sheathing tube, an inner needle, a tube, and a syringe, is provided in a state of being stored in one storage case in an operation room. Thus, an individual storage part is provided for each instrument in a storage case. Therefore, each instrument is stored in the individual storage part in the storage case, and is fixed to the individual storage part for each instrument.

However, in a case of providing each individual storage part of the storage case with a fixing structure to fix each instrument, problems of a complicated structure, a size increase, a cost increase, and the like of the storage case occur. Since the storage case is brought into an operation room in particular, the simplification of the structure and miniaturization are required from a perspective of garbage generation prevention and ease of handling. In addition, since the storage case is a disposable case that can be used in only one operation just as each instrument, cost reduction is also required.

The present invention is devised in view of such circumstances, and an object thereof is to provide a surgical system that can realize simplification of a structure of a storage case, miniaturization, and cost reduction.

According to an aspect of the present invention, there is provided a surgical system comprising an overtube that guides an insertion part of a medical instrument, which is to be inserted into a body cavity, into the body cavity, a sheathing tube that is sheathed to the overtube and passes through a body wall so as to be inserted into the body cavity, a syringe that is used in combination with the overtube and ejects and sucks a fluid from a nozzle, a tube that has one end connected to the overtube and the other end connected to the nozzle, an inner needle that is inserted into the overtube, the inner needle puncturing the body wall in a state of being combined with the overtube, and a storage case that has individual storage parts for individually storing the overtube, the sheathing tube, the syringe, the tube, and the inner needle, respectively. The storage case fixes a first instrument, which is any one of the overtube, the sheathing tube, the syringe, the tube, or the inner needle, to the individual storage part corresponding to the first instrument by using at least one of second instruments which are other instruments stored in the individual storage parts.

In the surgical system, since it is not necessary to additionally provide a structure for fixing the first instrument to the corresponding individual storage part in the storage case, simplification of the storage case, miniaturization, and cost reduction case can be realized.

In the surgical system according to another aspect of the present invention, the overtube comprises an overtube body that has a distal end, a proximal end, and a longitudinal axis, a first distal end opening and a second distal end opening that are provided at the distal end of the overtube body, a first proximal end opening and a second proximal end opening that are provided at the proximal end of the overtube body, a first insertion passage that is provided along the longitudinal axis of the overtube body and allows the first distal end opening and the first proximal end opening to communicate with each other, a second insertion passage that is provided along the longitudinal axis of the overtube body and allows the second distal end opening and the second proximal end opening to communicate with each other, and a coupling mechanism that has a first coupling part which is coupled to a first insertion part of a first medical instrument inserted in the first insertion passage and a second coupling part which is coupled to a second insertion part of a second medical instrument inserted in the second insertion passage. Accordingly, since any one of the first insertion part or the second insertion part can be moved forward and backward in an interlocking manner with forward and backward movement of the other one of the first insertion part or the second insertion part, an assistant can be made unnecessary. As a result, it is not necessary for an operator to serially give an instruction to an assistant, and thus a troublesome condition for the operator can be eliminated.

In the surgical system according to another aspect of the present invention, the coupling mechanism has a non-sensing region where any one of the first insertion part or the second insertion part is not interlocked with forward and backward movement of the other one of the first insertion part or the second insertion part and a sensing region where any one of the first insertion part or the second insertion part is interlocked with forward and backward movement of the other one of the first insertion part or the second insertion part. Accordingly, as intended by an operator, the operator can select whether or not to interlock any one of the first insertion part or the second insertion part with forward and backward movement of the other one of the first insertion part or the second insertion part.

In the surgical system according to another aspect of the present invention, the overtube comprises the overtube body, a slider that is provided inside the overtube body and is movable in an axial direction of the longitudinal axis, the slider having a pair of restricting parts disposed to be spaced apart from each other in the axial direction of the longitudinal axis, and a fixing tool that is provided in the slider, and is movable between the pair of restricting parts in the axial direction of the longitudinal axis. The slider comprises a first passage in which the fixing tool moves between the pair of restricting parts in the axial direction of the longitudinal axis, a second passage into which the first insertion part of the first medical instrument is inserted, and a first coupling part which is coupled to the first insertion part inserted in the second passage. The fixing tool comprises a third passage into which the second insertion part of the second medical instrument is inserted and a second coupling part which is coupled to the second insertion part inserted in the third passage. Accordingly, the overtube has the non-sensing region and the sensing region which are described above.

In the surgical system according to another aspect of the present invention, the coupling mechanism comprises a partition wall member that is provided inside the overtube body and extends along the longitudinal axis, the partition wall member having a partition wall between the first insertion passage and the second insertion passage, a first fixing tool that has the first coupling part and is movable forward and backward along the first insertion passage, a second fixing tool that has the second coupling part and is movable forward and backward along the second insertion passage, and a slider that is externally fitted to an outer peripheral part of the partition wall member and is movable forward and backward along the longitudinal axis with respect to the partition wall member, the slider having a sensing region where any one of the first fixing tool or the second fixing tool is moved forward and backward in an interlocking manner with forward and backward movement of the other one of the first fixing tool or the second fixing tool. Accordingly, any one of the first insertion part or the second insertion part can be interlocked with forward and backward movement of the other one of the first insertion part or the second insertion part.

In the surgical system according to another aspect of the present invention, the slider further has a non-sensing region where any one of the first fixing tool or the second fixing tool is not moved forward and backward with respect to forward and backward movement of the other one of the first fixing tool or the second fixing tool. Accordingly, as intended by an operator, the operator can select whether or not to interlock any one of the first insertion part or the second insertion part with forward and backward movement of the other one of the first insertion part or the second insertion part.

In the surgical system according to another aspect of the present invention, the slider has a first engaging part that is engaged with the first fixing tool and a second engaging part that is engaged with the second fixing tool. The first engaging part has a first restricting part that restricts forward and backward movement of the first fixing tool in a first range. The second engaging part has a second restricting part that restricts forward and backward movement of the second fixing tool in a second range different from the first range. Accordingly, the first fixing tool and the second fixing tool can be moved forward and backward in different ranges with respect to the slider. The ranges also include zero.

In the surgical system according to another aspect of the present invention, the slider has a first engaging part that is engaged with the first fixing tool and a second engaging part that is engaged with the second fixing tool. At least one of the first engaging part or the second engaging part allows movement of the corresponding fixing tool in a direction along the longitudinal axis. Accordingly, the slider has the non-sensing region described above.

In the surgical system according to another aspect of the present invention, the slider has a first engaging part that is engaged with the first fixing tool and a second engaging part that is engaged with the second fixing tool. At least one of the first engaging part or the second engaging part allows rotation of the corresponding fixing tool in a direction around an axis. Accordingly, at least one of the first insertion part or the second insertion part can be rotated in the direction around an axis.

In the surgical system according to another aspect of the present invention, the partition wall member has a first guide groove constituting a part of the first insertion passage and a second guide groove constituting a part of the second insertion passage. Accordingly, the first insertion part and the second insertion part are restrained from proceeding to a region other than the respective insertion passages.

In the surgical system according to another aspect of the present invention, the first insertion passage and the second insertion passage are disposed so as to be parallel to each other.

In the surgical system according to another aspect of the present invention, the first insertion passage and the second insertion passage are disposed so as to obliquely intersect each other. Accordingly, even in a case where an interval between the first insertion passage and the second insertion passage in the overtube is narrowed for diameter reduction, a distal end of the first insertion part inserted in the overtube and the distal end of the second insertion part can be spaced apart from each other.

In the surgical system according to another aspect of the present invention, the inner needle comprises a first needle part that has a first distal end part and is inserted into the first insertion passage, a second needle part that has a second distal end part and is inserted into the second insertion passage, a first cutting edge that is formed at the first distal end part and has a length component orthogonal to the longitudinal axis in a state where the overtube and the inner needle are combined, a second cutting edge that is formed at the second distal end part and has a length component orthogonal to the longitudinal axis in a state where the overtube and the inner needle are combined, and a positioning part that defines a position of the first distal end part with respect to the first distal end opening and a position of the second distal end part with respect to the second distal end opening in a state where the overtube and the inner needle are combined. In a case where the first cutting edge and the second cutting edge are projected on a plane perpendicular to the longitudinal axis in a state where the overtube and the inner needle are combined, the first cutting edge and the second cutting edge are disposed along the same straight line. In the combined state, the first distal end part is disposed closer to a proximal end side of the overtube body than the second distal end part is. Accordingly, with respect to the amount of inserting force required in a case of puncturing the body wall with the overtube and a penetration force required in a case where the overtube passes through the body wall, an effect of having the two insertion passages of the overtube can be made small, a necessary amount of inserting force and a necessary penetration force can be made small, and puncturing can be made easy for the overtube.

In the surgical system according to another aspect of the present invention, in a case where the first cutting edge and the second cutting edge are projected on the plane perpendicular to the longitudinal axis in a state where the overtube and the inner needle are combined, the first cutting edge and the second cutting edge are disposed on the same straight line. Accordingly, the necessary amount of inserting force and the penetration force which are described above can be made small, and puncturing can be made easy for the overtube. An insertion load in a case of puncturing the body wall with the overtube can be reduced without impairing a tearing task with respect to the body wall by linearly disposing each of the cutting edges.

In the surgical system according to another aspect of the present invention, a tapered part that tapers off toward a distal end of the overtube body is provided on a distal end side of the overtube body. The tapered part has the second distal end opening and the first distal end opening that is disposed closer to the proximal end side of the overtube body than the second distal end opening is. Accordingly, a shape of a distal end portion in a state where the overtube and the inner needle are combined can be made similar to a shape of a distal end portion of the overtube in a state where the inner needle having one needle part is mounted on the overtube having one insertion passage. As a result, the necessary amount of inserting force and the penetration force which are described above can be made small, and puncturing can be made easy for the overtube.

In the surgical system according to another aspect of the present invention, the second distal end opening is open in a direction perpendicular to the longitudinal axis, and the first distal end opening is open in an oblique direction with respect to the longitudinal axis. Accordingly, a shape of a distal end portion in a state where the overtube and the inner needle are combined can be made similar to a shape of a distal end portion of the overtube in a state where the inner needle having one needle part is mounted on the overtube having one insertion passage.

In the surgical system according to another aspect of the present invention, the second distal end part has an inclined surface that tapers off toward a distal end of the second distal end part, and the inclined surface is provided at a position protruding from the second distal end opening in a case of being positioned by the positioning part. A pair of the second cutting edges is provided on the inclined surface, and the pair of second cutting edges is disposed at positions symmetrical to each other with respect to a central axis of the second needle part. Accordingly, an insertion load in a case of puncturing the body wall with the overtube can be reduced without impairing a tearing task with respect to the body wall.

In the surgical system according to another aspect of the present invention, the first distal end part has a distal end surface disposed along an opening surface of the first distal end opening in a case of being positioned by the positioning part. The first cutting edge is provided on the distal end surface. Accordingly, an insertion load in a case of puncturing the body wall with the overtube can be reduced without impairing a tearing task with respect to the body wall.

In the surgical system according to another aspect of the present invention, the coupling mechanism comprises a partition wall member that is provided inside the overtube body and extends along the longitudinal axis, the partition wall member having a partition wall between the first insertion passage and the second insertion passage, a first fixing tool that has the first coupling part and is movable forward and backward along the first insertion passage, a second fixing tool that has the second coupling part and is movable forward and backward along the second insertion passage, and a slider that is externally fitted to an outer peripheral part of the partition wall member and is movable forward and backward along the longitudinal axis with respect to the partition wall member in a third range, the slider comprising the first fixing tool and the second fixing tool. Any one of the first insertion passage or the second insertion passage is an endoscope insertion passage into which an insertion part of an endoscope is inserted so as to be movable forward and backward. Any one of the first fixing tool or the second fixing tool is an endoscope fixing tool that moves along the endoscope insertion passage and is coupled to the insertion part of the endoscope. The overtube comprises a fluid passage including a fluid supply and discharge port that is open into the distal end side of the endoscope insertion passage and a proximal end side connection port that is connected to the one end of the tube. In a case where the slider moves to a proximal end of the third range in a state where the insertion part of the endoscope is coupled to the endoscope fixing tool, the slider positions a distal end of the insertion part of the endoscope at a position closer to a proximal end side than a distal end side end part of the fluid supply and discharge port. Accordingly, only with the feeling in the hand, the operator can position the distal end of the insertion part of the endoscope at a position closer to the proximal end side of the overtube body than the distal end side end part of the fluid supply and discharge port.

In the surgical system according to still another aspect of the present invention, the sheathing tube comprises a sheathing tube body that has a tubular shape of which a longitudinal axis is a central axis, the sheathing tube body being sheathed to an outer peripheral surface of the overtube, a rotation restricting part that is formed on an outer peripheral surface of the sheathing tube body and restricts rotation of the sheathing tube body with respect to the body wall in a rotation direction with the longitudinal axis as a center, and a movement restricting part that is formed on the outer peripheral surface of the sheathing tube body and restricts forward and backward movement of the sheathing tube body with respect to the body wall in an axial direction of the longitudinal axis. Accordingly, the operator can restrict unintended rotation of the overtube in a rotation direction and unintended forward and backward movement of the overtube in the axial direction.

The surgical system according to an embodiment of the present invention can realize simplification of a structure of a storage case, miniaturization, and cost reduction.

Figure 16:
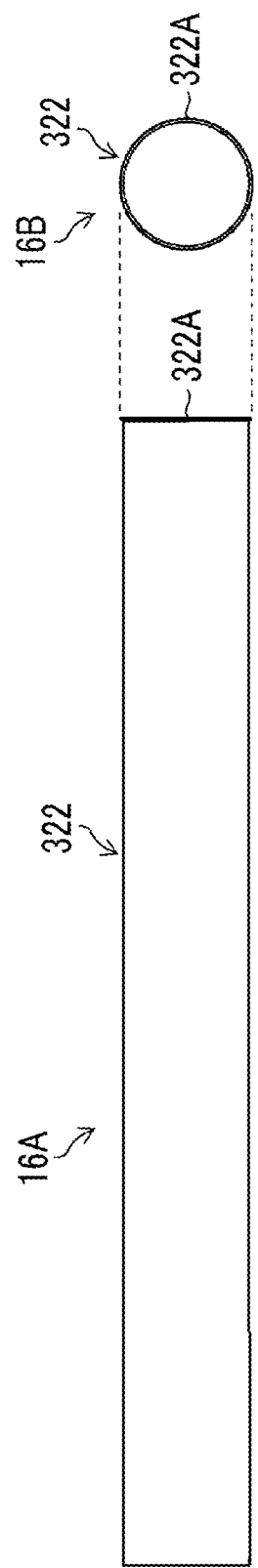

The reference sign 16A of FIG. 16 indicates a side view of the long tubular body of the overtube body, and the reference sign 16B of FIG. 16 indicates a rear view of the long tubular body seen from a proximal end side thereof.

Figure 17:
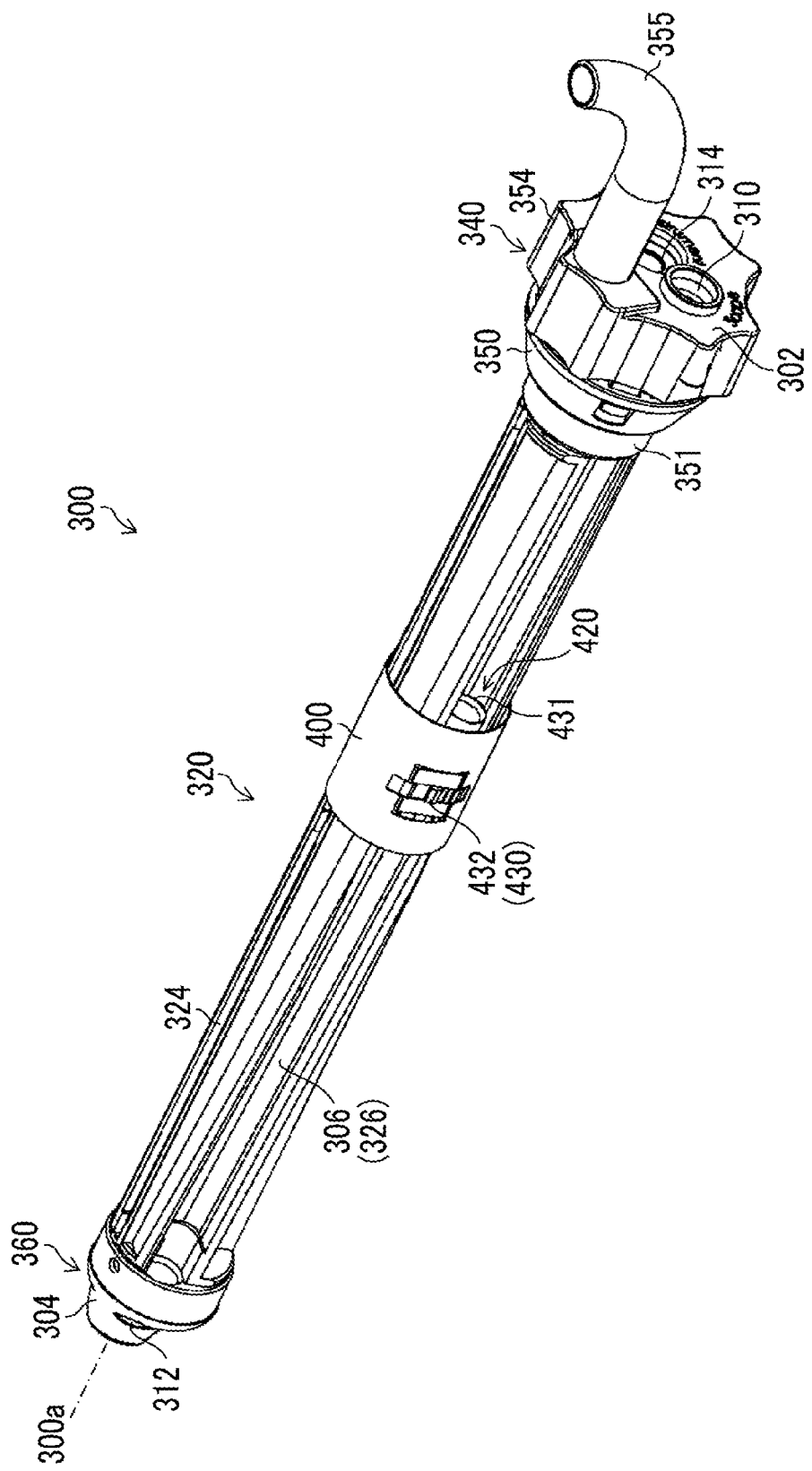

FIG. 17 is an external perspective view illustrating the overtube body with the long tubular body omitted.

Figure 18:
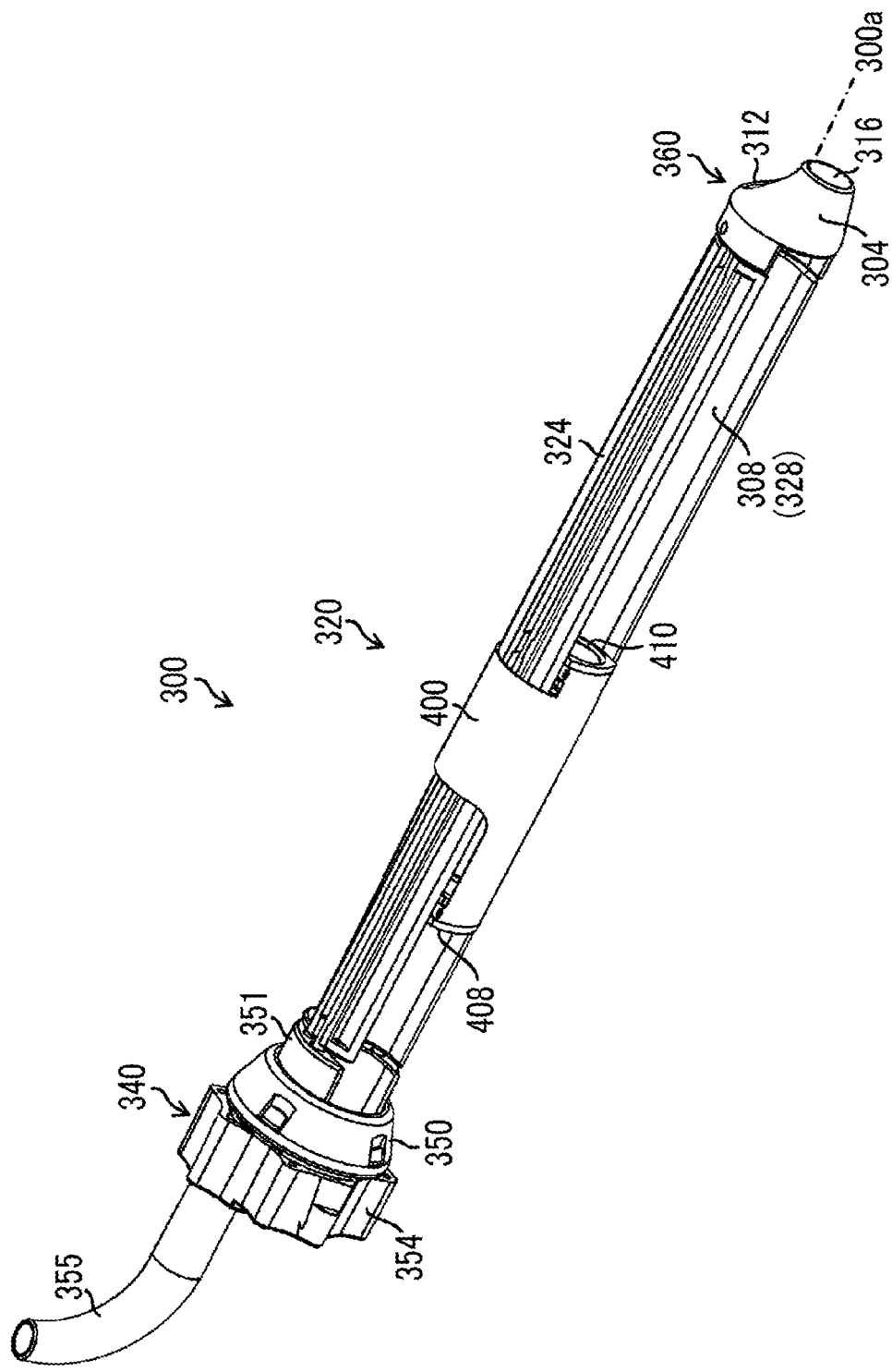

FIG. 18 is an external perspective view illustrating the overtube body with the long tubular body omitted.

Figure 19:
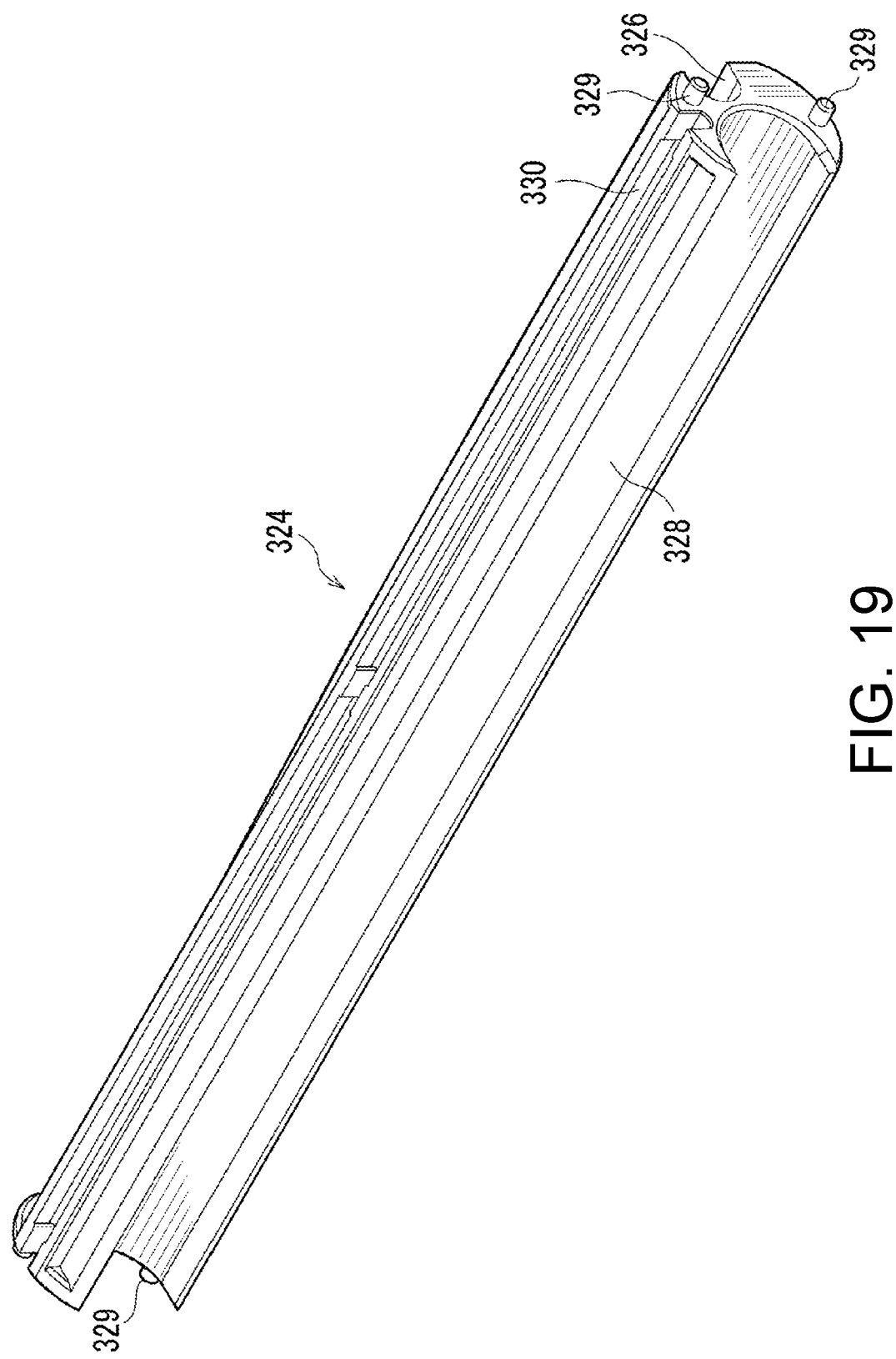

FIG. 19 is an external perspective view of a partition wall member seen from a distal end side thereof.

Figure 20:
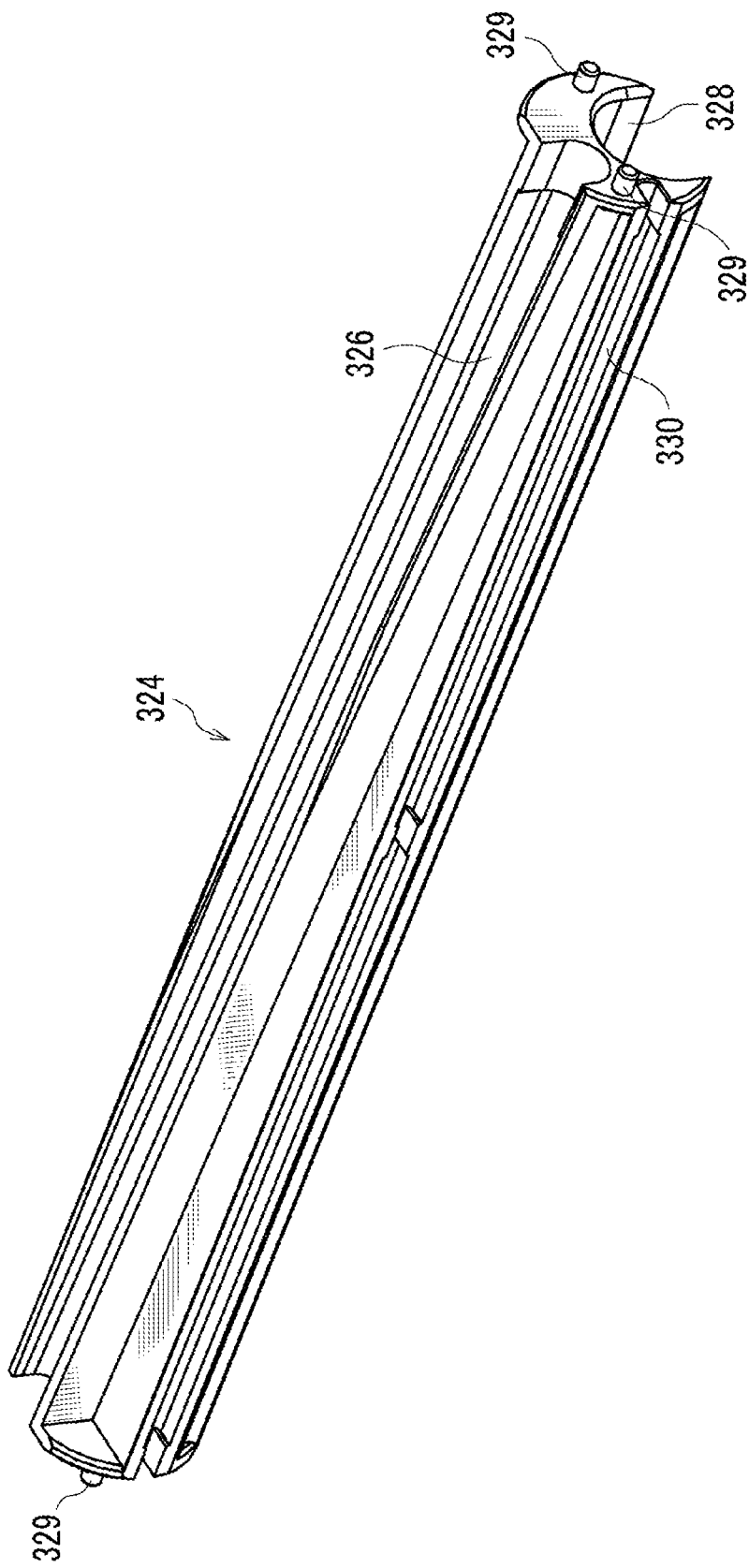

FIG. 20 is an external perspective view of the partition wall member seen from the distal end side thereof.

Figure 21:
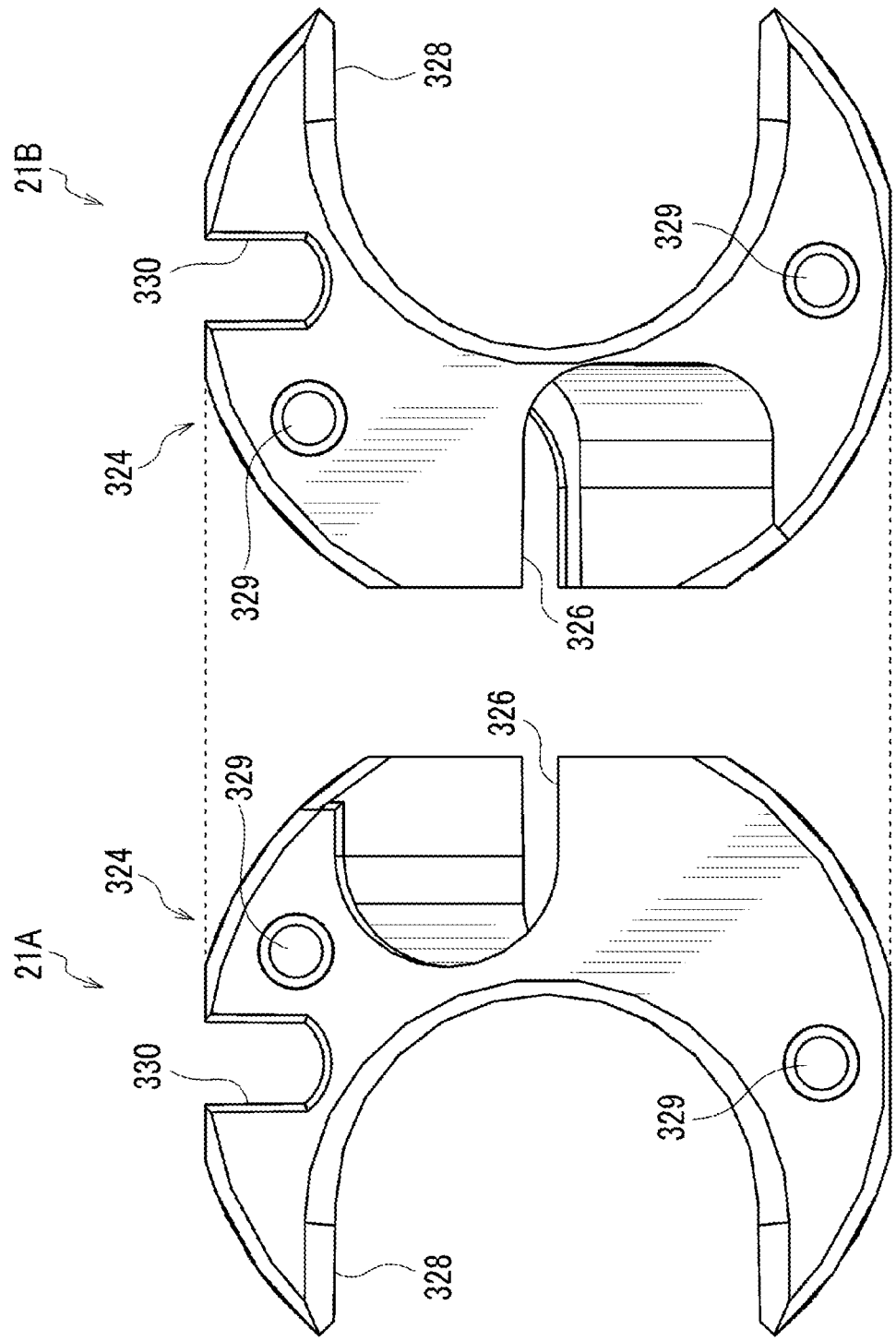

The reference sign 21A of FIG. 21 indicates a front view of the partition wall member seen from the distal end side thereof, and the reference sign 21B of FIG. 21 indicates a rear view of the partition wall member seen from a proximal end side thereof.

Figure 22:
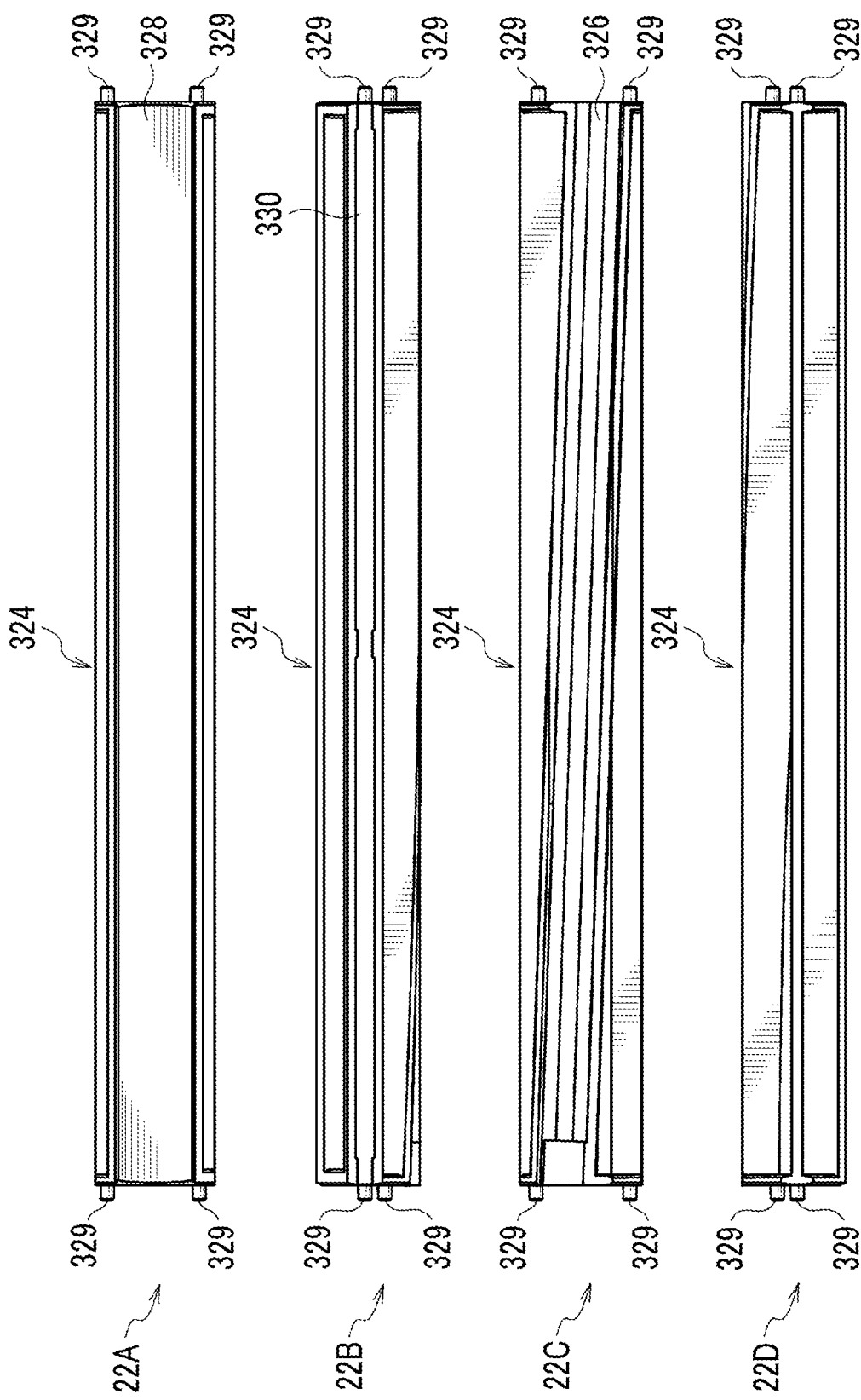

The reference sign 22A of FIG. 22 indicates a right side view of the partition wall member, the reference sign 22B of FIG. 22 indicates an upper side view of the partition wall member, the reference sign 22C of FIG. 22 indicates a left side view of the partition wall member, and the reference sign 22D of FIG. 22 indicates a lower side view of the partition wall member.

Figure 23:
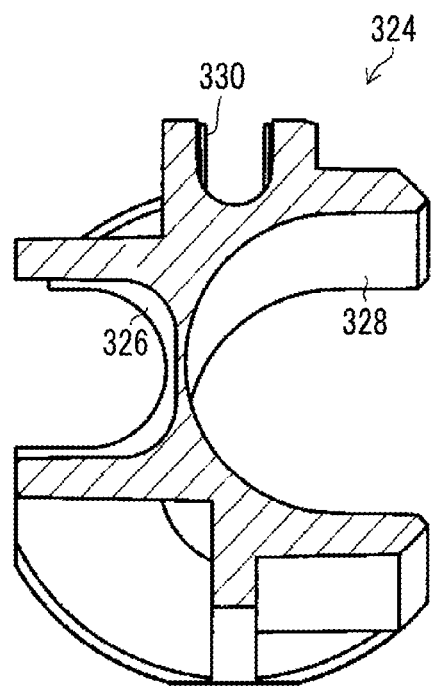

FIG. 23 is a cross-sectional view of the partition wall member taken along a plane perpendicular to a longitudinal axis, and is a cross-sectional view of the partition wall member seen from the proximal end side thereof.

Figure 24:
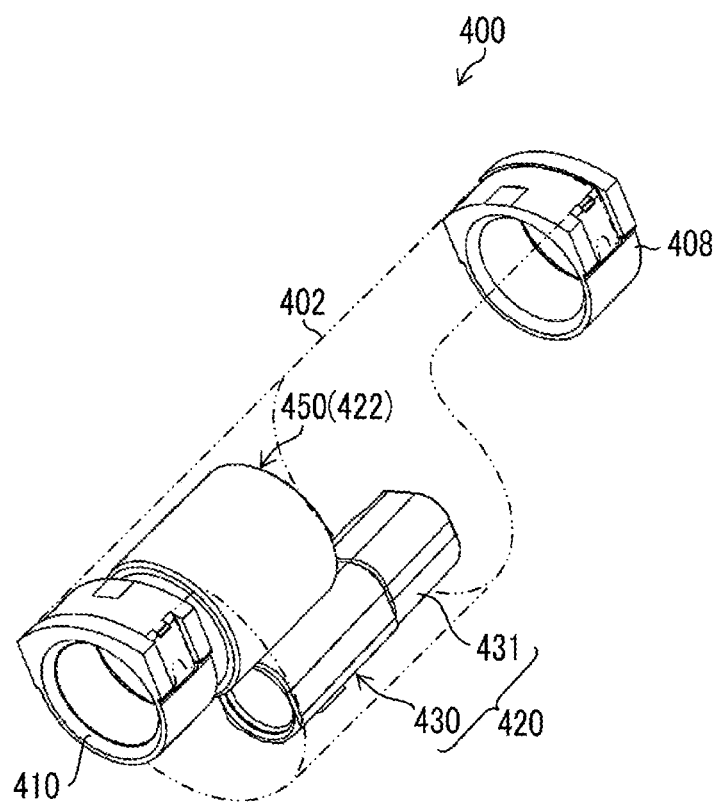

FIG. 24 is an external perspective view of a slider.

Figure 25:
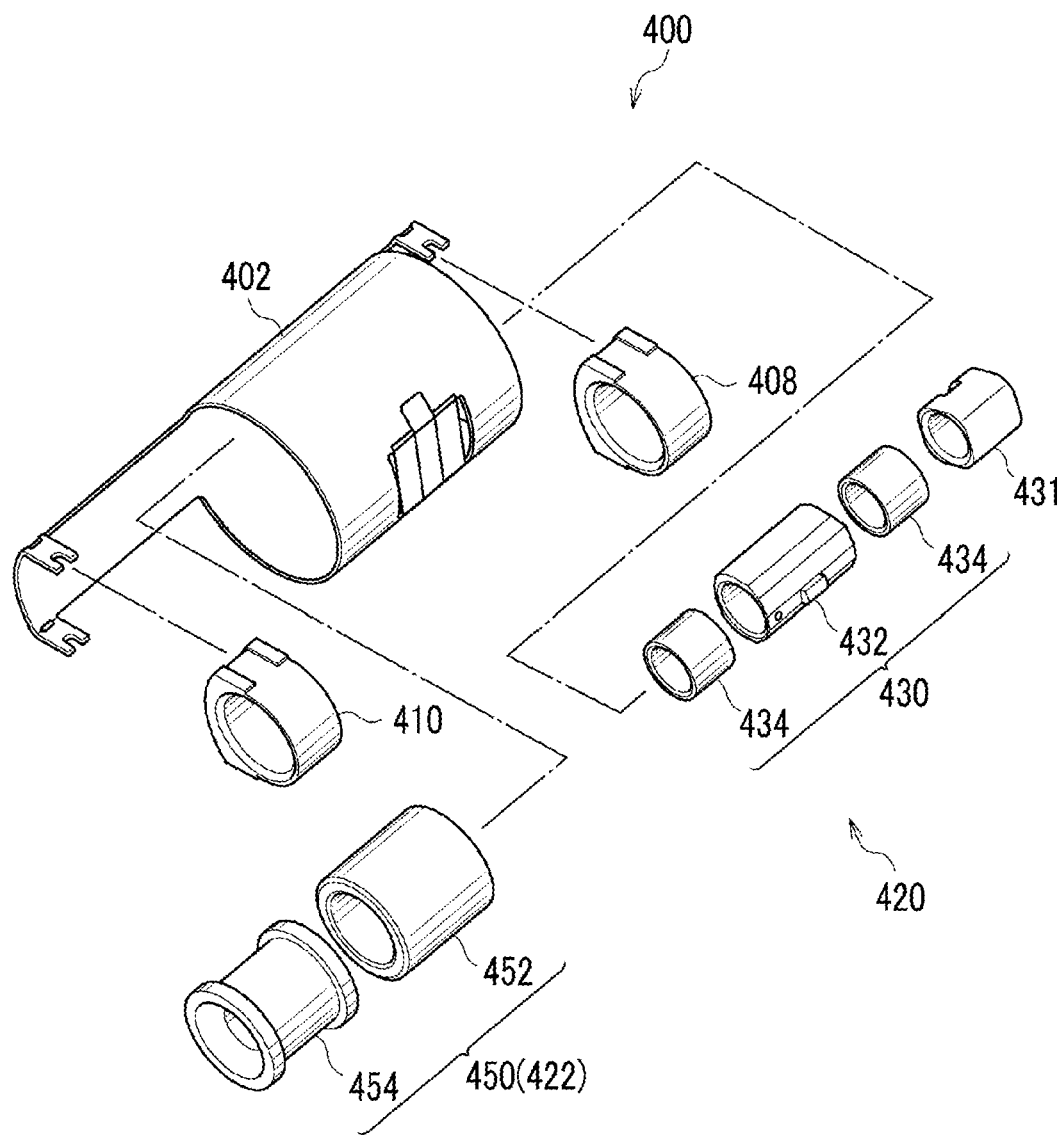

FIG. 25 is an exploded perspective view of the slider.

Figure 26:
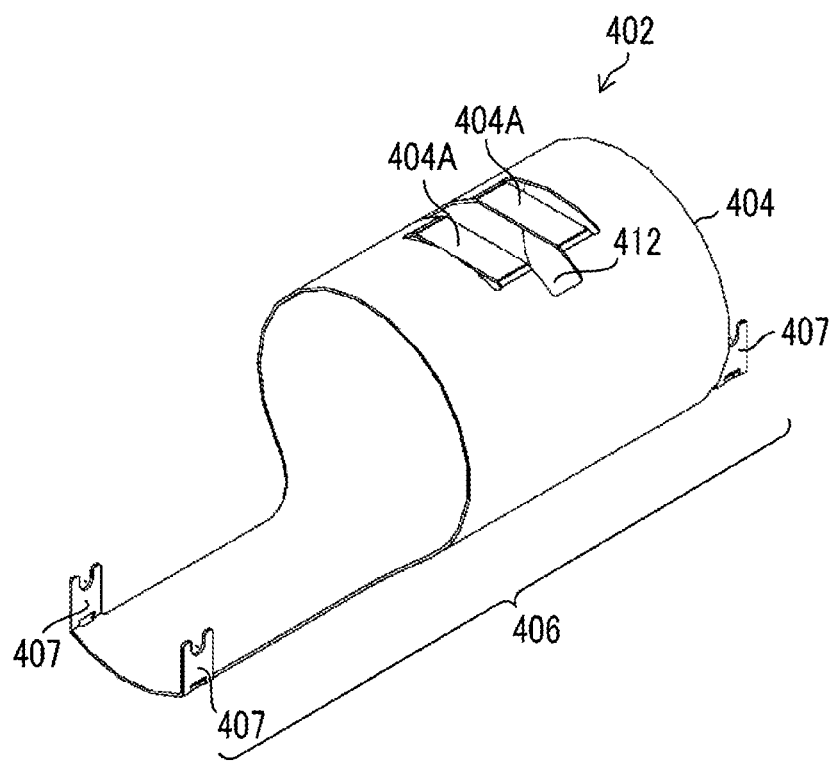

FIG. 26 is an external perspective view of a coupling ring.

Figure 27:
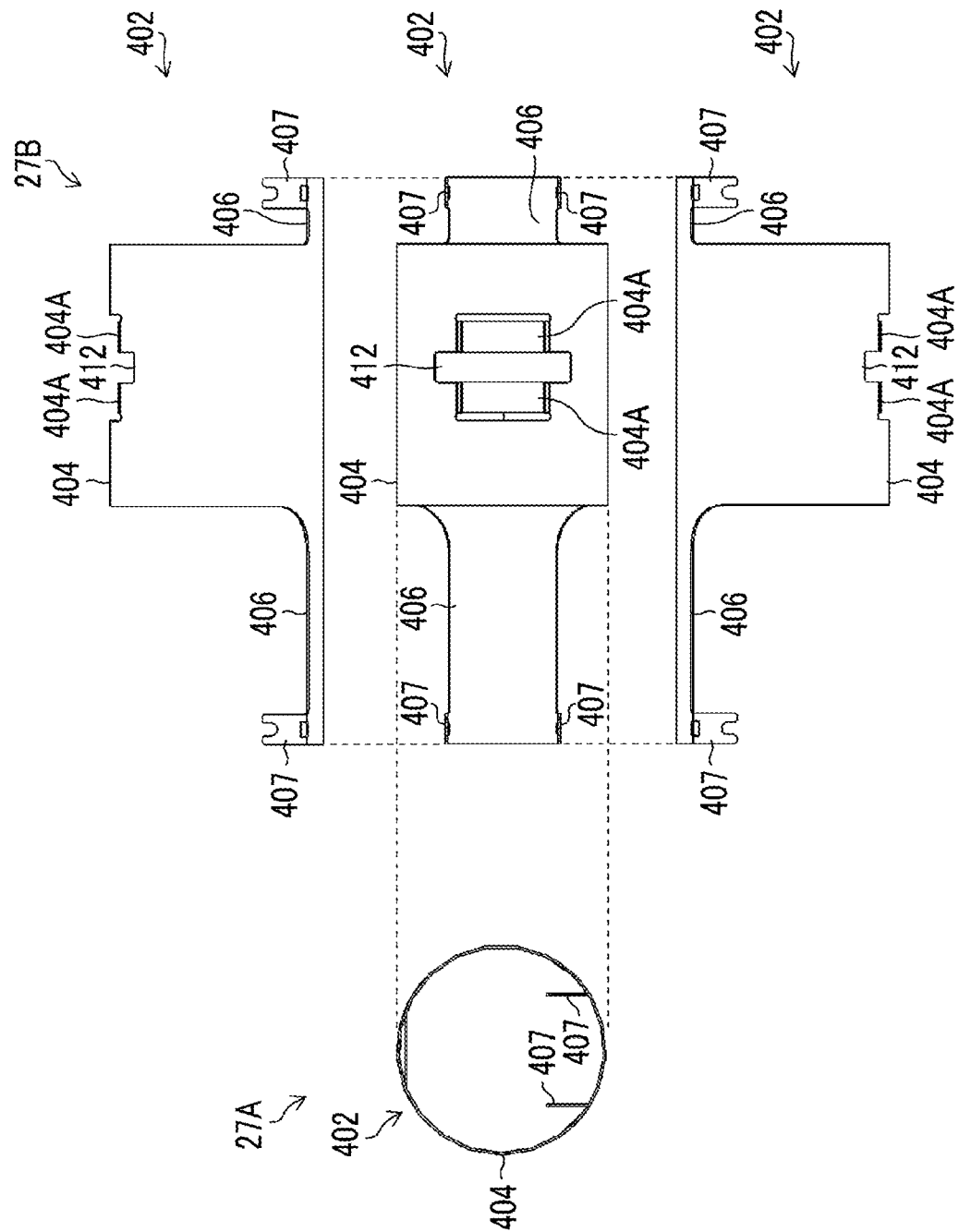

The reference sign 27A of FIG. 27 indicates a front view of the coupling ring seen from a distal end side thereof, and the reference sign 27B of FIG. 27 indicates a right-and-left side view and a top view of the coupling ring.

Figure 28:
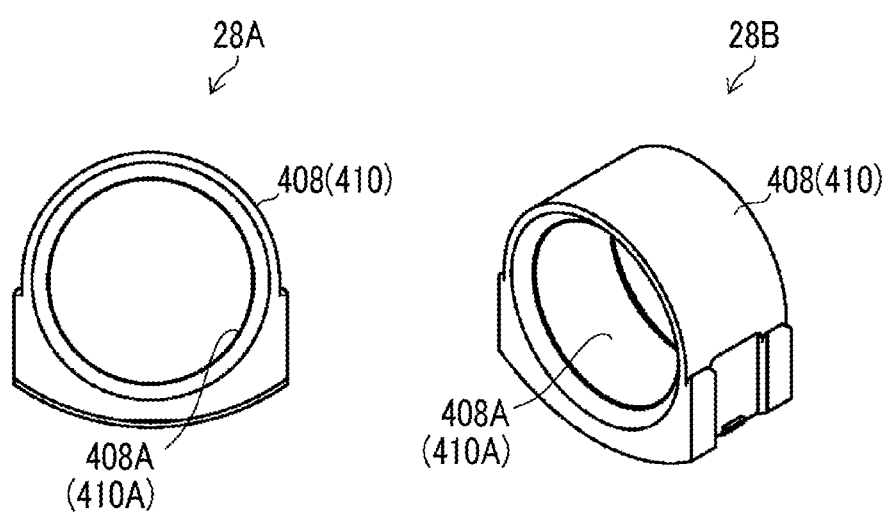

The reference sign 28A of FIG. 28 indicates a front view of a rear restriction end and a front restriction end, and the reference sign 28B of FIG. 28 indicates an external perspective view of the rear restriction end and the front restriction end.

Figure 29:
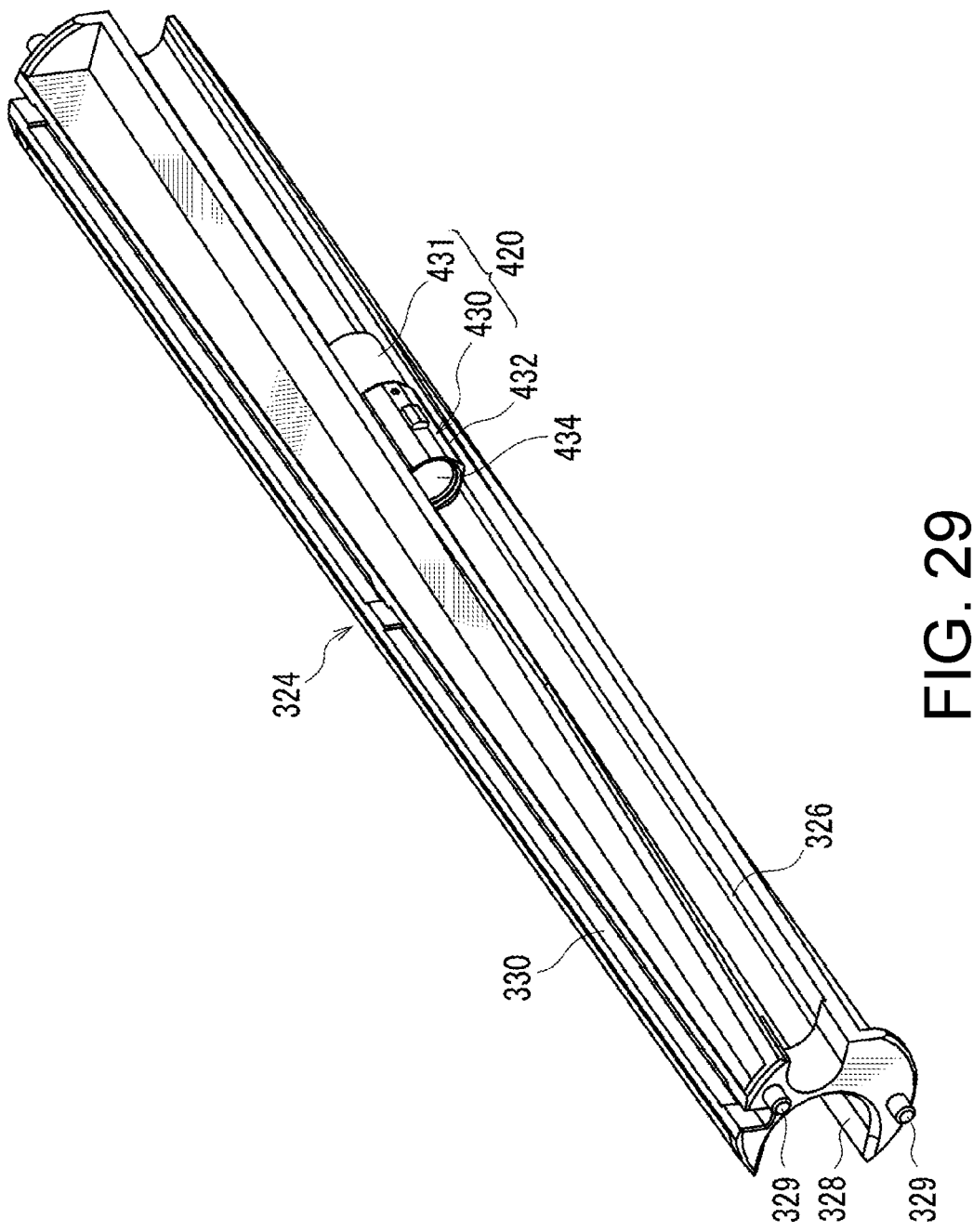

FIG. 29 is an external perspective view illustrating the partition wall member and an endoscope coupling part with the coupling ring omitted.

Figure 30:
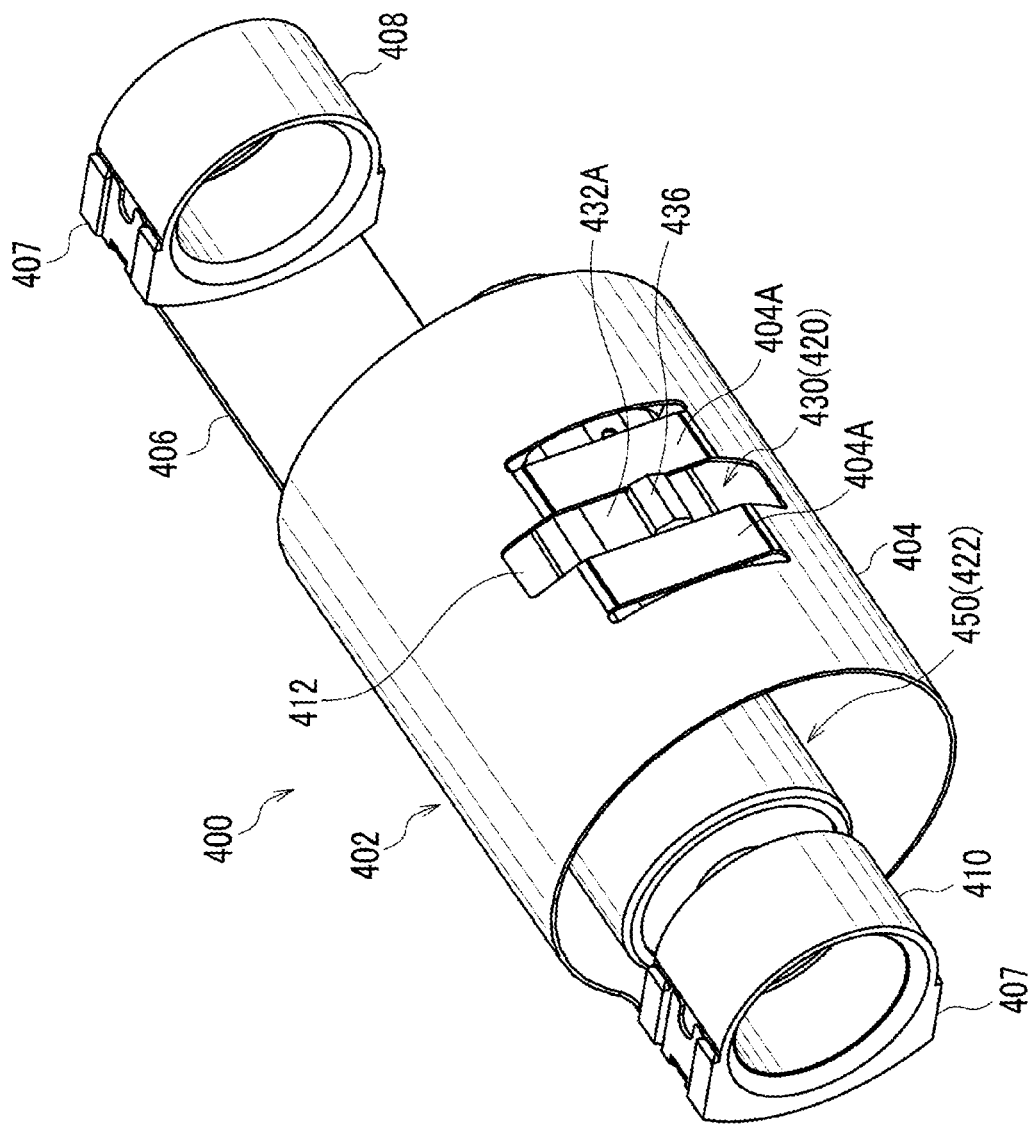

FIG. 30 is an external perspective view of the slider.

Figure 31:
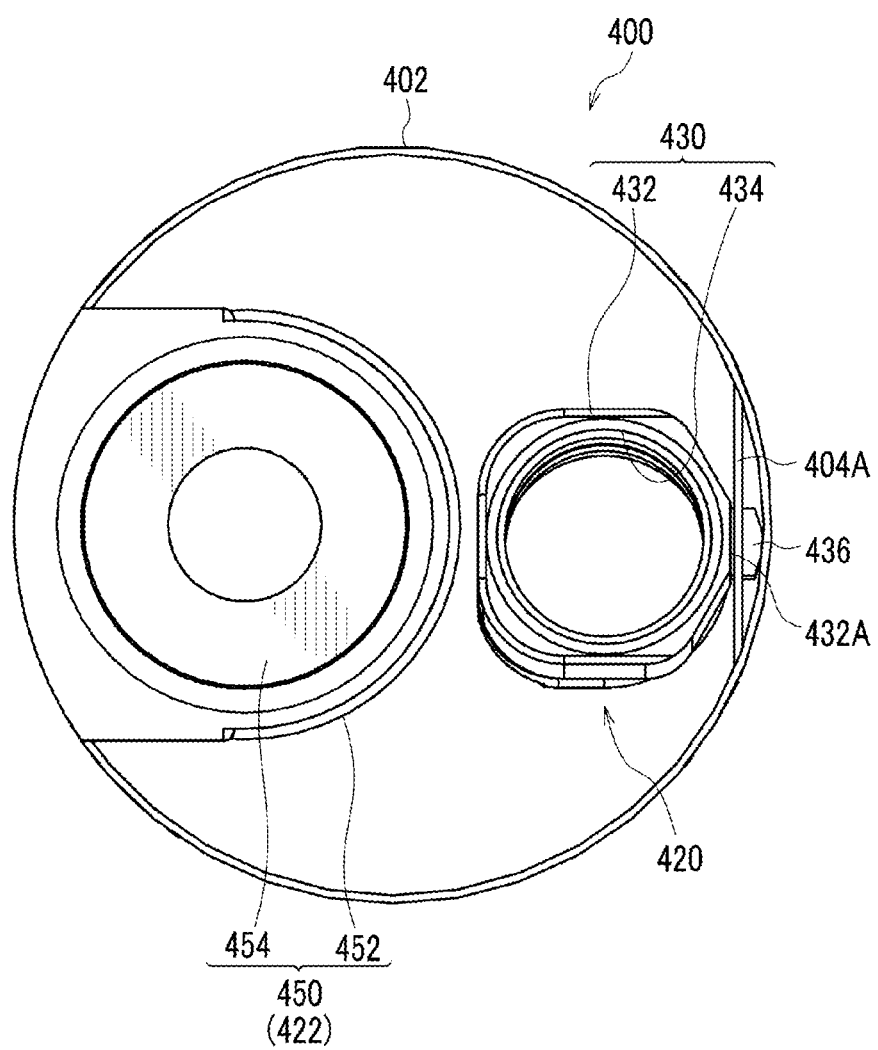

FIG. 31 is a front view of the slider seen from a distal end side thereof.

The reference sign 32A of FIG. 32 indicates an external perspective view of a holding frame of an endoscope fixing tool, and the reference sign 32B of FIG. 32 indicates a cross-sectional view of the holding frame taken along a forward-backward direction.

Figure 33:
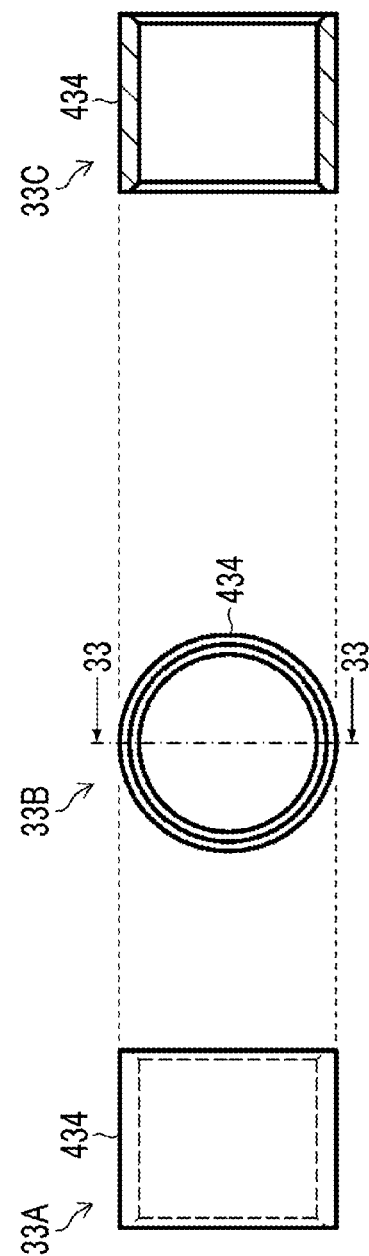

The reference sign 33A of FIG. 33 indicates a side view of an endoscope seal member, the reference sign 33B of FIG. 33 indicates a front view of the endoscope seal member, and the reference sign 33C of FIG. 33 indicates a cross-sectional view of the endoscope seal member shown with the reference sign 33B, which is taken along line "33"-"33".

Figure 34:
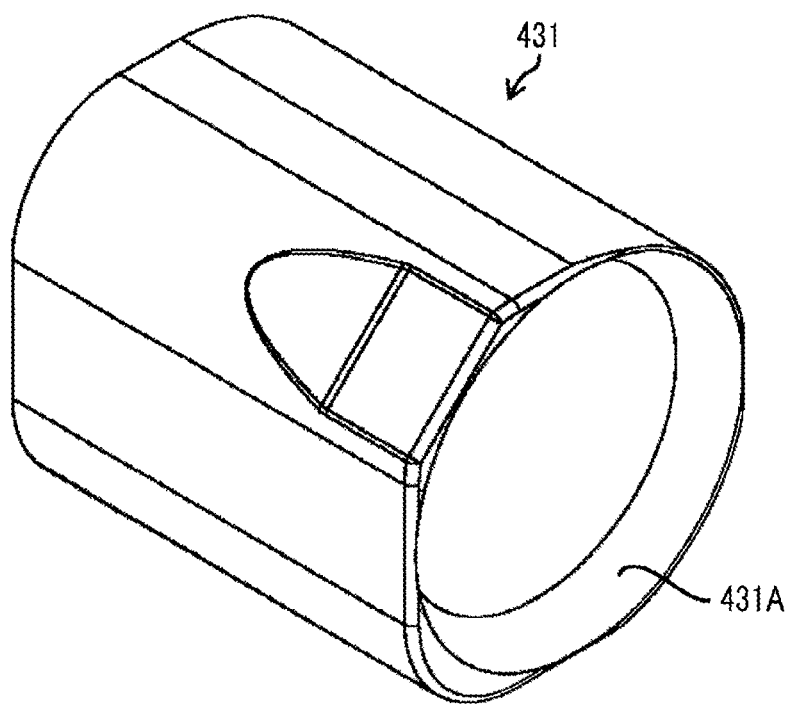

FIG. 34 is an external perspective view of a guide bush.

Figure 35:
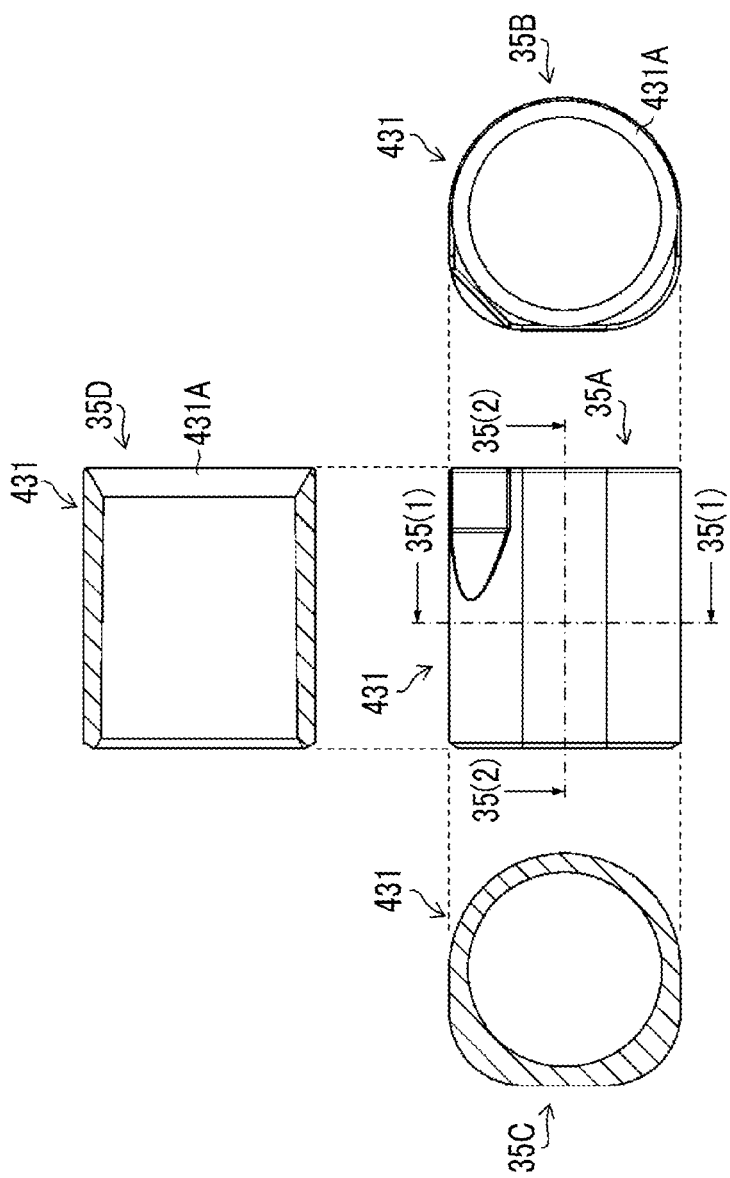

The reference sign 35A of FIG. 35 indicates a side view of the guide bush, the reference sign 35B of FIG. 35 indicates a rear view of the guide bush seen from a proximal end side thereof, the reference sign 35C of FIG. 35 indicates a cross-sectional view of the guide bush shown with the reference sign 35A, which is taken along line "35(1)"-"35(1)", and the reference sign 35D of FIG. 35 indicates a cross-sectional view of the same guide bush, which is taken along line "35(2)"-"35(2)".

Figure 36:
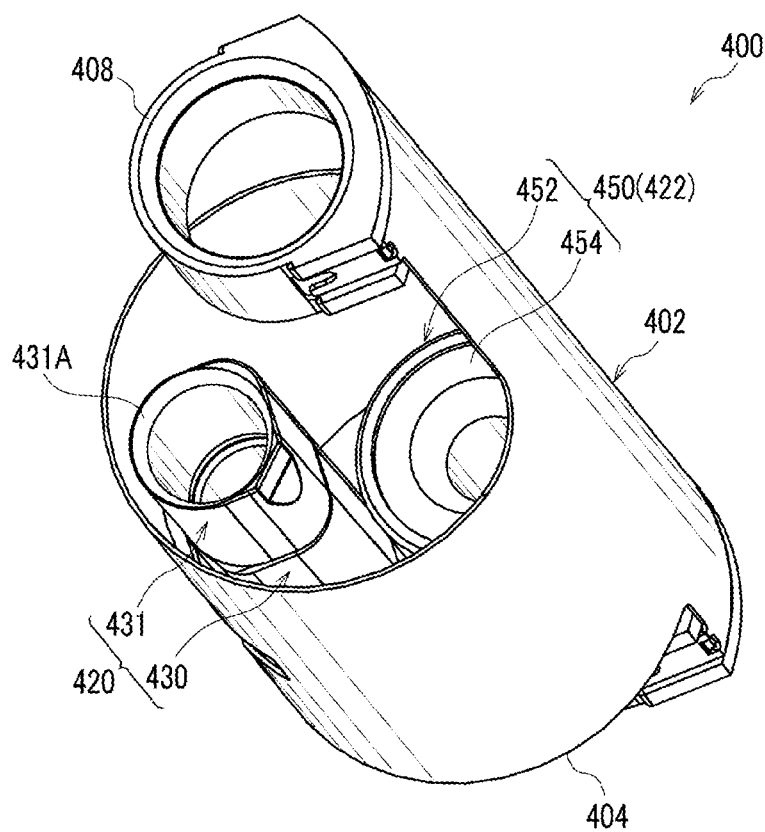

FIG. 36 is a rear perspective view of the guide bush seen from the proximal end side thereof.

Figure 37:
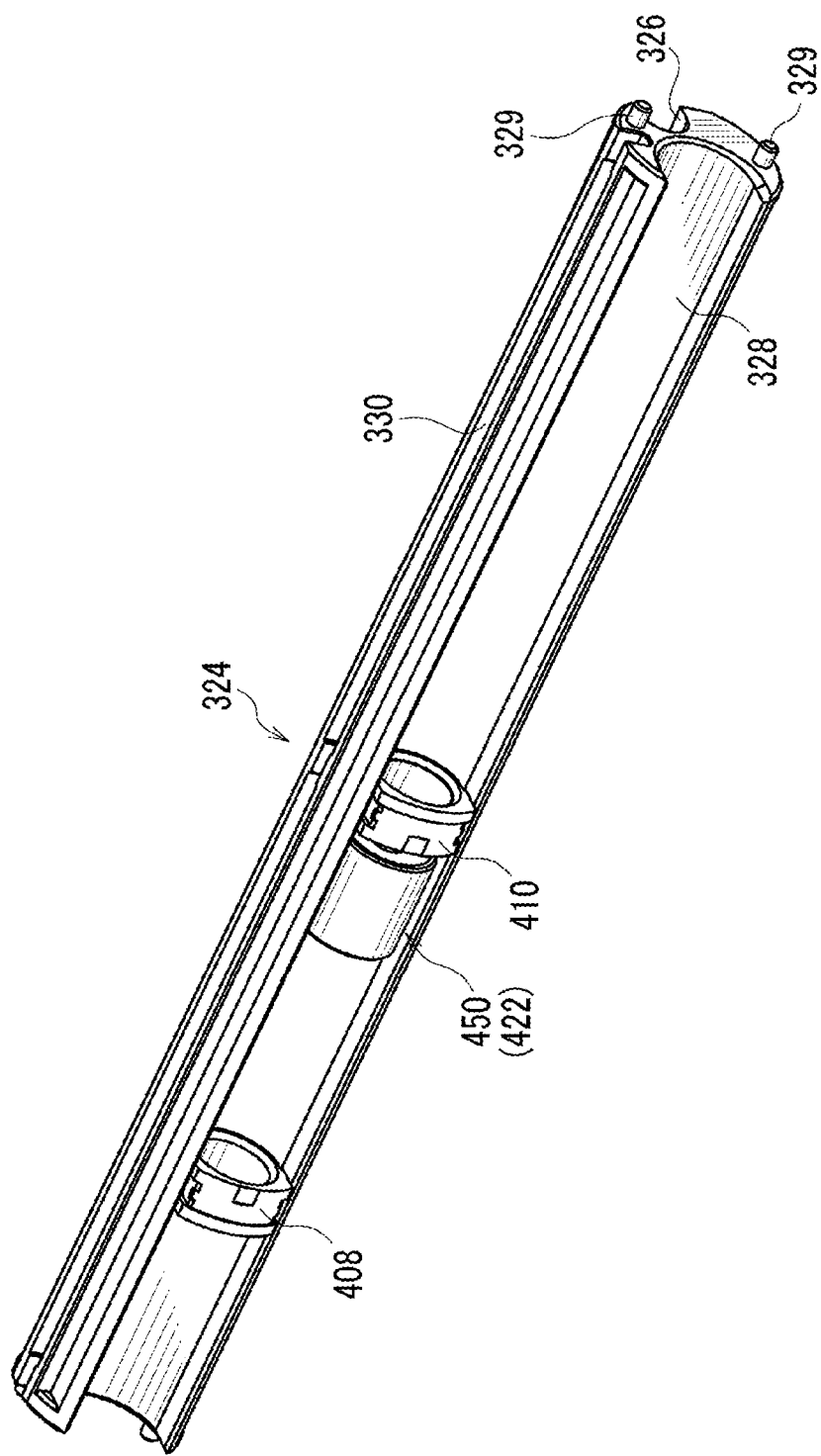

FIG. 37 is an external perspective view illustrating the partition wall member and a treatment tool fixing tool with the coupling ring omitted.

Figure 38:
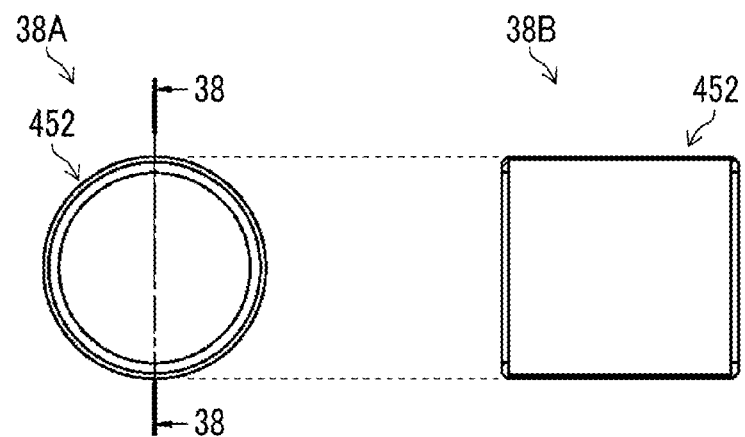

The reference sign 38A of FIG. 38 indicates a front view of a frame of the treatment tool fixing tool seen from a distal end side thereof, and the reference sign 38B of FIG. 38 indicates a cross-sectional view of the frame shown with the reference sign 38A, which is taken along line "38"-"38".

Figure 39:
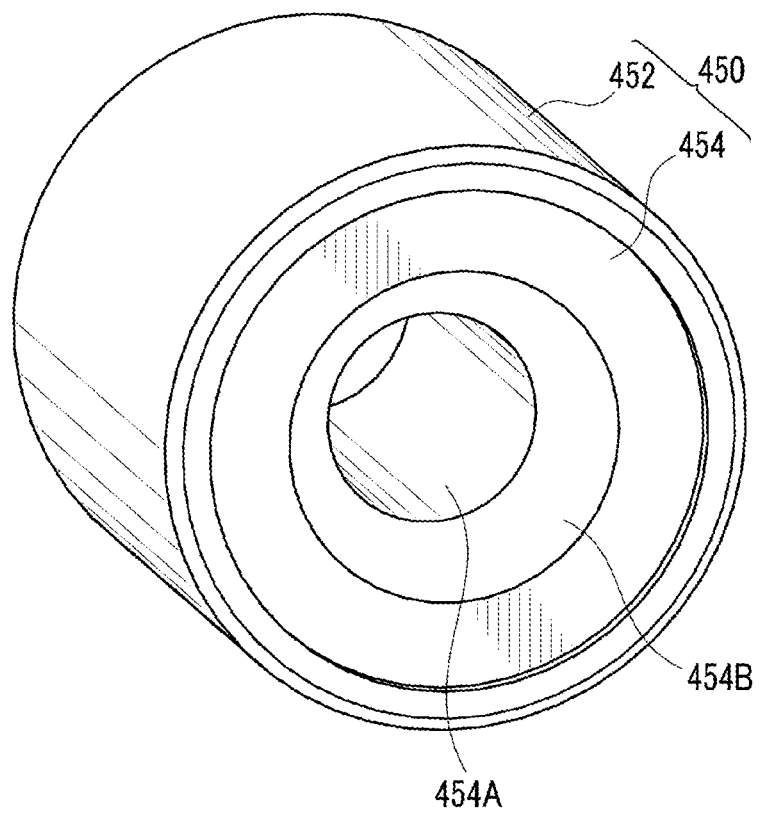

FIG. 39 is a rear perspective view of the frame of the treatment tool fixing tool and a treatment tool seal member of the treatment tool fixing tool seen from a proximal end side thereof.

Figure 40:
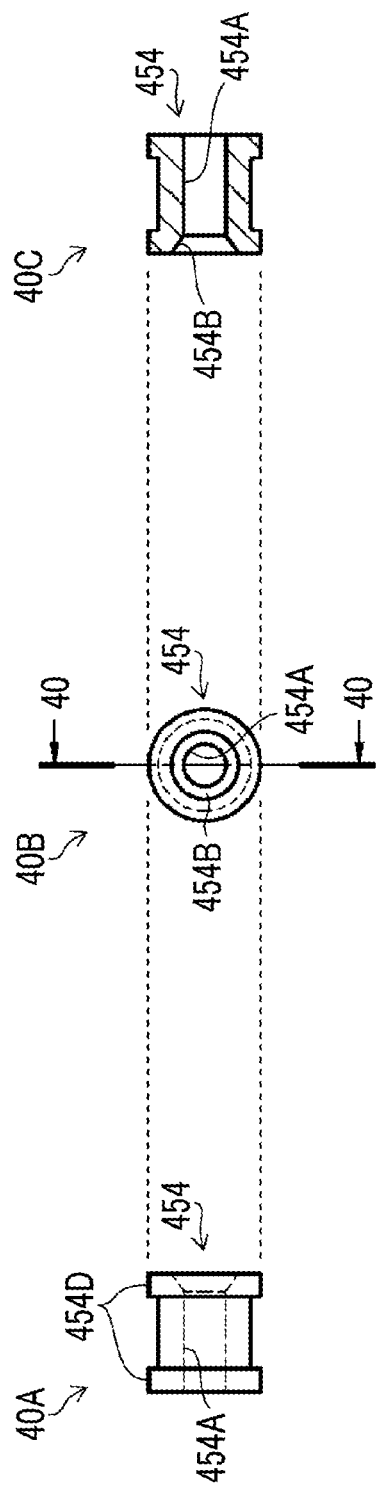

The reference sign 40A of FIG. 40 indicates a side view of the treatment tool seal member of the treatment tool fixing tool, the reference sign 40B of FIG. 40 indicates a rear view of the treatment tool seal member seen from the proximal end side thereof, and the reference sign 40C of FIG. 40 indicates a cross-sectional view of the treatment tool seal member shown with the reference sign 40B, which is taken along line "40"-"40".

Figure 41:
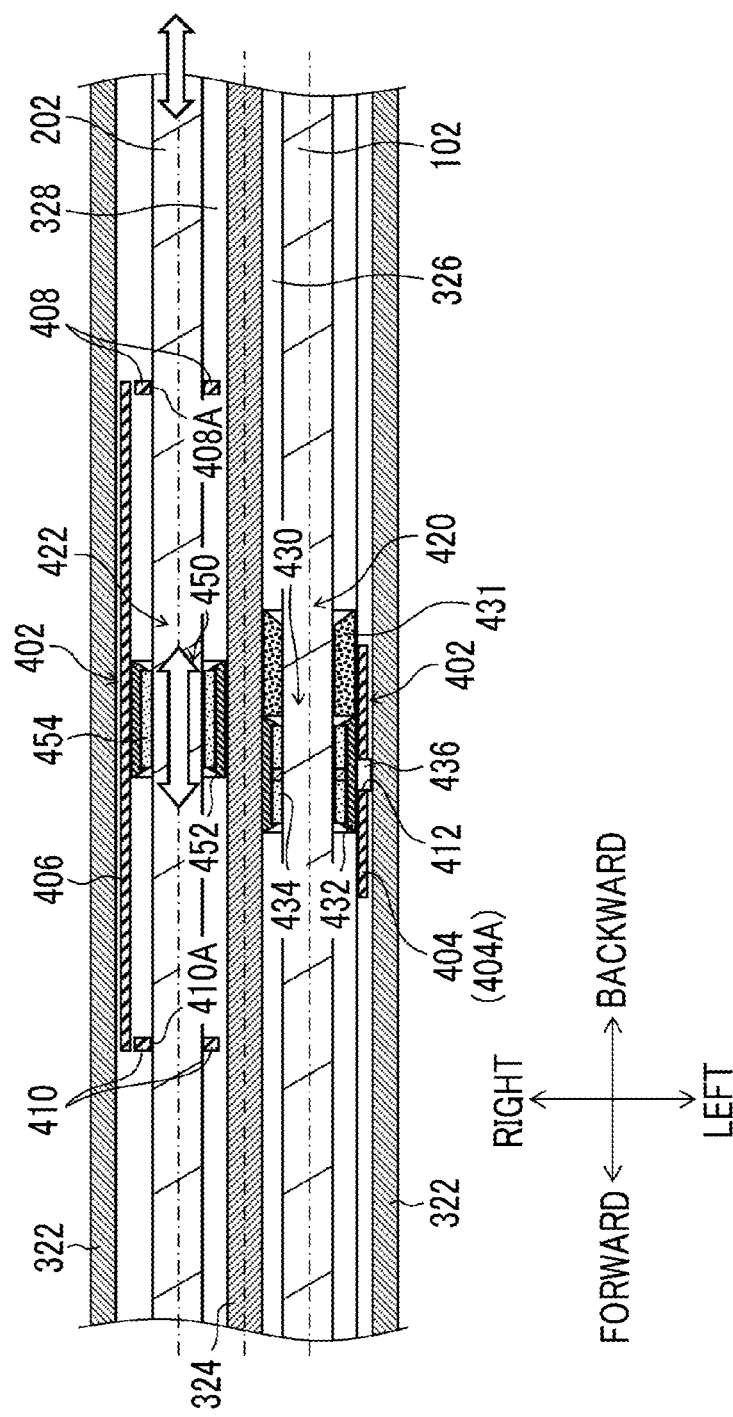

FIG. 41 is an explanatory view for illustrating a non-sensing region of the coupling ring.

Figure 42:
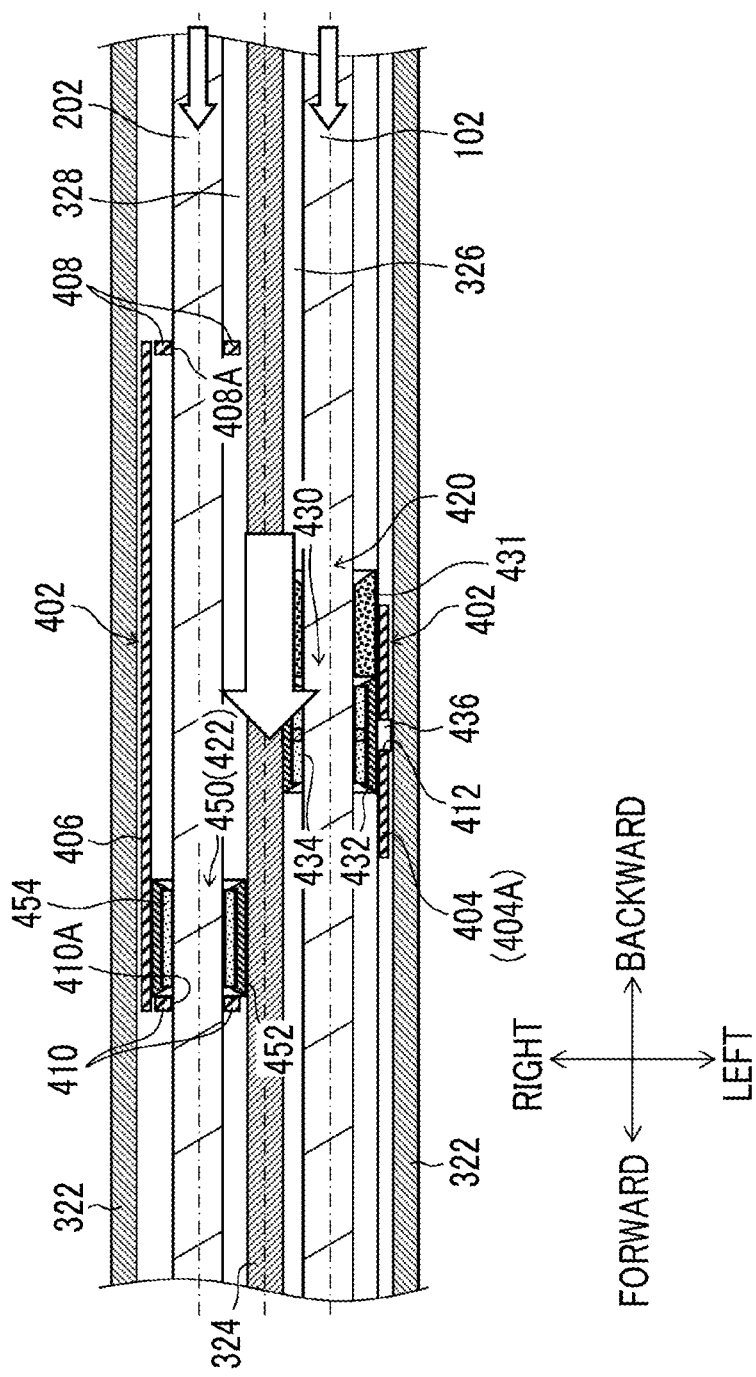

FIG. 42 is an explanatory view for illustrating a sensing region of the coupling ring.

Figure 43:
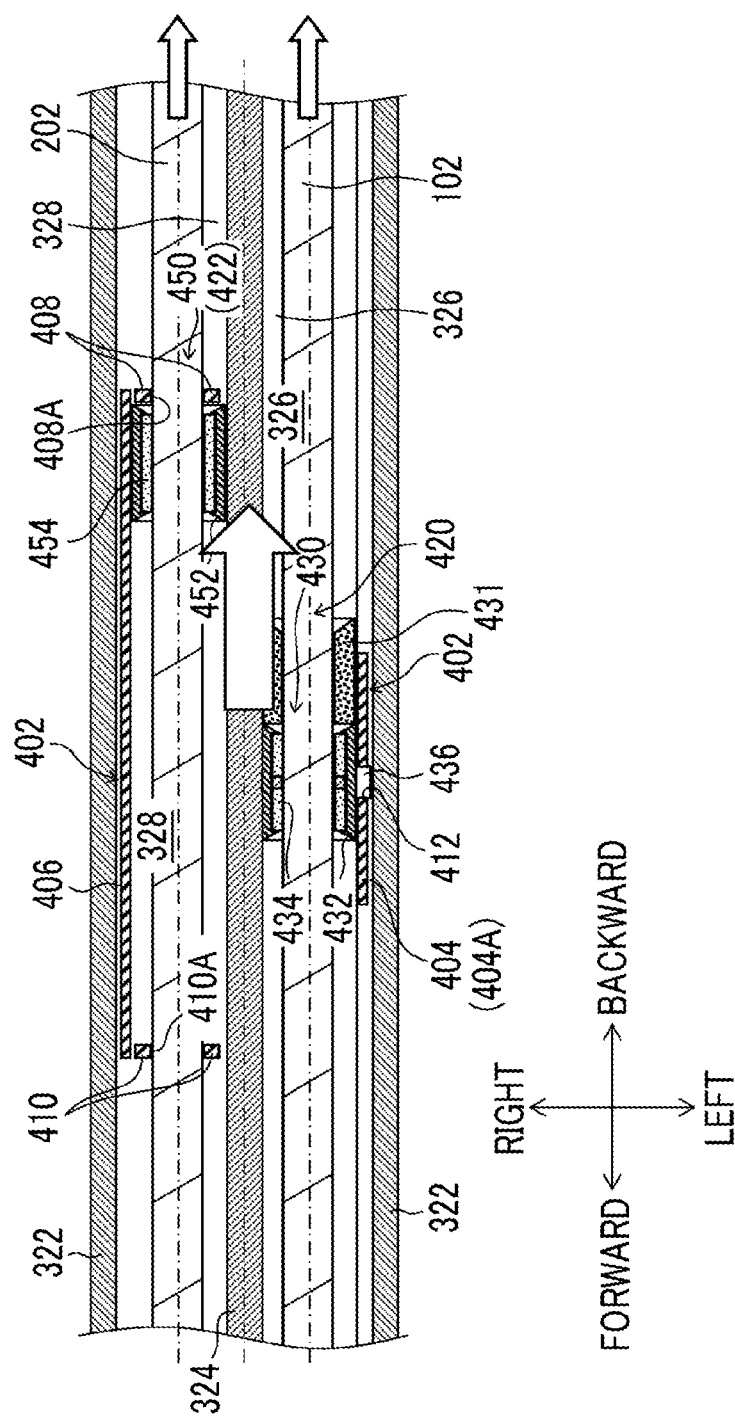

FIG. 43 is an explanatory view for illustrating the sensing region of the coupling ring.

Figure 44:
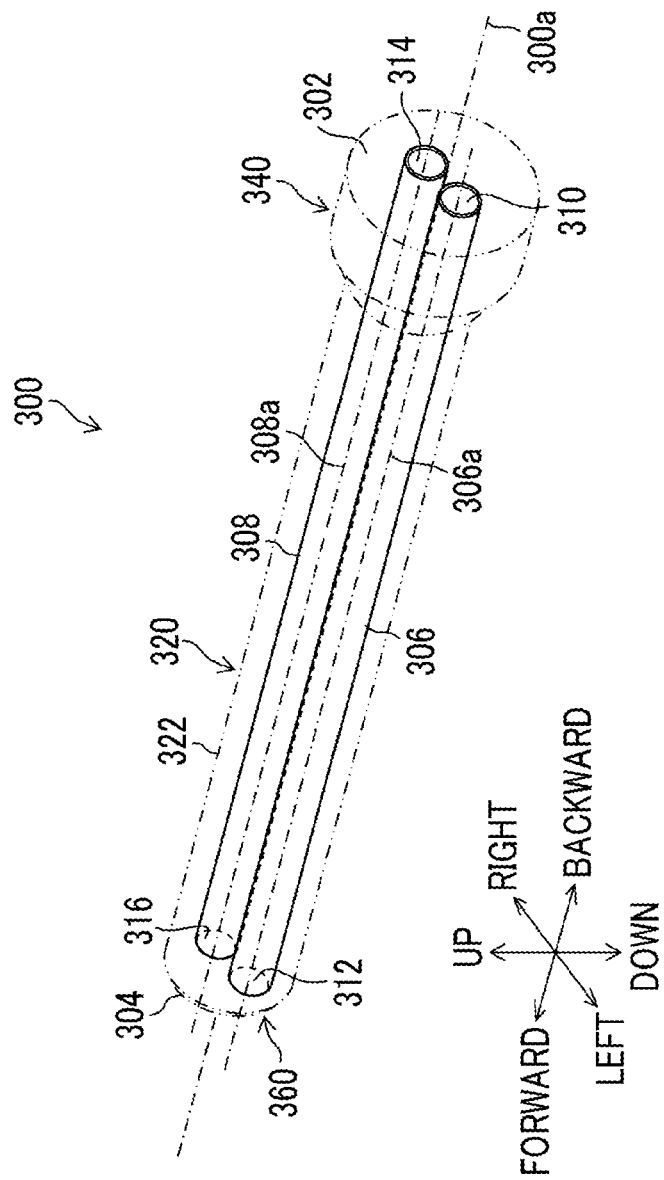

FIG. 44 is an explanatory view for illustrating a modification example of an endoscope insertion passage and a treatment tool insertion passage.

Figure 45:
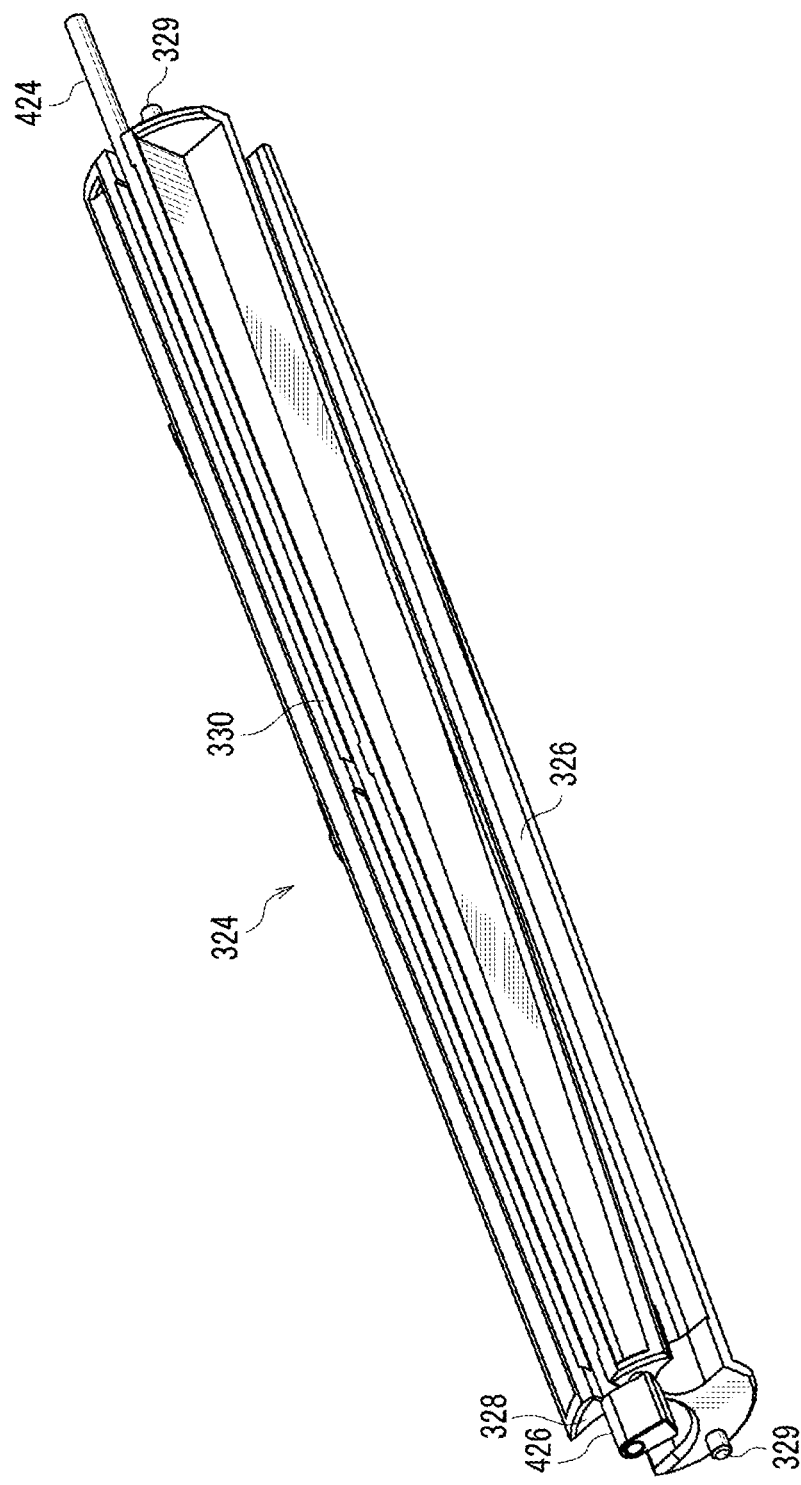

FIG. 45 is an external perspective view illustrating a liquid feeding tube and a cap connecting part in the overtube body with the long tubular body omitted.

The reference sign 46A of FIG. 46 indicates a front perspective view of the cap connecting part seen from a distal end side thereof, and the reference sign 46B of FIG.

46 indicates a rear perspective view of the cap connecting part seen from a proximal end side thereof.

Figure 47:
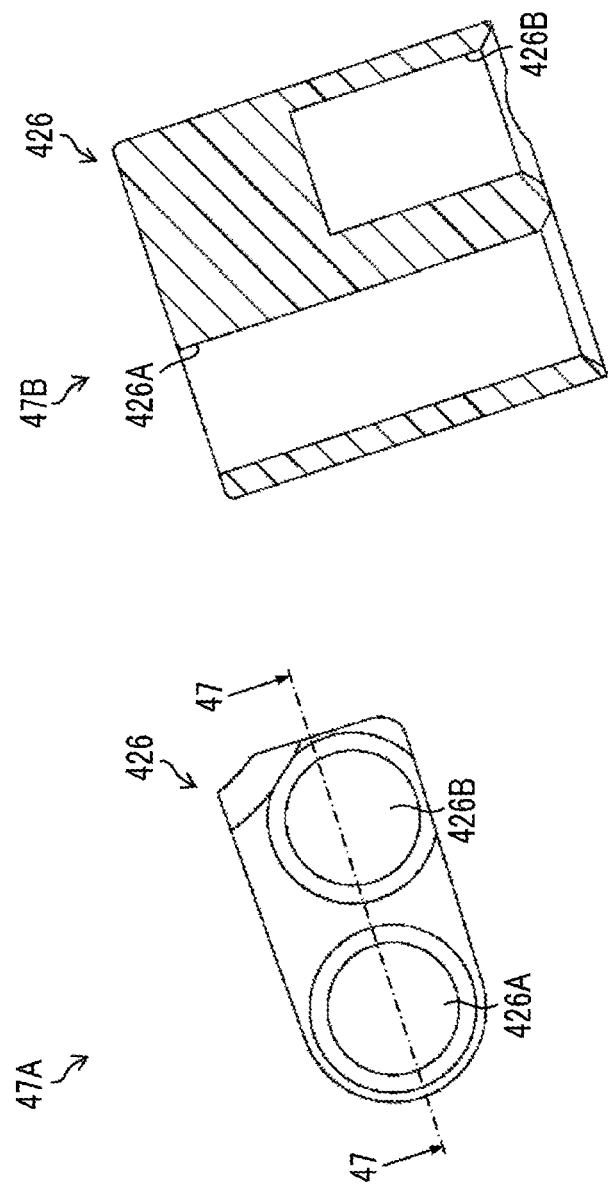

The reference sign 47A of FIG. 47 indicates a rear view of the cap connecting part seen from the proximal end side thereof, and the reference sign 47B of FIG. 47 indicates a cross-sectional view of the cap connecting part shown with the reference sign 47A, which is taken along line "47"-"47".

Figure 48:
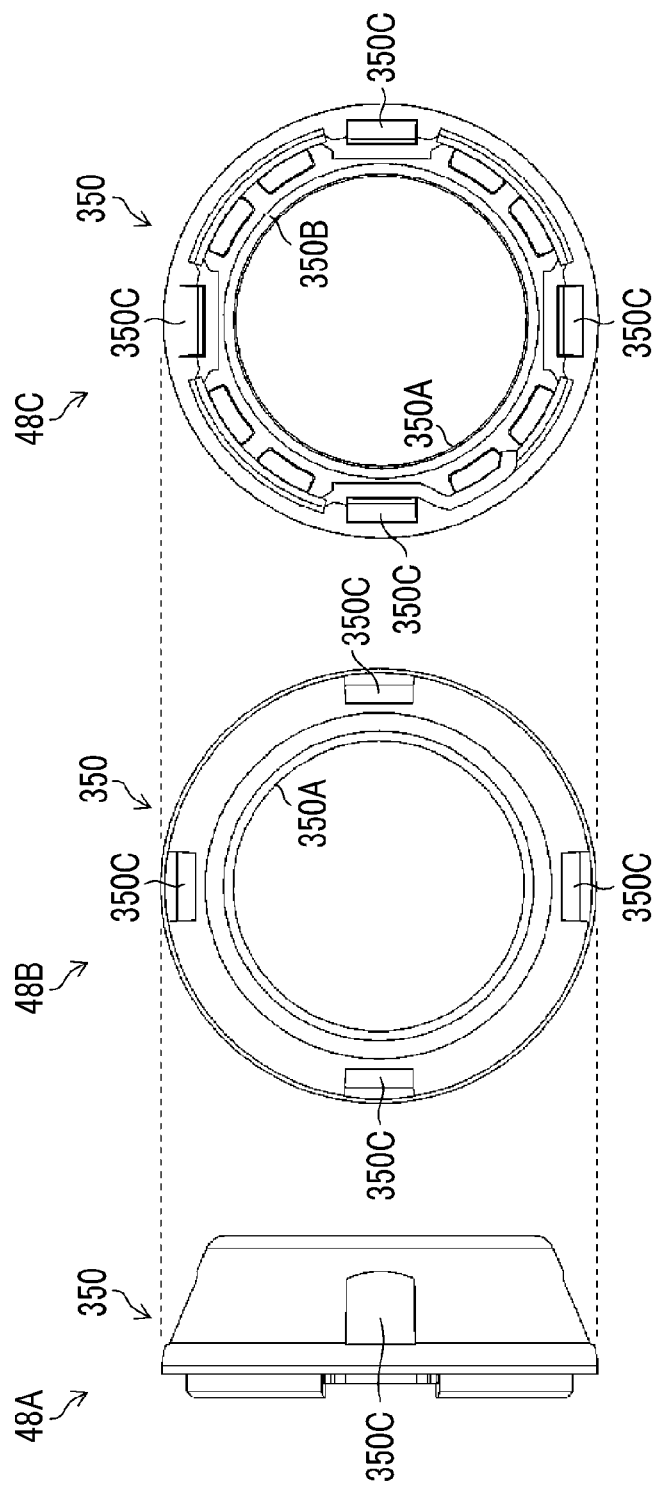

The reference sign 48A of FIG. 48 indicates a side view of a flange, the reference sign 48B of FIG. 48 indicates a front view of the flange seen from a distal end side thereof, and the reference sign 48C of FIG. 48 indicates a rear view of the flange seen from a proximal end side thereof.

Figure 49:
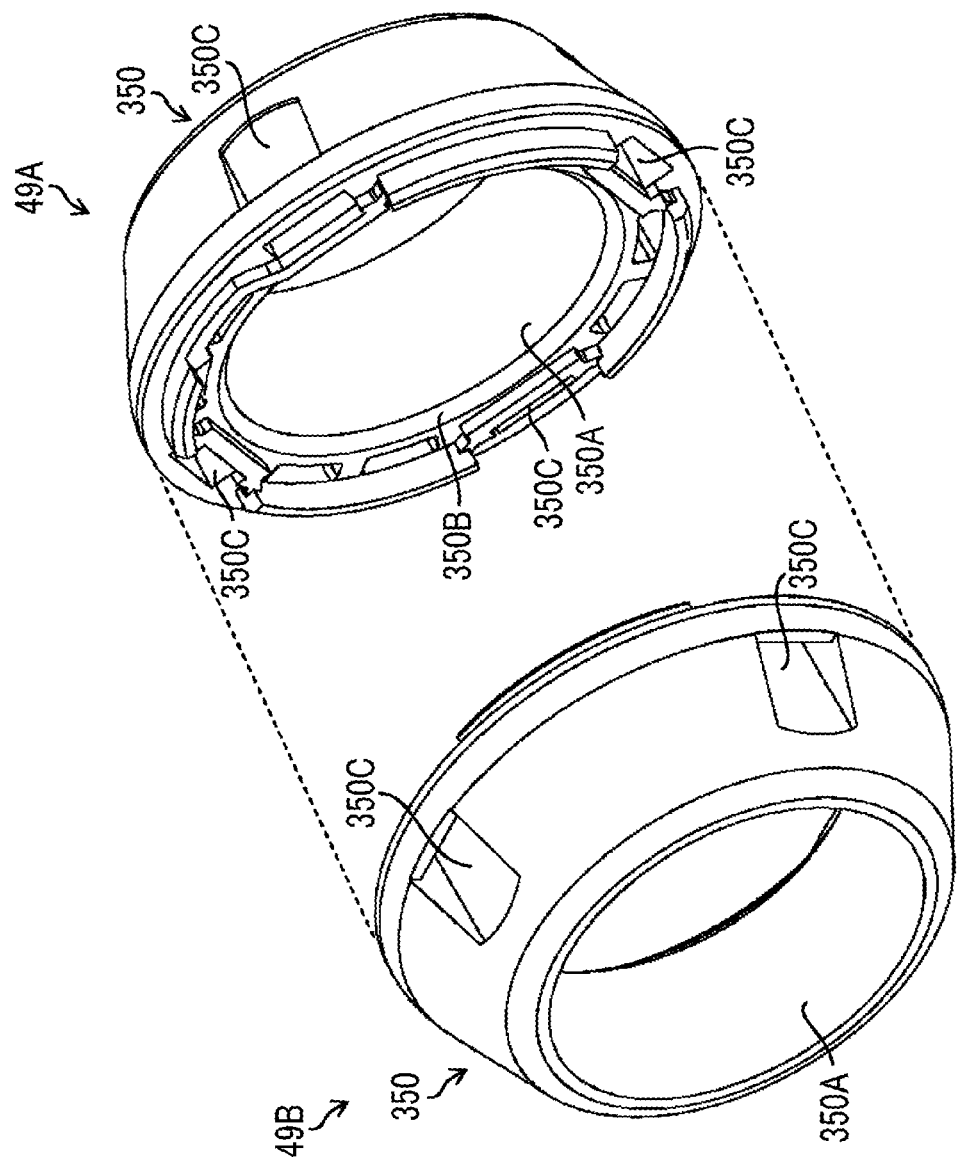

The reference sign 49A of FIG. 49 indicates a rear perspective view of the flange seen from the proximal end side thereof, and the reference sign 49B of FIG. 49 indicates a front perspective view of the flange seen from the distal end side thereof.

Figure 50:
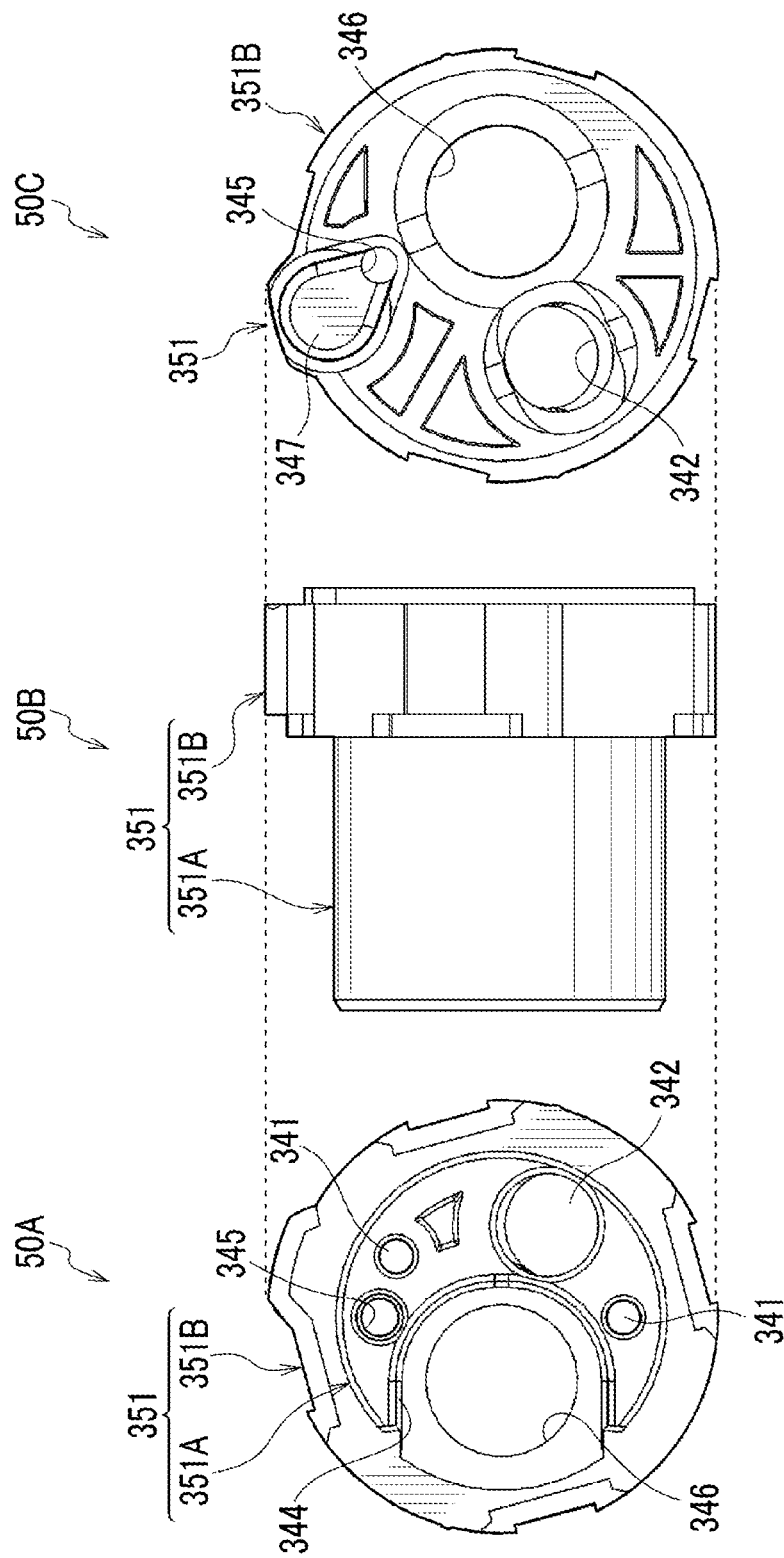

The reference sign 50A of FIG. 50 indicates a front view of a connector seen from a distal end side thereof, the reference sign 50B of FIG. 50 indicates a side view of the connector, and the reference sign 50C of FIG. 50 indicates a rear view of the connector seen from a proximal end side thereof.

Figure 51:
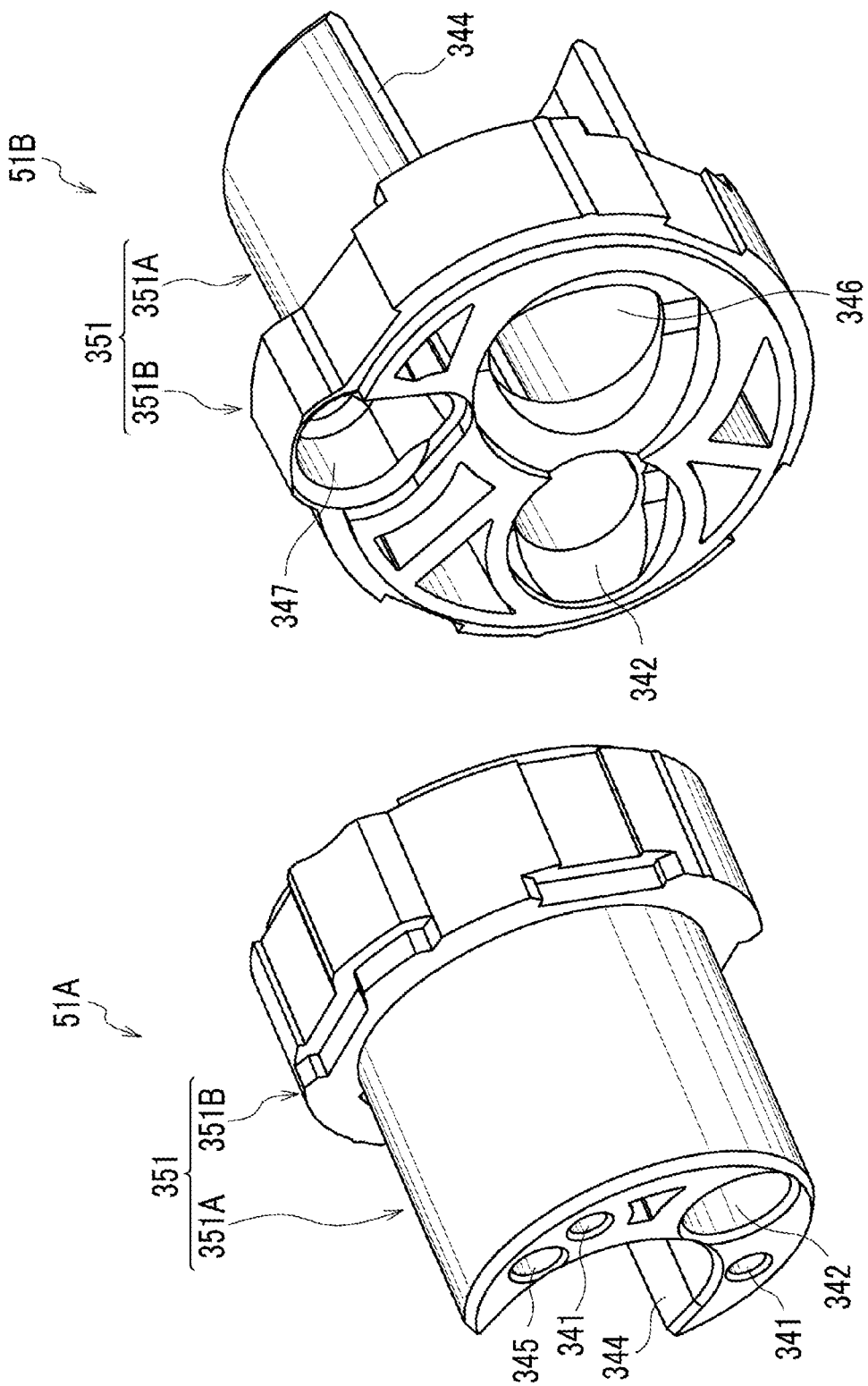

The reference sign 51A of FIG. 51 indicates a front perspective view of the connector seen from the distal end side thereof, and the reference sign 51B of FIG. 51 indicates a rear perspective view of the connector seen from the proximal end side thereof.

Figure 52:
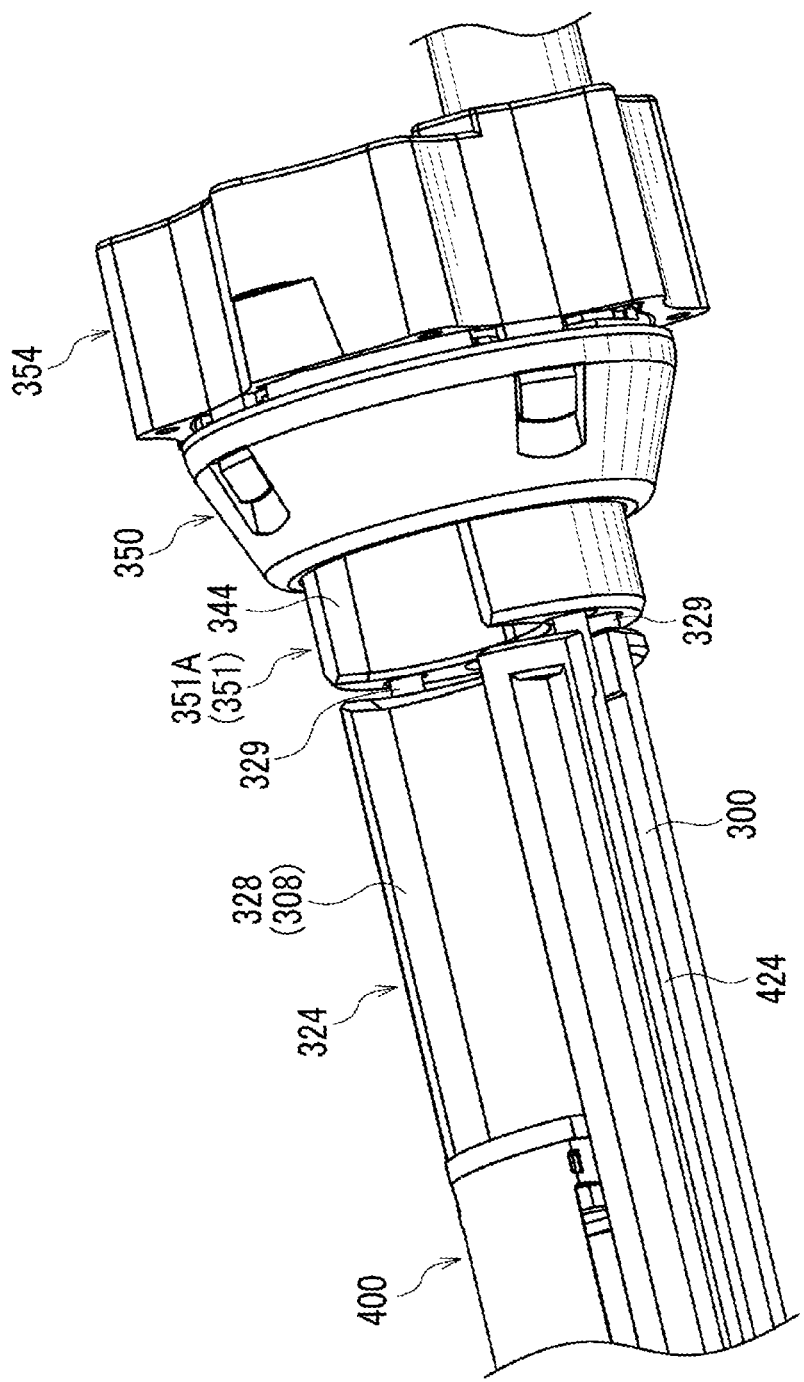

FIG. 52 is an external perspective view illustrating the partition wall member, the connector, and the like with the long tubular body omitted.

Figure 53:
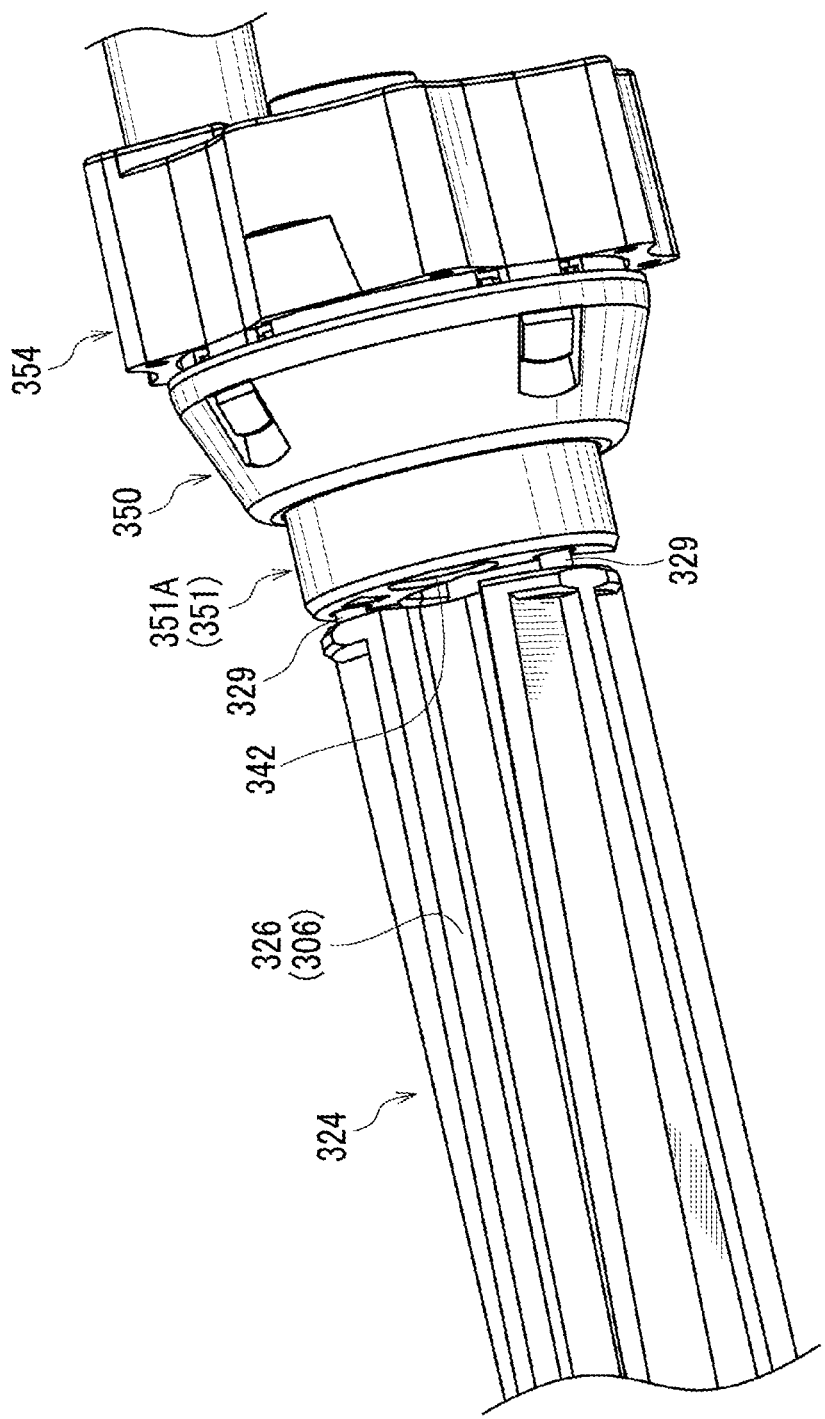

FIG. 53 is an external perspective view illustrating the partition wall member, the connector, and the like with the long tubular body omitted.

Figure 54:
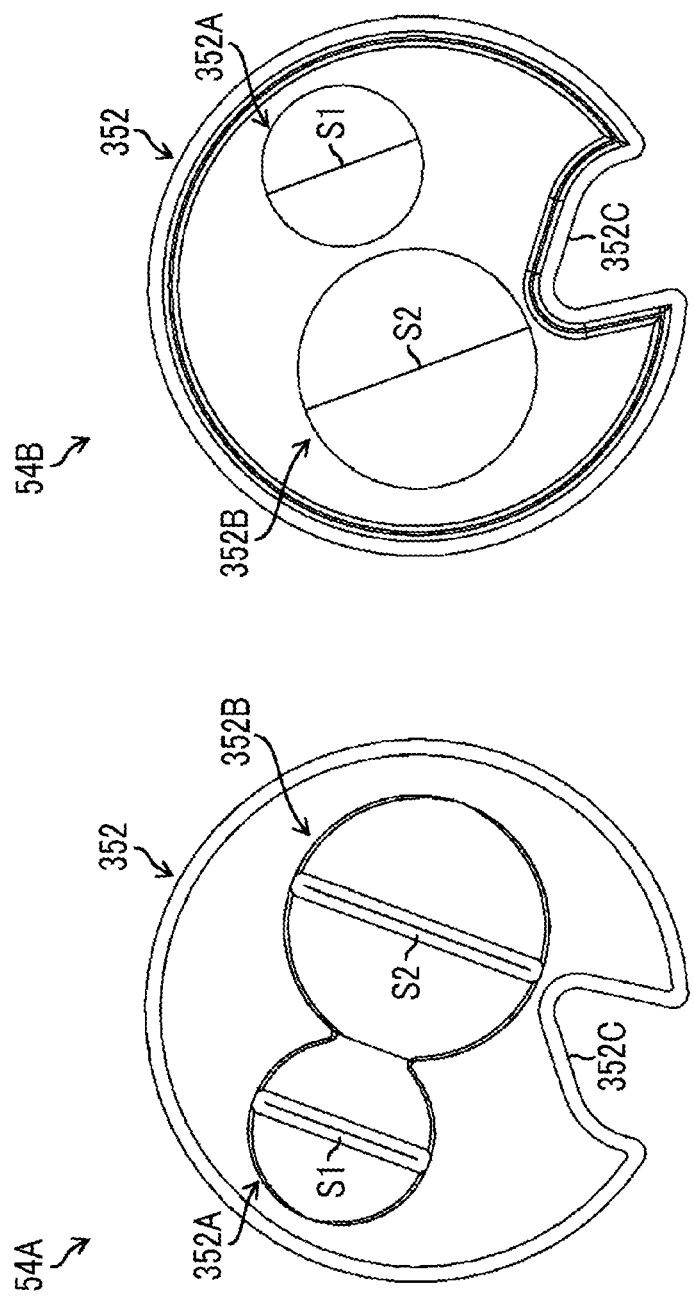

The reference sign 54A of FIG. 54 indicates a front view of a duckbill seal seen from a distal end side thereof, and the reference sign 54B of FIG. 54 indicates a rear view of the duckbill seal seen from a proximal end side thereof.

Figure 55:
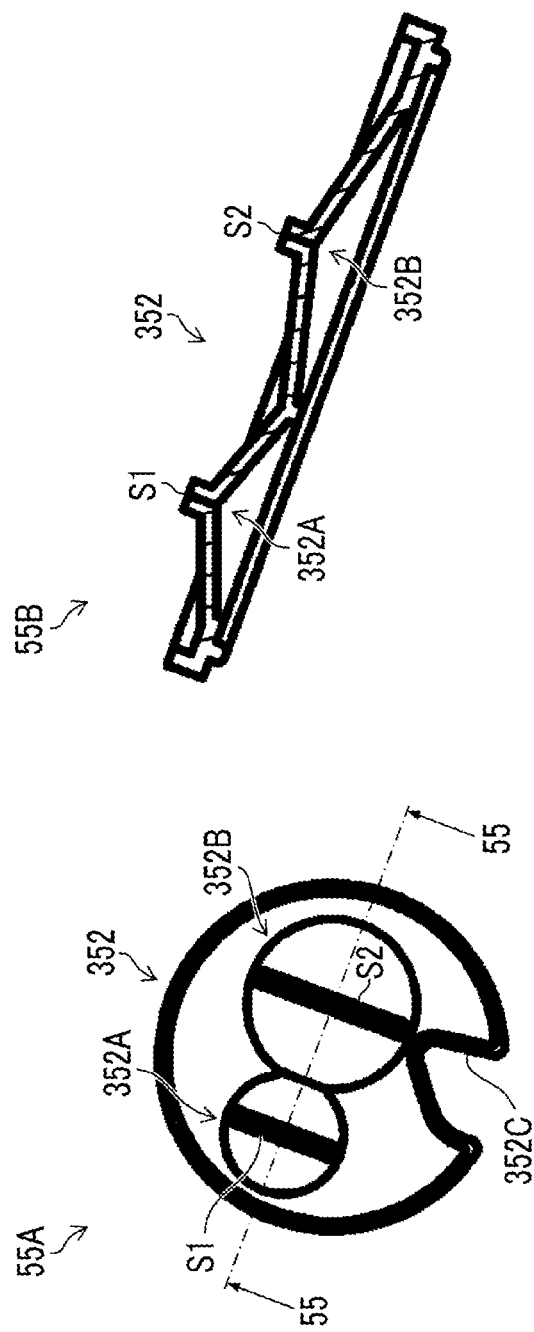

The reference sign 55A of FIG. 55 indicates a front view of the duckbill seal seen from the distal end side thereof, and the reference sign 55B of FIG. 55 indicates a cross-sectional view of the duckbill seal shown with the reference sign 55A, which is taken along line "55"-"55".

Figure 56:
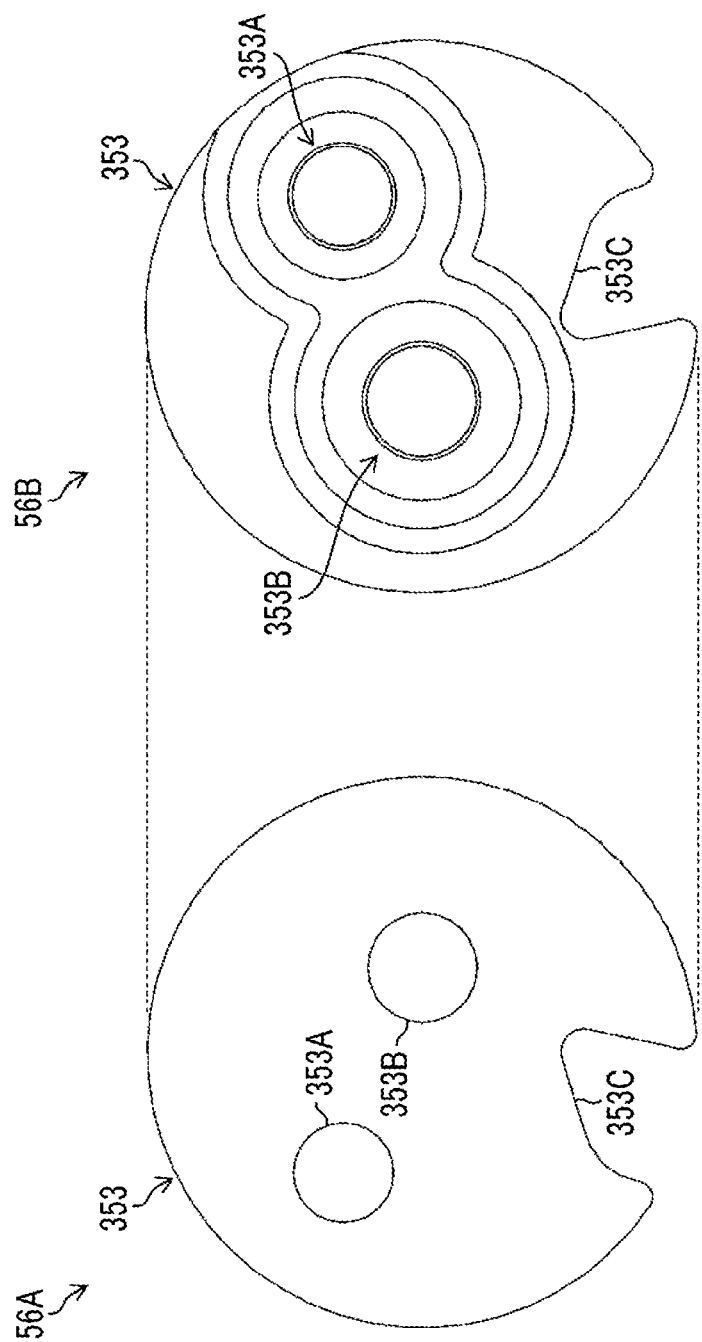

The reference sign 56A of FIG. 56 indicates a front view of an upper seal seen from a distal end side thereof, and the reference sign 56B of FIG. 56 indicates a rear view of the upper seal seen from a proximal end side thereof.

Figure 57:
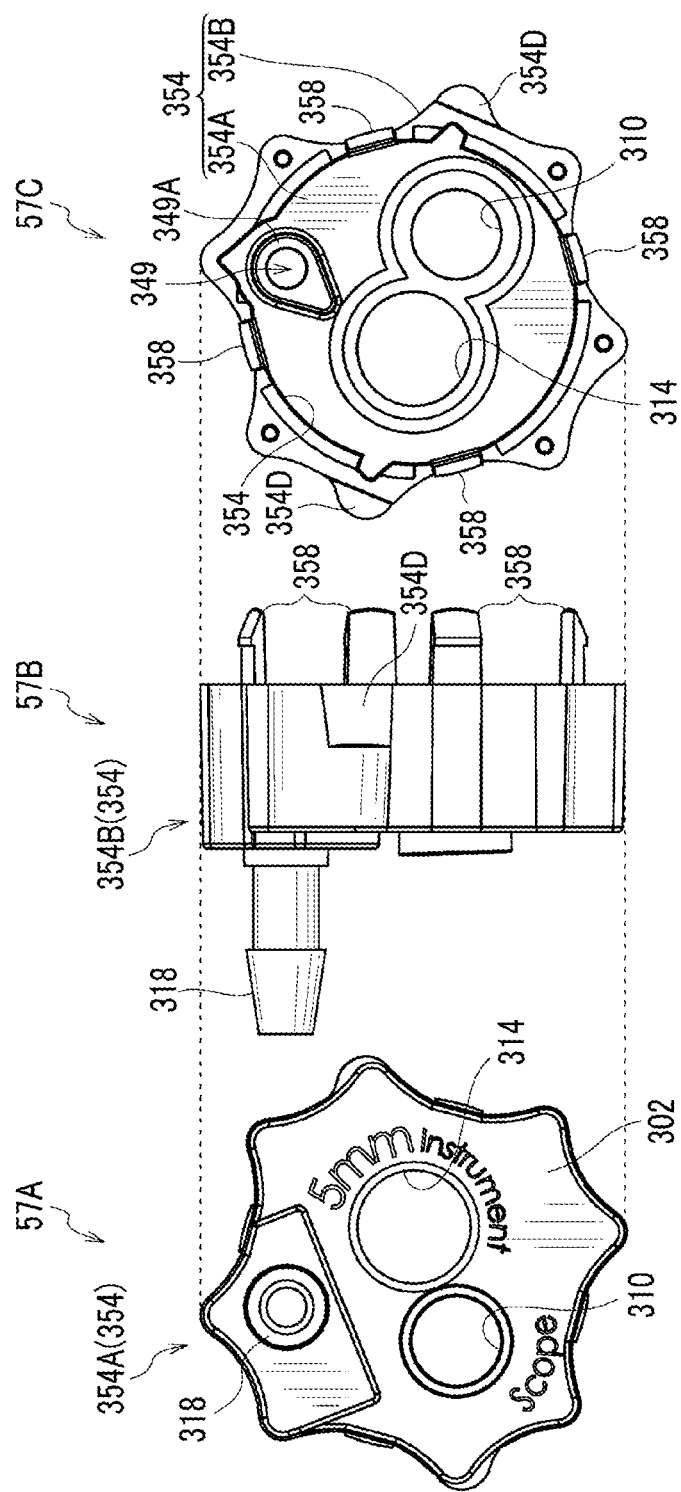

The reference sign 57A of FIG. 57 indicates a rear view of a cover member seen from a proximal end side thereof, the reference sign 57B of FIG. 57 indicates a side view of the cover member, and the reference sign 57C of FIG. 57 indicates a front view of the cover member seen from a distal end side thereof.

Figure 58:
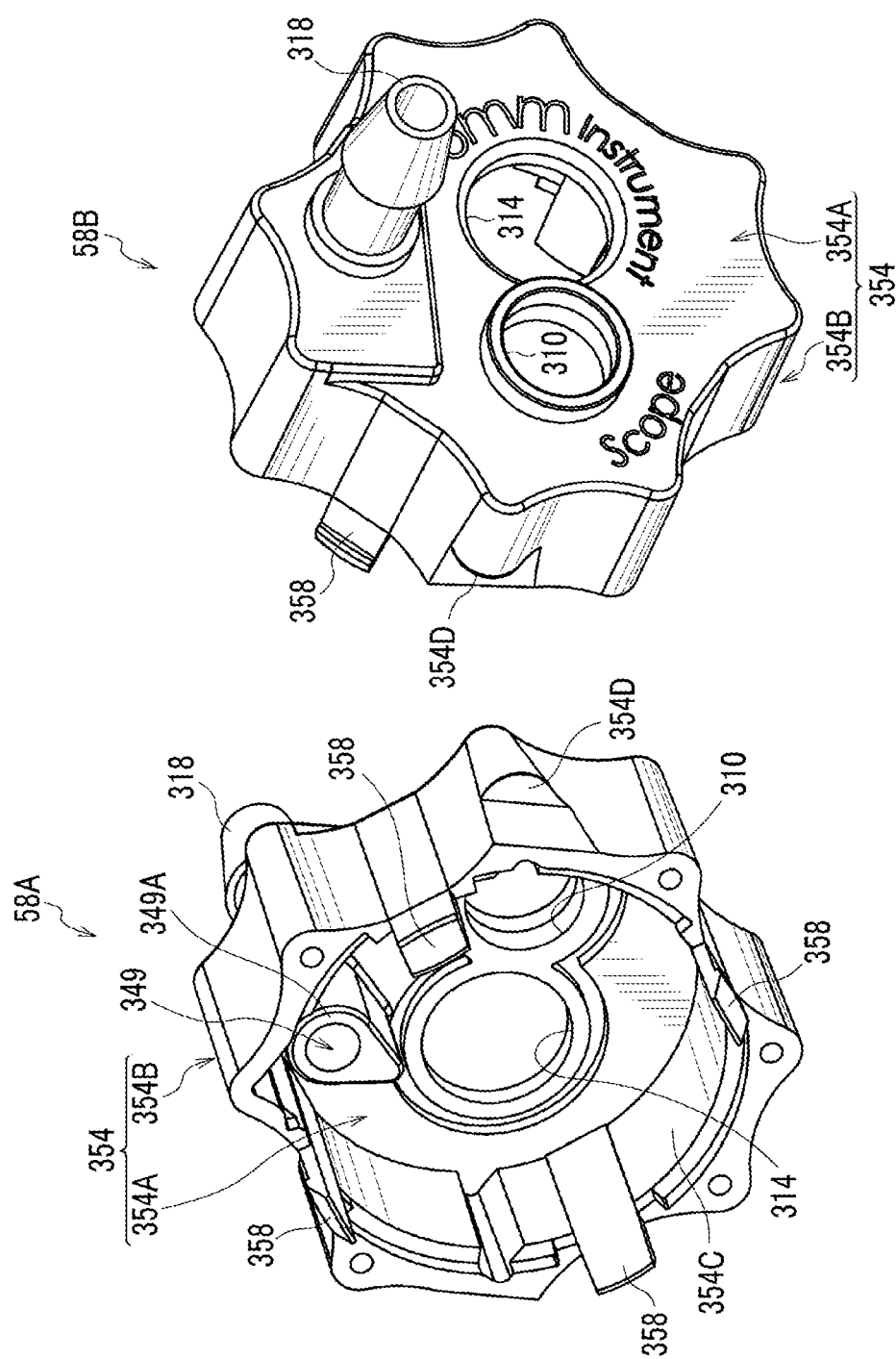

The reference sign 58A of FIG. 58 indicates a front perspective view of the cover member seen from the distal end side thereof, and the reference sign 58B of FIG. 58 indicates a rear perspective view of the cover member seen from the proximal end side thereof.

Figure 59:
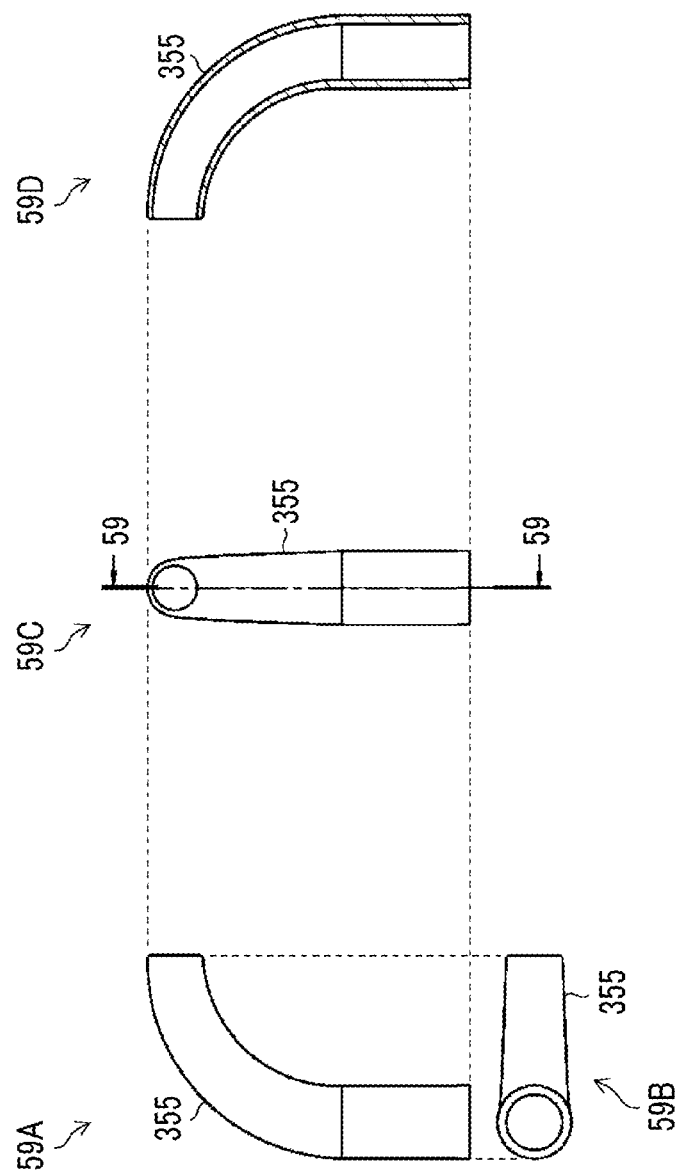

The reference sign 59A, the reference sign 59B, and the reference sign 59C of FIG. 59 are external views of a strain relief seen from directions different from each other, and the reference sign 59D of FIG. 59 is a cross-sectional view of the strain relief shown with the reference sign 59C, which is taken along line "59"-"59".

Figure 60:
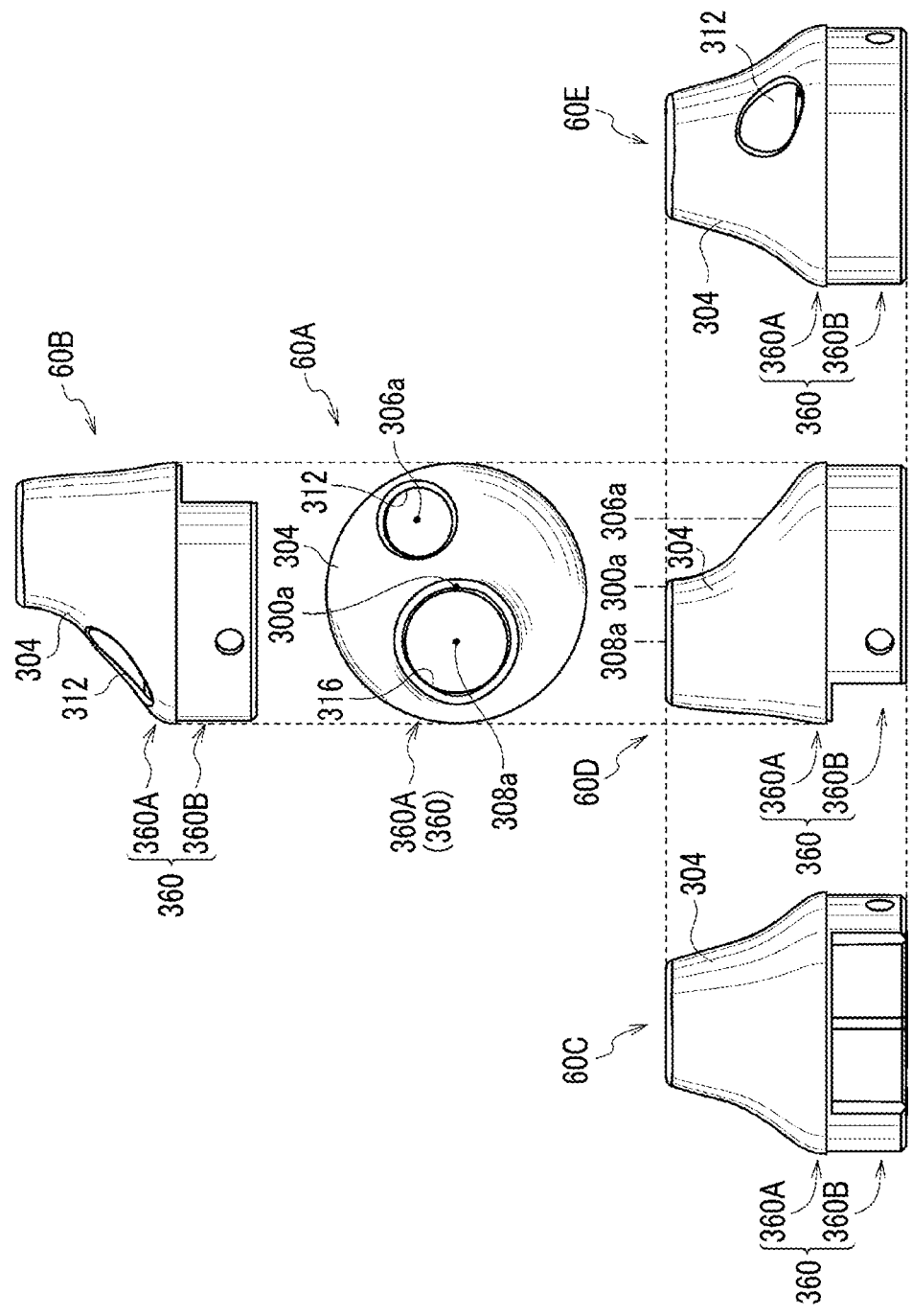

The reference sign 60A of FIG. 60 indicates a front view of a distal end cap part seen from a distal end side thereof, and the reference sign 60B, the reference sign 60C, the reference sign 60D, and the reference sign 60E of FIG. 60 indicate side views of the distal end cap part seen from directions different from each other.

Figure 61:
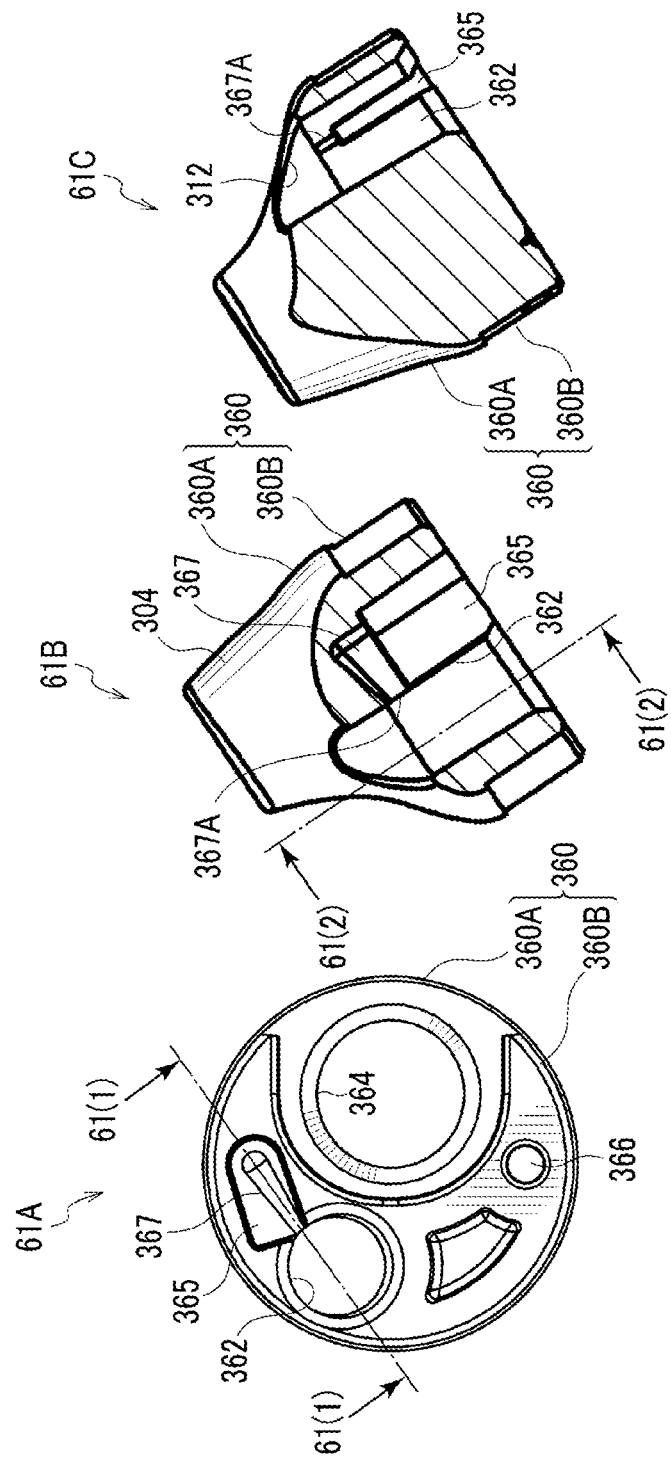

The reference sign 61A of FIG. 61 indicates a rear view of the distal end cap part seen from a proximal end side thereof, the reference sign 61B of FIG. 61 indicates a cross-sectional view of the distal end cap part shown with the reference sign 61A, which is taken along line "61(1)"-"61(1)", and the reference sign 61C of FIG. 61 indicates a cross-sectional view of the distal end cap part shown with the reference sign 61B, which is taken along line "61(2)"-"61(2)".

Figure 62:
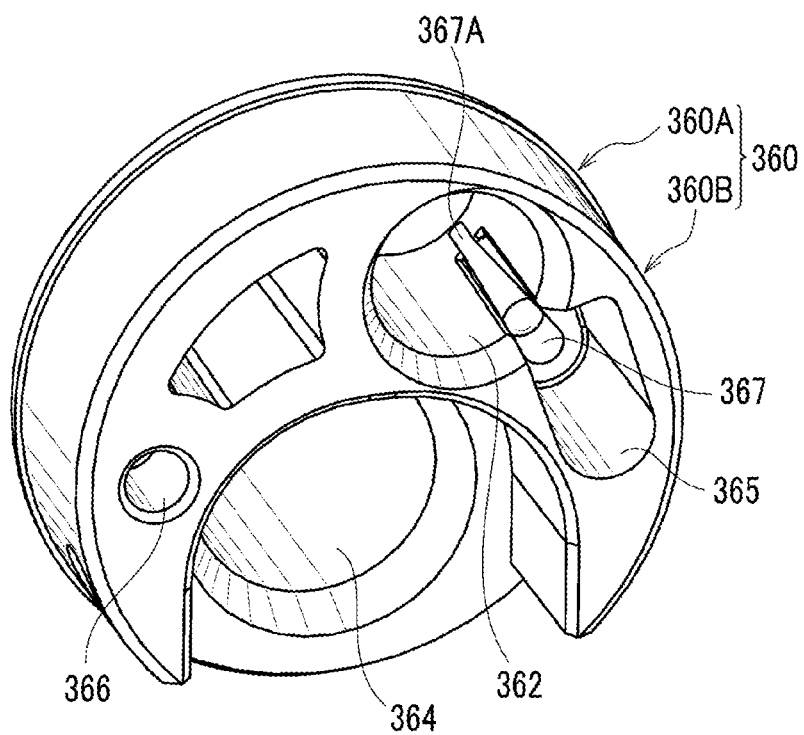

FIG. 62 is a rear perspective view of the distal end cap part seen from the proximal end side thereof.

Figure 63:
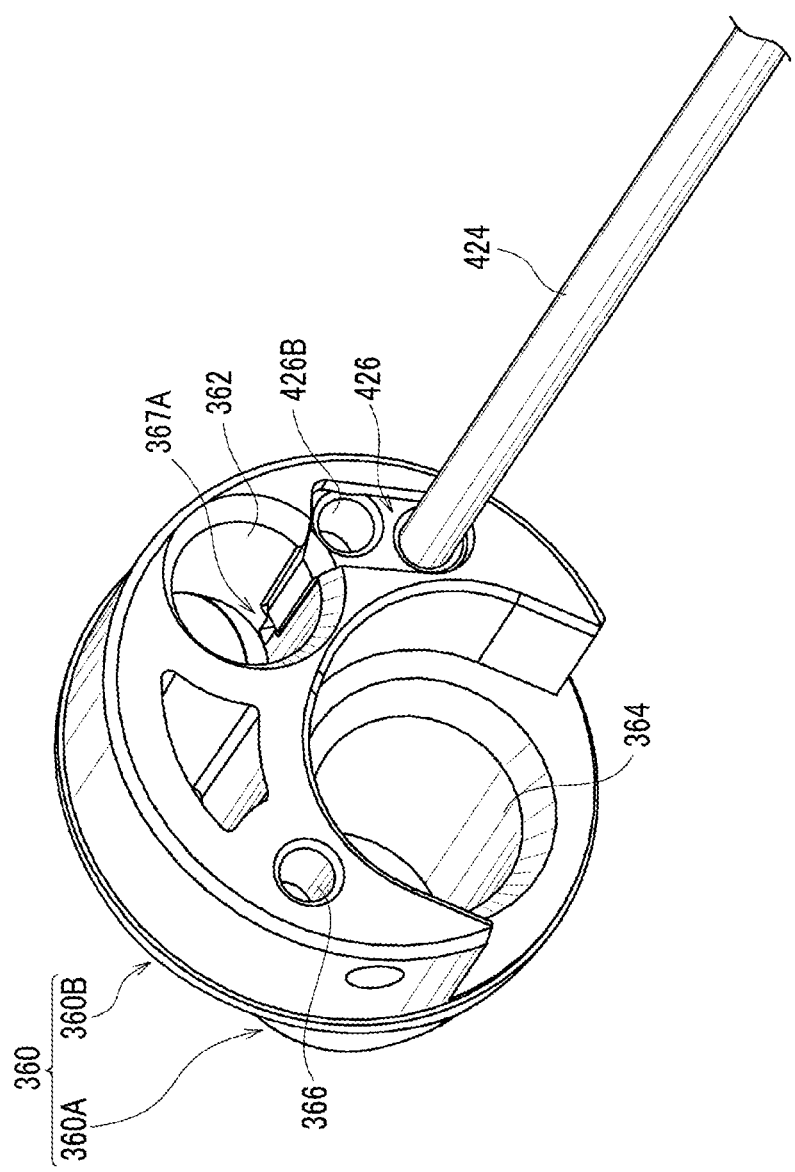

FIG. 63 is an external perspective view illustrating a state where the cap connecting part is attached to an attachment hole of the distal end cap part.

Figure 64:
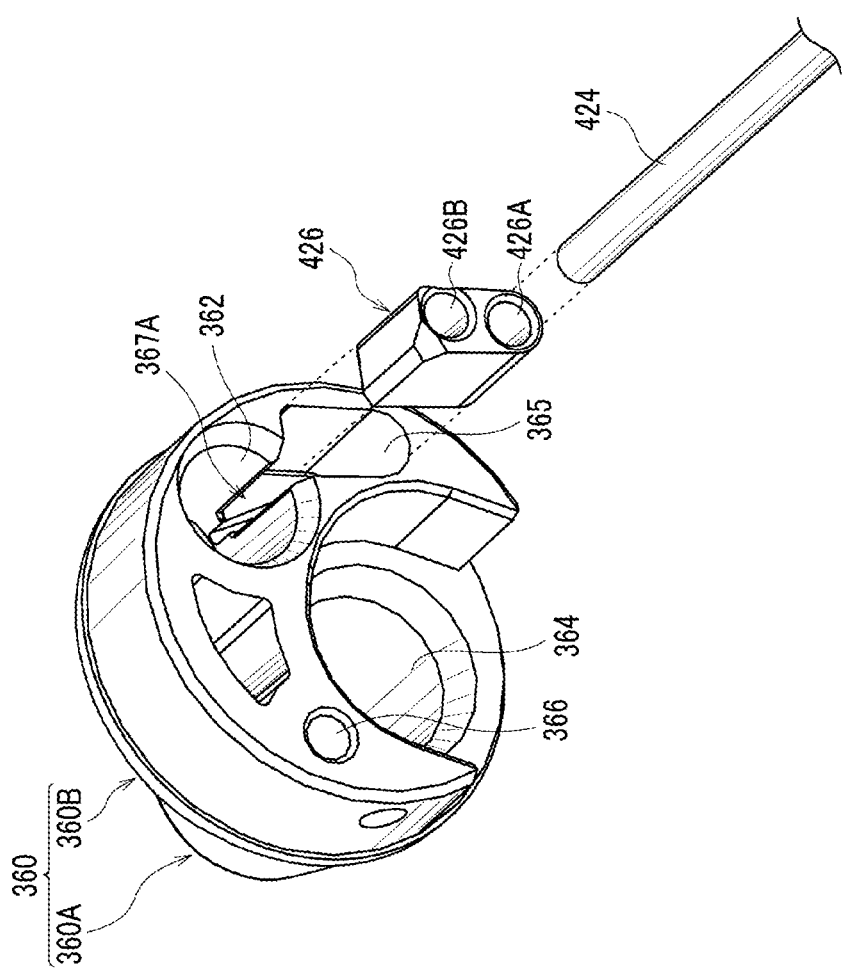

FIG. 64 is an exploded perspective view of the distal end cap part, the cap connecting part, and the like which are illustrated in FIG. 63.

Figure 65:
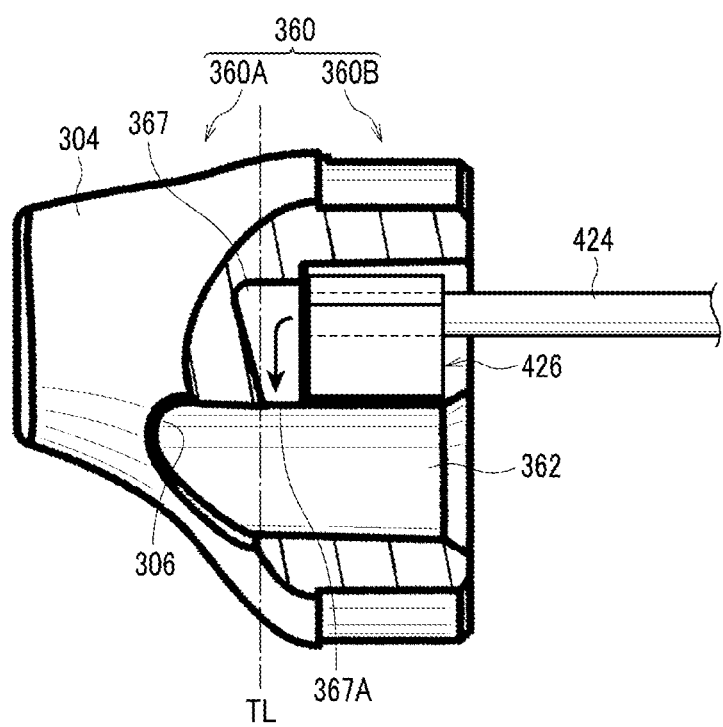

FIG. 65 is a cross-sectional view of the attachment hole and a liquid passage of the distal end cap part.

Figure 66:
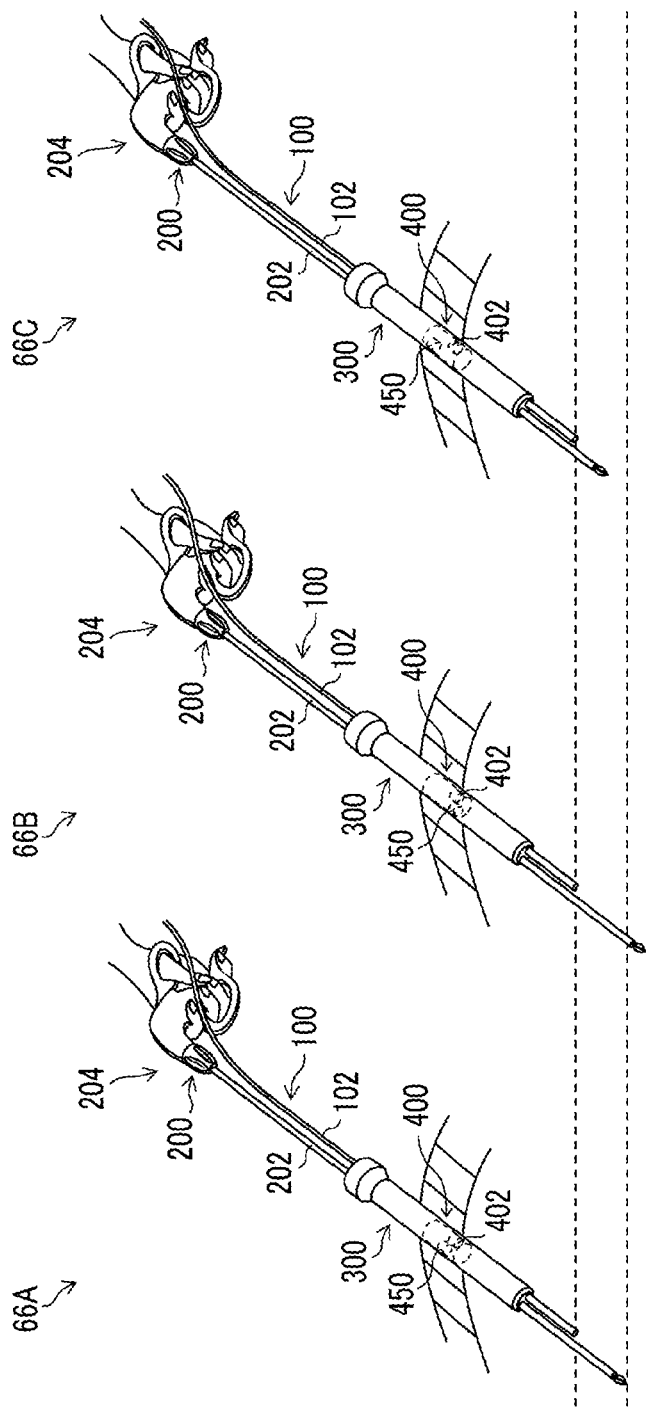

FIG. 66 is an explanatory view for illustrating the working of the overtube in a case of treating a diseased site in a patient's body cavity using a surgical device.

Figure 67:
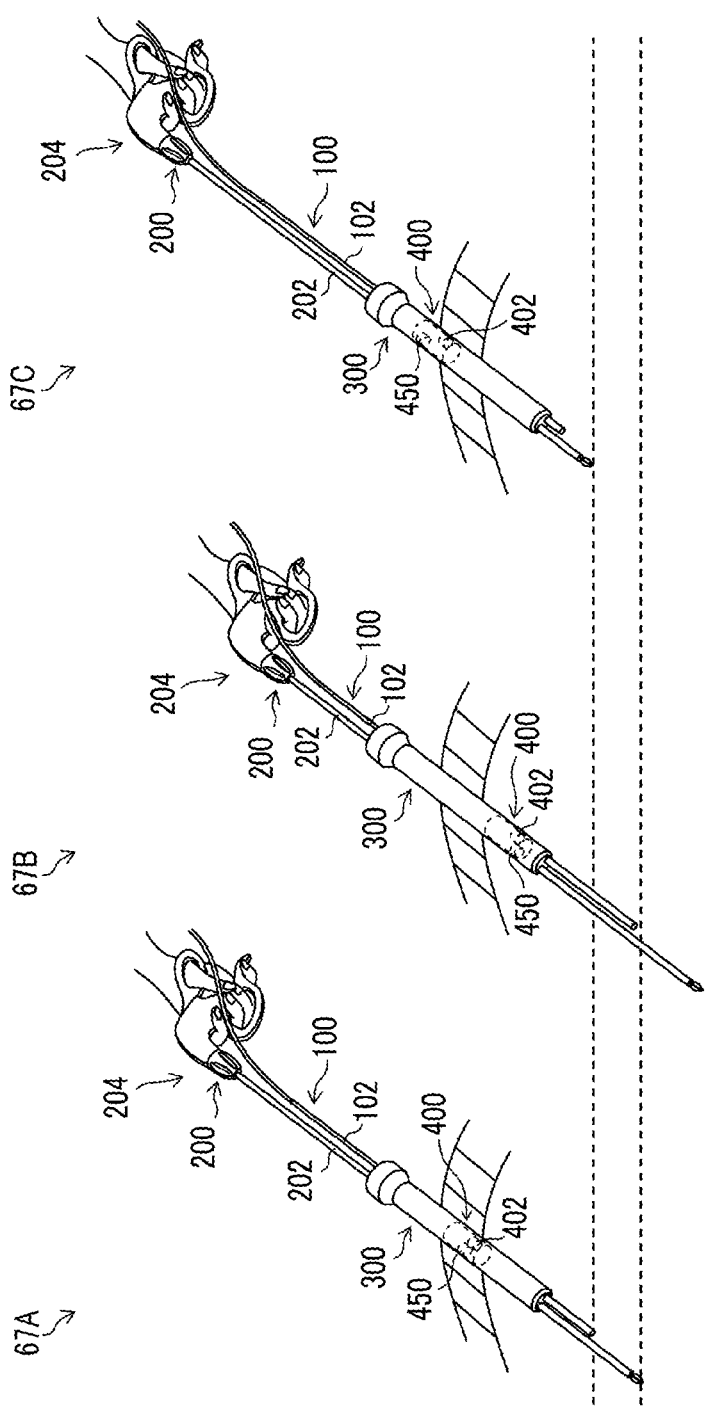

FIG. 67 is an explanatory view for illustrating the working of the overtube in a case of treating the diseased site in the patient's body cavity using the surgical device.

Figure 68:
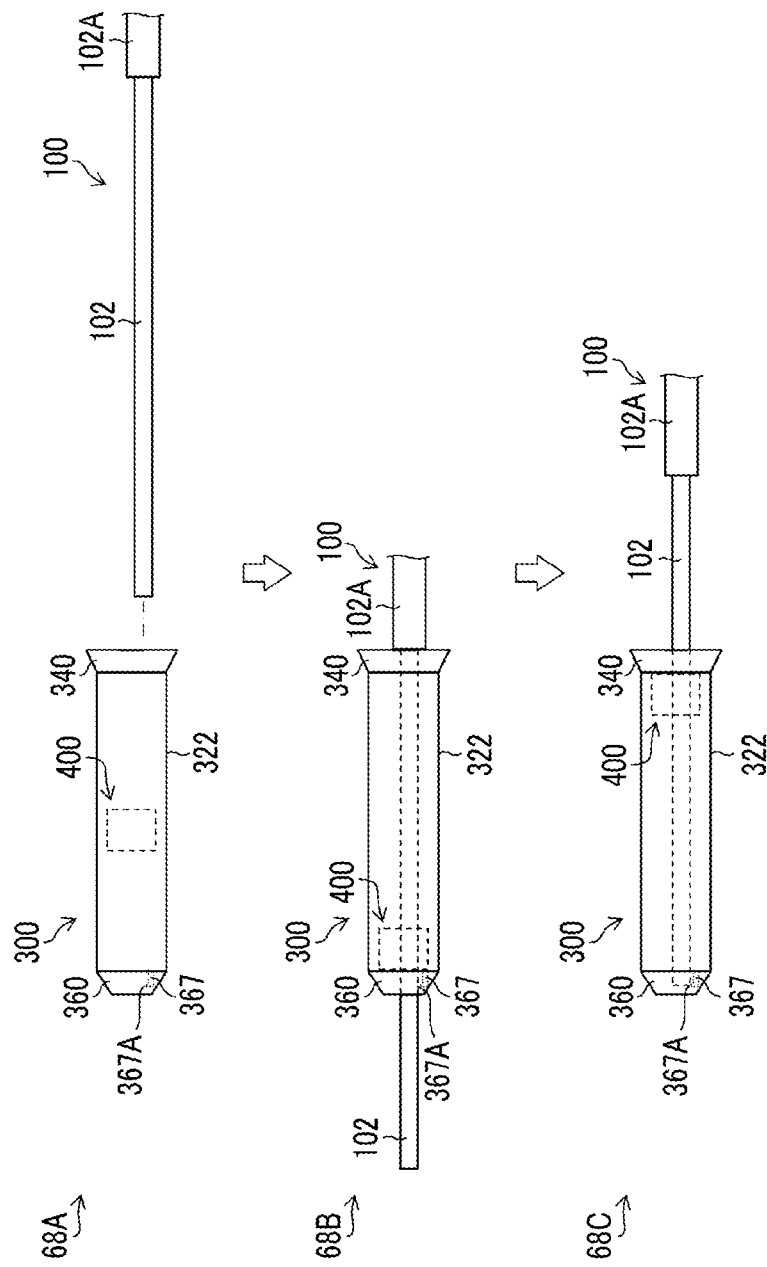

FIG. 68 is an explanatory view for illustrating the working of the overtube in a case of cleaning an observation window of the endoscope insertion part.

Figure 69:
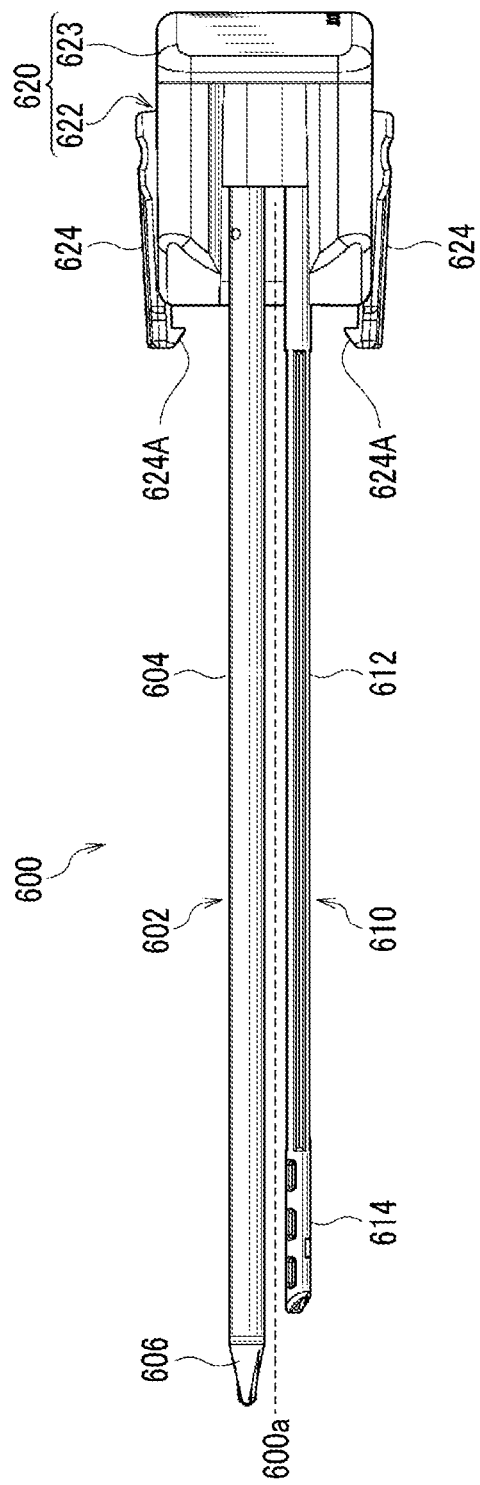

FIG. 69 is a side view of the inner needle mounted on the overtube in a case of forming a hole in the body wall and inserting the overtube and the sheathing tube into the hole.

Figure 70:
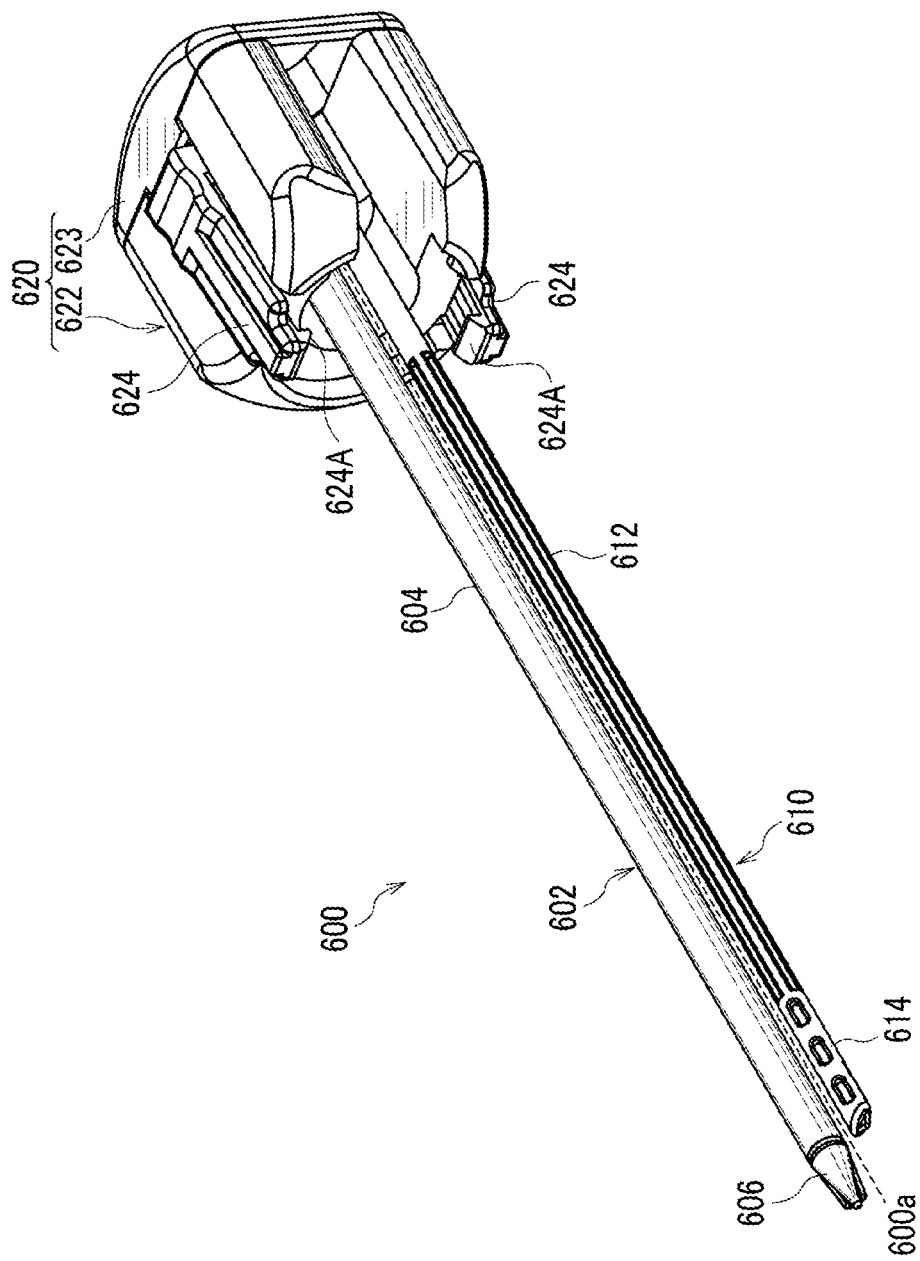

FIG. 70 is a front perspective view of the inner needle seen from a distal end side thereof.

Figure 71:
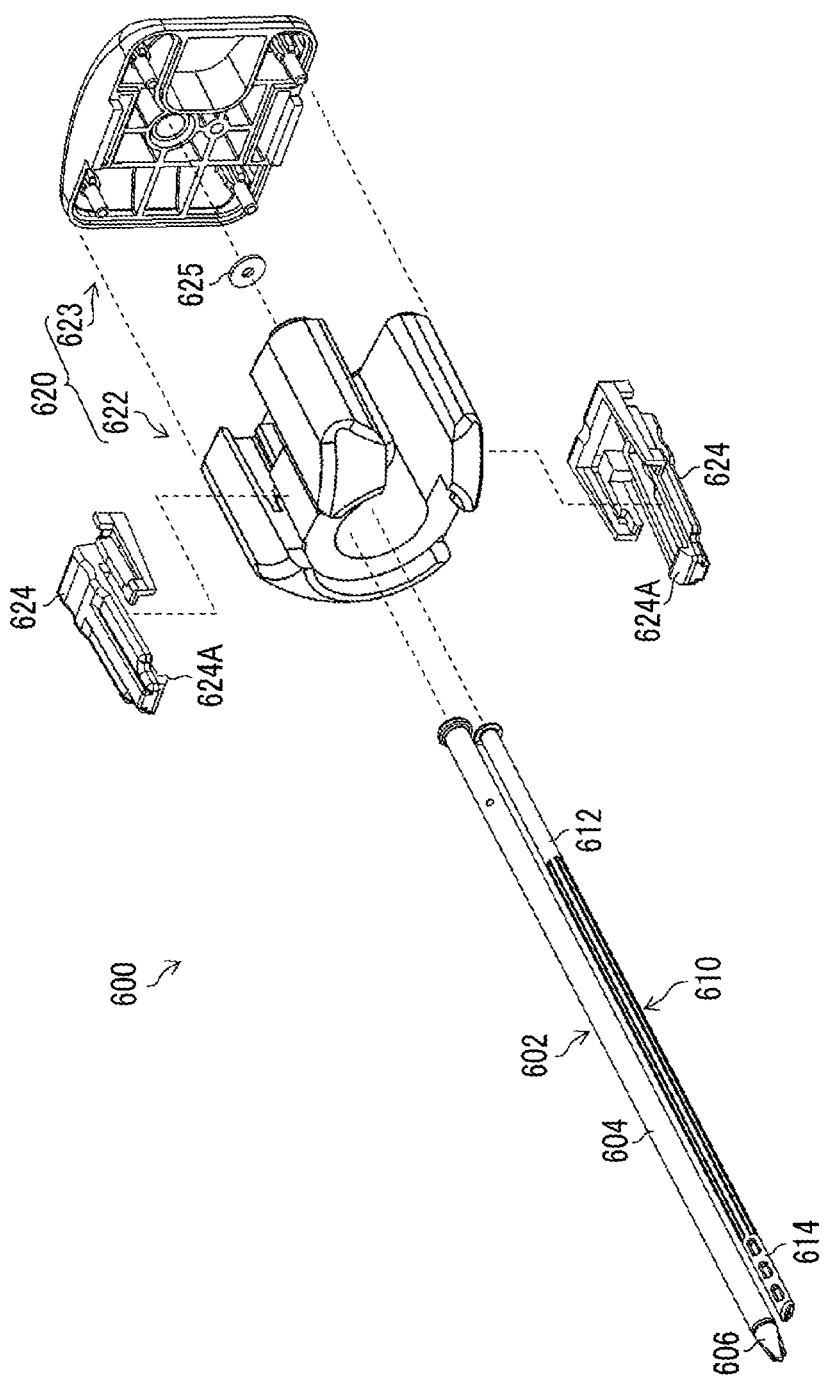

FIG. 71 is an exploded perspective view of the inner needle seen from the distal end side thereof.

Figure 72:
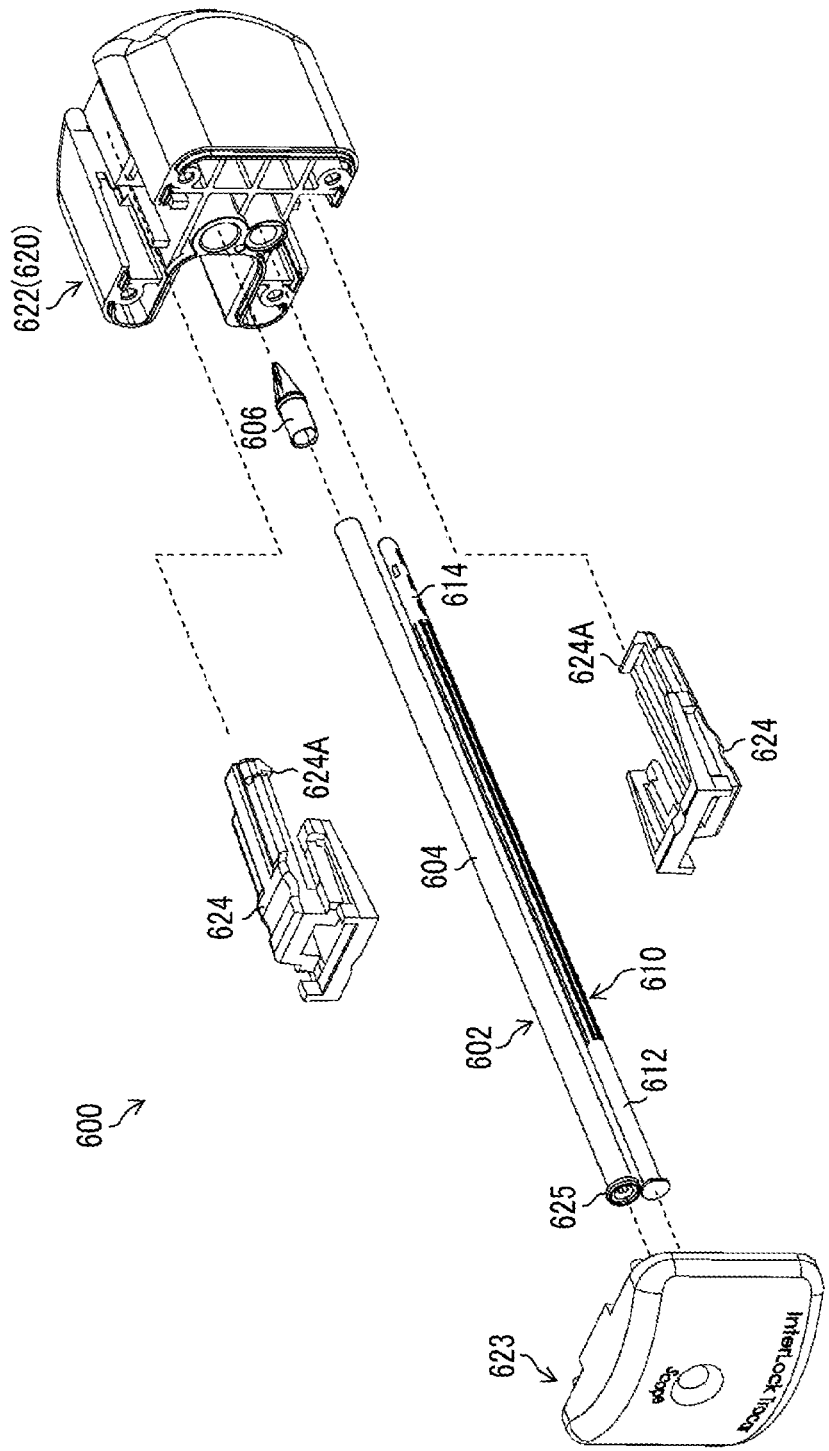

FIG. 72 is an exploded perspective view of the inner needle seen from a proximal end side thereof.

Figure 73:
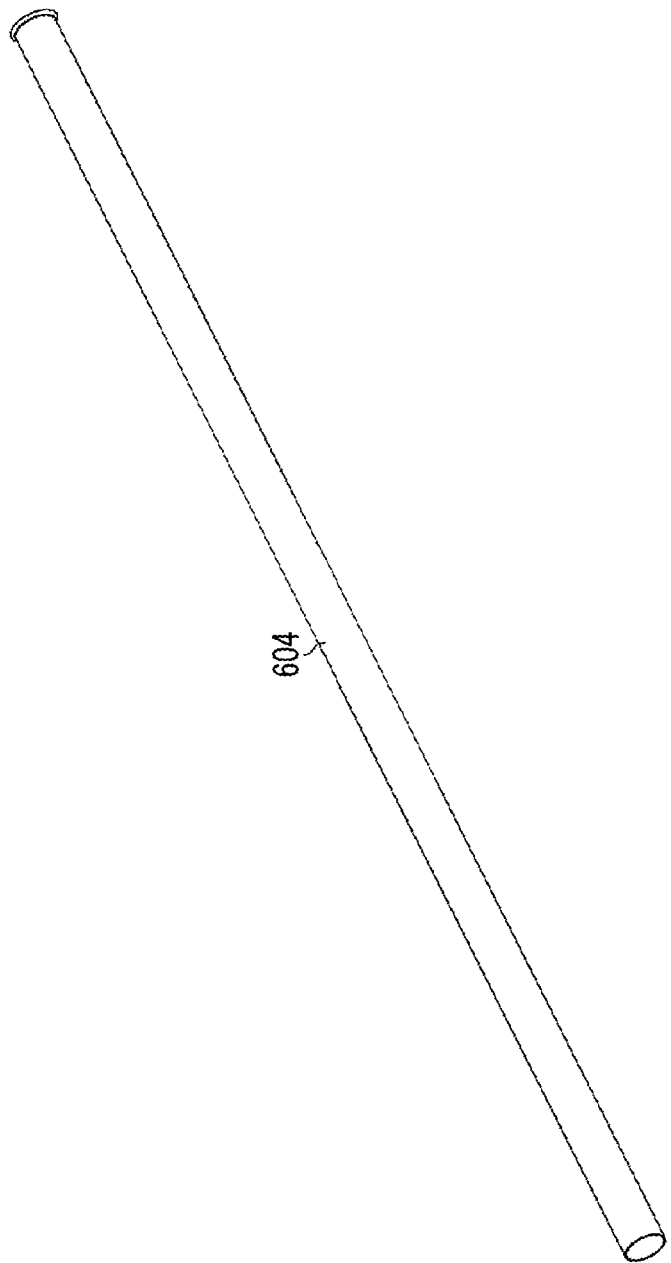

FIG. 73 is a front perspective view of a shaft part of a long needle part seen from a distal end side thereof.

Figure 74:
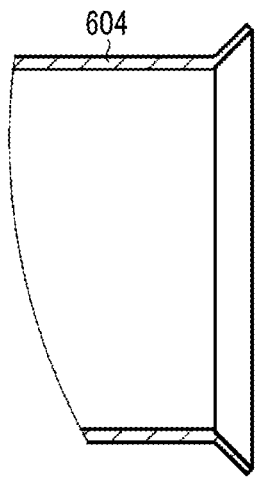

FIG. 74 is an enlarged cross sectional view of a proximal end side of the shaft part of the long needle part.

Figure 75:
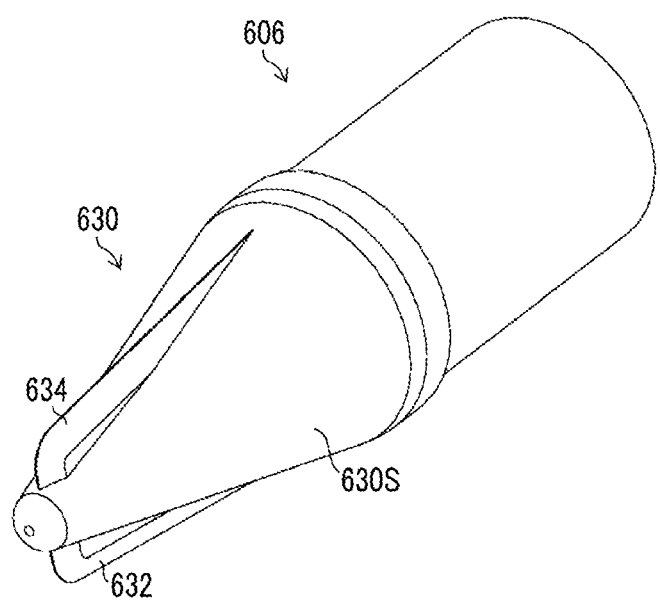

FIG. 75 is a front perspective view of a distal end part of the long needle part seen from a distal end side thereof.

Figure 76:
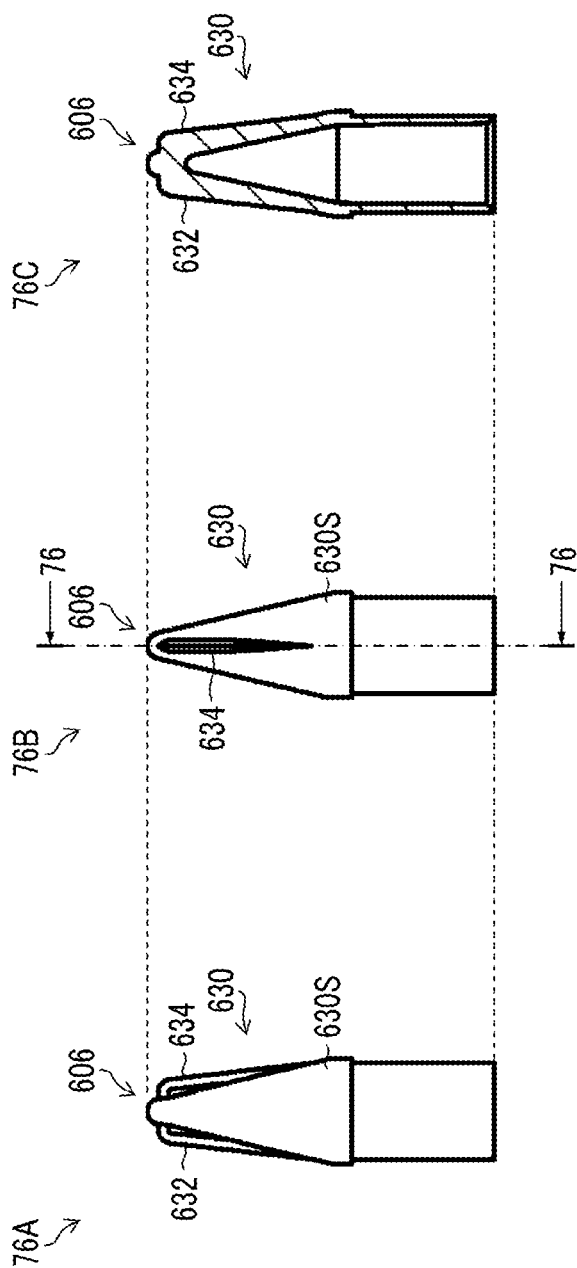

The reference sign 76A and the reference sign 76B of FIG. 76 indicate side views of the distal end part of the long needle part seen from directions different from each other, and the reference sign 76C of FIG. 76 is a cross-sectional view of the distal end part shown with the reference sign 76B, which is taken along line "76"-"76".

Figure 77:
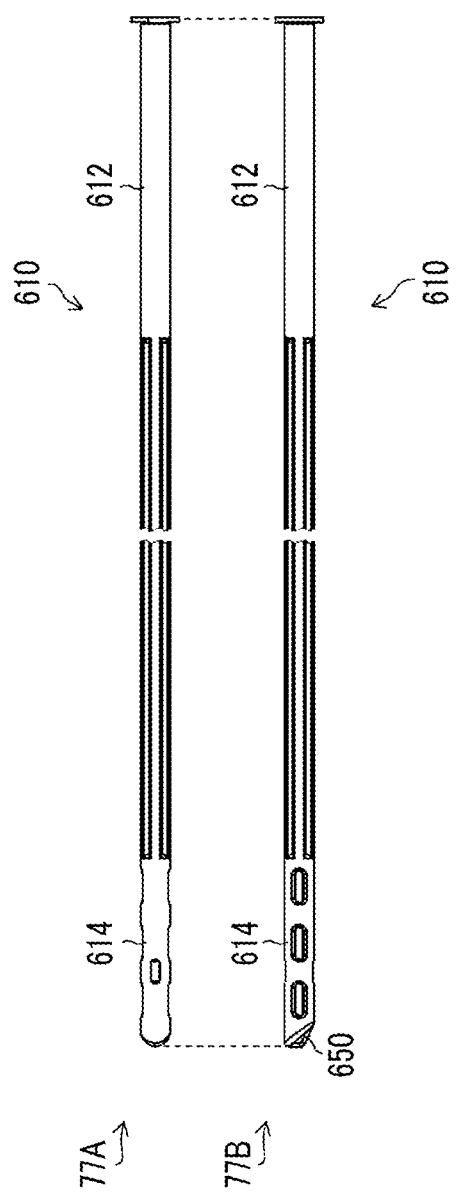

The reference sign 77A and the reference sign 77B of FIG. 77 indicate side views of a short needle part seen from directions different from each other.

Figure 78:
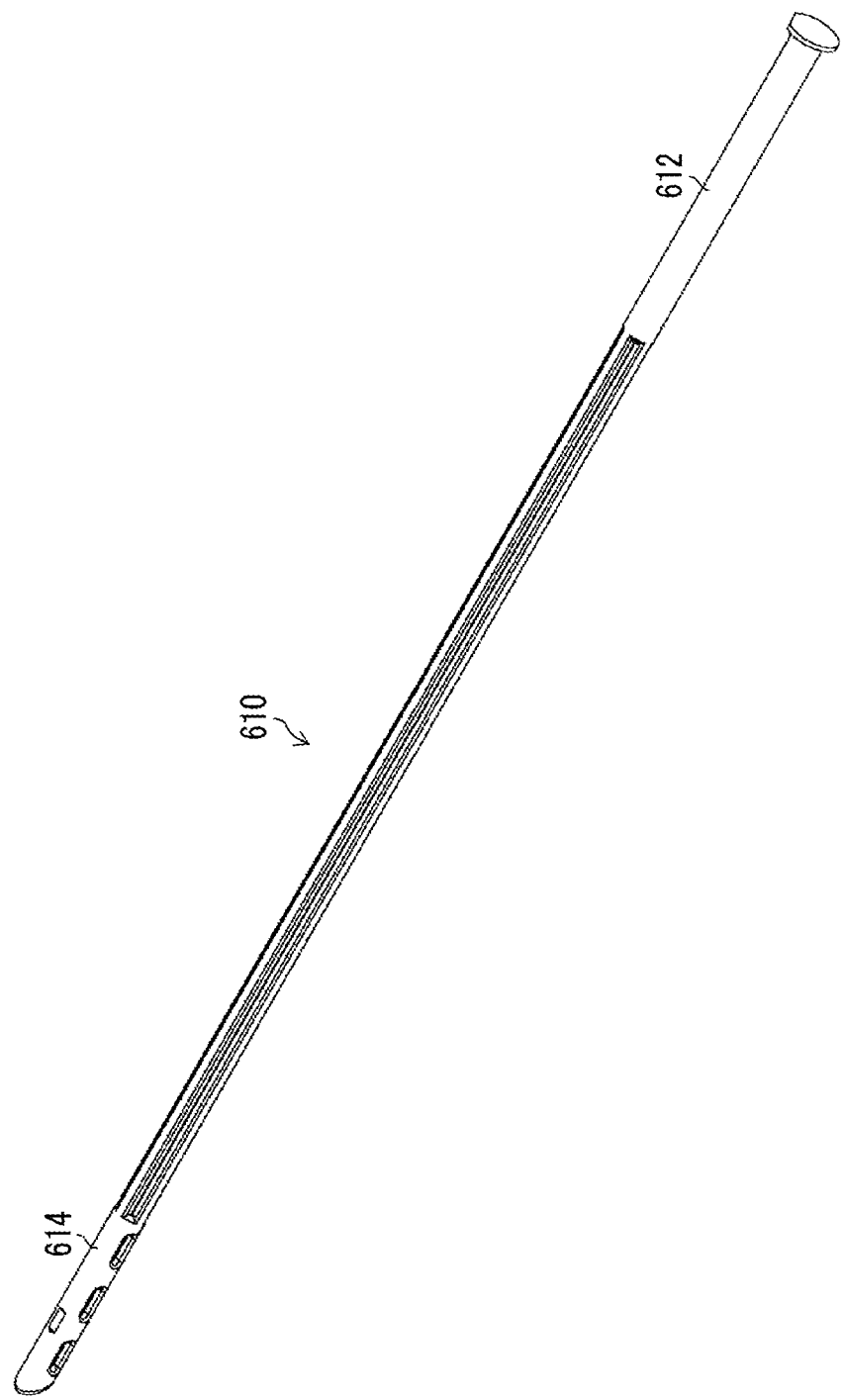

FIG. 78 is a rear perspective view of the short needle part seen from a proximal end side thereof.

Figure 79:
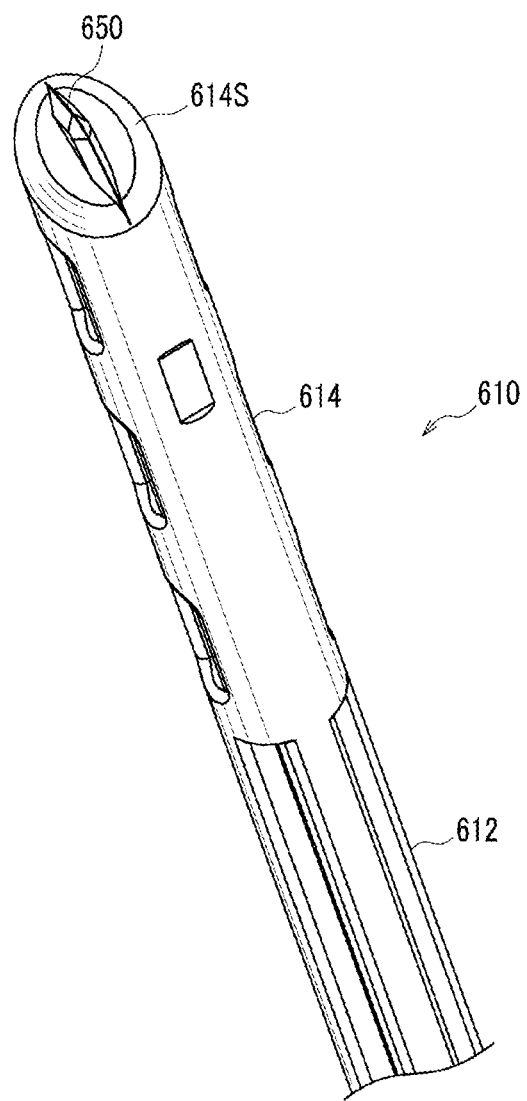

FIG. 79 is an enlarged perspective view of the distal end part of the short needle part.

Figure 80:
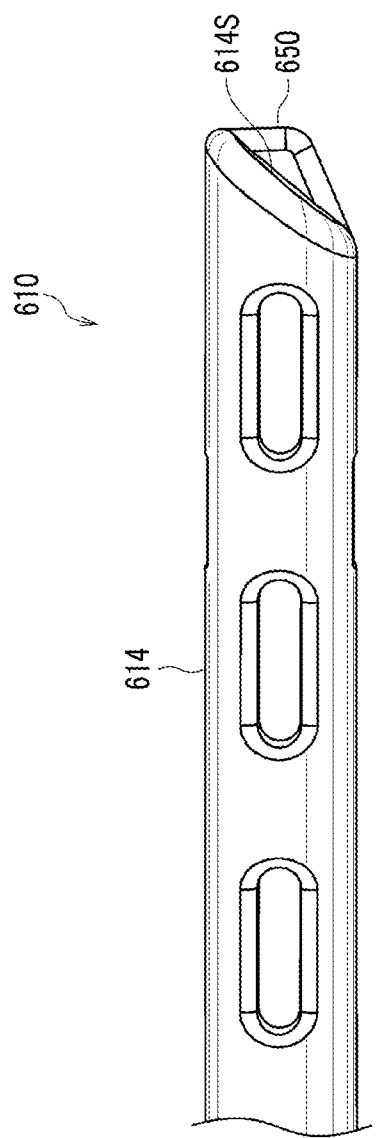

FIG. 80 is an enlarged side view of the distal end part of the short needle part.

Figure 81:
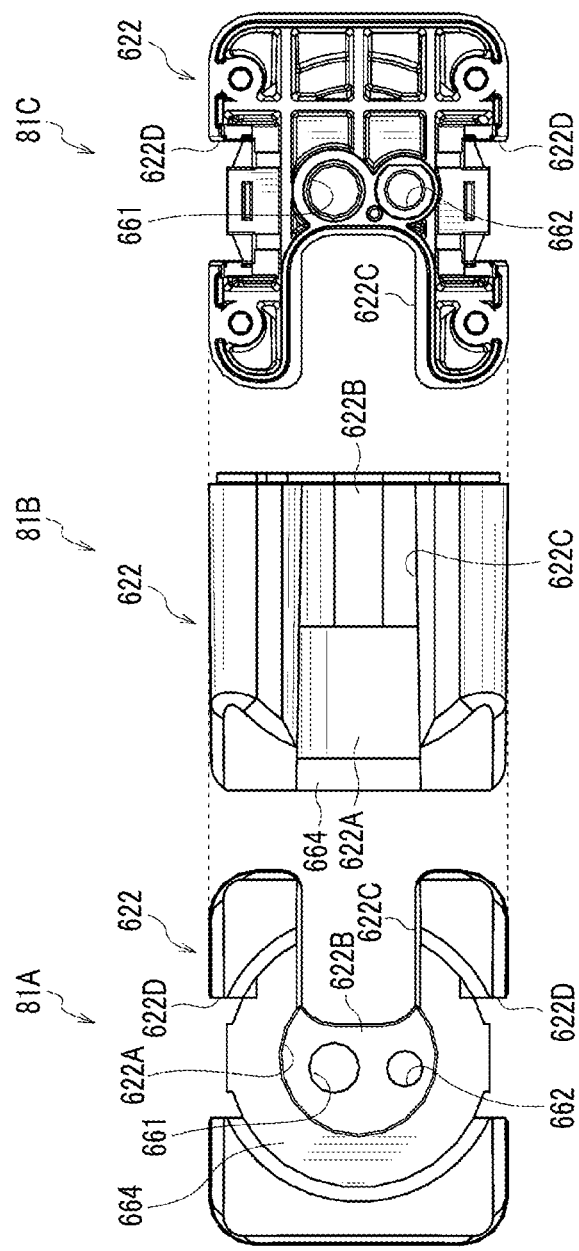

The reference sign 81A of FIG. 81 indicates a front view of a head body seen from a distal end side thereof, the reference sign 81B of FIG. 81 indicates a side view of the head body seen from the side, and the reference sign 81C of FIG. 81 indicates a rear view of the head body seen from a proximal end side thereof.

Figure 82:
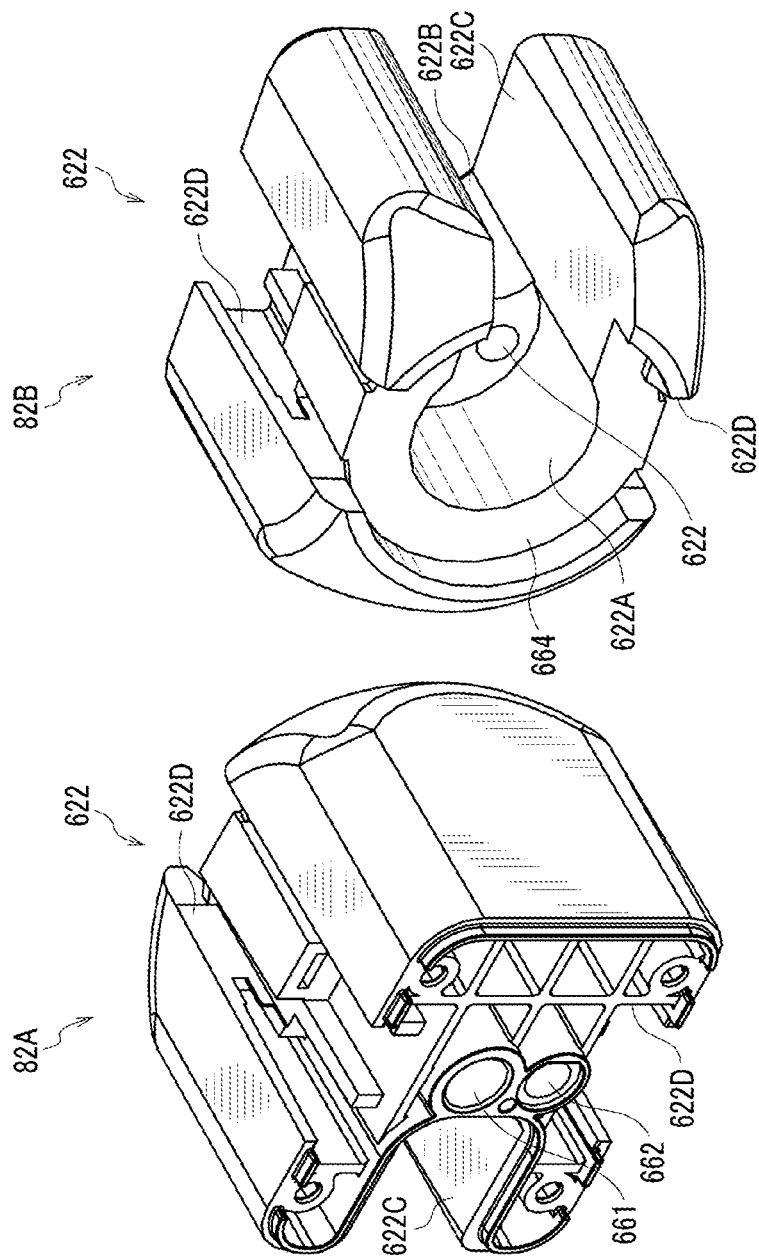

The reference sign 82A of FIG. 82 indicates a rear perspective view of the head body seen from the proximal end side thereof, and the reference sign 82B of FIG. 82 indicates a front perspective view of the head body seen from the distal end side thereof.

Figure 83:
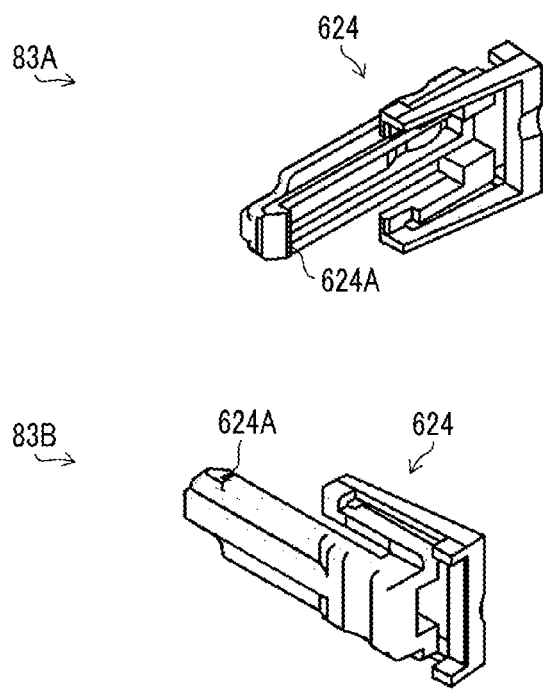

The reference sign 83A and the reference sign 83B of FIG. 83 indicate external perspective views of a lock lever seen from directions different from each other.

Figure 84:
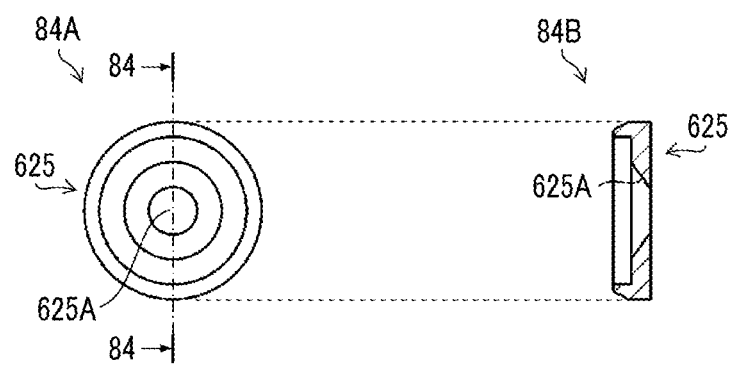

The reference sign 84A of FIG. 84 indicates a rear view of a seal member seen from a proximal end side thereof, and the reference sign 84B of FIG. 84 indicates a cross-sectional view of the seal member shown with the reference sign 84A, which is taken along line "84"-"84".

Figure 85:
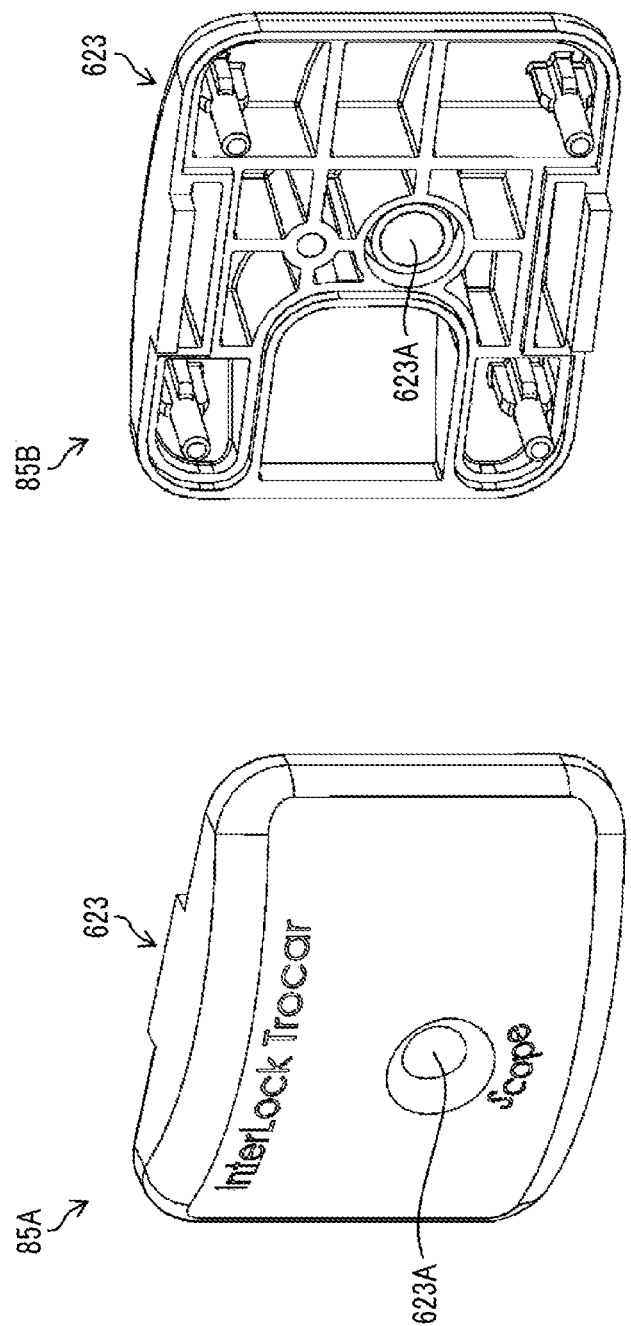

The reference sign 85A of FIG. 85 indicates a rear perspective view of a head cover seen from a proximal end side thereof, and the reference sign 85B of FIG. 85 indicates a front perspective view of the head cover seen from a distal end side thereof.

Figure 86:
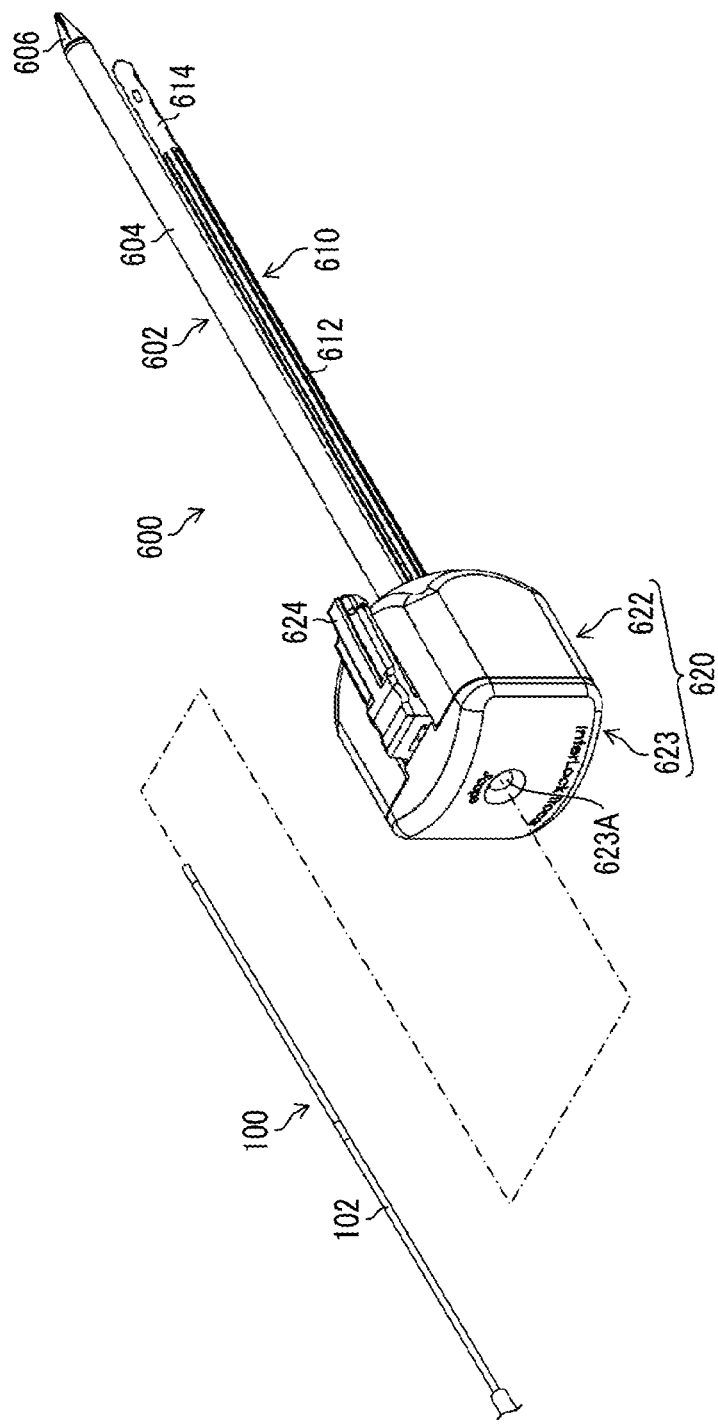

FIG. 86 is an explanatory view for illustrating insertion of an endoscope (endoscope insertion part) into the long needle part.

Figure 87:
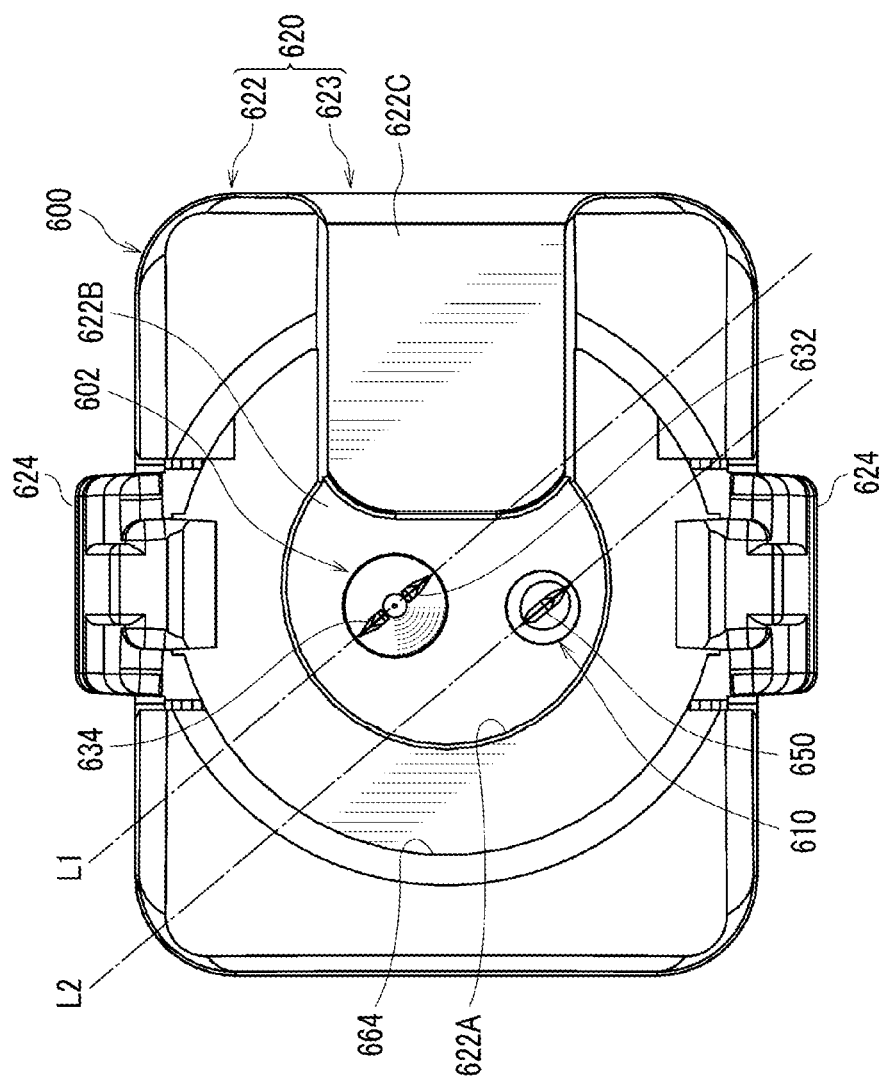

FIG. 87 is a front view of the inner needle seen from the distal end side thereof.

Figure 88:
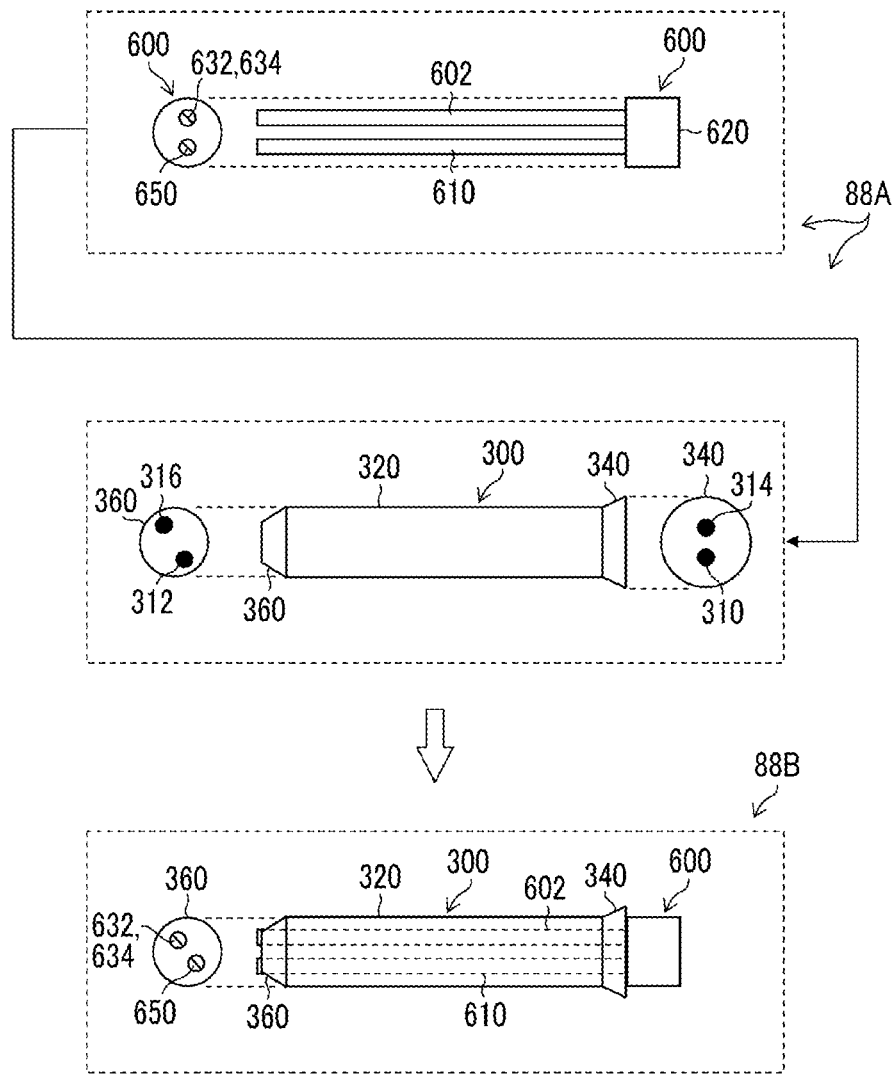

FIG. 88 is an explanatory view for illustrating a positional relationship between respective cutting edges before and after mounting the inner needle onto the overtube.

Figure 89:
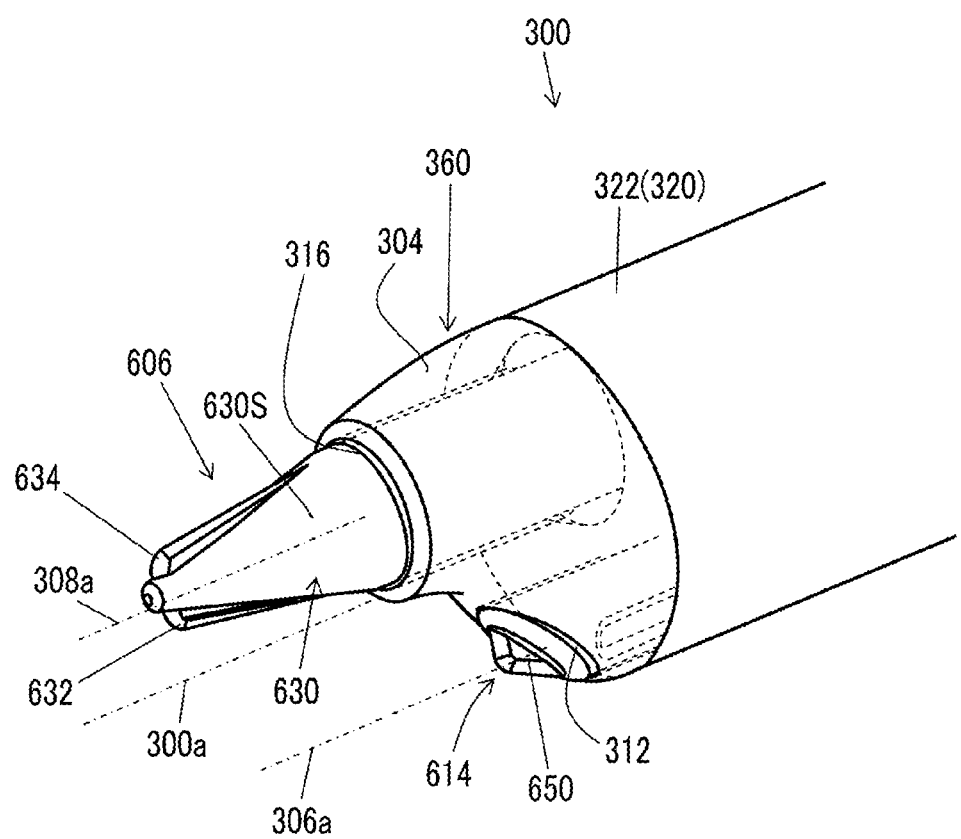

FIG. 89 is an external perspective view of each of the cutting edges in an inner needle mounted state.

Figure 90:
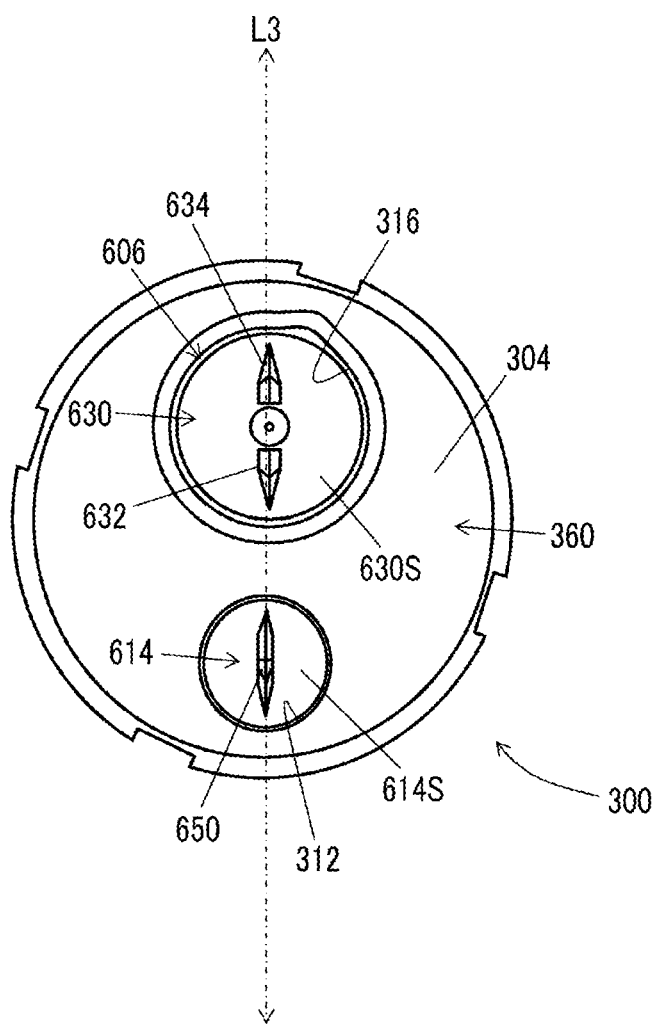

FIG. 90 is a front view of each of the cutting edges in the inner needle mounted state seen from a distal end side thereof.

Figure 91:
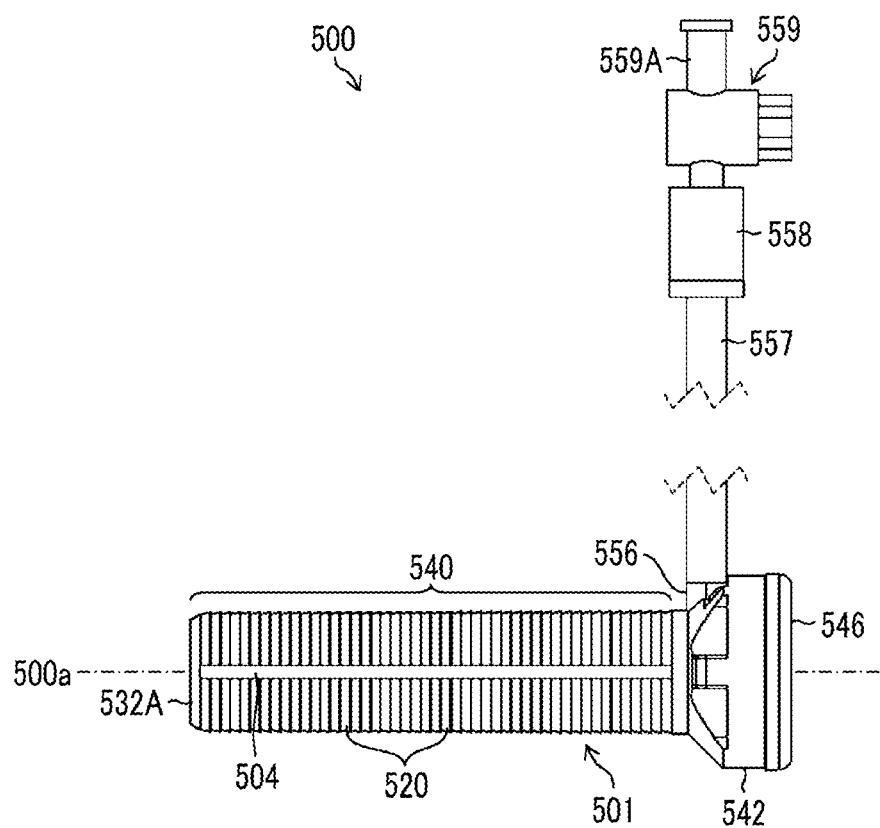

FIG. 91 is a side view of the sheathing tube.

Figure 92:
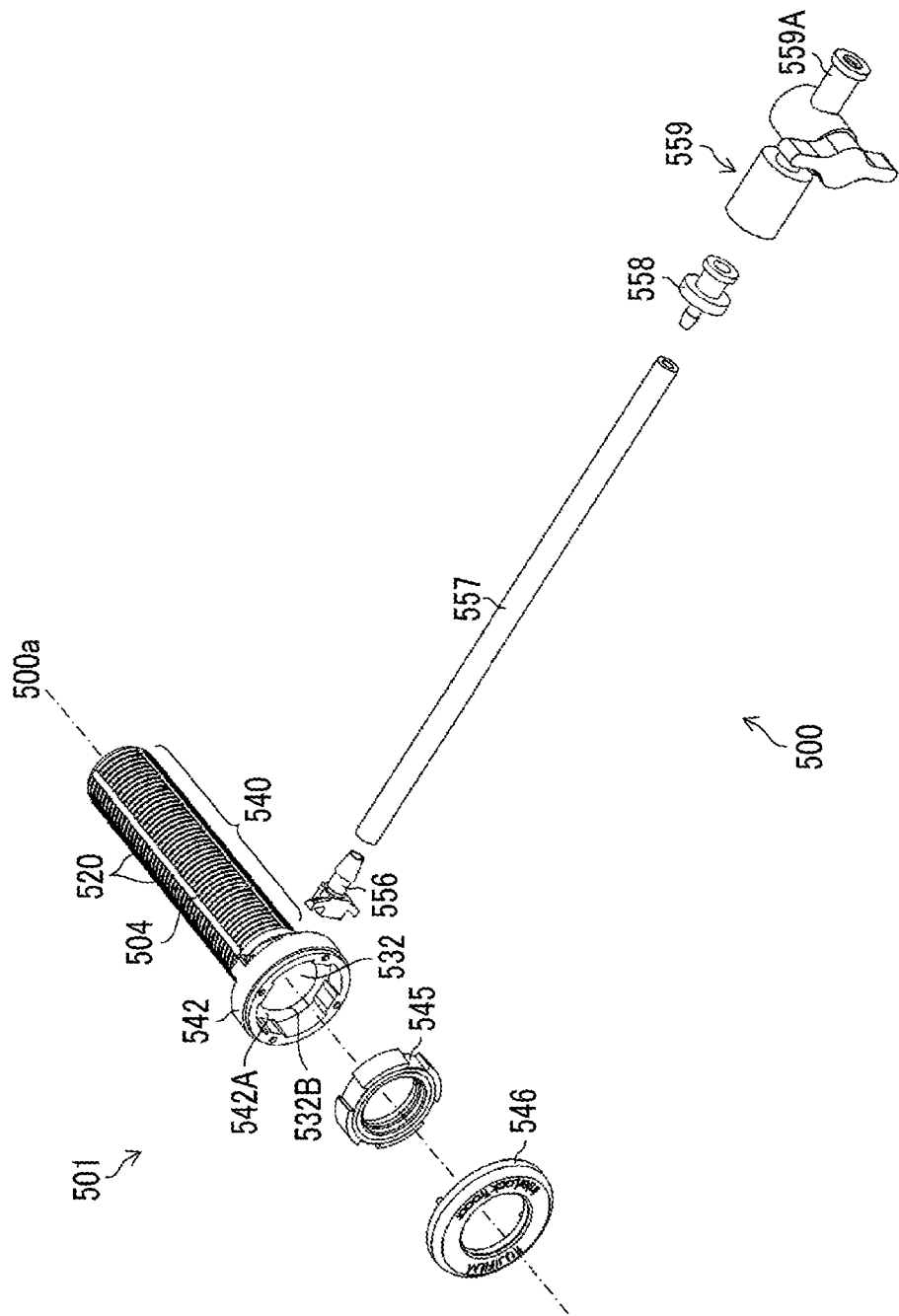

FIG. 92 is an exploded perspective view of the sheathing tube, in which the sheathing tube is seen from a proximal end side thereof.

Figure 93:
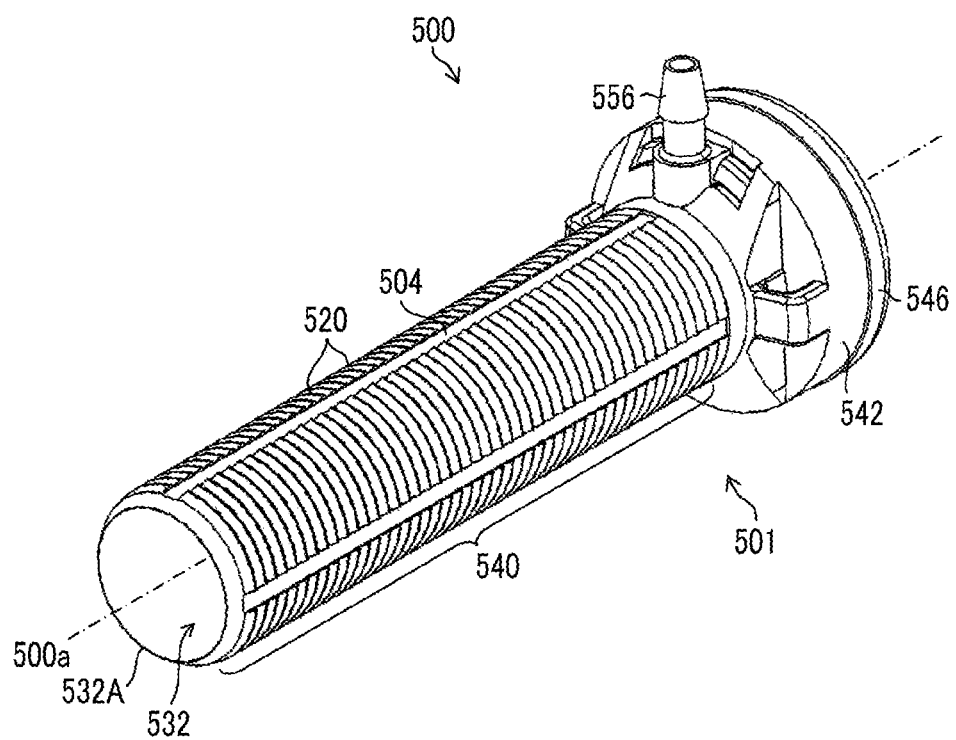

FIG. 93 is an external perspective view of important parts of the sheathing tube seen from a distal end side thereof.

Figure 94:
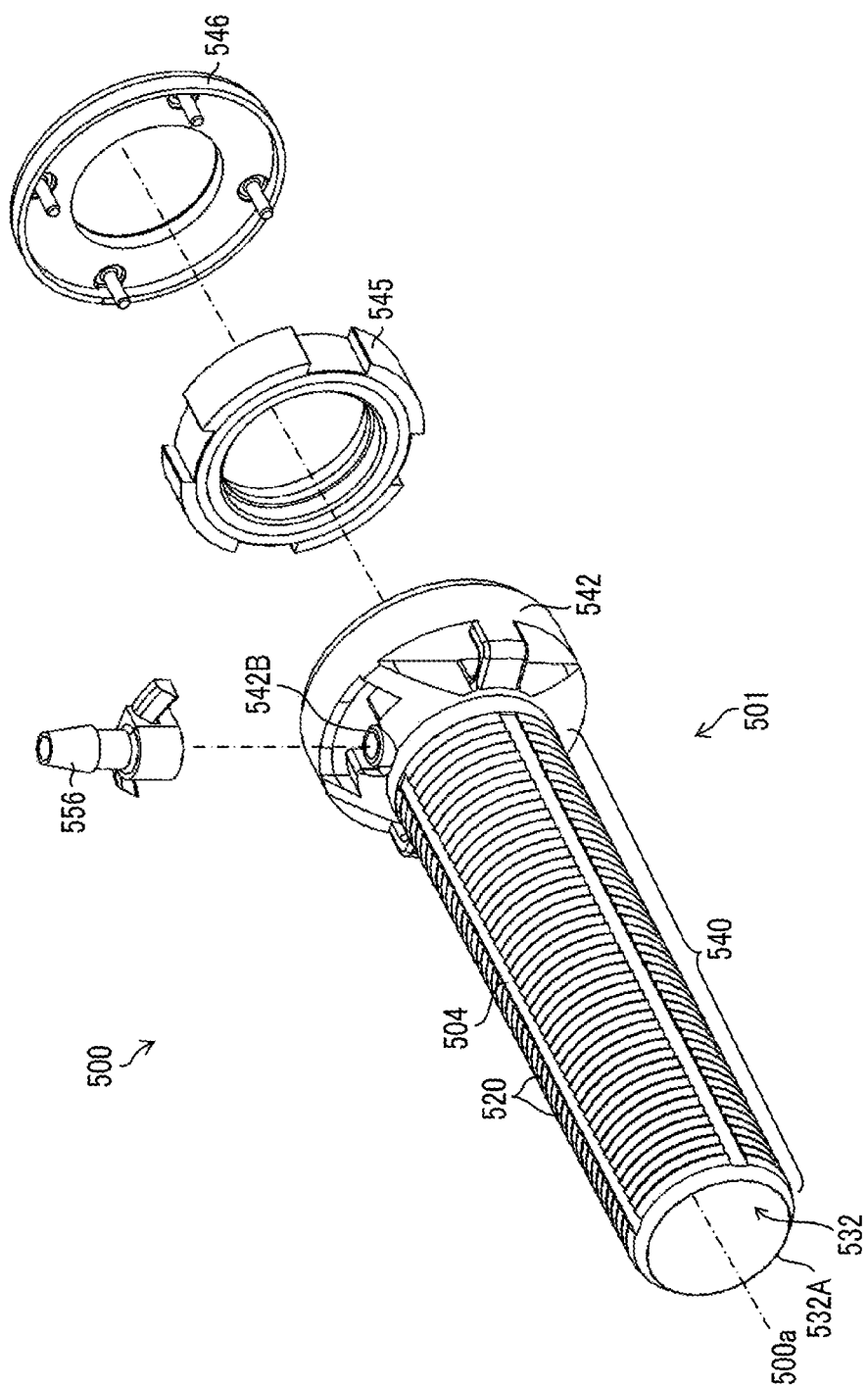

FIG. 94 is an exploded perspective view of the important parts of the sheathing tube.

Figure 95:
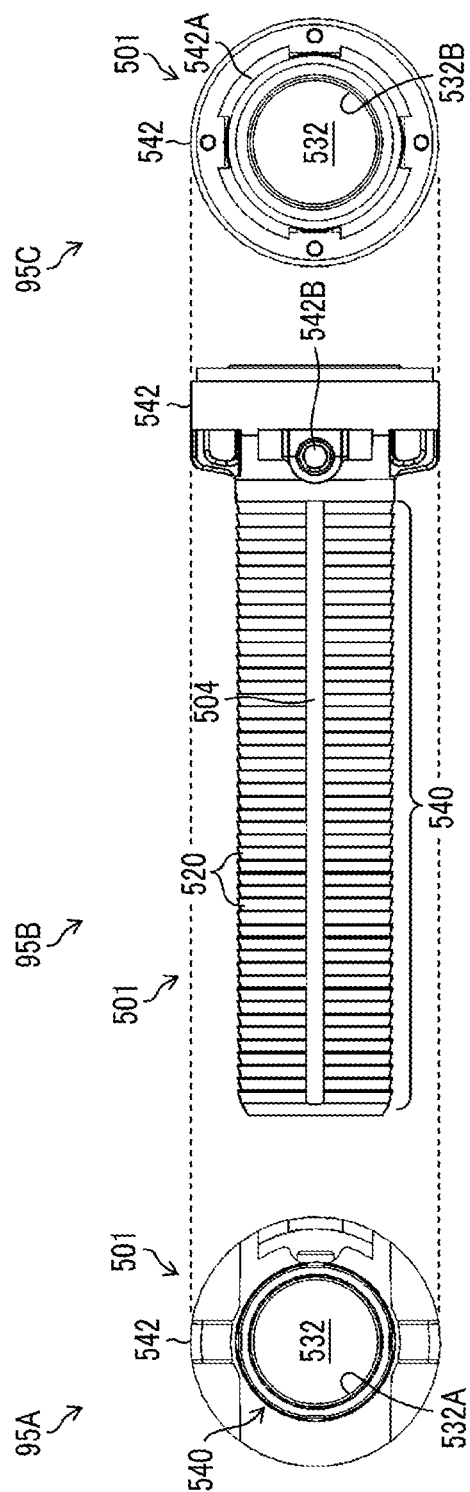

The reference sign 95A of FIG. 95 indicates a front view of a sheathing tube body seen from a distal end side thereof, the reference sign 95B of FIG. 95 indicates a side view of the sheathing tube body, and the reference sign 95C of FIG. 95 indicates a rear view of the sheathing tube body seen from a proximal end side thereof.

Figure 96:
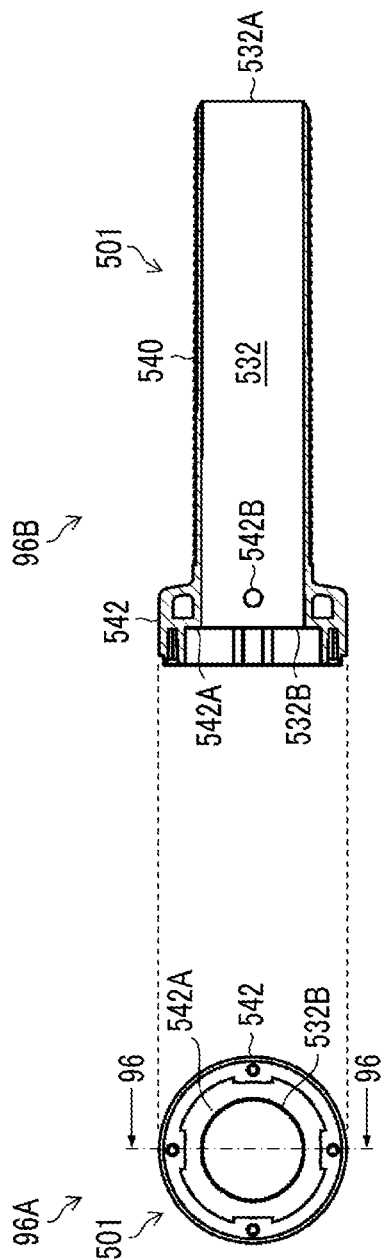

The reference sign 96A of FIG. 96 indicates a rear view of the sheathing tube body seen from the proximal end side thereof, and the reference sign 96B of FIG. 96 indicates a cross-sectional view of the sheathing tube body shown with the reference sign 96A, which is taken along line "96"-"96".

Figure 97:
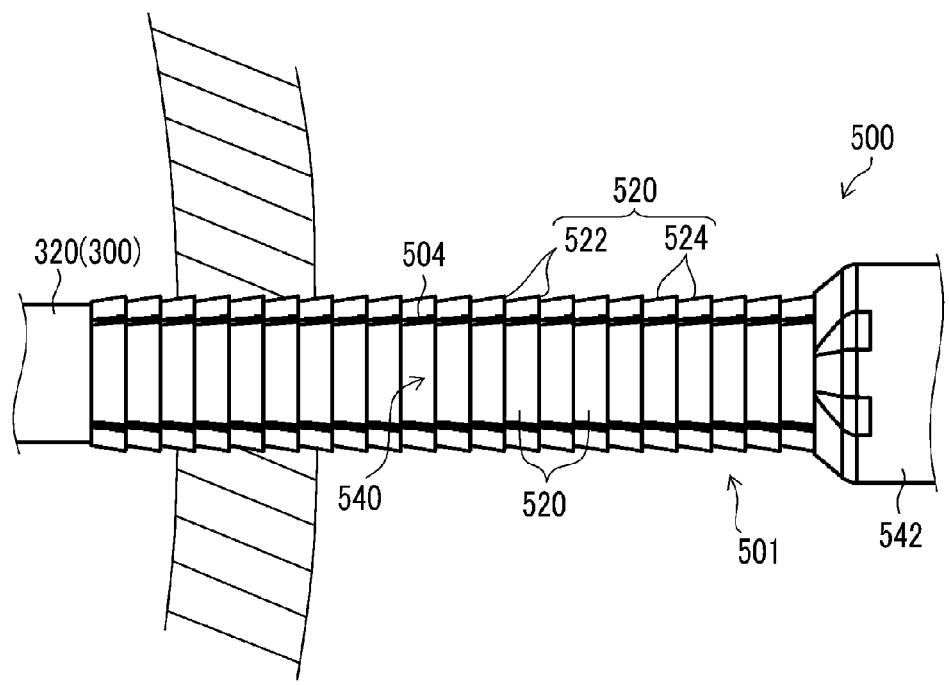

FIG. 97 is a schematic view of the sheathing tube body (sheathing tube) inserted in the body wall.

Figure 98:
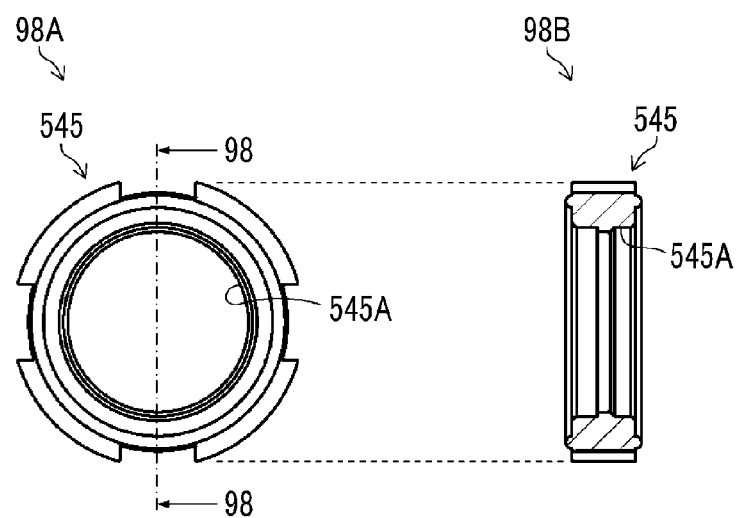

The reference sign 98A of FIG. 98 indicates a rear view of the seal member seen from the proximal end side thereof, and the reference sign 98B of FIG. 98 indicates a cross-sectional view of the seal member shown with the reference sign 98A, which is taken along line "98"-"98".

Figure 99:
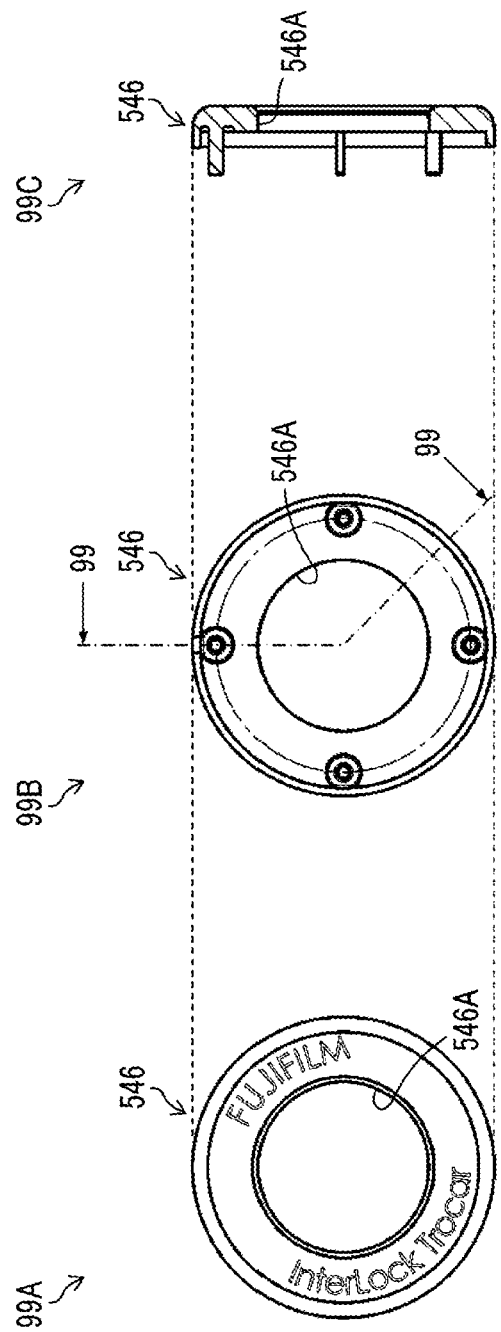

The reference sign 99A of FIG. 99 indicates a rear view of the cover member seen from the proximal end side thereof, the reference sign 99B of FIG. 99 indicates a front view of the cover member seen from the distal end side thereof, and the reference sign 99C of FIG. 99 indicates a cross-sectional view of the cover member shown with the reference sign 99B, which is taken along line "99"-"99".

Figure 100:
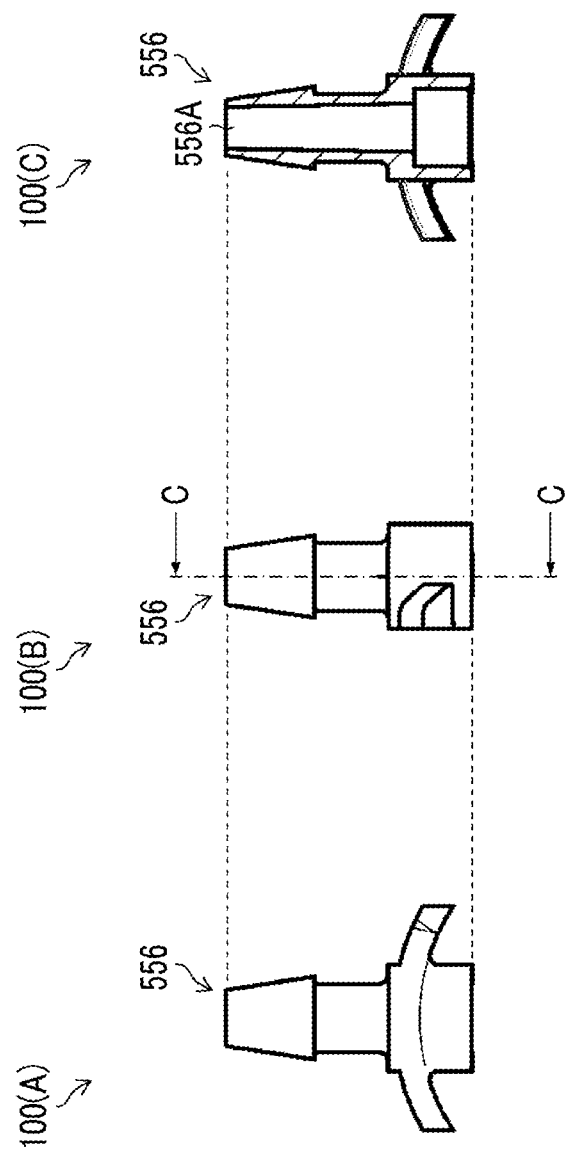

The reference sign 100(A) and the reference sign 100(B) of FIG. 100 indicate side views of a connection valve seen from directions different from each other, and the reference sign 100(C) of FIG. 100 is a cross-sectional view of the connection valve shown with the reference sign 100(B), which is taken along line "C"-"C".

Figure 101:
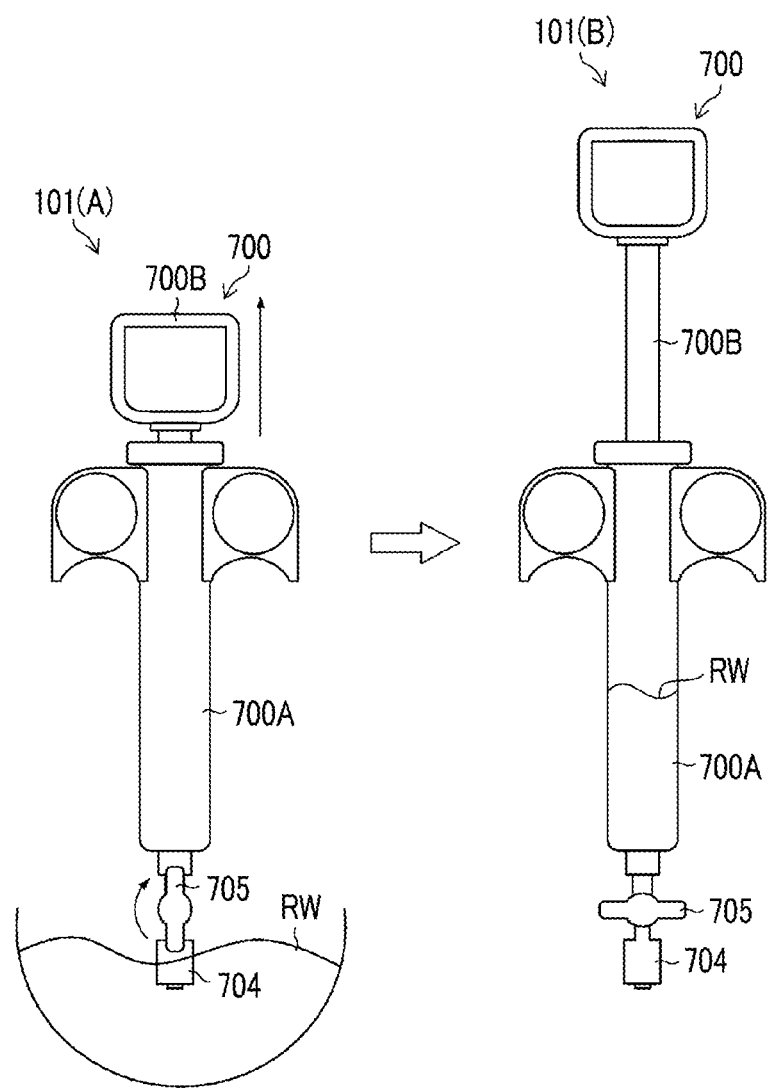

The reference sign 101(A) of FIG. 101 indicates a side view of the syringe before suction of the cleaning liquid, and the reference sign 101(B) of FIG. 101 indicates a side view of the syringe after suction of the cleaning liquid.

Figure 102:
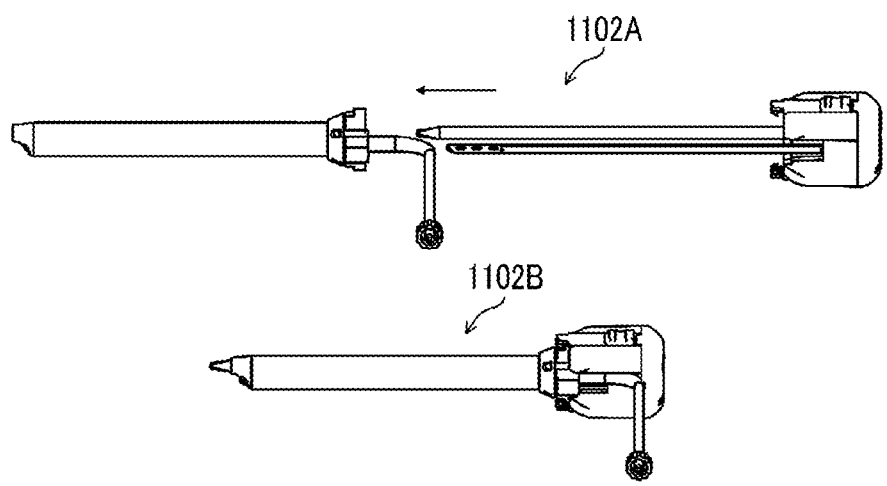

FIG. 102 is a view illustrating details of a using method and precautions of the surgical system.

Figure 103:
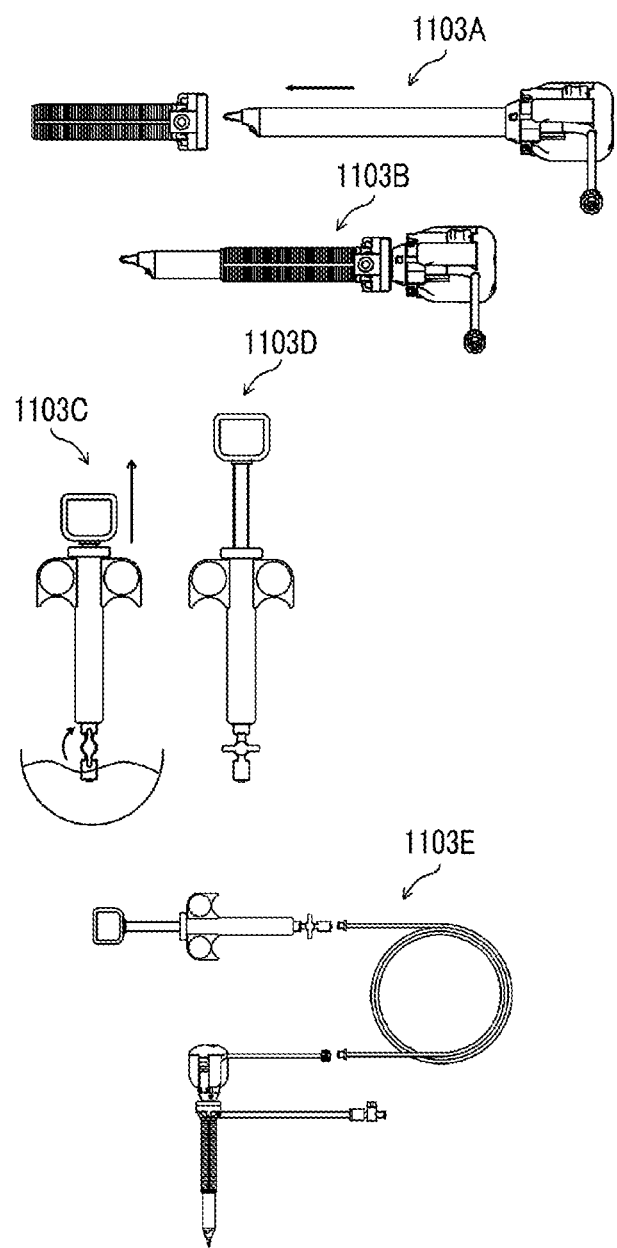

FIG. 103 is a view illustrating the details of the using method and the precautions of the surgical system.

Figure 104:
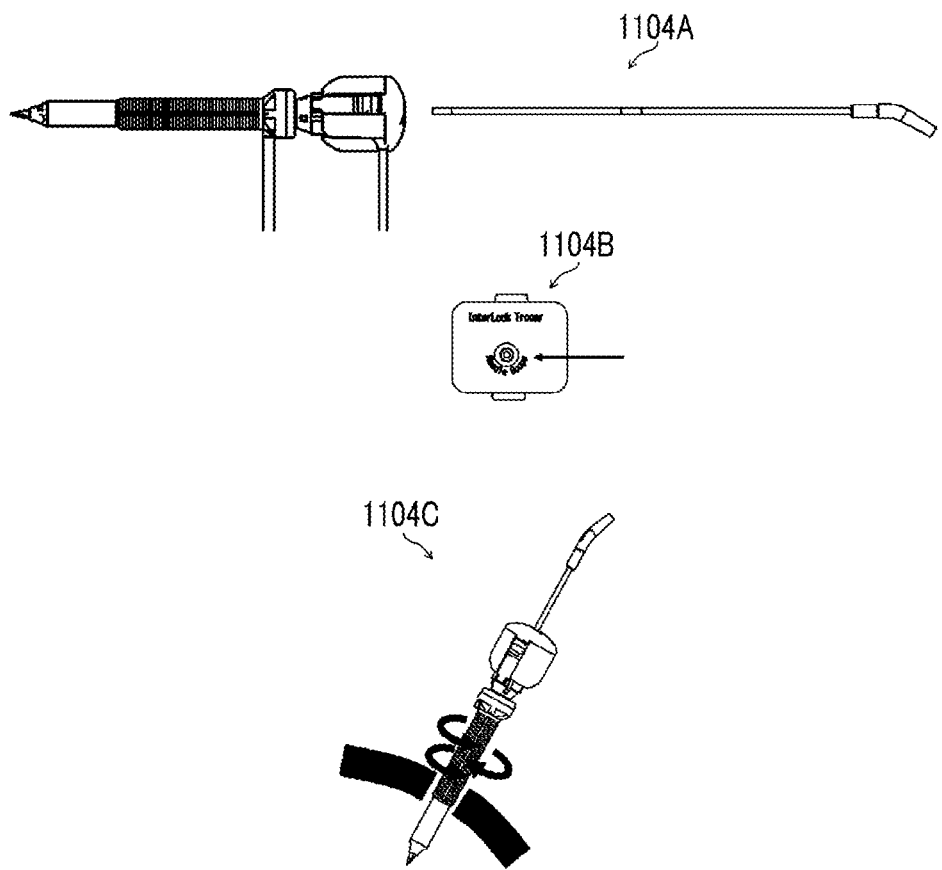

FIG. 104 is a view illustrating the details of the using method and the precautions of the surgical system.

Figure 105:
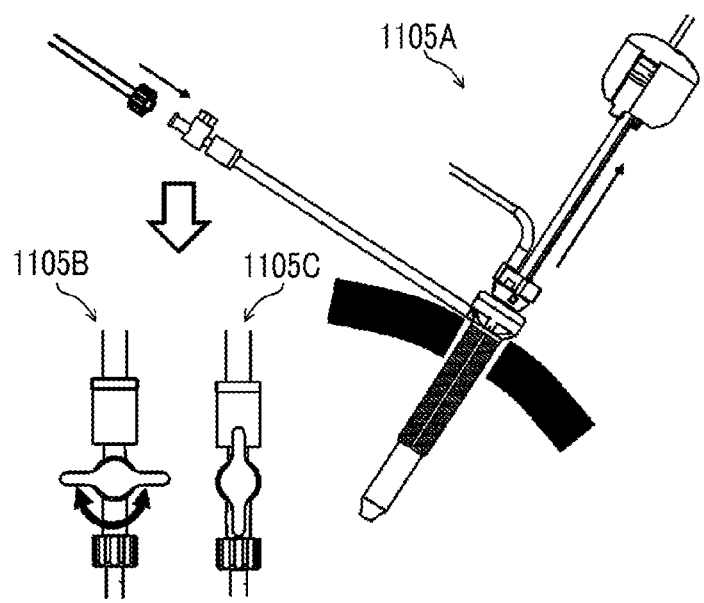

FIG. 105 is a view illustrating the details of the using method and the precautions of the surgical system.

Figure 106:
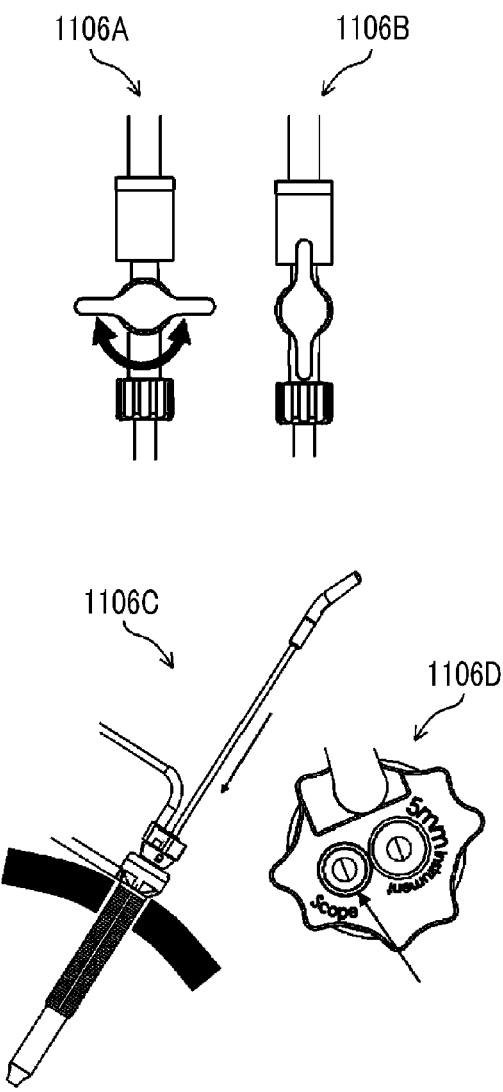

FIG. 106 is a view illustrating the details of the using method and the precautions of the surgical system.

Figure 107:
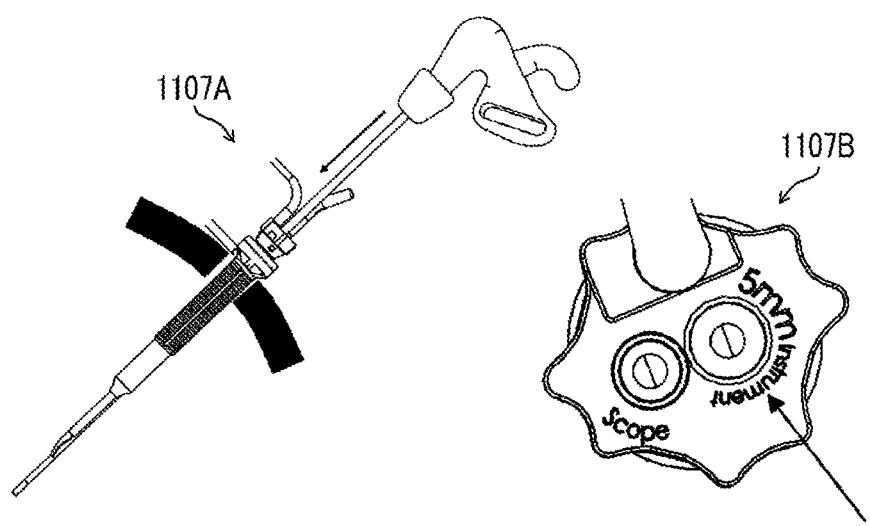

FIG. 107 is a view illustrating the details of the using method and the precautions of the surgical system.

Figure 108:
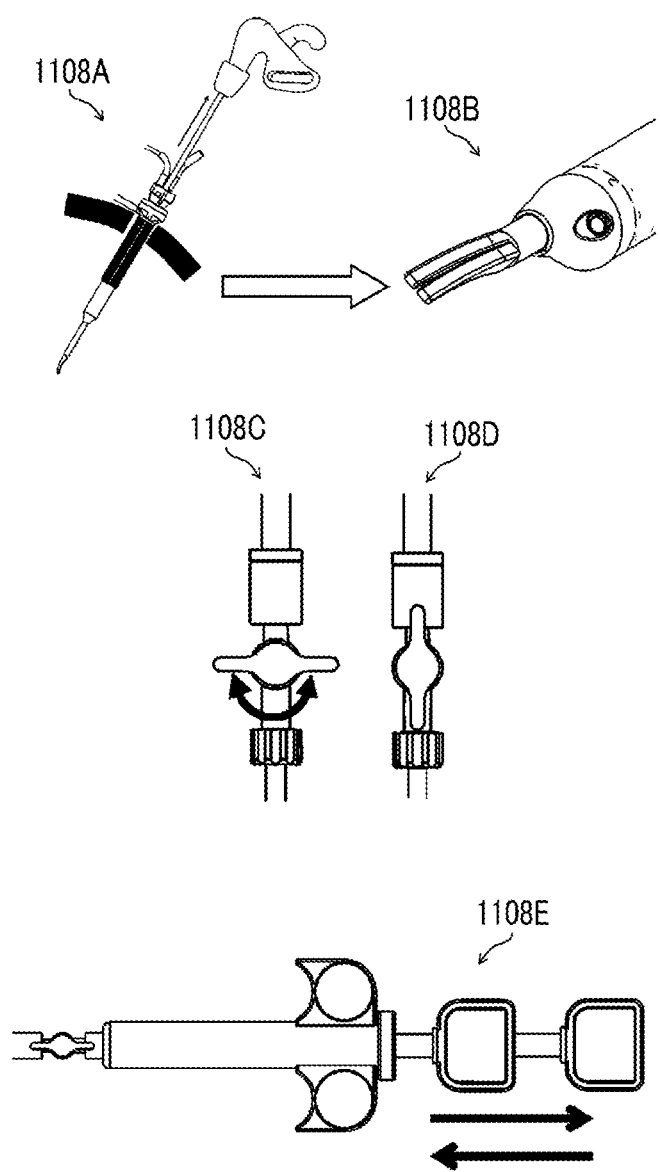

FIG. 108 is a view illustrating the details of the using method and the precautions of the surgical system.

Figure 109:
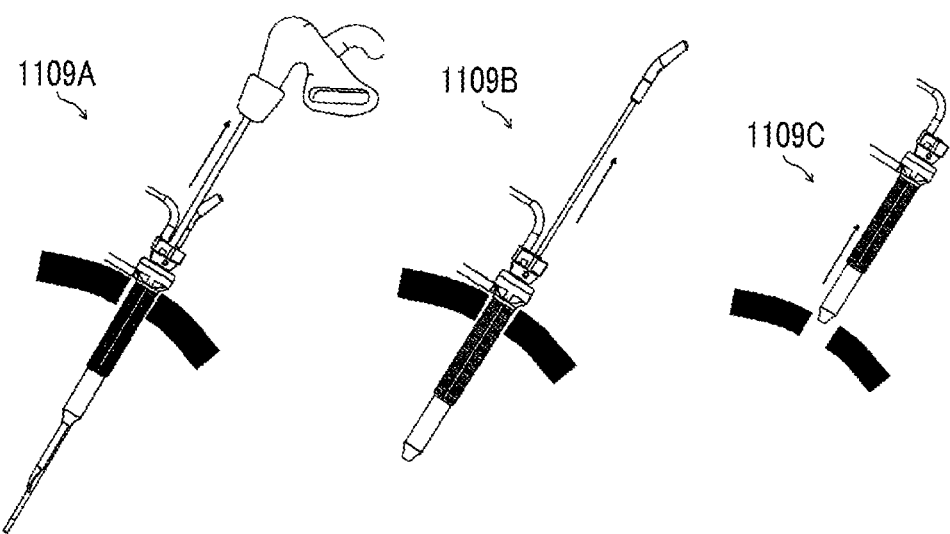

FIG. 109 is a view illustrating the details of the using method and the precautions of the surgical system.

DESCRIPTION OF THE PREFERRED EMBODIMENTS

[Schematic Configuration of Surgical System]

Figure 1:
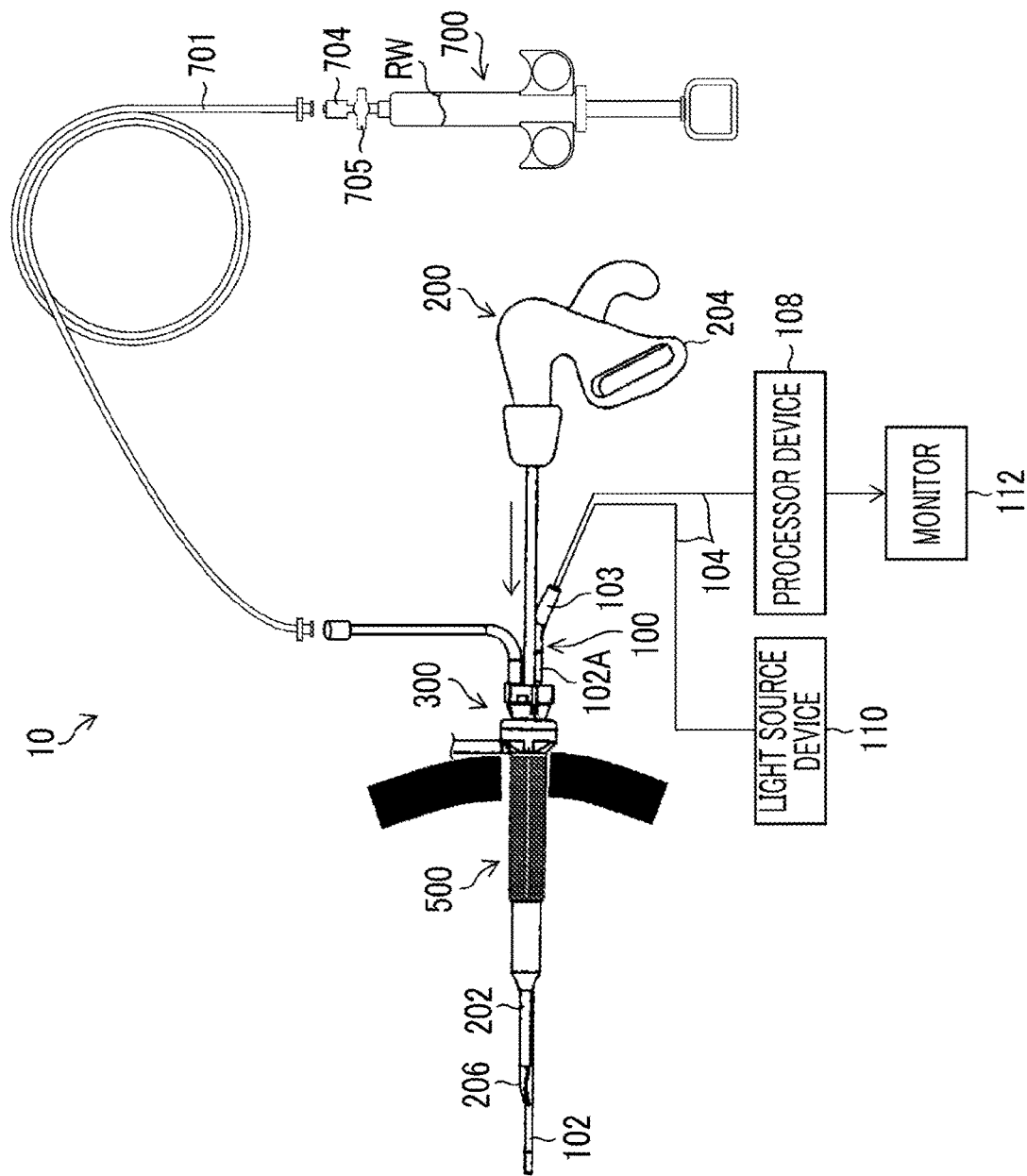
FIG. 1 is a schematic configuration view of a part of a surgical system according to an embodiment of the present invention.

FIG. 1 is a schematic configuration view of a part of a surgical system 10 according to an embodiment of the present invention. As illustrated in FIG. 1, in a case where the surgical system 10 performs observation and various types of treatments inside a patient's body cavity, the surgical system is configured to include an endoscope 100, a treatment tool 200, an overtube 300, a sheathing tube 500, a syringe 700, and a tube 701.

The endoscope 100 is one form of a first medical instrument (medical instrument) inserted into a body cavity. The endoscope 100 is, for example, a hard endoscope such as a laparoscope, and is inserted into the body cavity to observe the inside of the body cavity. The endoscope 100 comprises an elongated hard endoscope insertion part 102 that is inserted into the body cavity, a grip part 102A that is consecutively installed on a proximal end part of the endoscope insertion part 102 and has a diameter larger than a diameter of the endoscope insertion part 102, a connecting part 103 that is consecutively installed on a proximal end part of the grip part 102A, and a flexible cord part 104 that is connected to the endoscope insertion part 102 via the connecting part 103. The endoscope insertion part 102 corresponds to each of an insertion part of the medical instrument of the embodiment of the present invention, a first insertion part, and an insertion part of the endoscope.

An end part of the cord part 104 on an opposite side to the connecting part 103 is provided with a connector (not illustrated) attachably and detachably connected to each of a processor device 108 and a light source device 110. A monitor 112 is connected to the processor device 108 via a cable (not illustrated).

Figure 2:
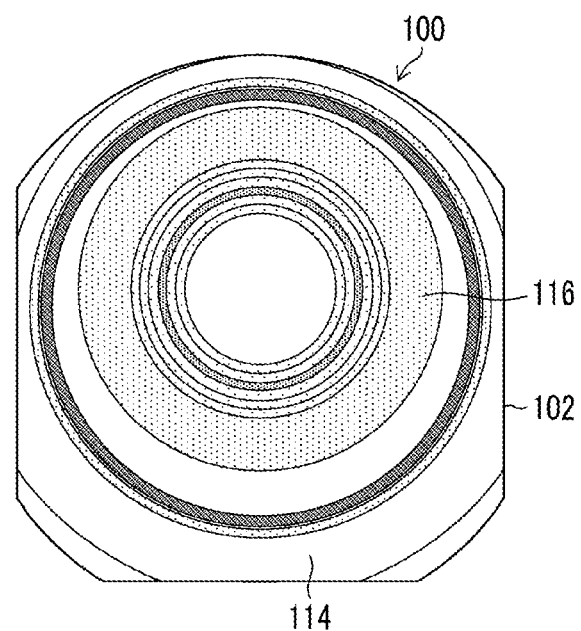
FIG. 2 is a front view of a distal end surface of an endoscope insertion part.

FIG. 2 is a front view of a distal end surface 114 of the endoscope insertion part 102. As illustrated in FIG. 2, the distal end surface 114 is provided with an observation window 116. Behind (inside) the observation window 116, an illumination part (not illustrated), an observation optical system (not illustrated), a solid image pickup element (not illustrated), and the like are provided.

One or a plurality of emission ends of a light guide (not illustrated) are disposed in the illumination part. The light guide is inserted into the endoscope insertion part 102, the connecting part 103, the cord part 104, and the like to extend up to the connector described above, and is connected to the light source device 110. Accordingly, illumination light emitted from the light source device 110 is radiated to the front of the endoscope insertion part 102 from the illumination part through the light guide. Accordingly, the inside of the patient's body cavity is irradiated with the illumination light. The illumination part may be provided behind an illumination window (not illustrated) provided in the distal end surface 114.

Subject light picked up from the observation window 116 is incident to an imaging surface of the solid image pickup element (not illustrated) by means of the observation optical system (not illustrated). The solid image pickup element is a solid image pickup element, such as a charge coupled device (CCD) image sensor and a complementary metal oxide semiconductor (CMOS) image sensor, and images the subject light incident to the imaging surface to output an image pickup signal. In addition, a signal cable (not illustrated) is connected to the solid image pickup element. The signal cable is inserted into the endoscope insertion part 102, the connecting part 103, the cord part 104, and the like to extend up to the connector described above, and is connected to the processor device 108. Accordingly, the processor device 108 causes the monitor 112 to display an endoscopic image (an observation image of the inside of the body cavity) based on the image pickup signal input from the solid image pickup element.

Referring back to FIG. 1, the treatment tool 200 is one form of a second medical instrument (medical instrument) inserted into a body cavity. For example, an electric scalpel, a forceps, a laser probe, a suture device, a needle holder, an ultrasonic device, an aspirator, or the like is used as the treatment tool 200, and the treatment tool is inserted into the body cavity to examine or treat a diseased site in the body cavity. The treatment tool 200 comprises an elongated treatment tool insertion part 202 inserted into the body cavity, an operating part 204 that is provided on a proximal end side of the treatment tool insertion part 202 and is gripped by an operator, and a treatment part 206 that is provided on a distal end of the treatment tool insertion part 202 and is operable by the operation of the operating part 204. The treatment tool insertion part 202 corresponds to the insertion part of the medical instrument of the embodiment of the present invention and a second insertion part.

The overtube 300 allows the endoscope insertion part 102 and the treatment tool insertion part 202 to be inserted therein from the proximal end side and to be delivered from the distal end side. By inserting the overtube 300 into a hole formed in a body wall and having a proximal end side thereof disposed outside the body and a distal end side thereof disposed within the body cavity, the endoscope insertion part 102 and the treatment tool insertion part 202 are guided into the body cavity with one overtube 300. In addition, as will be described below in detail, the overtube 300 includes an interlocking function of moving the endoscope insertion part 102 and the treatment tool insertion part 202 forward and backward in an interlocking manner. Accordingly, for example, the endoscope insertion part 102 can also be moved forward and backward by the forward and backward movement operation of only the treatment tool insertion part 202, and a suitable endoscopic image can be obtained without performing the forward and backward movement operation of the endoscope insertion part 102.

The sheathing tube 500 is formed in a tubular shape, and is sheathed to the overtube 300 described above. In a state of being sheathed to the overtube 300 (in a state where the overtube 300 is inserted in the sheathing tube 500), the sheathing tube 500 is inserted into the hole formed in the body wall along with the overtube 300, and passes through a body wall so as to be inserted into a body cavity. In addition, as will be described below in detail, the sheathing tube 500 has a wall surface that prevents rotation and forward and backward movement with respect to the body wall. For this reason, by sheathing the sheathing tube 500 to the overtube 300, unintended rotation and forward and backward movement of the overtube 300 with respect to the body wall can be prevented. In addition, as will be described below in detail, the sheathing tube 500 is connected to an air supply device (not illustrated). Accordingly, the sheathing tube 500 receives supply of a pneumoperitoneum gas (a carbon dioxide gas or the like) from the air supply device, and fills the body cavity with the pneumoperitoneum gas by supplying the pneumoperitoneum gas into the body cavity.

The syringe 700 is configured to eject and suck a cleaning liquid RW (corresponds to a fluid according to the embodiment of the present invention) from a nozzle 704 with one-handed operation by an operator or the like, and is used in combination with the overtube 300 described above. The cleaning liquid RW ejected and sucked from the nozzle 704 of the syringe 700 is used in cleaning the observation window 116 of the endoscope 100 inserted in the overtube 300. The type of the cleaning liquid RW is not particularly limited, and a known liquid is used.

The nozzle 704 is provided with a stopcock 705 that opens and closes the nozzle 704. The stopcock 705 opens the nozzle 704 in a posture parallel to the nozzle 704, and closes the nozzle 704 in a posture perpendicular to the nozzle 704. A known configuration other than the stopcock 705 may be used as an opening and closing structure for the nozzle 704.

A tube 701 is a flexible tubular body, and connects the nozzle 704 of the syringe 700 to the overtube 300. Accordingly, the cleaning liquid RW can be ejected from the syringe 700 to the overtube 300 via the tube 701, and the ejected cleaning liquid RW can be sucked by the syringe 700.

Figure 3:
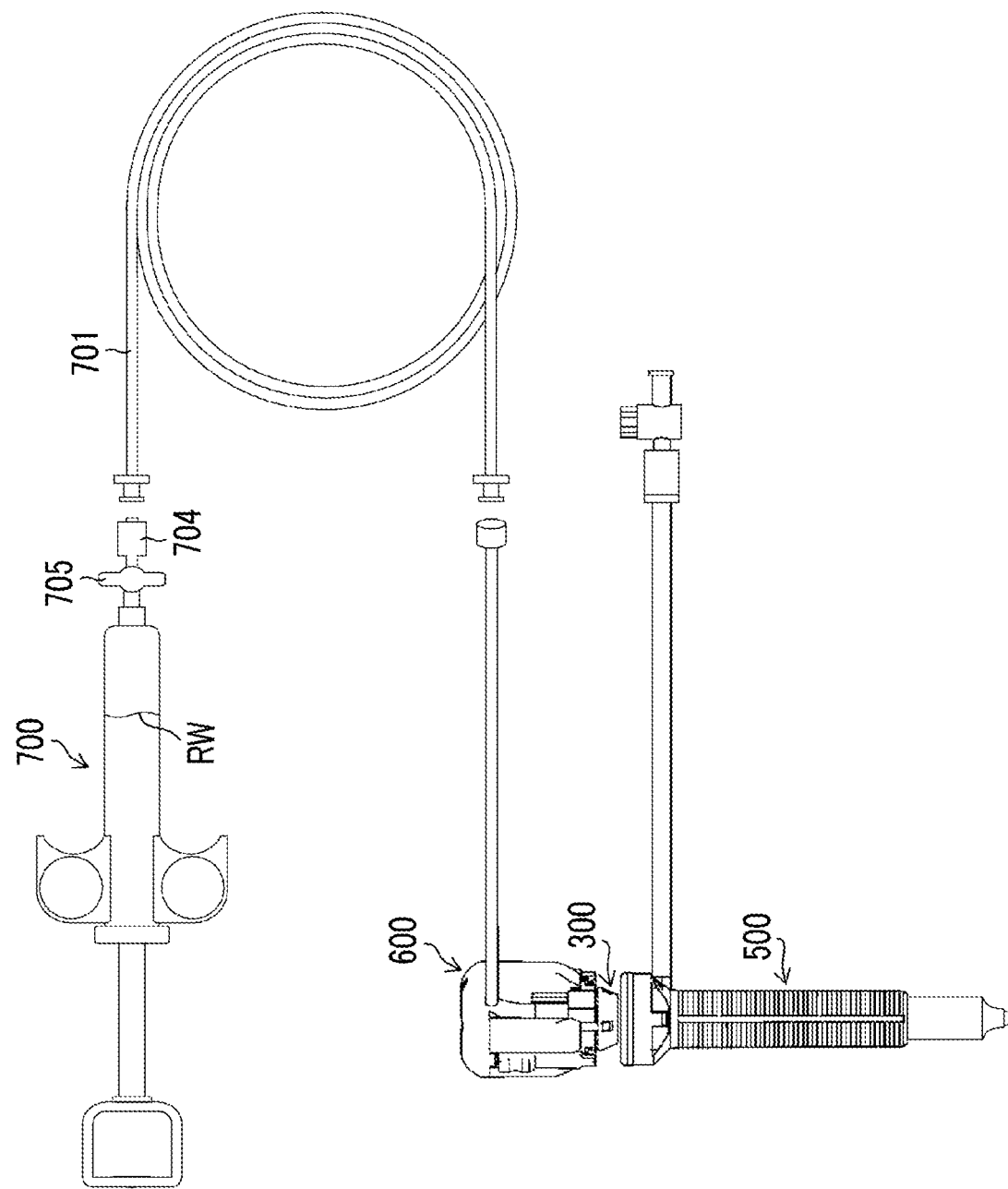
FIG. 3 is a schematic configuration view of the surgical system in a case of forming a hole in a body wall and inserting an overtube and a sheathing tube into the hole.

FIG. 3 is a schematic configuration view of the surgical system 10 in a case of forming a hole in a body wall and inserting the overtube 300 and the sheathing tube 500 into the hole. As illustrated in FIG. 3, in a case of forming the hole in the body wall and inserting the overtube 300 and the sheathing tube 500 into the hole prior to observation and various types of treatments inside a patient's body cavity, the surgical system 10 comprises an inner needle 600 instead of the endoscope 100 and the treatment tool 200 out of respective configurations described above.

Figure 4:
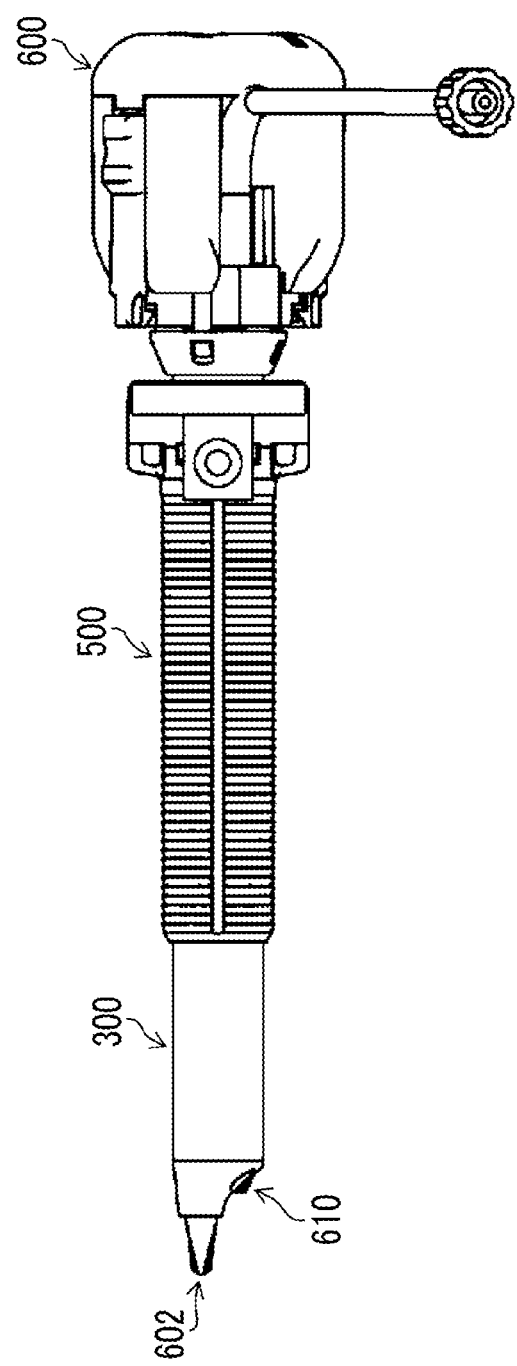
FIG. 4 is an enlarged view of the overtube, the sheathing tube, and an inner needle.
Figure 5:
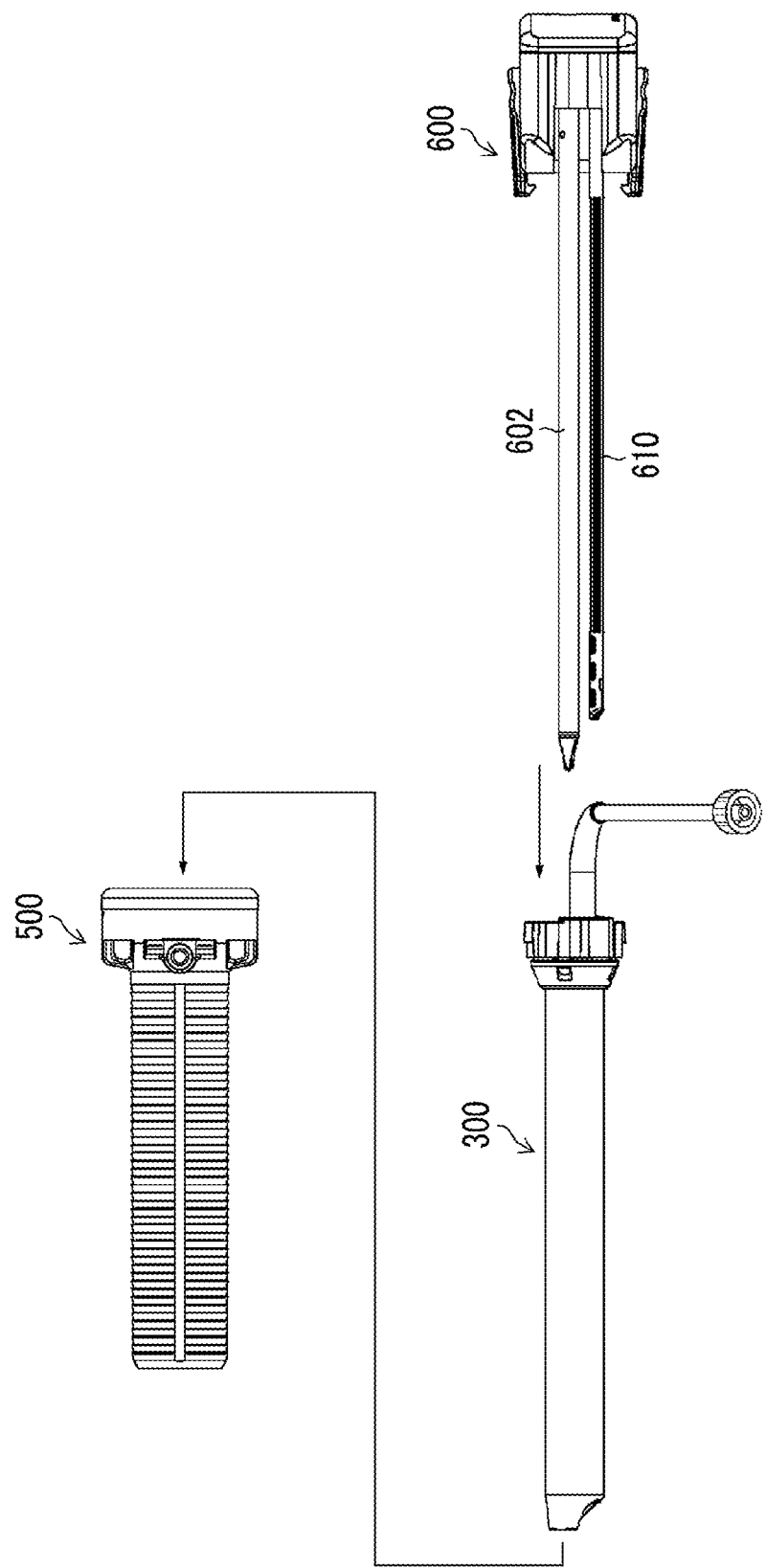
FIG. 5 is an exploded view of the overtube, the sheathing tube, and the inner needle.

FIG. 4 is an enlarged view of the overtube 300, the sheathing tube 500, and the inner needle 600 of FIG. 3. FIG. 5 is an exploded view of the overtube 300, the sheathing tube 500, and the inner needle 600. As illustrated in FIGS. 4 and 5, in a state of being inserted in the overtube 300 and being combined with the overtube 300, the inner needle 600 punctures the body wall. The inner needle 600 has two needle parts (a long needle part 602 and a short needle part 610) that are inserted into the overtube 300 from a proximal end side thereof and protrude from a distal end side, and a tapered distal end part of each needle part is disposed to protrude from a distal end of the overtube 300. Then, after the overtube 300 on which the inner needle 600 is mounted punctures the body wall along with the sheathing tube 500, the inner needle 600 is removed from the overtube 300.

Accordingly, a hole is formed in the body wall, and the overtube 300 and the sheathing tube 500 are inserted into the hole.

[Configuration of Storage Case]

Figure 6:
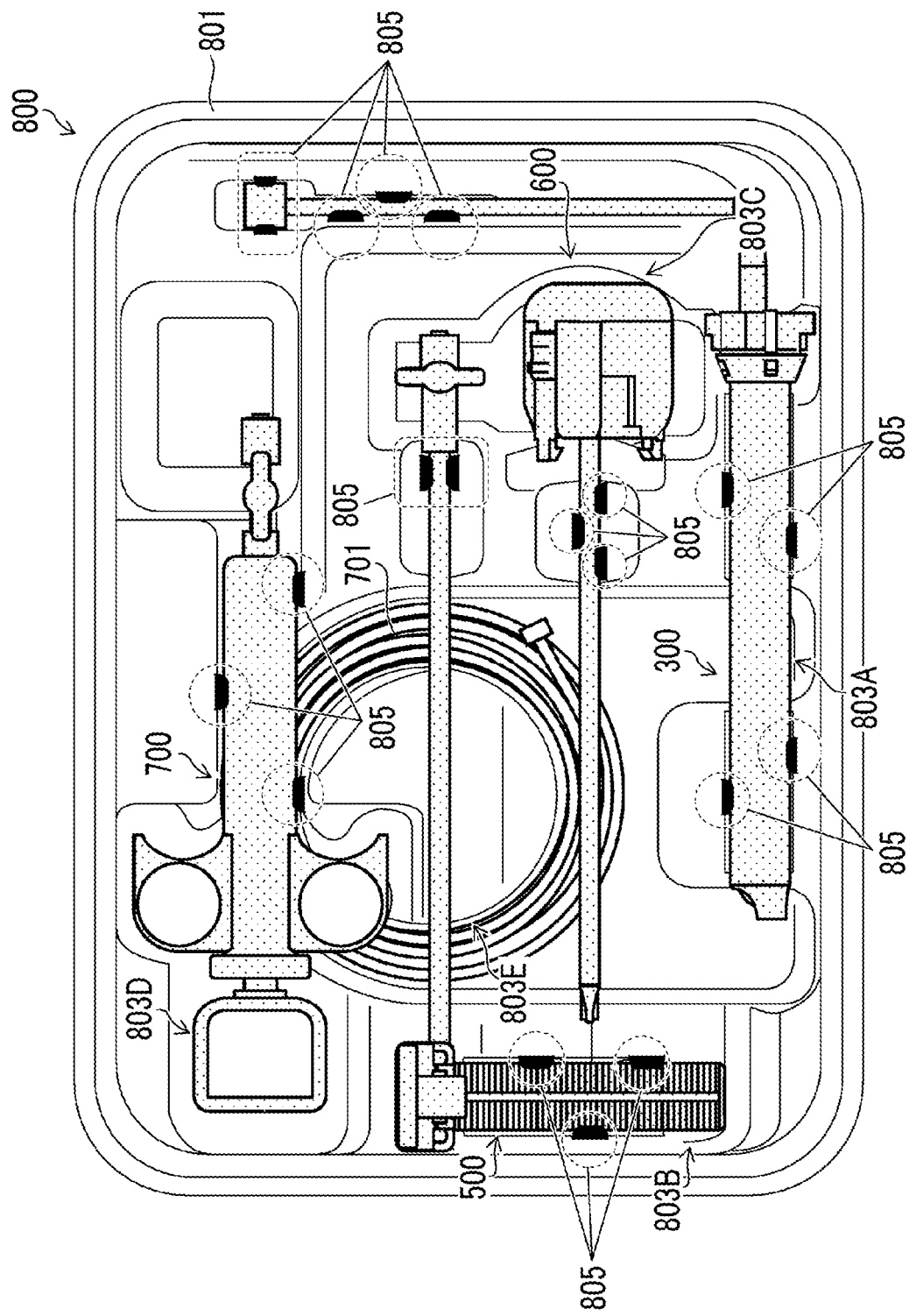
FIG. 6 is a front view of a case body of a storage case that stores each of the overtube, the sheathing tube, a syringe, and a tube.

The overtube 300, the sheathing tube 500, the inner needle 600, the syringe 700, and the tube 701, which are illustrated in FIG. 3, are instruments disposed for one time of endoscopic surgery, and are brought into an operation room or the like in a state of being stored in a storage case 800 (refer to FIG. 6). For this reason, the storage case 800 configures the surgical system according to the embodiment of the present invention along with the overtube 300, the sheathing tube 500, the inner needle 600, the syringe 700, and the tube 701.

Figure 7:
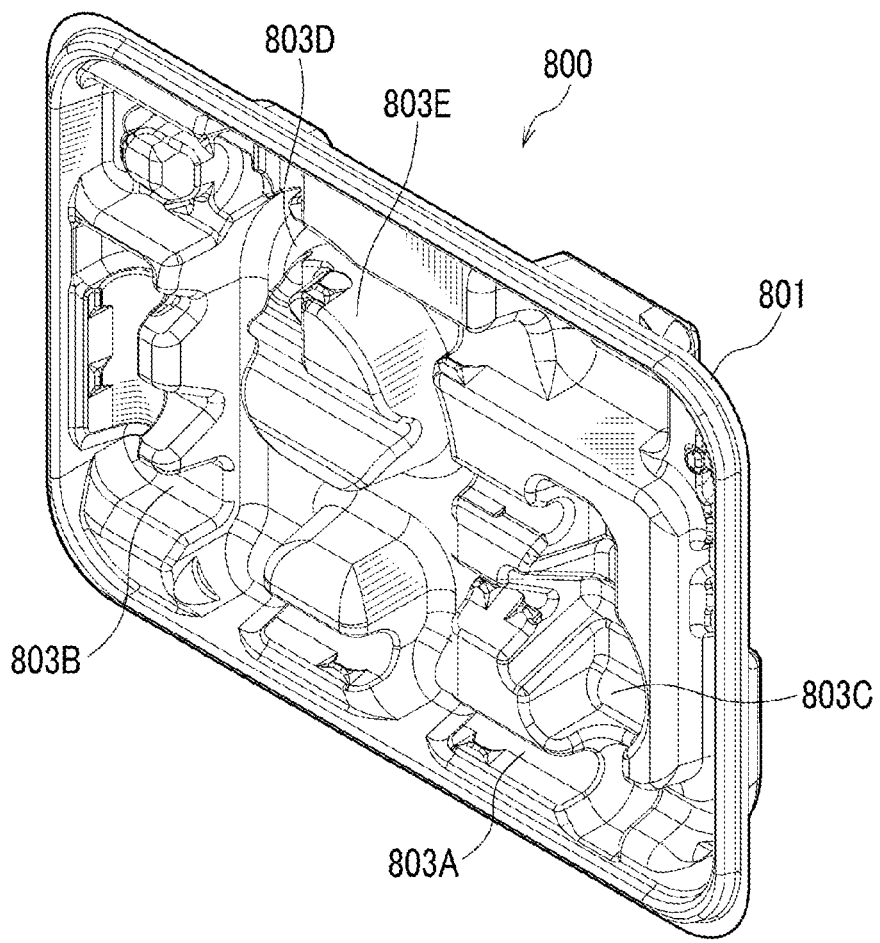
FIG. 7 is a front perspective view of the case body of the storage case.

FIG. 6 is a front view of a case body 801 of the storage case 800 that stores each of the overtube 300, the sheathing tube 500, the inner needle 600, the syringe 700, and the tube 701. FIG. 7 is a front perspective view of the case body 801 of the storage case 800.

As illustrated in FIGS. 6 and 7, the case body 801 has a container-like shape of which one surface is open. The case body 801 is provided with an individual storage part 803A, an individual storage part 803B, an individual storage part 803C, an individual storage part 803D, and an individual storage part 803E that individually store instruments of the overtube 300, the sheathing tube 500, the inner needle 600, the syringe 700, and the tube 701, respectively. To seal the inside of the case body 801, an opening part of the case body 801 is covered with a lid (not illustrated), or is packaged with a package (not illustrated).

The individual storage part 803A has a hollow shape into which the overtube 300 is fitted, and stores the overtube 300. The individual storage part 803B has a hollow shape into which the sheathing tube 500 is fitted, and stores the sheathing tube 500. The individual storage part 803C has a hollow shape into which the inner needle 600 is fitted, and stores the inner needle 600. The individual storage part 803D has a hollow shape into which the syringe 700 is fitted, and stores the syringe 700.

Each of the individual storage parts 803A to 803D is provided with an engagement claw 805 (shown with a black portion in a dotted circle in FIG. 6) that is engaged with each of the instruments of the overtube 300, the sheathing tube 500, the inner needle 600, and the syringe 700 and fixes each instrument. A fixing part (fixing structure) that fixes each instrument to each of the individual storage parts 803A to 803D is not limited to the engagement claw 805, and a known fixing part may be used.

The individual storage part 803E is provided in a region in the case body 801, which overlaps a part of each of the individual storage parts 803B to 803D, the region being positioned closer to a bottom side of the case body 801 than each of the individual storage parts 803B to 803D is. The individual storage part 803E is formed in a substantially circular groove shape. Accordingly, in a state of being wound around a central part of the individual storage part 803E in a coil shape (loop shape), the flexible tube 701 is stored in the individual storage part 803E. The tube 701 is clipped in order to maintain a coil-shaped state.

As described above, the individual storage part 803E overlaps a part of each of the other individual storage parts 803B to 803D, and is positioned closer to the bottom side of the case body 801 than each of the individual storage parts is. For this reason, in a state where the tube 701 is stored in the individual storage part 803E first, each of the sheathing tube 500, the inner needle 600, and the syringe 700 can be stored and fixed in each of the individual storage parts 803B to 803D. Accordingly, since the tube 701 in the individual storage part 803E is pressed down by the sheathing tube 500, the inner needle 600, and the syringe 700, the tube 701 is fixed in the individual storage part 803E. In this case, the tube 701 corresponds to the first instrument according to the embodiment of the present invention, and the sheathing tube 500, the inner needle 600, and the syringe 700 correspond to the second instrument according to the embodiment of the present invention.

As described above, the tube 701 can be fixed in the individual storage part 803E by using the sheathing tube 500, the inner needle 600, and the syringe 700 that are stored in the individual storage parts 803B to 803D. For this reason, it is not necessary for the storage case 800 to be additionally provided with a fixing part such as the engagement claw 805 or the like for fixing the tube 701 in the individual storage part 803E. As a result, since the structure of the storage case 800 is simplified, costs of the storage case 800 can be reduced. In addition, by the individual storage part 803E partially overlapping the regions of the other individual storage parts 803B to 803D, the storage case 800 is miniaturized. Accordingly, since simplification, miniaturization, and cost reduction of the storage case 800 can be realized, garbage generation in an operation room reduces and ease of handling improves.

Although the tube 701 in the individual storage part 803E is fixed by the sheathing tube 500, the inner needle 600, and the syringe 700 in the embodiment, the present invention is not limited thereto. For example, the layout of each of the individual storage parts 803A to 803E is changed, and any one first instrument (or a plurality of first instruments) of the overtube 300, the sheathing tube 500, the inner needle 600, the syringe 700, or the tube 701 may be fixed by using at least one of the other second instruments.

In addition, any one instrument of the overtube 300, the sheathing tube 500, the inner needle 600, the syringe 700, or the tube 701 may be fixed by another instrument while simultaneously fixing other instruments. That is, the first instrument and the second instrument according to the embodiment of the present invention may be the same instrument.

[Configuration of Overtube]

Figure 8:
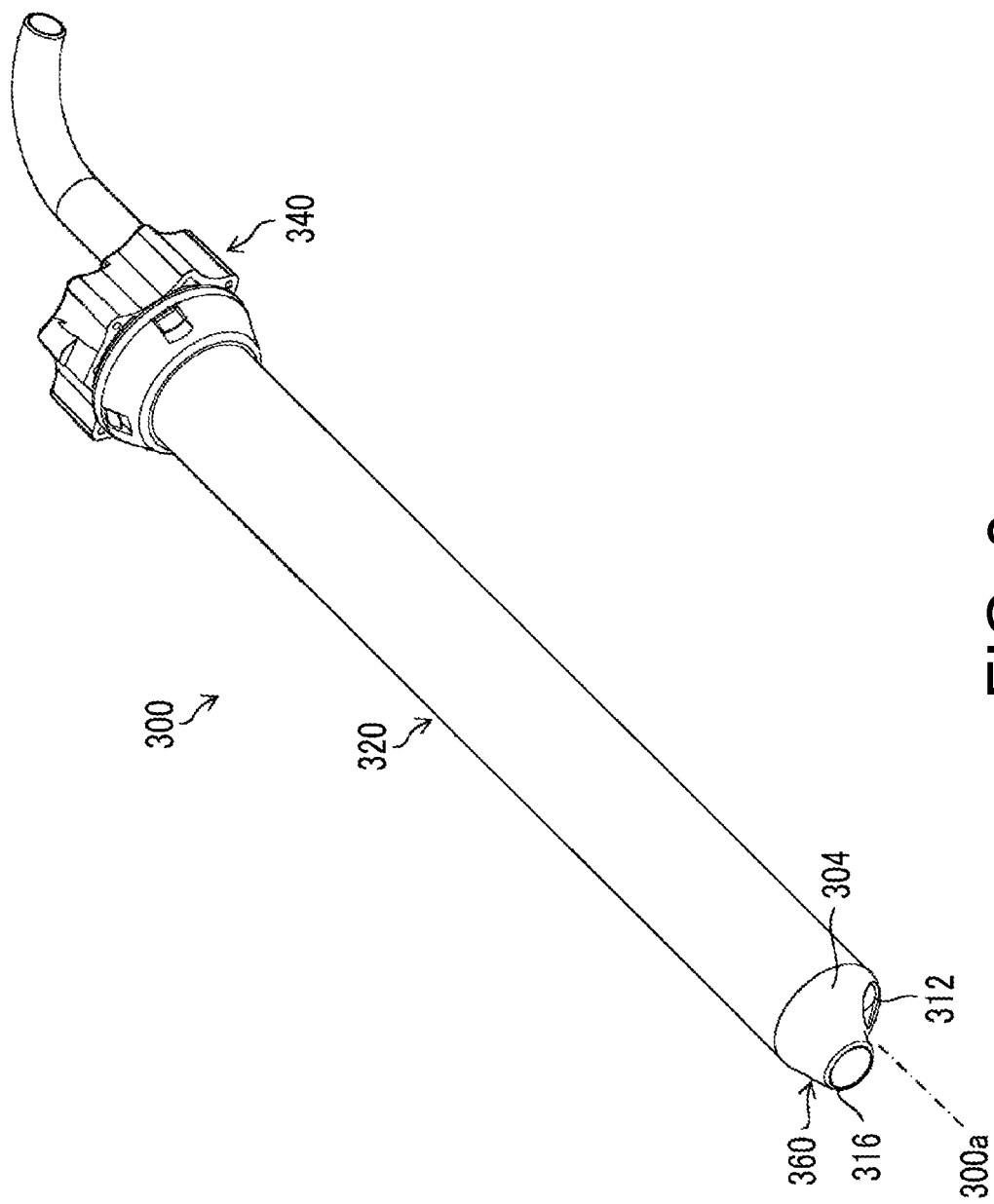
FIG. 8 is an external perspective view of the overtube.
Figure 9:
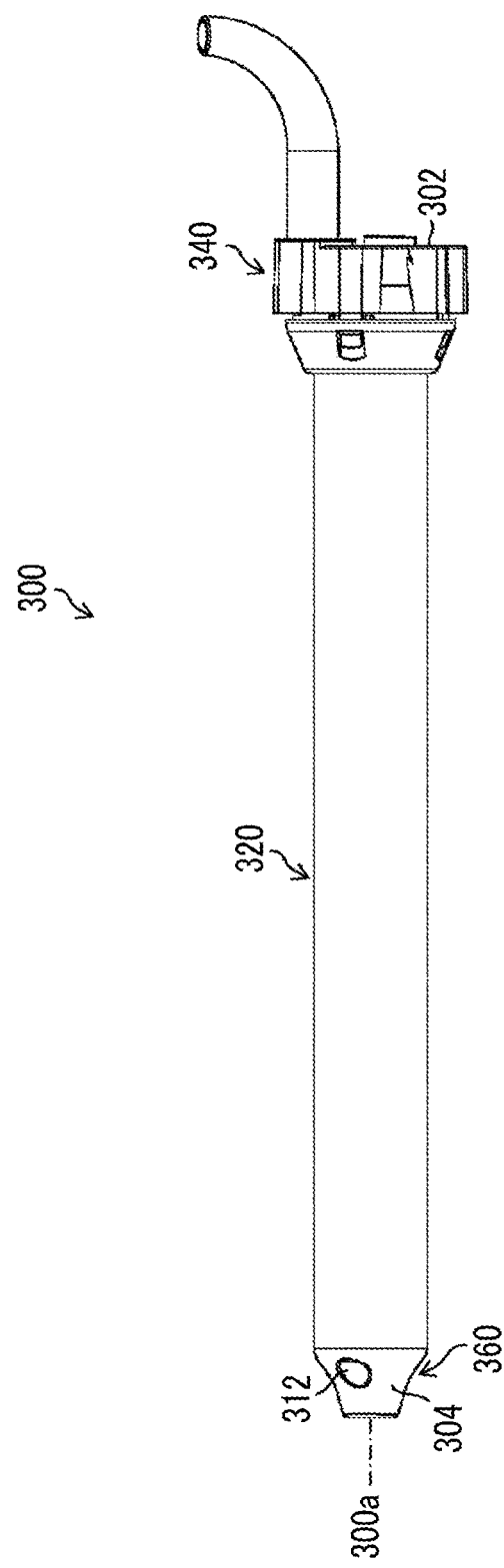
FIG. 9 is a side view of the overtube.
Figure 10:
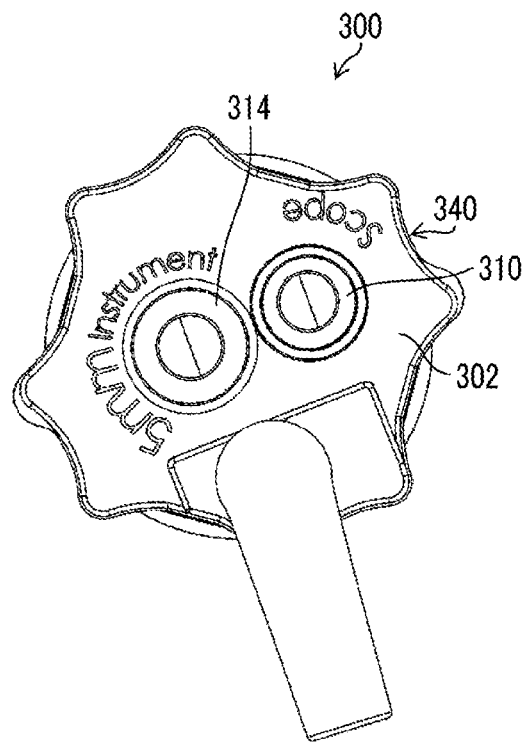
FIG. 10 is a rear view of the overtube seen from a proximal end side thereof.
Figure 11:
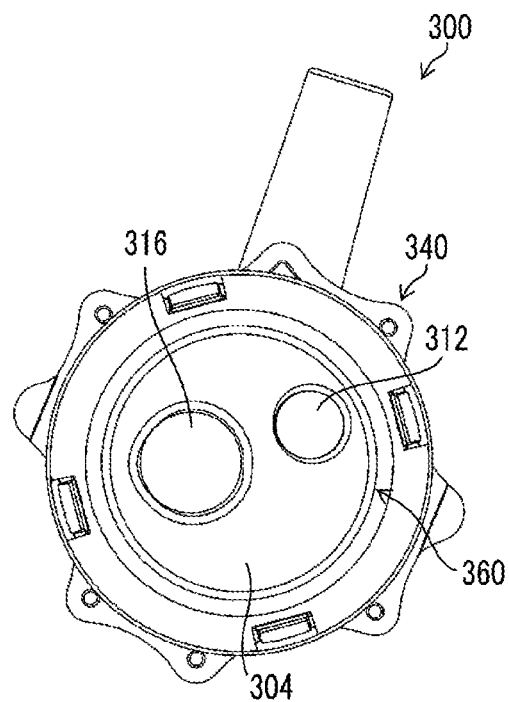
FIG. 11 is a front view of the overtube seen from a distal end side thereof.
Figure 13:
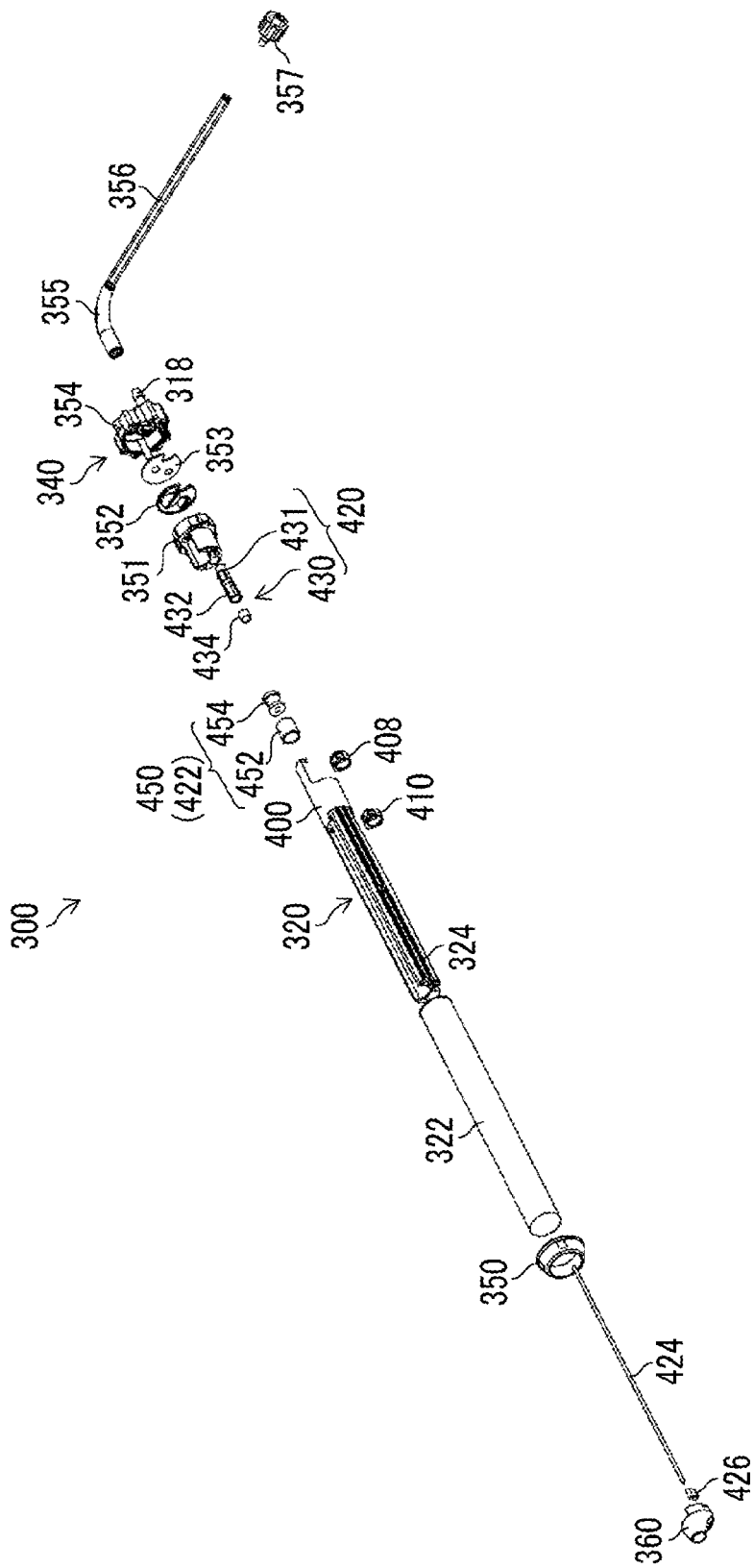
FIG. 13 is an overall exploded perspective view of the overtube.

FIG. 8 is an external perspective view of the overtube 300. FIG. 9 is a side view of the overtube 300. FIG. 10 is a rear view of the overtube 300 seen from the proximal end side thereof. FIG. 11 is a front view of the overtube 300 seen from the distal end side thereof. In FIGS. 8 to 11, the illustration of a liquid feeding tube 356 and a liquid feeding connector 357, which are to be described below and are illustrated in FIG. 13, is omitted.

As illustrated in FIGS. 8 to 11, the overtube 300 has an elongated cylindrical shape as a whole, and has a distal end, a proximal end, and a longitudinal axis 300a. The overtube 300 has an overtube body 320 that has a shape extending along the longitudinal axis 300a, a proximal end cap part 340 attached to a proximal end side of the overtube body 320, and a distal end cap part 360 attached to a distal end side of the overtube body 320.

A proximal end surface 302, which is an end surface of the proximal end cap part 340 on the proximal end side, is provided with a first proximal end opening 310, which is a proximal end opening allowing the endoscope insertion part 102 to be inserted into the overtube body 320, and a second proximal end opening 314, which is a proximal end opening allowing the treatment tool insertion part 202 to be inserted into the overtube body 320 (refer to FIG. 10). In addition, a distal end surface 304, which is an end surface of the distal end cap part 360 on the distal end side, is provided with a first distal end opening 312, which is a distal end opening allowing the endoscope insertion part 102 inserted in the overtube body 320 to be delivered forward, and a second distal end opening 316, which is a distal end opening allowing the treatment tool insertion part 202 inserted in the overtube body 320 to be delivered forward (refer to FIG. 11 and the like).

Figure 12:
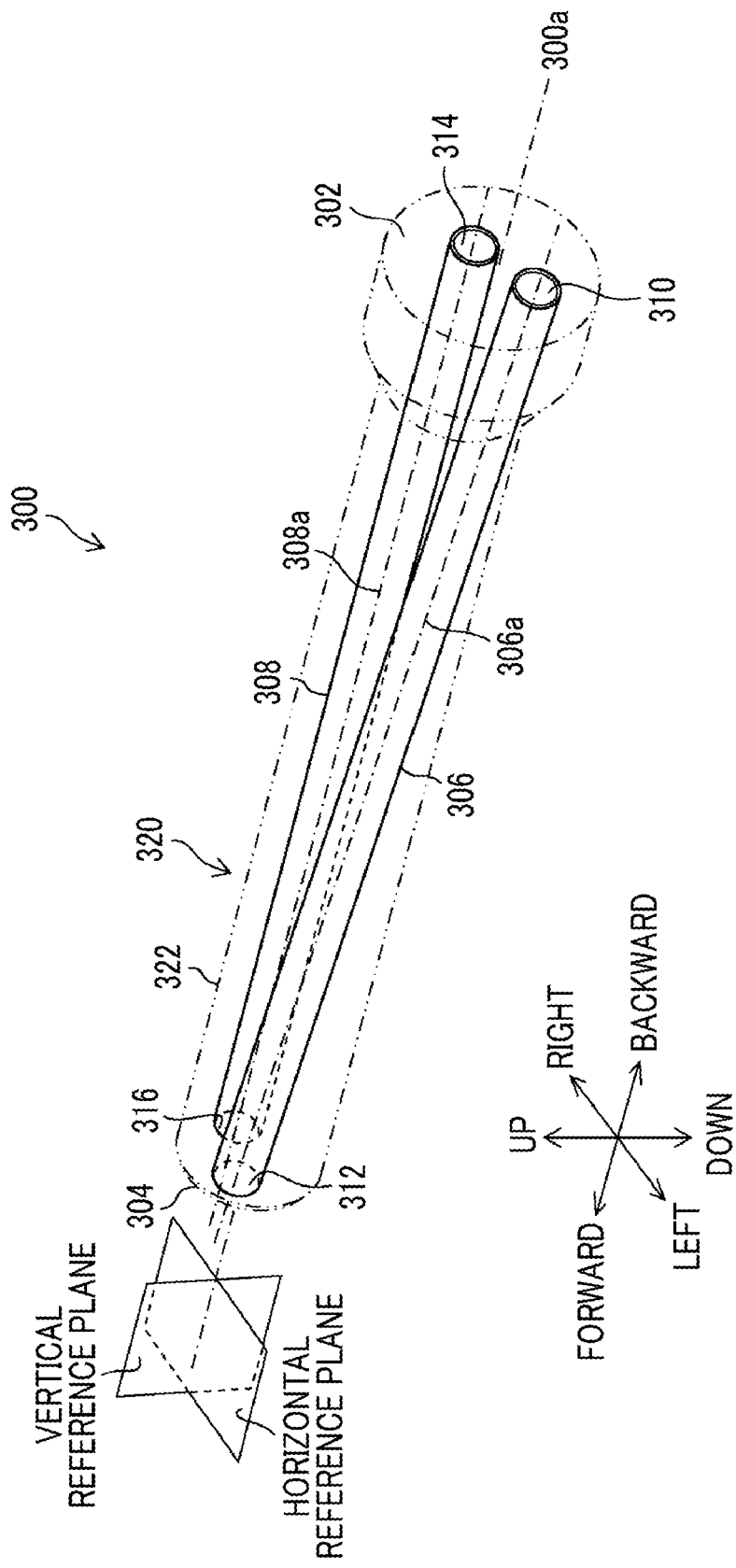
FIG. 12 is an explanatory view for illustrating an endoscope insertion passage and a treatment tool insertion passage in the overtube.

FIG. 12 is an explanatory view for illustrating an endoscope insertion passage 306 and a treatment tool insertion passage 308 in the overtube 300. Herein, in order to prevent the drawing from becoming complicated, an external shape of the overtube 300 is simplified.

Regarding the position and orientation of a space where the overtube 300 is disposed, terms called "forward", "backward", "left", "right", "up", and "down" are used with an orientation from the proximal end surface 302 to the distal end surface 304 in a direction along the longitudinal axis 300a defined as forward and with an orientation from the longitudinal axis 300a to a treatment tool insertion axis 308a defined as the right. In addition, as for each part and each member configuring the overtube 300, the "distal end side" refers to the distal end side of the overtube 300 (a distal end surface 304 side), and the "proximal end side" refers to the proximal end side of the overtube 300 (a proximal end surface 302 side). In addition, as for each part and each member configuring each of instruments of the inner needle 600 and the sheathing tube 500 to be described below, the "distal end side" refers to the distal end side of each instrument, the "proximal end side" refers to the proximal end side of each instrument, and a relationship between the "distal end side" and the "proximal end side" of each of the instruments is in accordance with a relationship between the "distal end side" and the "proximal end side" of the overtube 300, which is shown in FIG. 4.

As illustrated in FIG. 12, the overtube 300 has, along the longitudinal axis 300a, the endoscope insertion passage 306 into which the endoscope insertion part 102 is inserted so as to be movable forward and backward and the treatment tool insertion passage 308 into which the treatment tool insertion part 202 is inserted so as to be movable forward and backward. The reference sign "306a" in FIG. 12 is an endoscope insertion axis that corresponds to a central axis of the endoscope insertion passage 306. In addition, the reference sign "308a" in FIG. 12 is a treatment tool insertion axis that corresponds to a central axis of the treatment tool insertion passage 308.

The endoscope insertion passage 306 is one form of the first insertion passage according to the embodiment of the present invention, allows the first distal end opening 312 and the first proximal end opening 310 to communicate with each other, and thereby the endoscope insertion part 102 is inserted into the endoscope insertion passage so as to be movable forward and backward. In a case where the inner needle 600 to be described below is mounted on the overtube 300, the short needle part 610 of the inner needle 600 is inserted into the endoscope insertion passage 306. In addition, the treatment tool insertion passage 308 is one form of the second insertion passage according to the embodiment of the present invention, allows the second distal end opening 316 and the second proximal end opening 314 to communicate with each other, and thereby the treatment tool insertion part 202 is inserted into the treatment tool insertion passage so as to be movable forward and backward. In a case where the inner needle 600 is mounted on the overtube 300, the long needle part 602 of the inner needle 600 is inserted into the treatment tool insertion passage 308.

In the embodiment, the treatment tool insertion axis 308a of the treatment tool insertion passage 308 is disposed parallel to the longitudinal axis 300a of the overtube 300. On the other hand, an endoscope insertion axis 306a of the endoscope insertion passage 306 obliquely intersects the longitudinal axis 300a.

That is, in a case where a plane along an upward-downward direction including the longitudinal axis 300a is referred to as a vertical reference plane and a plane along a leftward-rightward direction including the longitudinal axis 300a is referred to as a horizontal reference plane, the treatment tool insertion axis 308a is parallel to both the horizontal reference plane and the vertical reference plane.

On the other hand, the endoscope insertion axis 306a is parallel to the vertical reference plane, is not parallel to the horizontal reference plane, and is obliquely inclined with respect to the horizontal reference plane. In addition, the endoscope insertion axis 306a is inclined from a rear lower side toward a front upper side, and for example, intersects the horizontal reference plane at a substantially intermediate position of the overtube 300 in a forward-backward direction. For this reason, the endoscope insertion passage 306 and the treatment tool insertion passage 308 are disposed to obliquely intersect each other.

Figure 14:
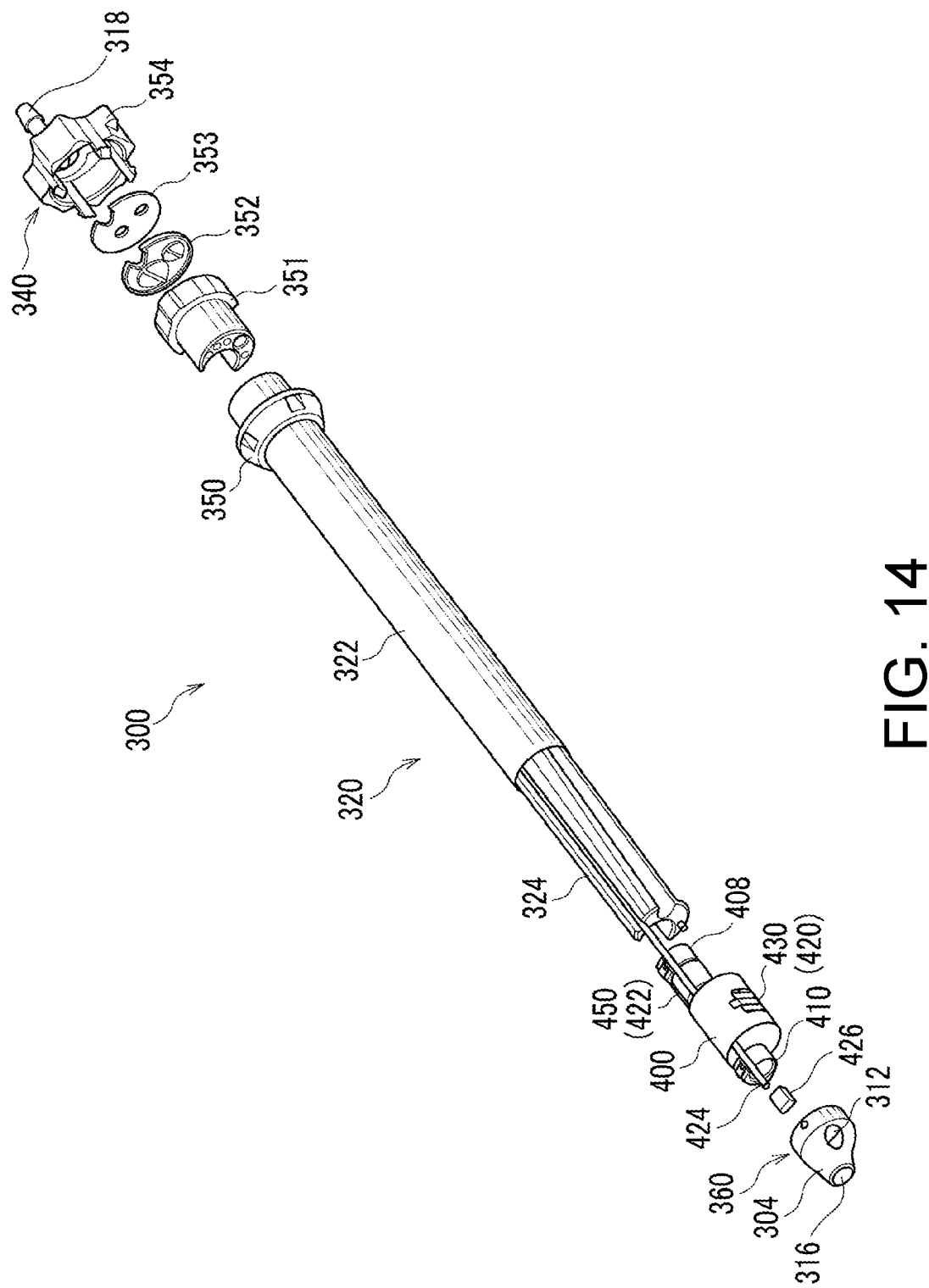
FIG. 14 is an exploded perspective view of important parts of the overtube.

FIG. 13 is an overall exploded perspective view of the overtube 300. FIG. 14 is an exploded perspective view of important parts of the overtube 300.

As illustrated in FIGS. 13 and 14, the overtube body 320 of the overtube 300 comprises a long tubular body 322, a partition wall member 324, a slider 400, a rear restriction end 408 and a front restriction end 410 that are provided in the slider 400, an endoscope coupling part 420, a treatment tool coupling part 422, a liquid feeding tube 424, and a cap connecting part 426.

The endoscope coupling part 420 is configured by an endoscope fixing tool 430 and a guide bush 431. The endoscope fixing tool 430 comprises a holding frame 432 and endoscope seal members 434. In addition, the treatment tool coupling part 422 is configured by a treatment tool fixing tool 450. The treatment tool fixing tool 450 comprises a holding frame 452 and a treatment tool seal member 454.

The proximal end cap part 340 of the overtube 300 comprises a flange 350, a connector 351, a duckbill seal 352, an upper seal 353, a cover member 354 having a connector for cleaning 318, a strain relief 355, the liquid feeding tube 356, and the liquid feeding connector 357.

As described above, the distal end cap part 360 of the overtube 300 has the distal end surface 304, the first distal end opening 312, and the second distal end opening 316.

<Configuration of Overtube Body>

(Long Tubular Body)

Figure 15:
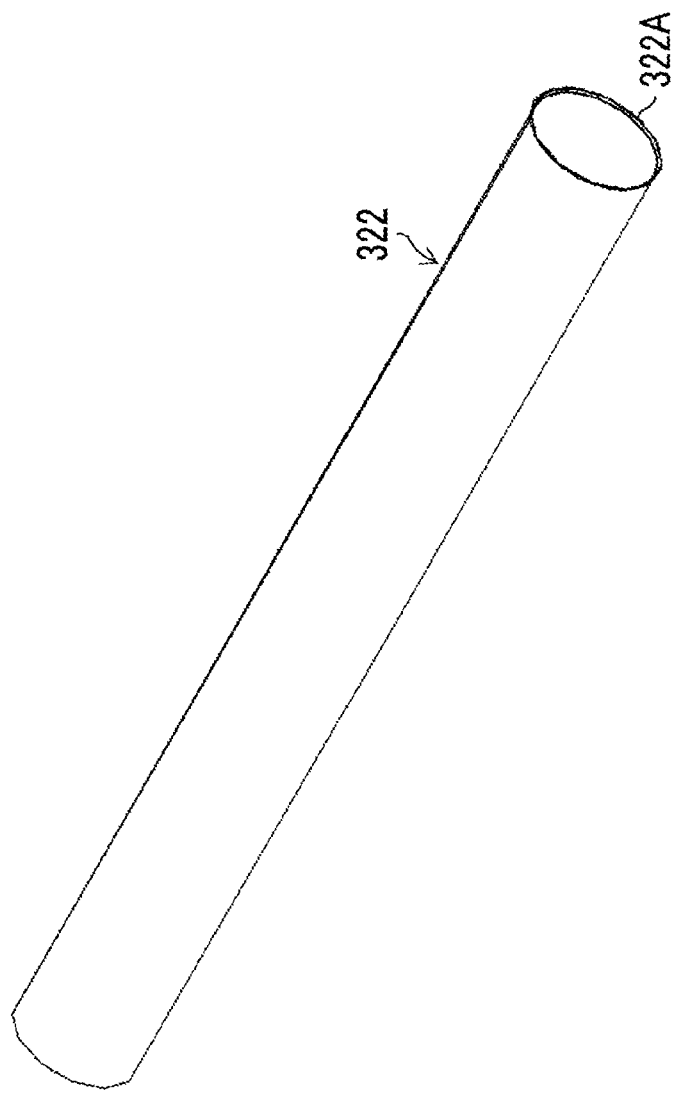
FIG. 15 is an external perspective view of a long tubular body of an overtube body.

FIG. 15 is an external perspective view of the long tubular body 322 of the overtube body 320. The reference sign 16A of FIG. 16 indicates a side view of the long tubular body 322 of the overtube body 320, and the reference sign 16B indicates a rear view of the long tubular body 322 seen from a proximal end side thereof.

As illustrated in FIGS. 15 and 16, the long tubular body 322 is formed of, for example, stainless steel [stainless steel 304 (SUS304 specified in Japanese Industrial Standards) or the like] in a cylindrical shape extending with the longitudinal axis 300a described above as a central axis. A tapered portion 322A of which a diameter is larger than diameters of other portions of the long tubular body 322 is formed at a proximal end of the long tubular body 322 in order to improve assemblability.

(Partition Wall Member)

FIGS. 17 and 18 are external perspective views illustrating the overtube body 320 with the long tubular body 322 omitted. As illustrated in FIGS. 17 and 18, inside the long tubular body 322 of the overtube body 320, there are the endoscope insertion passage 306, the treatment tool insertion passage 308, the substantially cylindrical partition wall member 324 that extends along the longitudinal axis 300a, and the slider 400 that is a coupling mechanism which interlocks the endoscope insertion part 102 and the treatment tool insertion part 202 so as to move forward and backward in a direction of the longitudinal axis 300a. The slider 400 is guided by the partition wall member 324, and is supported so as to be movable forward and backward in the forward-backward direction.

FIGS. 19 and 20 are external perspective views of the partition wall member 324 seen from a distal end side thereof. The reference sign 21A of FIG. 21 indicates a front view of the partition wall member 324 seen from the distal end side thereof, and the reference sign 21B of FIG. 21 indicates a rear view of the partition wall member 324 seen from the proximal end side thereof. The reference sign 22A of FIG. 22 indicates a right side view of the partition wall member 324, the reference sign 22B indicates an upper side view of the partition wall member 324, the reference sign 22C indicates a left side view of the partition wall member 324, and the reference sign 22D indicates a lower side view of the partition wall member 324. FIG. 23 is a cross-sectional view of the partition wall member 324 taken along a plane perpendicular to the longitudinal axis 300a, and is a cross-sectional view of the partition wall member 324 seen from the proximal end side thereof.

As illustrated in FIGS. 19 to 23, the partition wall member 324 is a solid insulator formed of, for example, a resin material [polyphenylene sulfide (PPS)], and extends from the proximal end cap part 340 to the distal end cap part 360 inside the long tubular body 322. In a left side surface of the partition wall member 324, an endoscope guide groove 326 (corresponds to a first guide groove according to the embodiment of the present invention) that is not parallel to the longitudinal axis 300a described above is formed from the proximal end to the distal end of the partition wall member 324. In addition, in a right side surface of the partition wall member 324, a treatment tool guide groove 328 (corresponds to a second guide groove according to the embodiment of the present invention) that is parallel to the longitudinal axis 300a is formed from the proximal end to the distal end of the partition wall member 324. For this reason, the endoscope guide groove 326 and the treatment tool guide groove 328 obliquely intersect each other.

The endoscope guide groove 326 forms a part of the endoscope insertion passage 306 described above, and the treatment tool guide groove 328 forms a part of the treatment tool insertion passage 308 described above. In addition, the partition wall member 324 forms a partition wall between the endoscope insertion passage 306 and the treatment tool insertion passage 308.

By virtue of the partition wall member 324, the endoscope insertion part 102 and the treatment tool insertion part 202 inserted in the overtube 300 reliably proceed through the insertion passages without falling out of the regions of the endoscope insertion passage 306 and the treatment tool insertion passage 308 corresponding thereto, respectively. Accordingly, an insertion task of the endoscope insertion part 102 and the treatment tool insertion part 202 with respect to the overtube 300 becomes easy.

In addition, the partition wall member 324 prevents the endoscope insertion part 102 inserted in the endoscope insertion passage 306 and the treatment tool insertion part 202 inserted in the treatment tool insertion passage 308 from coming into contact with each other inside the overtube 300, and electrically insulates the partition wall member and the treatment tool insertion part from each other. For that reason, even in a case where the treatment tool 200 uses electricity, generation of electrical leakage (high-frequency electricity or the like) from the treatment tool 200 to the endoscope 100, electrical noise, or the like can be prevented, and damage or the like to the endoscope 100 can be prevented in advance.

Each of a distal end surface and a proximal end surface (rear surface) of the partition wall member 324 is provided with a pair of attaching pins 329. The pair of attaching pins 329 provided on the distal end surface of the partition wall member 324 is fitted to each of the distal end cap part 360 and the cap connecting part 426 to be described below. In addition, the pair of attaching pins 329 provided on the distal end surface of the partition wall member 324 is fitted to the connector 351 to be described below.

A tube attaching groove 330 parallel to the longitudinal axis 300a from the proximal end to the distal end of the partition wall member 324 is formed in an upper surface of the partition wall member 324. The liquid feeding tube 424 to be described below is attached to the tube attaching groove 330.

(Slider)

Referring back to FIGS. 17 and 18, the slider 400 is externally fitted to an outer peripheral part of the partition wall member 324 inside the long tubular body 322. The slider 400 is a ring-shaped moving body that moves forward and backward (movable) with respect to the partition wall member 324 along the direction of the longitudinal axis 300a. In addition, the slider 400 functions as an interlocking member having a first coupling part coupled to the endoscope insertion part 102 (first insertion part) and a second coupling part coupled to the treatment tool insertion part 202 (second insertion part), and configures the coupling mechanism according to the embodiment of the present invention along with the partition wall member 324.

FIG. 24 is an external perspective view of the slider 400. FIG. 25 is an exploded perspective view of the slider 400. As illustrated in FIGS. 24 and 25 and FIGS. 17 and 18, which are described above, the slider 400 comprises the endoscope coupling part 420 disposed inside the endoscope guide groove 326, the treatment tool coupling part 422 disposed inside the treatment tool guide groove 328, a coupling ring 402 that integrally interlocks the endoscope coupling part 420 and the treatment tool coupling part 422, and the rear restriction end 408 and the front restriction end 410 which are provided in the coupling ring 402.

The endoscope coupling part 420 functions as the first coupling part according to the embodiment of the present invention, and the treatment tool coupling part 422 functions as the second coupling part according to the embodiment of the present invention. As described above, the endoscope coupling part 420 comprises the endoscope fixing tool 430 and the guide bush 431. The endoscope fixing tool 430 corresponds to the first fixing tool according to the embodiment of the present invention, and comprises the holding frame 432 and the endoscope seal members 434. In addition, the treatment tool coupling part 422 comprises the treatment tool fixing tool 450. The treatment tool fixing tool 450 configures the fixing tool provided in the second fixing tool and the slider according to the embodiment of the present invention, and comprises the holding frame 452 and the treatment tool seal member 454.

FIG. 26 is an external perspective view of the coupling ring 402. The reference sign 27A of FIG. 27 indicates a front view of the coupling ring 402 seen from a distal end side thereof, and the reference sign 27B indicates a right-and-left side view and a top view of the coupling ring 402.

As illustrated in FIGS. 26 and 27, the coupling ring 402 is formed of, for example, stainless steel (SUS304 or the like), and has a tubular ring part 404, which surrounds an outer periphery of the partition wall member 324 in a circumferential direction, and an arm part 406. The ring part 404 comes into contact with or approaches a portion of an outer peripheral surface of the partition wall member 324 other than the endoscope guide groove 326 and the treatment tool guide groove 328.

The arm part 406 extends from a portion of the ring part 404 facing the treatment tool guide groove 328 in the forward-backward direction along the treatment tool guide groove 328 (refer to FIG. 18).

Each of both ends of the arm part 406 is provided with an attaching part 407 to which each of the rear restriction end 408 and the front restriction end 410 that are disposed to be inserted inside the treatment tool guide groove 328 is attached. The front restriction end 410 is attached to the attaching part 407 on a distal end side of the arm part 406, and the rear restriction end 408 is attached to the attaching part 407 on a proximal end side of the arm part 406 (refer to FIG. 30).

On the other hand, two flat first engaging parts 404A that are parallel to an opening of the endoscope guide groove 326 are formed at an interval in the forward-backward direction in a portion of the ring part 404 facing the endoscope guide groove 326 (refer to FIG. 17). Each of the first engaging parts 404A is formed, for example, by making a notch in the cylindrical ring part 404 and then performing flattening (pressing).

Referring back to FIGS. 26 and 27, the rotation of the coupling ring 402 in a direction around an axis, with the longitudinal axis 300a as reference, with respect to the partition wall member 324 is restricted by each of the first engaging parts 404A and the rear restriction end 408 and the front restriction end 410 which are to be described below. In addition, an engagement hole 412 is formed between the respective first engaging parts 404A. The engagement hole 412 is formed as an elongated hole that extends in the circumferential direction of the ring part 404 beyond a range of each of the first engaging parts 404A.

The reference sign 28A of FIG. 28 indicates a front view of the rear restriction end 408 and the front restriction end 410, and the reference sign 28B indicates an external perspective view of the rear restriction end 408 and the front restriction end 410. As illustrated in FIG. 28, the rear restriction end 408 is provided with an opening 408A into which the treatment tool insertion part 202 is inserted, and the front restriction end 410 is provided with an opening 410A into which the treatment tool insertion part 202 is inserted.

Referring back to FIGS. 18 and 24, the rear restriction end 408 and the front restriction end 410 are disposed to be spaced apart from each other in an axial direction of the longitudinal axis 300a, and restrict forward and backward movement of the treatment tool coupling part 422 (treatment tool fixing tool 450), which is disposed therebetween inside the treatment tool guide groove 328, in the forward-backward direction. That is, the arm part 406, which combines the rear restriction end 408 and the front restriction end 410 together, acts as the second engaging part that is engaged with the treatment tool fixing tool 450, which is the second fixing tool according to the embodiment of the present invention, and the rear restriction end 408 and the front restriction end 410 function as a pair of restricting parts and a second restricting part according to the embodiment of the present invention. In addition, a movement range of the treatment tool fixing tool 450 between the rear restriction end 408 and the front restriction end 410 corresponds to a second range according to the embodiment of the present invention.

The coupling ring 402 is supported by the partition wall member 324 so as to be movable forward and backward in the forward-backward direction, and is supported by the partition wall member 324 in a state where movement in the upward-downward direction and in the leftward-rightward direction and rotation in all directions (directions around three axes including a forward-backward axis, a leftward-rightward axis, and an upward-downward axis) are restricted (in a state where at least rotation around the longitudinal axis is impossible). In addition, the coupling ring 402 moves forward and backward within a movable range having a position where the rear restriction end 408 abuts against the proximal end cap part 340 as a rear end and having a position where the front restriction end 410 abuts against the distal end cap part 360 as a front end, that is, moves forward and backward in a third range according to the embodiment of the present invention.

(Endoscope Coupling Part)

FIG. 29 is an external perspective view illustrating the partition wall member 324 and the endoscope coupling part 420 with the coupling ring 402 omitted. FIG. 30 is an external perspective view of the slider 400. FIG. 31 is a front view of the slider 400 seen from a distal end side thereof.

As illustrated in FIGS. 29 to 31, the endoscope coupling part 420 is disposed in the endoscope guide groove 326, and is coupled to (engaged with) the endoscope insertion part 102 inserted in the endoscope guide groove 326.

The endoscope coupling part 420 is disposed inside the endoscope guide groove 326, and has the endoscope fixing tool 430 and the guide bush 431 that are movable forward and backward in the forward-backward direction along the endoscope insertion passage 306 formed by the endoscope guide groove 326. The endoscope fixing tool 430 holds the endoscope 100 (endoscope insertion part 102) in the slider 400. The endoscope fixing tool 430 is configured by the metal tubular holding frame 432, which approaches or comes into contact with an inner wall surface of the endoscope guide groove 326, and the tubular (cyclic) endoscope seal members 434, each of which is an O-ring or the like, which is fixed inside the holding frame 432 and is formed of an elastic material, such as elastic rubber.

The reference sign 32A of FIG. 32 indicates an external perspective view of the holding frame 432 of the endoscope fixing tool 430, and the reference sign 32B indicates a cross-sectional view of the holding frame 432 taken along the forward-backward direction. As illustrated in FIG. 32, the holding frame 432 is formed of, for example, stainless steel [stainless steel 303 (SUS303 specified in Japanese Industrial Standards)]. An outer peripheral surface of the holding frame 432 is provided with a flat part 432A, which is parallel to an opening (and the first engaging parts 404A) at a position facing the opening of the endoscope guide groove 326, and a protrusion 436 that protrudes toward the outside of the opening. In addition, inside the holding frame 432, two endoscope seal members 434 are arranged and fixed in the forward-backward direction.

The flat part 432A abuts against the first engaging part 404A (refer to FIG. 31). Accordingly, the holding frame 432 (endoscope fixing tool 430) becomes impossible to rotate inside the endoscope guide groove 326. Since the holding frame 432 has a shape that makes it impossible to rotate in the endoscope guide groove 326 as described above, only forward and backward movement in the forward-backward direction is allowed for the endoscope fixing tool 430 in the endoscope guide groove 326.

The protrusion 436 is inserted into the engagement hole 412 formed between the respective first engaging parts 404A, and is locked in the forward-backward direction by each of the first engaging parts 404A (refer to FIGS. 30 and 31). That is, since each of the first engaging parts 404A is engaged with the holding frame 432 via the protrusion 436, the first engaging part functions as the first restricting part according to the embodiment of the present invention. Accordingly, since the relative forward and backward movement of the endoscope fixing tool 430 in the forward-backward direction with respect to the coupling ring 402 is restricted, a first range where the endoscope fixing tool 430 can move forward and backward with respect to the coupling ring 402 becomes zero. Therefore, the coupling ring 402 and the endoscope fixing tool 430 integrally move forward and backward in the forward-backward direction.

Two cyclic grooves (not illustrated) to which the endoscope seal members 434 are fitted and fixed are formed in the forward-backward direction in an inner peripheral surface of the holding frame 432. Accordingly, even in a case where the endoscope seal members 434 each contain oil and cannot be fixed inside the holding frame 432 with an adhesive, the endoscope seal members 434 can be fixed inside the holding frame 432.

The reference sign 33A of FIG. 33 indicates a side view of the endoscope seal member 434, the reference sign 33B indicates a front view of the endoscope seal member 434, and the reference sign 33C indicates a cross-sectional view of the endoscope seal member 434 shown with the reference sign 33B, which is taken along line "33"-"33".

As illustrated in FIG. 33, the endoscope seal members 434 each are formed of, for example, silicon rubber, and elastically hold an outer peripheral surface of the endoscope insertion part 102 inserted therein by being brought into pressure contact with (engaged with) the outer peripheral surface. Accordingly, an insertion part longitudinal axis (central axis) of the endoscope insertion part 102 is disposed substantially coaxially with the endoscope insertion axis 306a. Since inner peripheral surfaces of the endoscope seal members 434 are brought into pressure contact with the outer peripheral surface of the endoscope insertion part 102 by an elastic force, the rotation of the endoscope insertion part 102 in the circumferential direction is allowed. In addition, the endoscope seal members 434 can freely adjust a holding position of the endoscope insertion part 102 in the forward-backward direction. The inside of each of the endoscope seal members 434 corresponds to a second passage according to the embodiment of the present invention into which the endoscope insertion part 102 that corresponds to the first insertion part according to the embodiment of the present invention is inserted.

FIG. 34 is an external perspective view of the guide bush 431. The reference sign 35A of FIG. 35 indicates a side view of the guide bush 431, and the reference sign 35B indicates a rear view of the guide bush 431 seen from a proximal end side thereof. In addition, the reference sign 35C of FIG. 35 indicates a cross-sectional view of the guide bush 431 shown with the reference sign 35A, which is taken along line "35(1)"-"35(1)", and the reference sign 35D indicates a cross-sectional view of the same guide bush 431, which is taken along line "35(2)"-"35(2)". FIG. 36 is a rear perspective view of the guide bush 431 seen from a proximal end side thereof.

As illustrated in FIGS. 34 to 36 and FIGS. 24 and 29 which are described above, the guide bush 431 is formed of, for example, a resin material [polycarbonate or the like] in a substantially tubular shape, and is provided to abut against a proximal end side of the endoscope fixing tool 430 (holding frame 432). A gap may be formed between the guide bush 431 and the endoscope fixing tool 430. In addition, a position of a central axis of the guide bush 431 matches (includes substantially matching) a position of a central axis of the endoscope fixing tool 430.

In addition, a chamfer 431A is formed on an opening edge of the guide bush 431 on the proximal end side. Accordingly, an opening diameter of the guide bush 431 on the proximal end side is larger than inner diameters of other portions of the guide bush 431 and inner diameters of the endoscope seal members 434.

The guide bush 431 aligns a distal end of the endoscope insertion part 102 inserted in the endoscope insertion passage 306 from the first proximal end opening 310 of the proximal end cap part 340 at the position of the central axis of the endoscope fixing tool 430 by means of the chamfer 431A. Accordingly, in a state of being aligned at the position of the central axis of the endoscope fixing tool 430, the distal end of the endoscope insertion part 102 is inserted (guided) into the endoscope seal members 434. Since the holding frame 432 of the endoscope fixing tool 430 is formed of stainless steel as described above, there is a possibility that the distal end of the endoscope insertion part 102 comes into contact with the holding frame 432 and becomes damaged in a case where alignment is not performed by the guide bush 431. For this reason, the distal end of the endoscope insertion part 102 is prevented from coming into contact with the holding frame 432 by the guide bush 431 performing alignment as in the embodiment.

The endoscope guide groove 326 (endoscope insertion passage 306) is not parallel to the longitudinal axis 300a as described above. For this reason, the endoscope fixing tool 430 disposed inside the endoscope guide groove 326 moves forward and backward in the forward-backward direction, and moves also in the upward-downward direction with respect to the partition wall member 324 and the coupling ring 402. As a result, also the protrusion 436 formed on an outer peripheral part of the endoscope fixing tool 430 moves in the upward-downward direction with respect to the coupling ring 402 according to a position of the endoscope fixing tool 430 in the forward-backward direction.

Thus, as illustrated in FIGS. 26 and 30 or the like described above, the engagement hole 412 formed in the coupling ring 402 is formed in a shape to be engaged with the protrusion 436 at any position in a movement range of the protrusion 436 in the upward-downward direction, that is, the engagement hole is formed as an elongated hole extending in the circumferential direction (upward-downward direction) of the ring part 404 beyond the ranges of the first engaging parts 404A.

In addition, since each of the first engaging parts 404A of the coupling ring 402 has a flat shape orthogonal to the leftward-rightward direction, a distance between an outer peripheral surface of the endoscope fixing tool 430 and each of the first engaging part 404A is uniformly maintained regardless of the movement of the endoscope fixing tool 430 in the upward-downward direction with respect to the coupling ring 402. For that reason, the amount of protrusion of the protrusion 436 can be reduced, and the diameter of the overtube body 320 can be reduced.

In a case where the endoscope guide groove 326 is obliquely formed with respect to the longitudinal axis 300a, the opening of the endoscope guide groove 326 deviates from a position facing the first engaging parts 404A. Thus, a range of the partition wall member 324 through which the first engaging parts 404A pass due to the movement of the coupling ring 402 in the forward-backward direction is cut out along a flat surface so as not to interfere with the first engaging parts 404A.

(Treatment Tool Coupling Part)

FIG. 37 is an external perspective view illustrating the partition wall member 324 and the treatment tool fixing tool 450 (treatment tool coupling part 422) with the coupling ring 402 omitted.

As illustrated in FIG. 37 and FIGS. 30 and 31, which are described above, the treatment tool coupling part 422 is disposed in the treatment tool guide groove 328, and is coupled to (engaged with) the treatment tool insertion part 202 inserted in the treatment tool guide groove 328.

The treatment tool coupling part 422 has the treatment tool fixing tool 450 disposed in a passage between the rear restriction end 408 and the front restriction end 410, which are both ends of the arm part 406 described above, inside the treatment tool guide groove 328. The treatment tool fixing tool 450 holds the treatment tool 200 (treatment tool insertion part 202) in the slider 400. In other words, the treatment tool 200 is locked to the slider 400 by means of the treatment tool fixing tool 450. The treatment tool fixing tool 450 is movable forward and backward in the forward-backward direction between the rear restriction end 408 and the front restriction end 410 along the treatment tool guide groove 328. The treatment tool guide groove 328 positioned between the rear restriction end 408 and the front restriction end 410 corresponds to the first passage according to the embodiment of the present invention, through which the treatment tool fixing tool 450 moves in the axial direction of the longitudinal axis 300a.

The treatment tool fixing tool 450 comprises the metal holding frame 452, which approaches or comes into contact with an inner wall surface of the treatment tool guide groove 328, and the treatment tool seal member 454, which is fixed inside the holding frame 452 and is formed of spongy elastic rubber.

The reference sign 38A of FIG. 38 indicates a front view of the holding frame 452 of the treatment tool fixing tool 450 seen from a distal end side thereof, and the reference sign 38B indicates a cross-sectional view of the holding frame 452 shown with the reference sign 38A, which is taken along line "38"-"38". In addition, FIG. 39 is a rear perspective view of the holding frame 452 and the treatment tool seal member 454 of the treatment tool fixing tool 450 seen from a proximal end side thereof.

As illustrated in FIGS. 38 and 39, the holding frame 452 is formed of, for example, stainless steel (SUS304 or the like) in a substantially cylindrical shape. The holding frame 452 is in contact with the treatment tool seal member 454 via a holding surface 454D (refer to FIG. 40) of the treatment tool seal member 454 to be described below. Although not illustrated, a cyclic groove to which the treatment tool seal member 454 is fitted and fixed is formed in an inner peripheral surface of the holding frame 452. Accordingly, the treatment tool seal member 454 can be fixed inside the holding frame 452 without using an adhesive.

The reference sign 40A of FIG. 40 indicates a side view of the treatment tool seal member 454 of the treatment tool fixing tool 450, the reference sign 40B indicates a rear view of the treatment tool seal member 454 seen from a proximal end side thereof, and the reference sign 40C indicates a cross-sectional view of the treatment tool seal member 454 shown with the reference sign 40B, which is taken along line "40"-"40".

As illustrated in FIG. 40 and FIG. 39 which is described above, the treatment tool seal member 454 is formed of spongy elastic rubber, for example, ethylene propylene diene monomers rubber (EPDM rubber or the like), in a substantially cylindrical shape and in an H-shape as illustrated in the side view of the reference sign 40A. Each of outer peripheral surfaces of both ends of the treatment tool seal member 454 in the forward-backward direction is the holding surface 454D described above. Since the treatment tool seal member 454 is formed of spongy elastic rubber and is formed in an H-shape seen from the side, it is possible to insert and fix (elastically hold) even the treatment tool insertion part 202 of the treatment tool 200 having a different outline. The treatment tool seal member 454 has a treatment tool insertion passage 454A (corresponds to a third passage according to the embodiment of the present invention), into which the treatment tool insertion part 202 inserted in the treatment tool insertion passage 308 from the second proximal end opening 314 of the proximal end cap part 340 is inserted.

The treatment tool seal member 454 elastically holds the treatment tool insertion part 202 inserted in the treatment tool insertion passage 454A as described above. Accordingly, a central axis (longitudinal axis) of the treatment tool insertion part 202 is disposed substantially coaxially with the treatment tool insertion axis 308a. In this case, since a wall surface of the treatment tool insertion passage 454A comes into contact with an outer peripheral surface of the treatment tool insertion part 202 only by the elastic force, a holding position of the treatment tool insertion part 202 in the forward-backward direction by the treatment tool seal member 454 can be freely adjusted.

In addition, a chamfer 454B is formed on an opening edge of the treatment tool seal member 454 on the proximal end side. Accordingly, an opening diameter of the treatment tool seal member 454 on the proximal end side is larger than a diameter of the treatment tool insertion passage 454A. Accordingly, the distal end of the endoscope insertion part 102 inserted in the treatment tool insertion passage 308 from the second proximal end opening 314 is guided into the treatment tool insertion passage 454A by the chamfer 454B.

Referring back to FIG. 37, the treatment tool fixing tool 450 integrally moves forward and backward in an interlocking manner with the forward and backward movement of the treatment tool insertion part 202 in the forward-backward direction. In this case, the treatment tool fixing tool 450 is movable forward and backward in the forward-backward direction between the rear restriction end 408 and the front restriction end 410 along the treatment tool guide groove 328. That is, the arm part 406 (corresponding to the second engaging part according to the embodiment of the present invention), which combines the rear restriction end 408 and the front restriction end 410, allows the forward and backward movement of the treatment tool fixing tool 450 in the forward-backward direction with respect to the coupling ring 402 in a range from a position where the treatment tool fixing tool 450 abuts against the rear restriction end 408 to a position where the treatment tool fixing tool abuts against the front restriction end 410 (corresponding to the second range according to the embodiment of the present invention), and restricts the forward and backward movement to the range.

In addition, the treatment tool fixing tool 450 rotates in the treatment tool guide groove 328 in an interlocking manner with the rotation of the treatment tool insertion part 202 in a direction around an axis with the longitudinal axis as reference. That is, the arm part 406 of the slider 400 allows the rotation of the treatment tool fixing tool 450 in the direction around the axis.

(Non-Sensing Region and Sensing Region of Coupling Ring)

FIG. 41 is an explanatory view for illustrating a non-sensing region of the coupling ring 402. As illustrated in FIG. 41, in a case where a range where the endoscope fixing tool 430 is movable forward and backward with respect to the coupling ring 402 is set as the first range and a range where the treatment tool fixing tool 450 is movable forward and backward with respect to the coupling ring 402 is set as the second range, the first range becomes zero since the forward and backward movement of the endoscope fixing tool 430 in the forward-backward direction with respect to the first engaging parts 404A of the coupling ring 402 is restricted. On the contrary, the second range is a range between the rear restriction end 408 and the front restriction end 410 as described above. Accordingly, the coupling ring 402 has a non-sensing region where the forward and backward movement of any one of the treatment tool fixing tool 450 or the endoscope fixing tool 430 is not interlocked with the forward and backward movement of the other.

Since the endoscope 100 does not move forward and backward with respect to forward and backward movement operation in the non-sensing region (forward and backward movement in a range where the treatment tool fixing tool 450 and the rear restriction end 408 or the front restriction end 410 do not abut against each other), a range of an observation site, such as a distal end site of the treatment tool 200 and a body cavity inner site, which is to be displayed on the monitor 112 as an endoscopic image, does not vary, and the size of an image of the observation site is prevented from fluctuating according to minute displacement of the treatment tool 200. Accordingly, a sense of perspective can be suitably maintained, and a stable endoscopic image can be obtained.

FIGS. 42 and 43 are explanatory views for illustrating a sensing region of the coupling ring 402. As illustrated in FIGS. 42 and 43, in a case where the treatment tool fixing tool 450 has moved forward and backward in the forward-backward direction, or in a case where the coupling ring 402 has moved forward and backward in the forward-backward direction along with the endoscope fixing tool 430, the treatment tool fixing tool 450 abuts against the rear restriction end 408 or the front restriction end 410. In this state, the coupling ring 402 has a sensing region where the forward and backward movement of any one of the endoscope fixing tool 430 or the treatment tool fixing tool 450 (the forward and backward movement in a direction where the treatment tool fixing tool 450 and the rear restriction end 408 or the front restriction end 410 are not spaced apart from each other) is interlocked with forward and backward movement of the other.

Since the endoscope 100 moves forward and backward with respect to forward and backward movement operation in the sensing region, a range of an observation site that appears in an endoscopic image displayed on the monitor 112 is continuously changed so as to follow the forward and backward movement of the treatment tool 200. Accordingly, since the sizes of images of observation sites other than the distal end site of the treatment tool 200 that appears in the endoscopic image and the size of the range of the observation site vary according to the operation of the treatment tool 200, an operator can simply obtain a desired image.

As described above, the slider 400 has a non-sensing region where the forward and backward movement of any one of the endoscope insertion part 102 coupled to the endoscope fixing tool 430 or the treatment tool insertion part 202 coupled to the treatment tool fixing tool 450 in the forward-backward direction (axial direction) is not interlocked with the forward and backward movement of the other and a sensing region where the forward and backward movement of any one of the endoscope insertion part or the treatment tool insertion part is interlocked with the forward and backward movement of the other. That is, the endoscope insertion part 102 is interlocked with the forward and backward movement of the treatment tool insertion part 202 in the axial direction at a distance by the slider 400.

(Effect of Obliquely Intersecting Endoscope Guide Groove and Treatment Tool Guide Groove)

In addition, in the overtube 300 of the embodiment, the endoscope guide groove 326 (endoscope insertion passage 306) and the treatment tool guide groove 328 (treatment tool insertion passage 308) obliquely intersect each other. For this reason, even in a case where an interval between the endoscope insertion passage 306 and the treatment tool insertion passage 308 in the overtube 300 is narrowed for diameter reduction, the distal end of the endoscope insertion part 102 inserted in the overtube 300 and the distal end of the treatment tool insertion part 202 can be spaced apart from each other. Accordingly, a distal end (treatment part 206) of the treatment tool 200 can be observed in bird's-eye view, and there is an advantage that the state of this distal end is easily observed by the endoscope 100.

(Modification Example of Partition Wall Member, Slider, and the Like)

Although the first range where the endoscope fixing tool 430 is movable forward and backward with respect to the coupling ring 402 is zero in the embodiment, the forward and backward movement of the endoscope fixing tool 430 with respect to the coupling ring 402 together with the treatment tool fixing tool 450 or instead of the treatment tool fixing tool 450 may be allowed, and the first range may have a magnitude other than zero. That is, a configuration in which the forward and backward movement of at least one of the endoscope fixing tool 430 or the treatment tool fixing tool 450 with respect to the coupling ring 402 is allowed may be adopted.

In addition, in a case of allowing forward and backward movement of the endoscope fixing tool 430 with respect to the coupling ring 402, a form in which the range of the engagement hole 412 of the first engaging part 404A that is engaged with the protrusion 436 of the endoscope fixing tool 430 is increased in the forward-backward direction may be adopted. Accordingly, the endoscope fixing tool 430 can be made movable forward and backward with respect to the coupling ring 402 with a length range of the engagement hole 412 in the forward-backward direction as the first range. By using the same configuration as the rear restriction end 408 and the front restriction end 410 of the arm part 406 with respect to the treatment tool fixing tool 450, the endoscope fixing tool 430 can be made movable forward and backward with respect to the coupling ring 402.

In addition, the endoscope fixing tool 430 may be made rotatable in a direction around an axis with the endoscope insertion axis 306a as reference within the endoscope insertion passage 306. In this case, the configuration of the arm part 406 of the coupling ring 402 with respect to the treatment tool fixing tool 450 can be adopted for the endoscope fixing tool 430.

FIG. 44 is an explanatory view for illustrating a modification example of the endoscope insertion passage 306 and the treatment tool insertion passage 308. Although the endoscope insertion passage 306 (endoscope guide groove 326) and the treatment tool insertion passage 308 (treatment tool guide groove 328) are disposed to obliquely intersect each other in the embodiment, for example, both of the passages may be disposed to be parallel to each other and parallel to the longitudinal axis 300a as illustrated in FIG. 44. Although the longitudinal axis 300a, the endoscope insertion axis 306a, and the treatment tool insertion axis 308a are disposed on the same plane in FIG. 44, a configuration of being disposed on the same plane does not necessarily have to be adopted.

Insofar as the partition wall member 324 at least forms a partition wall between the endoscope insertion passage 306 and the treatment tool insertion passage 308, the partition wall member does not necessarily have to be formed in a shape illustrated in FIGS. 19 and 20 and the like.

(Liquid Feeding Tube and Cap Connecting Part)

FIG. 45 is an external perspective view illustrating the liquid feeding tube 424 and the cap connecting part 426 in the overtube body 320 with the long tubular body 322 omitted.

As illustrated in FIG. 45, the liquid feeding tube 424 configures a part of a fluid passage according to the embodiment of the present invention, and is formed of, for example, stainless steel (SUS304 or the like) in a tubular shape. The liquid feeding tube 424 is attached to the tube attaching groove 330 of the partition wall member 324. In addition, the liquid feeding tube 424 has a distal end side connected to the distal end cap part 360 via the cap connecting part 426 to be described below and a proximal end side connected to the syringe 700 via the proximal end cap part 340, the tube 701, and the like which are to be described below. That is, the liquid feeding tube 424 is a pipe line that allows the distal end cap part 360 and the proximal end cap part 340 to communicate with each other inside the overtube 300, and the cleaning liquid RW that is ejected or sucked by the syringe 700 flows therein.

A distal end part of the liquid feeding tube 424 is connected to the cap connecting part 426, and is open on a distal end surface of the cap connecting part 426. In addition, a proximal end part of the liquid feeding tube 424 is connected to the connector 351 to be described below (refer to FIG. 14).

The reference sign 46A of FIG. 46 indicates a front perspective view of the cap connecting part 426 seen from a distal end side thereof, and the reference sign 46B indicates a rear perspective view of the cap connecting part 426 seen from a proximal end side thereof. In addition, the reference sign 47A of FIG. 47 indicates a rear view of the cap connecting part 426 seen from the proximal end side thereof, and the reference sign 47B indicates a cross-sectional view of the cap connecting part 426 shown with the reference sign 47A, which is taken along line "47"-"47".

As illustrated in FIGS. 46 and 47, the cap connecting part 426 is formed of, for example, stainless steel (SUS304 or the like), and functions as a connector that connects the distal end part of the liquid feeding tube 424 to the distal end cap part 360. In the cap connecting part 426, a through hole 426A that passes through the cap connecting part 426 in the forward-backward direction and a pin attachment hole 426B, which is a non-through hole extending in the forward-backward direction are formed.

The distal end part of the liquid feeding tube 424 is inserted into the through hole 426A from a proximal end side thereof. The distal end part of the liquid feeding tube 424 inserted in the through hole 426A is open on the distal end surface of the cap connecting part 426.

The pin attachment hole 426B is open to a proximal end surface side of the cap connecting part 426. One of the pair of attaching pins 329 provided on the distal end surface of the partition wall member 324 is connected to the pin attachment hole 426B (refer to FIG. 45). Accordingly, a position of the cap connecting part 426 in a direction around an axis with a central axis of the liquid feeding tube 424 as reference is positioned (refer to FIG. 45).

<Configuration of Proximal End Cap Part>

The proximal end cap part 340 comprises the flange 350, the connector 351, the duckbill seal 352, the upper seal 353, the cover member 354 having the connector for cleaning 318, the strain relief 355, the liquid feeding tube 356, and the liquid feeding connector 357 as illustrated in FIGS. 13 and 14 which are described above.

(Flange)

The reference sign 48A of FIG. 48 indicates a side view of the flange 350, the reference sign 48B indicates a front view of the flange 350 seen from a distal end side thereof, and the reference sign 48C indicates a rear view of the flange 350 seen from a proximal end side thereof. In addition, the reference sign 49A of FIG. 49 indicates a rear perspective view of the flange 350 seen from the proximal end side thereof, and the reference sign 49B indicates a front perspective view of the flange 350 seen from the distal end side thereof.

As illustrated in FIGS. 48 and 49 and FIGS. 13 and 14, which are described above, the flange 350 is formed of, for example, a resin material (polycarbonate or the like) in a cyclic shape surrounding an outer circumference of the long tubular body 322 in the circumferential direction. An insertion hole 350A into which the long tubular body 322 is inserted is formed in the flange 350.

A chamfer 350B against which the tapered portion 322A (refer to FIGS. 15 and 16) of the long tubular body 322 abuts is formed on an opening edge on a proximal end side of the insertion hole 350A, for example, by chamfering. By the chamfer 350B abutting against the tapered portion 322A, relative movement to the proximal end side of the flange 350 with respect to the long tubular body 322 is prohibited, and thus the flange 350 is retained.

Engagement holes 350C, into which engagement claws 358 (refer to FIG. 57) of the cover member 354 to be described below are inserted from proximal end sides thereof and are engaged therewith, are formed in an outer peripheral surface of the flange 350. Although four engagement holes 350C are formed at equal intervals in the outer peripheral surface of the flange 350 in the embodiment, the number and formation positions of the engagement holes 350C may be changed as appropriate.

(Connector)

The reference sign 50A of FIG. 50 indicates a front view of the connector 351 seen from a distal end side thereof, the reference sign 50B indicates a side view of the connector 351, and the reference sign 50C indicates a rear view of the connector 351 seen from a proximal end side thereof. In addition, the reference sign 51A of FIG. 51 indicates a front perspective view of the connector 351 seen from the distal end side thereof, and the reference sign 51B indicates a rear perspective view of the connector 351 seen from the proximal end side thereof.

As illustrated in FIGS. 50 and 51, the connector 351 is formed of, for example, a resin material (polycarbonate or the like), and has a substantially columnar long tubular body insertion part 351A and a substantially disk-shaped connector head 351B.

The long tubular body insertion part 351A has a diameter corresponding to an inner diameter of the long tubular body 322, and is inserted into the long tubular body 322 from an opening on the proximal end side of the long tubular body 322 (refer to FIGS. 13 and 14). A pair of pin attachment holes 341, an endoscope guide hole 342, a treatment tool guide groove 344, and a liquid feeding tube attachment hole 345 are formed in the long tubular body insertion part 351A.

FIGS. 52 and 53 are external perspective views illustrating the partition wall member 324, the connector 351, and the like with the long tubular body 322 omitted.

As illustrated in FIGS. 52 and 53 and FIGS. 50 and 51, which are described above, the pair of pin attachment holes 341 is formed in a distal end surface of the long tubular body insertion part 351A. In a case where the long tubular body insertion part 351A is inserted into the long tubular body 322 from the opening on the proximal end side of the long tubular body 322, the pair of attaching pins 329 formed on the proximal end surface of the partition wall member 324 is respectively inserted into the pair of pin attachment holes 341. Accordingly, a position of the connector 351 in a direction around an axis with a central axis (longitudinal axis 300a) of the long tubular body 322 as reference is positioned.

The endoscope guide hole 342 configures a part of the endoscope insertion passage 306 described above, and passes through the long tubular body insertion part 351A and a connector head 351B to be described below in the forward-backward direction. The endoscope insertion part 102 inserted from the first proximal end opening 310 is inserted into the endoscope guide hole 342. In a case where the pair of attaching pins 329 of the partition wall member 324 is respectively inserted in the pair of pin attachment holes 341 of the long tubular body insertion part 351A, a distal end side of the endoscope guide hole 342 communicates with a proximal end side of the endoscope guide groove 326.

The treatment tool guide groove 344 configures a part of the treatment tool insertion passage 308 described above, and is formed in a side surface of the long tubular body insertion part 351A along the forward-backward direction. The treatment tool insertion part 202 inserted from the second proximal end opening 314 is inserted into the treatment tool guide groove 344. In a case where the pair of attaching pins 329 of the partition wall member 324 is respectively inserted in the pair of pin attachment holes 341 of the long tubular body insertion part 351A, a distal end side of the treatment tool guide groove 344 communicates with a proximal end side of the treatment tool guide groove 328.

The liquid feeding tube attachment hole 345 passes through the long tubular body insertion part 351A in the forward-backward direction. In a case where the pair of attaching pins 329 of the partition wall member 324 is respectively inserted in the pair of pin attachment holes 341 of the long tubular body insertion part 351A, the proximal end part of the liquid feeding tube 424 is inserted into the liquid feeding tube attachment hole 345. The proximal end part of the liquid feeding tube 424 is open on the proximal end side of the liquid feeding tube attachment hole 345.

Referring back to FIGS. 50 and 51, the connector head 351B is formed to have a diameter larger than a diameter of the long tubular body insertion part 351A, and abuts against the proximal end of the long tubular body 322 in a case where the long tubular body insertion part 351A is inserted inside the long tubular body 322. A proximal end part of the endoscope guide hole 342 described above is open to a proximal end surface of the connector head 351B. In addition, a treatment tool guide hole 346 and a liquid feeding passage 347 are formed in the connector head 351B.

The treatment tool guide hole 346 configures a part of the treatment tool insertion passage 308 described above, and the treatment tool insertion part 202 inserted from the second proximal end opening 314 is inserted thereto. An opening on a distal end side of the treatment tool guide hole 346 communicates with the proximal end side of the treatment tool guide groove 344 described above. In addition, a proximal end side of the treatment tool guide hole 346 is open on the proximal end surface of the connector head 351B.

The liquid feeding passage 347 configures a part of the fluid passage according to the embodiment of the present invention, and the cleaning liquid RW ejected or sucked by the syringe 700 flows therein. A distal end side of the liquid feeding passage 347 communicates with the liquid feeding tube attachment hole 345 described above. Accordingly, the liquid feeding tube 424 which is open in the liquid feeding tube attachment hole 345 communicates with the liquid feeding passage 347. In addition, a proximal end side of the liquid feeding passage 347 is open on the proximal end surface of the connector head 351B.

(Duckbill Seal)

The reference sign 54A of FIG. 54 indicates a front view of the duckbill seal 352 seen from a distal end side thereof, and the reference sign 54B indicates a rear view of the duckbill seal 352 seen from a proximal end side thereof. The reference sign 55A of FIG. 55 indicates a front view of the duckbill seal 352 seen from the distal end side thereof, and the reference sign 55B indicates a cross-sectional view of the duckbill seal 352 shown with the reference sign 55A, which is taken along line "55"-"55".

As illustrated in FIGS. 54 and 55 and FIGS. 13 and 14, which are described above, the duckbill seal 352 is formed of, for example, silicon rubber, in a shape corresponding to the proximal end surface of the connector head 351B, and is provided on the proximal end surface of the connector head 351B. An endoscope inserting part 352A, a treatment tool inserting part 352B, and a notch 352C are formed in the duckbill seal 352.

The endoscope inserting part 352A is formed in a substantially disk shape that covers an opening of the endoscope guide hole 342, which is open above the proximal end surface of the connector head 351B, and has one slit S1 formed along a radial direction perpendicular to the longitudinal axis 300a. As illustrated in the cross-sectional view of the reference sign 55B, the endoscope inserting part 352A is formed to have a V-shaped cross section having the slit S1 as a bottom thereof. In a case where the endoscope insertion part 102 inserted from the first proximal end opening 310 is inserted into the slit S1, the endoscope inserting part 352A is open. In addition, the endoscope inserting part 352A secures the airtightness of a space on the distal end side of the duckbill seal 352 by closing the slit S1 when the endoscope insertion part 102 is not inserted.

The treatment tool inserting part 352B is formed in a substantially disk shape that covers an opening of the treatment tool guide hole 346, which is open above the proximal end surface of the connector head 351B, and has one slit S2 formed along the radial direction perpendicular to the longitudinal axis 300a. The treatment tool inserting part 352B is formed to have a V-shaped cross section as the endoscope inserting part 352A. In a case where the treatment tool insertion part 202 inserted from the second proximal end opening 314 is inserted into the slit S2, the treatment tool inserting part 352B is open. In addition, the treatment tool inserting part 352B secures the airtightness of the space on the distal end side of the duckbill seal 352 by closing the slit S2 when the treatment tool insertion part 202 is not inserted.

The notch 352C opens an opening of the liquid feeding passage 347, which is open above the proximal end surface of the connector head 351B.

(Upper Seal)

The reference sign 56A of FIG. 56 indicates a front view of the upper seal 353 seen from a distal end side thereof, and the reference sign 56B indicates a rear view of the upper seal 353 seen from a proximal end side thereof.

As illustrated in FIG. 56 and FIGS. 13 and 14, which are described above, the upper seal 353 is formed of, for example, silicon rubber, in a shape that is substantially the same as the shape of the duckbill seal 352 described above, and is provided on a proximal end surface side of the duckbill seal 352. An endoscope inserting part 353A, a treatment tool inserting part 353B, and a notch 353C are formed in the upper seal 353.

The endoscope inserting part 353A is an insertion hole of the endoscope insertion part 102 provided between the first proximal end opening 310 and the endoscope inserting part 352A described above, and is formed to have a diameter smaller than the diameter of the endoscope insertion part 102. In a case where the endoscope insertion part 102 inserted from the first proximal end opening 310 is inserted, the diameter of the endoscope inserting part 353A increases and the endoscope inserting part is closely attached to the outer peripheral surface thereof without a substantial gap.

The treatment tool inserting part 353B is an insertion hole of the treatment tool insertion part 202 provided between the second proximal end opening 314 and the treatment tool inserting part 352B described above, and is formed to have a diameter smaller than the diameter of the treatment tool insertion part 202. In a case of inserting the treatment tool insertion part 202 inserted from the second proximal end opening 314, the diameter of the treatment tool inserting part 353B increases and the treatment tool inserting part is closely attached to the outer peripheral surface thereof without a substantial gap.

As the notch 352C described above, the notch 353C opens the opening of the liquid feeding passage 347, which is open above the proximal end surface of the connector head 351B.

By providing the duckbill seal 352 and the upper seal 353 on the proximal end surface side of the connector head 351B as described above, the airtightness of the spaces on the distal end sides of both seals is secured. As a result, the leakage or the like of a pneumoperitoneum gas injected into the body cavity to the outside of the body is reduced.

(Cover Member)

The reference sign 57A of FIG. 57 indicates a rear view of the cover member 354 seen from a proximal end side thereof, the reference sign 57B indicates a side view of the cover member 354, and the reference sign 57C indicates a front view of the cover member 354 seen from a distal end side thereof. In addition, the reference sign 58A of FIG. 58 indicates a front perspective view of the cover member 354 seen from the distal end side thereof, and the reference sign 58B indicates a rear perspective view of the cover member 354 seen from the proximal end side thereof.

As illustrated in FIGS. 57 and 58 and FIGS. 13 and 14, which are described above, the cover member 354 is formed of, for example, a resin material (polycarbonate or the like) in a substantially cap shape having a bottom surface part 354A and a side surface part 354B. The cover member 354 comprises the plurality of engagement claws 358, a liquid feeding passage 349, the first proximal end opening 310, the second proximal end opening 314, and the connector for cleaning 318.

The bottom surface part 354A faces the proximal end surface of the connector head 351B via the upper seal 353 and the duckbill seal 352. A surface of the bottom surface part 354A on a proximal end side becomes the proximal end surface 302 described above. The side surface part 354B is provided along an outer peripheral part of a distal end surface of the bottom surface part 354A. Accordingly, a fitting hole 354C to which the connector head 351B is fitted is formed by the side surface part 354B.

Four engagement claws 358 are formed along a circumferential direction of the side surface part 354B at equal intervals so as to correspond to the engagement holes 350C (refer to FIG. 48 or the like) of the flange 350 described above. Each of the engagement claws 358 extends forward. Each of the engagement claws 358 is inserted into each of the engagement holes 350C of the flange 350 from each proximal end side and is engaged therewith. Accordingly, in a state of covering the connector head 351B, the duckbill seal 352, and the upper seal 353, the cover member 354 is attached to the proximal end side of the flange 350. Simultaneously, the connector head 351B, the duckbill seal 352, and the upper seal 353 are fitted to the fitting hole 354C of the cover member 354. As a result, a position of the cover member 354 in the direction around the axis with the longitudinal axis 300a of the long tubular body 322 as reference is positioned.

The liquid feeding passage 349 configures a part of the fluid passage according to the embodiment of the present invention. The liquid feeding passage 349 is a liquid passage that allows the liquid feeding passage 347 of the connector head 351B to communicate with the connector for cleaning 318 to be described below, and the cleaning liquid RW ejected or sucked by the syringe 700 flows therein. Specifically, the liquid feeding passage 349 passes through the bottom surface part 354A in the forward-backward direction and has a shape that protrudes from a distal end surface side of the bottom surface part 354A to the distal end side (connector head 351B side). A distal end part 349A of the liquid feeding passage 349 has a shape that can be fitted to the opening of the liquid feeding passage 347, which is open above the proximal end surface of the connector head 351B. For this reason, in a case where the cover member 354 is attached to the proximal end side of the flange 350, the distal end part 349A is fitted to the proximal end side of the opening of the liquid feeding passage 347 via the notches 352C and 353C.

Each of the first proximal end opening 310 and the second proximal end opening 314 passes through the bottom surface part 354A in the forward-backward direction. In a case where the cover member 354 is attached to the flange 350, the first proximal end opening 310 is set at a position facing the endoscope guide hole 342 of the connector head 351B via the endoscope inserting parts 352A and 353A of the seals 352 and 353 respectively. Accordingly, the endoscope insertion part 102 can be inserted from the first proximal end opening 310 into the endoscope insertion passage 306.

Meanwhile, in a case where the cover member 354 is attached to the flange 350, the second proximal end opening 314 is set at a position facing the treatment tool guide hole 346 of the connector head 351B via the treatment tool inserting parts 352B and 353B of the seals 352 and 353 respectively. Accordingly, the treatment tool insertion part 202 can be inserted from the second proximal end opening 314 into the treatment tool insertion passage 308.

The connector for cleaning 318 configures a part of the fluid passage according to the embodiment of the present invention, and the cleaning liquid RW ejected or sucked by the syringe 700 flows therein. The connector for cleaning 318 is provided on the proximal end surface 302 of the bottom surface part 354A, and is formed in a substantially cylindrical shape protruding backward from the proximal end surface 302. In addition, the connector for cleaning 318 communicates with a proximal end side of the liquid feeding passage 349. Therefore, the connector for cleaning 318 communicates with the liquid feeding tube 424, which is open in the liquid feeding tube attachment hole 345, via the liquid feeding passage 349 and the liquid feeding passage 347.

An engaged part 354D that is engaged with a lock lever 624 (refer to FIG. 69 or the like) of the inner needle 600 in a case of mounting the inner needle 600 described below onto the overtube 300 is formed on the side surface part 354B of the cover member 354.

(Strain Relief)

The reference sign 59A, the reference sign 59B, and the reference sign 59C of FIG. 59 are external views of the strain relief 355 seen from directions different from each other, and the reference sign 59D is a cross-sectional view of the strain relief 355 shown with the reference sign 59C, which is taken along line "59"-"59".

As illustrated in FIG. 59 and FIG. 13, which is described above, the strain relief 355 configures a part of the fluid passage according to the embodiment of the present invention, and the cleaning liquid RW ejected or sucked by the syringe 700 flows therein. The strain relief 355 is formed of, a material that has appropriate flexibility (elasticity) and stiffness, for example, silicon rubber, in a substantially tubular shape, and reduces a force applied to the connector for cleaning 318 from the liquid feeding tube 356 and the like. A distal end part of the strain relief 355 is connected to the connector for cleaning 318 described above. In addition, a proximal end part of the strain relief 355 has a shape curved by approximately 90° with respect to the distal end part of the strain relief 355, and is connected to the liquid feeding tube 356 (refer to FIG. 13). The strain relief 355 reduces interference between the treatment tool 200, the endoscope 100, and the tube 701 by the tube 701 staying outside the overtube 300.

(Liquid Feeding Tube and Liquid Feeding Connector)

Referring back to FIG. 13, the liquid feeding tube 356 is a tubular body configuring a part of the fluid passage according to the embodiment of the present invention, and the cleaning liquid RW ejected or sucked by the syringe 700 flows therein. The liquid feeding tube 356 is formed of, for example, a resin material, and has one end connected to the strain relief 355 and the other end connected to the liquid feeding connector 357.

The liquid feeding connector 357 configures a part of the fluid passage according to the embodiment of the present invention, and functions as a proximal end side connection port according to the embodiment of the present invention. The cleaning liquid RW ejected or sucked by the syringe 700 flows therein. The liquid feeding connector 357 has one end connected to the liquid feeding tube 356, and the other end connected to the tube 701. Accordingly, the liquid feeding tube 424 and the syringe 700 communicate with each other via the tube 701, the liquid feeding connector 357, the liquid feeding tube 356, the strain relief 355, the connector for cleaning 318, the liquid feeding passage 349, the liquid feeding passage 347, and the liquid feeding tube attachment hole 345.

<Configuration of Distal End Cap Part>

The reference sign 60A of FIG. 60 indicates a front view of the distal end cap part 360 seen from a distal end side thereof, and the reference sign 60B, the reference sign 60C, the reference sign 60D, and the reference sign 60E indicate side views of the distal end cap part 360 seen from directions different from each other. The reference sign 61A of FIG. 61 indicates a rear view of the distal end cap part 360 seen from a proximal end side thereof, the reference sign 61B indicates a cross-sectional view of the distal end cap part 360 shown with the reference sign 61A, which is taken along line "61(1)"-"61(1)", and the reference sign 61C indicates a cross-sectional view of the distal end cap part 360 shown with the reference sign 61B, which is taken along line "61(2)"-"61(2)". FIG. 62 is a rear perspective view of the distal end cap part 360 seen from the proximal end side thereof.

As illustrated from FIGS. 60 to 62 and FIGS. 13 and 14, which are described above, the distal end cap part 360 is attached to the distal end side of the overtube body 320, and configures a distal end of the overtube body 320. The distal end cap part 360 is formed of, for example, a resin material (polycarbonate or the like). The distal end cap part 360 has a tapered part 360A that tapers off toward the distal end side thereof, a substantially columnar long tubular body insertion part 360B provided on a proximal end side of the tapered part 360A, and two holes including a first through hole 362 and a second through hole 364 that pass through the tapered part 360A and the long tubular body insertion part 360B in the forward-backward direction.

The tapered part 360A has the distal end surface 304 formed on the basis of a tapered shape protruding from each point of an outer peripheral edge of the distal end of the overtube body 320 (long tubular body 322) to a distal end side of each point. The first distal end opening 312, which is a distal end opening of the first through hole 362, and the second distal end opening 316, which is a distal end opening of the second through hole 364, are formed in the distal end surface 304.

The first through hole 362 forms a part of the endoscope insertion passage 306. In a case where the inner needle 600 to be described below is mounted on the overtube 300, the short needle part 610 of the inner needle 600 is inserted into the first through hole 362. In addition, the second through hole 364 forms a part of the treatment tool insertion passage 308. In a case where the inner needle 600 is mounted on the overtube 300, the long needle part 602 of the inner needle 600 is inserted into the second through hole 364.

The first distal end opening 312 is formed such that a central position thereof is positioned at a position where the endoscope insertion axis 306a passes through, and is formed closer to the proximal end side than the second distal end opening 316 is.

In addition, the first distal end opening 312 is open in an oblique direction with respect to the longitudinal axis 300a. That is, the first distal end opening 312 has an oblong surface of an intersecting portion between a plane obliquely intersecting the longitudinal axis 300a and the endoscope insertion axis 306a along an inclination of the distal end surface 304 and the first through hole 362 as an opening surface. For example, the opening surface goes along a plane that is perpendicular to the horizontal reference plane which goes along the leftward-rightward direction including the longitudinal axis 300a and obliquely intersects the vertical reference plane which goes along the upward-downward direction including the longitudinal axis 300a from the right front to the left rear. Therefore, the opening surface of the first distal end opening 312 is inclined with a side close to the longitudinal axis 300a and the treatment tool insertion axis 308a as the front side.

The second distal end opening 316 is formed such that a central position thereof is positioned at a position where the treatment tool insertion axis 308a passes through, and is formed closer to the distal end side than the first distal end opening 312 is.

In addition, the second distal end opening 316 is open in a direction perpendicular to the longitudinal axis 300a. That is, the second distal end opening has a circular surface of an intersecting portion between a plane, which is substantially perpendicular to the longitudinal axis 300a and the treatment tool insertion axis 308a, and the second through hole 364 as an opening surface. Therefore, the opening surface of the second distal end opening 316 is substantially orthogonal to the longitudinal axis 300a and the treatment tool insertion axis 308a.

The long tubular body insertion part 360B has a diameter corresponding to the inner diameter of the long tubular body 322, and is inserted into the long tubular body 322 from an opening of the long tubular body 322 on the distal end side. In a proximal end surface side of the long tubular body insertion part 360B, openings of the first through hole 362 and the second through hole 364 on the proximal end sides are formed, and an attachment hole 365 of the cap connecting part 426 described above (refer to FIGS. 45 to 47) and a pin attachment hole 366 are formed. In addition, a liquid passage 367 is formed on a distal end side (inside) of the attachment hole 365.

FIG. 63 is an external perspective view illustrating a state where the cap connecting part 426 is attached to the attachment hole 365 of the distal end cap part 360. FIG. 64 is an exploded perspective view of the distal end cap part 360, the cap connecting part 426, and the like, which are illustrated in FIG. 63. FIG. 65 is a cross-sectional view of the attachment hole 365 and the liquid passage 367 of the distal end cap part 360.

As illustrated from FIGS. 61 to 65, the attachment hole 365 is a non-through hole formed along the first through hole 362 in the long tubular body insertion part 360B. Although the attachment hole 365 and the first through hole 362 communicate with each other in the embodiment, a partition wall or the like may be formed between both of the holes. In a case where the long tubular body insertion part 360B is inserted into the long tubular body 322, the cap connecting part 426 (refer to FIG. 45) is inserted and attached to the attachment hole 365.

In this case, out of the pair of attaching pins 329 formed on the distal end surface of the partition wall member 324, the other pin (refer to FIG. 45) that is not inserted in the cap connecting part 426 is inserted into the pin attachment hole 366 open to a proximal end surface of the long tubular body insertion part 360B. As described above, a position of the distal end cap part 360 in the direction around the axis with the longitudinal axis 300a of the long tubular body 322 as reference is positioned by attaching the cap connecting part 426 to the attachment hole 365 and attaching the attaching pin 329 to the pin attachment hole 366.

The liquid passage 367 configures a part of the fluid passage according to the embodiment of the present invention, and allows the cleaning liquid RW ejected or sucked by the syringe 700 to be ejected (jetted) to the first through hole 362 or the ejected cleaning liquid RW to be sucked. The liquid passage 367 has a shape extending from a position facing the distal end surface of the cap connecting part 426 (that is, an opening part of the liquid feeding tube 424) in the attachment hole 365 to the first through hole 362. The liquid passage 367 has a cleaning liquid supply and discharge port 367A (corresponds to a fluid supply and discharge port according to the embodiment of the present invention) that is open above a wall surface of the first through hole 362, that is, into the distal end side of the endoscope insertion passage 306.

The cleaning liquid supply and discharge port 367A of the liquid passage 367 communicates with the syringe 700 via the liquid feeding tube 424, the tube 701, and the like. Accordingly, in a case where the distal end of the endoscope insertion part 102 is positioned on the proximal end side of a distal end side end part (refer to a one-dot chain line TL in FIG. 65) of the cleaning liquid supply and discharge port 367A, the cleaning liquid RW is ejected from the cleaning liquid supply and discharge port 367A to the observation window 116 of the endoscope insertion part 102 inserted in the first through hole 362, and the cleaning liquid RW ejected through the cleaning liquid supply and discharge port 367A is sucked.

<Working of Overtube in a Case of Treating Diseased Site>

FIGS. 66 and 67 are explanatory views for illustrating the working of the overtube 300 in a case of treating a diseased site in a patient's body cavity using the surgical system 10. In order to prevent the drawing from becoming complicated, the overtube 300 is simplified and illustrated herein.

As shown with the reference sign 66A of FIG. 66, after the overtube 300 is inserted into a patient's body wall, the endoscope 100 (endoscope insertion part 102) and the treatment tool 200 (treatment tool insertion part 202) are respectively inserted into the endoscope insertion passage 306 and the treatment tool insertion passage 308 of the overtube 300, and the endoscope insertion part 102 and the treatment tool insertion part 202 are mounted onto the overtube 300.

At this time, the endoscope insertion part 102 is reliably guided to a position, at which the endoscope fixing tool 430 of the slider 400 is inserted, by the endoscope guide groove 326 of the partition wall member 324, and is coupled to the endoscope fixing tool 430. The coupling of the endoscope insertion part 102 to the endoscope fixing tool 430 will be described in more detail with reference to FIG. 68 to be described below.

In addition, the treatment tool insertion part 202 is guided reliably to a position, at which the treatment tool fixing tool 450 of the slider 400 is inserted, by the treatment tool guide groove 328 of the partition wall member 324, and is coupled to the treatment tool fixing tool 450.

Although the sheathing tube 500 is not illustrated in FIGS. 66 and 67, the sheathing tube 500 is sheathed (fitted) to the overtube 300 as illustrated in FIG. 1 and the like, and the body cavity is filled with a pneumoperitoneum gas by introducing the pneumoperitoneum gas into the body cavity via the sheathing tube 500. However, it is also possible to use the overtube 300 without sheathing the sheathing tube 500 thereto.

The state shown with the reference sign 66A of FIG. 66 is a state illustrated in FIG. 41 described above. At this time, in a case where the operator minutely moves the treatment tool insertion part 202 forward with his/her hand that is gripping the operating part 204 of the treatment tool 200, only the treatment tool fixing tool 450 moves forward within the movable range thereof with respect to the coupling ring 402, and the coupling ring 402 does not move with respect to the overtube 300 (overtube body 320).

For that reason, with respect to the forward movement of the treatment tool insertion part 202 until the treatment tool fixing tool 450 reaches a front end (front restriction end 410) of the movable range thereof with respect to the coupling ring 402, as shown with reference sign 66B of FIG. 66, only the treatment tool insertion part 202 moves forward in a state where the endoscope insertion part 102 is stationary. That is, the slider 400 has the non-sensing region where the endoscope insertion part 102 is not interlocked with the forward and backward movement of the treatment tool insertion part 202, and the forward movement operation of the treatment tool 200 at this time becomes forward and backward movement operation of the slider 400 in the non-sensing region.

Similarly, in a case where the operator minutely moves the treatment tool insertion part 202 backward with his/her hand that is gripping the operating part 204 of the treatment tool 200 in the state illustrated in FIG. 41 described above, only the treatment tool fixing tool 450 moves backward within the movable range thereof with respect to the coupling ring 402, and the coupling ring 402 does not move with respect to the overtube 300 (overtube body 320).

For that reason, with respect to the backward movement of the treatment tool insertion part 202 until the treatment tool fixing tool 450 reaches the rear end (rear restriction end 408) of the movable range thereof with respect to the coupling ring 402, as shown with the reference sign 66C of FIG. 66, only the treatment tool insertion part 202 moves backward in a state where the endoscope insertion part 102 is stationary. That is, the backward movement operation of the treatment tool 200 of this case becomes the backward movement operation of the slider 400 in the non-sensing region.

Hence, since the endoscope 100 does not move forward and backward with respect to the minute forward and backward movement operation of the treatment tool 200, that is, the forward and backward movement operation thereof in the non-sensing region, the range of an observation site, such as the range of a distal end site of the treatment tool 200 or a body cavity inner site, to be displayed on the monitor 112 as an endoscopic image does not vary, and the size of an image of the observation site can be prevented from fluctuating according to minute displacement of the treatment tool 200. Accordingly, a sense of perspective can be suitably maintained, and a stable endoscopic image is obtained.

Meanwhile, in a case where the operator greatly moves the treatment tool insertion part 202 forward with his/her hand that is gripping the operating part 204 of the treatment tool 200 in the state illustrated in FIG. 41 described above, a state where the treatment tool fixing tool 450 has reached the front end (front restriction end 410) of the movable range thereof with respect to the coupling ring 402 as illustrated in FIG. 42 described above is brought about after the forward movement of the treatment tool fixing tool 450 of the slider 400 in the non-sensing region until it abuts against the front end (front restriction end 410) of the movable range. Then, in a case where the treatment tool insertion part 202 further moves forward, the treatment tool fixing tool 450 and the coupling ring 402 move forward with respect to the overtube body 320 together with the treatment tool insertion part 202.

Then, the endoscope fixing tool 430 moves forward together with the coupling ring 402, and the endoscope insertion part 102 moves forward together with the endoscope fixing tool 430. Accordingly, the endoscope insertion part 102 moves forward in an interlocking manner with the treatment tool insertion part 202.

For that reason, with respect to the forward movement of the treatment tool insertion part 202 after the treatment tool fixing tool 450 has reached the front end (front restriction end 410) of the movable range thereof with respect to the coupling ring 402, the endoscope insertion part 102 moves forward in an interlocking manner with the treatment tool insertion part 202 as shown with the reference sign 67B of FIG. 67, from the state shown with the reference sign 67A of FIG. 67 (the same state as the reference sign 66A of FIG. 66). That is, the slider 400 has the sensing region where the endoscope insertion part 102 is interlocked with the forward and backward movement of the treatment tool insertion part 202, and the forward movement operation of the treatment tool 200 at this time becomes the forward movement operation of the slider 400 in the sensing region.

Similarly, in a case where the operator greatly moves the treatment tool insertion part 202 backward with his/her hand that is gripping the operating part 204 of the treatment tool 200 in the state illustrated in FIG. 41 described above, a state where the treatment tool fixing tool 450 has reached the rear end (rear restriction end 408) of the movable range thereof with respect to the coupling ring 402 as illustrated in FIG. 43 described above is brought about after the backward movement of the treatment tool fixing tool 450 of the slider 400 in the non-sensing region until it abuts against the rear end (rear restriction end 408) of the movable range. Then, in a case where the treatment tool insertion part 202 further moves backward, the treatment tool fixing tool 450 and the coupling ring 402 moves backward with respect to the overtube body 320 together with the treatment tool insertion part 202. Then, the endoscope fixing tool 430 moves backward together with the coupling ring 402, and the endoscope insertion part 102 moves backward together with the endoscope fixing tool 430. Accordingly, the endoscope insertion part 102 moves backward in an interlocking manner with the treatment tool insertion part 202.

For that reason, with respect to the backward movement of the treatment tool insertion part 202 after the treatment tool fixing tool 450 has reached the rear end (rear restriction end 408) of the movable range thereof with respect to the coupling ring 402, as shown with the reference sign 67C of FIG. 67, the endoscope insertion part 102 moves backward in an interlocking manner with the treatment tool insertion part 202. That is, the backward movement operation of the treatment tool 200 of this case becomes the backward movement operation of the slider 400 in the sensing region.

Hence, since the endoscope 100 moves forward and backward with respect to large forward and backward movement operation of the treatment tool 200, that is, the forward and backward movement operation thereof in the sensing region, the range of an observation site that appears in an endoscopic image displayed on the monitor 112 is continuously changed so as to follow the forward and backward movement of the treatment tool 200. Accordingly, since the sizes of images of observation sites other than the distal end site of the treatment tool 200 that appears in the endoscopic image and the size of the range of the observation site vary according to the operation of the treatment tool 200, the operator simply obtains a desired image.

As described above, in a case where the displacement of the treatment tool insertion part 202 in the axial direction is large (in a case where a large amplitude of forward and backward movement operation has been performed) when an operator has moved the treatment tool insertion part 202 forward and backward in the axial direction, the endoscope insertion part 102 also moves forward, backward, up, down, right, and left in an interlocking manner. Thus, the visual field, orientation, and the like of the endoscope 100 can be changed as intended by an operator. Additionally, the visual field is always given to pick up an image of the distal end site of the treatment tool 200 and consequently, an image that is optimal for treatment is automatically provided. In a case where it is desired to check sites other than a site to be treated, the checking can be performed by moving the treatment tool insertion part 202, and an operator can perform operation as desired. Hence, an assistant (endoscopic technician) who operates the endoscope 100 apart from the operator can be made unnecessary, and thus it is not necessary for the operator to serially instruct an assistant about the visual field, orientation, and the like of the endoscope 100. As a result, a troublesome condition for the operator can be eliminated.

Additionally, in a case where the displacement of the treatment tool insertion part 202 in the axial direction is small (in a case where a small amplitude of forward and backward movement has been performed), the endoscope insertion part 102 is not interlocked. Therefore, an endoscopic image can be prevented from fluctuating needlessly, a sense of perspective can be suitably maintained, and a stable endoscopic image can be provided.

Additionally, in the overtube 300 of the embodiment, the insertion passage into which the endoscope 100 (endoscope insertion part 102) is inserted is used as the first insertion passage, and the insertion passage into which the treatment tool 200 (treatment tool insertion part 202) is inserted is used as the second insertion passage. The present invention can be applied to an overtube comprising the first insertion passage into which the first insertion part of the first medical instrument out of the first medical instrument and the second medical instrument, which are any types of two medical instruments, is inserted, and the second insertion passage into which the second insertion passage of the second medical instrument is inserted.

In addition, in the embodiment, the configuration of the slider 400, which is an interlocking member having the first coupling part that is movable forward and backward inside the overtube 300 and is coupled to the first insertion part of the first medical instrument inserted in the first insertion passage and the second coupling part that is coupled to the second insertion part of the second medical instrument inserted in the second insertion passage, and the configuration of the coupling mechanism formed by the partition wall member 324 and the slider 400 are merely examples, and a slider and a coupling mechanism that have other configurations may be adopted.

In addition, although the slider 400 of the embodiment has the non-sensing region, the present invention can be applied even in a case where the slider 400 has only the sensing region without the non-sensing region. In the present invention, the overtube 300 may not include a coupling mechanism such as the slider 400, and may simply have the first insertion passage and the second insertion passage, into which two medical instruments are inserted.

<Working of Overtube in a Case of Cleaning Observation Window>

FIG. 68 is an explanatory view for illustrating the working of the overtube 300 in a case of cleaning the observation window 116 of the endoscope insertion part 102. In order to prevent the drawing from becoming complicated in FIG. 68, the illustration of each part of the overtube 300 is simplified or the illustration is omitted.

As shown with the reference sign 68A of FIG. 68, in a case where the endoscope 100 is inserted into the endoscope insertion passage 306 of the overtube 300, the endoscope insertion part 102 is reliably guided to a position, at which the endoscope insertion part abuts against the endoscope fixing tool 430 of the slider 400, by the endoscope guide groove 326 of the partition wall member 324 or the like. In a case where the endoscope insertion part 102 is continued to be inserted further, the slider 400 and the distal end of the endoscope insertion part 102 integrally move to the distal end side. Then, in a case where the slider 400 moves to a position where a distal end of the third range according to the embodiment of the present invention, that is, the front restriction end 410 of the coupling ring 402 abuts against the distal end cap part 360, further movement of the slider 400 to the distal end side is restricted.

In a case where the endoscope insertion part 102 is continued to be inserted in this state, the endoscope insertion part 102 is inserted into the endoscope fixing tool 430 as shown with the reference sign 68B of FIG. 68. The endoscope insertion part 102 is continued to be inserted until the grip part 102A abuts against the proximal end cap part 340. Accordingly, a predetermined coupled part (held part) of the endoscope insertion part 102 is coupled (held) to the endoscope fixing tool 430. By forming the coupled part of the endoscope insertion part 102 of an insulating material, insulation between the endoscope 100 and the treatment tool 200 is secured even in a case where the slider 400 (coupling ring 402 or the like) is formed of a metal. For this reason, even in a case where the treatment tool 200 uses electricity, electrical leakage (high-frequency electricity or the like) from the treatment tool 200 to the endoscope 100 is prevented.

In a case of cleaning the observation window 116 of the endoscope insertion part 102, the operator moves the endoscope insertion part 102 backward with a minute force. In a case where the treatment tool 200 is mounted on the overtube 300, the operator may move the endoscope insertion part 102 backward by moving the treatment tool insertion part 202 backward, due to interlocking between the treatment tool insertion part 202 and the endoscope insertion part 102 via the slider 400. Accordingly, the slider 400 and the endoscope insertion part 102 integrally move to the proximal end side of the overtube body 320. Then, as shown with the reference sign 68C of FIG. 68, in a case where the slider 400 moves to a position where a proximal end of the third range according to the embodiment of the present invention, that is, the rear restriction end 408 of the coupling ring 402 abuts against the proximal end cap part 340, further movement of the slider 400 to the proximal end side of the overtube body 320 is restricted. In this case, by adjusting a position of the coupled part (held part) of the endoscope insertion part 102, the movement range of the slider 400, and the like in advance in the embodiment, the distal end of the endoscope insertion part 102 is positioned at a position closer to the proximal end side of the overtube body 320 than the distal end side end part of the cleaning liquid supply and discharge port 367A (one-dot chain line TL in FIG. 65).

As a result, it is possible to eject the cleaning liquid RW from the cleaning liquid supply and discharge port 367A to the observation window 116 of the endoscope insertion part 102, and to suck the ejected cleaning liquid RW through the cleaning liquid supply and discharge port 367A. Accordingly, only with the feeling in the hand, the operator can position the distal end of the endoscope insertion part 102 at a cleaning position closer to the proximal end side of the overtube body 320 than the distal end side end part of the cleaning liquid supply and discharge port 367A is.

[Configuration of Inner Needle]

FIG. 69 is a side view of the inner needle 600 mounted on the overtube 300 in a case of forming a hole in a body wall and inserting the overtube 300 and the sheathing tube 500 into the hole. FIG. 70 is a front perspective view of the inner needle 600 seen from a distal end side thereof. FIG. 71 is an exploded perspective view of the inner needle 600 seen from the distal end side of the inner needle 600. FIG. 72 is an exploded perspective view of the inner needle 600 seen from a proximal end side of the inner needle 600.

As illustrated in FIG. 4 and the like, which are described above, an axis of the inner needle 600 disposed coaxially with the longitudinal axis 300a of the overtube 300 in a state where the inner needle 600 is mounted on the overtube 300 is set as a longitudinal axis 600a. In addition, a relationship of forward, backward, right, left, up, and down of the inner needle 600 follows a relationship of forward, backward, right, left, up, and down of the overtube 300 in a state of being mounted on the overtube 300 as in FIG. 4.

As illustrated in FIGS. 69 to 72, and FIGS. 4 and 5, which are described above, the inner needle 600 comprises the long needle part 602 and the short needle part 610, which are two needle parts extending in the forward-backward direction, a head 620, which comprises a head body 622 and a head cover 623, the lock lever 624, and a seal member 625.

The long needle part 602 corresponds to the second needle part according to the embodiment of the present invention, and is inserted into the treatment tool insertion passage 308 corresponding to the second insertion passage according to the embodiment of the present invention. The short needle part 610 corresponds to the first needle part according to the embodiment of the present invention, and is inserted into the endoscope insertion passage 306 corresponding to the first insertion passage according to the embodiment of the present invention. The short needle part 610 is formed to have a length shorter than the long needle part 602.

The head 620 holds proximal end sides of the long needle part 602 and the short needle part 610. In addition, the head 620 defines a position of a distal end part of the short needle part 610 with respect to the first distal end opening 312 and a position of a distal end part of the long needle part 602 with respect to the second distal end opening 316 respectively in a state where the overtube 300 and the inner needle 600 are combined, that is, a state where the inner needle 600 is mounted on the overtube 300 (hereinafter, referred to as an inner needle mounted state) (refer to FIG. 4). For this reason, the head 620 corresponds to a positioning part according to the embodiment of the present invention.

The long needle part 602 comprises a shaft part 604 and a distal end part 606, which is provided on a distal end side of the shaft part 604 and corresponds to a second distal end part according to the embodiment of the present invention. In addition, the short needle part 610 comprises a shaft part 612 and a distal end part 614, which is provided on a distal end side of the shaft part 612 and corresponds to the first distal end part according to the embodiment of the present invention.

(Long Needle Part)

FIG. 73 is a front perspective view of the shaft part 604 of the long needle part 602 seen from the distal end side thereof. FIG. 74 is an enlarged cross sectional view of a proximal end side of the shaft part 604 of the long needle part 602. As illustrated in FIGS. 69 to 74, the shaft part 604 is a hollow tubular body that is formed of, for example, stainless steel (SUS304 or the like) and extends from the head 620 to the distal end side thereof. The shaft part 604 is disposed at a position where a central axis of the shaft part 604 is disposed substantially coaxially with the treatment tool insertion axis 308a of the overtube 300 in the inner needle mounted state.

In addition, the shaft part 604 has a diameter that allows to be insertable into the treatment tool insertion passage 308. In a case where the long needle part 602 is inserted up to a defined position in the treatment tool insertion passage 308 in the inner needle mounted state, the shaft part 604 has a length that allows a distal end of the shaft part 604 to substantially match the opening surface of the second distal end opening 316 in the distal end surface 304 of the overtube 300.

A proximal end portion of the shaft part 604 is formed in a tapered shape of which a diameter is larger than other portions of the shaft part 604, and is open. In a case of puncturing a body wall with the overtube 300 on which the inner needle 600 is mounted, the endoscope 100 (also referred to as a needle scope) having a diameter that allows to be insertable in the shaft part 604 is inserted into the shaft part 604.

FIG. 75 is a front perspective view of the distal end part 606 of the long needle part 602 seen from a distal end side thereof. The reference sign 76A and the reference sign 76B of FIG. 76 indicate side views of the distal end part 606 of the long needle part 602 seen from directions different from each other, and the reference sign 76C is a cross-sectional view of the distal end part 606 shown with the reference sign 76B, which is taken along line "76"-"76".

As illustrated in FIGS. 75 and 76, the distal end part 606 is formed of, for example, a resin material (polycarbonate or the like), and has a tapered shape (substantially a cone) having an inclined surface that tapers off toward a distal end of the distal end part 606. The head 620 to be described below positions the distal end part 606 at a position protruding from the second distal end opening 316 in the inner needle mounted state (refer to FIG. 4). In addition, the distal end part 606 has a structure that allows the endoscope 100 inserted in the shaft part 604 to observe a state in front of the distal end part 606, that is, a light-transmitting property, and is formed to be hollow except for the distal end side of the distal end part 606.

The distal end part 606 comprises a tapered (substantially conical) needle tip 630, which is installed consecutively on the distal end side of the shaft part 604 and on which an inclined surface 630S tapering off toward the distal end side of the distal end part 606 is formed. A distal end of the needle tip 630 is rounded.

In addition, a pair of cutting edges 632 and 634, which linearly extends to a rear side (proximal end side of the needle tip 630) along the inclined surface 630S from a position slightly closer to a proximal end side thereof than the distal end of the needle tip 630 is, is provided on the inclined surface 630S of the needle tip 630 as a second cutting edge according to the embodiment of the present invention. The pair of cutting edges 632 and 634 is disposed at positions symmetrical to each other with respect to a central axis of the long needle part 602 (shaft part 604). In addition, the cutting edges 632 and 634 each are disposed to protrude in a thin plate shape at a position that goes along a plane parallel to the longitudinal axes 300a and 600a.

Accordingly, the cutting edges 632 and 634 each have a length component orthogonal to the central axis of the long needle part 602.

(Short Needle Part)

The reference sign 77A and the reference sign 77B of FIG. 77 indicate side views of the short needle part 610 seen from directions different from each other. FIG. 78 is a rear perspective view of the short needle part 610 seen from the proximal end side thereof.

As illustrated in FIGS. 77 and 78, the short needle part 610 is formed of, for example, a resin material (polycarbonate or the like). The shaft part 612 of the short needle part 610 is a rod-like member extending from the head 620 to the distal end side thereof. The shaft part 612 is disposed at a position where a central axis of the shaft part 612 is disposed substantially coaxially with the endoscope insertion axis 306a of the overtube 300 in the inner needle mounted state.

In addition, the shaft part 612 has a diameter that allows to be insertable into the endoscope insertion passage 306. In a case where the short needle part 610 is inserted up to a defined position in the endoscope insertion passage 306 in the inner needle mounted state, the shaft part 612 has a length that allows a distal end of the shaft part 612 substantially to match the opening surface of the first distal end opening 312 in the distal end surface 304 of the overtube 300.

Since an inner diameter of the endoscope insertion passage 306 is smaller than an inner diameter of the treatment tool insertion passage 308 in the embodiment, the short needle part 610 has a diameter smaller than the long needle part 602.

The distal end part 614 having a cutting edge 650 is provided at the distal end of the shaft part 612 as the first distal end part according to the embodiment of the present invention. The head 620 to be described below positions the distal end part 614 at a position protruding from the first distal end opening 312 in the inner needle mounted state. In this case, the distal end part 614 is disposed at a position behind the distal end part 606 described above, that is, a position on the proximal end side of the overtube body 320.

FIG. 79 is an enlarged perspective view of the distal end part 614 of the short needle part 610. FIG. 80 is an enlarged side view of the distal end part 614 of the short needle part 610. As illustrated in FIGS. 79 and 80, a flat distal end surface 614S which is obliquely inclined with respect to the central axis of the shaft part 612 is provided at a distal end of the distal end part 614 of the short needle part 610. The cutting edge 650 linearly extending along the distal end surface 614S is provided on the distal end surface 614S as a first cutting edge according to the embodiment of the present invention.

The cutting edge 650 is disposed to protrude in a thin plate shape at a position that goes along the plane parallel to the longitudinal axes 300a and 600a. Accordingly, the cutting edge 650 has a length component orthogonal to a central axis of the short needle part 610. In addition, the cutting edge 650 protrudes in a triangular shape as illustrated in FIG. 80, and is formed such that a vertex protruding from the distal end surface 614S and a vertex on a distal end side of the distal end surface 614S, out of the other two vertexes on the distal end surface 614S, are at the substantially same positions with respect to the forward-backward direction.

(Head)

Referring back to FIGS. 69 to 72, the head 620 corresponding to the positioning part according to the embodiment of the present invention comprises the head body 622 that holds the proximal end sides of the long needle part 602 and the short needle part 610 and the head cover 623 that covers a proximal end surface side of the head body 622.

The reference sign 81A of FIG. 81 indicates a front view of the head body 622 seen from a distal end side thereof, the reference sign 81B indicates a side view of the head body 622 seen from the side, and the reference sign 81C indicates a rear view of the head body 622 seen from a proximal end side thereof. The reference sign 82A of FIG. 82 indicates a rear perspective view of the head body 622 seen from the proximal end side thereof, and the reference sign 82B indicates a front perspective view of the head body 622 seen from the distal end side thereof.

As illustrated in FIGS. 81 and 82, the head body 622 is formed of, for example, a resin material (polycarbonate or the like). A non-through hole 622A is formed in a distal end surface of the head body 622 toward the rear thereof. A long needle part insertion hole 661, into which the long needle part 602 is inserted and which extends in the forward-backward direction, and a short needle part insertion hole 662, into which the short needle part 610 is inserted and which extends in the forward-backward direction, are formed in a bottom part 622B of the non-through hole 622A.

In addition, by denting an opening peripheral edge on a distal end side of the non-through hole 622A to the proximal end side thereof, a cover member attachment hole 664 is formed in the distal end surface of the head body 622. The cover member 354 of the overtube 300 (proximal end cap part 340) is inserted and held in the inner needle mounted state in the cover member attachment hole 664 (refer to FIG. 4).

In addition, a through groove 622C that passes through the head body 622 in the forward-backward direction, the through groove 622C being connected to the non-through hole 622A and the cover member attachment hole 664, is formed in a side surface of the head body 622. In the inner needle mounted state, the strain relief 355 and the connector for cleaning 318 of the overtube 300 (proximal end cap part 340) are inserted into the through groove 622C.

In addition, lock lever attaching parts 622D on which the long plate-shaped lock lever 624 (refer to FIGS. 69 to 72) extending in the forward-backward direction is mounted are formed on upper and lower surfaces of the head body 622 in FIGS. 81 and 82.

The reference sign 83A and the reference sign 83B of FIG. 83 indicate external perspective views of the lock lever 624 seen from directions different from each other. As illustrated in FIG. 83 and FIGS. 69 to 72, which are described above, the lock lever 624 is formed of, for example, a resin material (polycarbonate or the like). In a state where a distal end part thereof is attached to the head body 622, the lock lever extends more forward than the head body 622 does. In addition, the lock lever 624 is held such that the distal end part thereof and a proximal end part thereof are swingable in the upward-downward direction (direction perpendicular to a provision surface of the lock lever 624) with near a center in the forward-backward direction as a fulcrum. The distal end part of the lock lever 624 is biased against a longitudinal axis 600a side by biasing means, and the proximal end part of the lock lever 624 is biased against an opposite direction to the longitudinal axis 600a side.

On a surface side of the distal end part of the lock lever 624, which faces the longitudinal axis 600a, a locking claw 624A projects. The locking claw 624A engages with the engaged part 354D (refer to FIGS. 57 and 58) of the cover member 354 of the overtube 300 (proximal end cap part 340)

in the inner needle mounted state (refer to FIG. 4). Accordingly, the inner needle 600 is mounted on the overtube 300.

As illustrated in FIGS. 69 to 72 and FIGS. 81 and 82, the long needle part 602 is inserted into the long needle part insertion hole 661 of the bottom part 622B of the head body 622 from the proximal end side thereof. In this case, a proximal end part of the long needle part 602 is formed to have a diameter larger than a diameter of the long needle part insertion hole 661 and to have a tapered shape (refer to FIG. 74), and the proximal end part abuts against an opening edge of the long needle part insertion hole 661 on the proximal end side. Accordingly, the proximal end side of the long needle part 602 is held by the bottom part 622B. The seal member 625 is provided on the proximal end side of the long needle part 602 inserted in the long needle part insertion hole 661.

On the contrary, the short needle part 610 is inserted into the short needle part insertion hole 662 of the bottom part 622B from the proximal end side thereof. In this case, a proximal end part of the short needle part 610 is formed to have a diameter larger than a diameter of the short needle part insertion hole 662 and to have a substantially disk shape, and the proximal end part abuts against an opening edge of the short needle part insertion hole 662 on the proximal end side. Accordingly, the proximal end side of the short needle part 610 is held by the bottom part 622B. As for the opening edge of the short needle part insertion hole 662 on the proximal end side and the proximal end part of the short needle part 610, the latter has a shape that makes rotation impossible but can be fitted with respect to the former. Accordingly, a position (that is, the orientation of the cutting edge 650) of the short needle part 610 in a direction around an axis with the central axis of the short needle part 610 as reference is positioned.

The reference sign 84A of FIG. 84 indicates a rear view of the seal member 625 seen from a proximal end side thereof, and the reference sign 84B indicates a cross-sectional view of the seal member 625 shown with the reference sign 84A, which is taken along line "84"-"84". As illustrated in FIG. 84 and FIGS. 71 and 72, which are described above, the seal member 625 is formed of, for example, silicon rubber (BLUESTAR 4765 made by Bluestar Silicones or the like), and covers an opening part of the long needle part 602 on the proximal end side.

The seal member 625 has an insertion hole 625A into which the endoscope insertion part 102 of the endoscope 100 inserted in the long needle part 602 is inserted. The seal member 625 elastically holds the outer peripheral surface of the endoscope insertion part 102 inserted in the insertion hole 625A by being brought into pressure contact with (engaged with) the outer peripheral surface. Accordingly, a central axis of the endoscope insertion part 102 is disposed substantially coaxially with the central axis of the long needle part 602. Since an inner peripheral surface of the seal member 625 is brought into pressure contact with the outer peripheral surface of the endoscope insertion part 102 by an elastic force, the rotation of the endoscope insertion part 102 in the circumferential direction is allowed. In addition, the seal member 625 can freely adjust the holding position of the endoscope insertion part 102 in the forward-backward direction.

The reference sign 85A of FIG. 85 indicates a rear perspective view of the head cover 623 seen from a proximal end side thereof, and the reference sign 85B indicates a front perspective view of the head cover 623 seen from a distal end side thereof. As illustrated in FIG. 85 and FIGS. 69 to 72, which are described above, the head cover 623 is formed of, for example, a resin material (polycarbonate or the like), and is attached to the head body 622 in a state where an opening part of the head body 622 on the proximal end side is covered after attaching the long needle part 602 and the short needle part 610 to the bottom part 622B of the head body 622. The head cover 623 has a proximal end opening 623A that communicates with the inside of the long needle part 602 via the insertion hole 625A of the seal member 625.

FIG. 86 is an explanatory view for illustrating insertion of the endoscope 100 (endoscope insertion part 102) into the long needle part 602. As illustrated in FIG. 86, the endoscope insertion part 102 can be inserted into the long needle part 602 through the insertion hole 625A of the seal member 625 from the proximal end opening 623A of the head cover 623. Accordingly, in a case of puncturing a body wall with the overtube 300 on which the inner needle 600 is mounted, a state in front of the distal end part 606 can be observed with the endoscope 100.

(Cutting Edges of Long Needle Part and Short Needle Part)

FIG. 87 is a front view of the inner needle 600 seen from the distal end side thereof. As illustrated in FIG. 87, in a case where the pair of cutting edges 632 and 634 of the long needle part 602 is projected on a plane perpendicular to the longitudinal axes 300a and 600a in a state before the inner needle mounted state, that is, a state where the inner needle 600 is not mounted on the overtube 300, the cutting edges 632 and 634 are disposed along a straight line L1. In contrast, in a case where the cutting edge 650 of the short needle part 610 is projected on the plane perpendicular to the longitudinal axes 300a and 600a, the cutting edge 650 is disposed along another straight line L2 parallel to the straight line L1. That is, in a state before the inner needle mounted state, the cutting edges 632 and 634 and the cutting edge 650 are parallel to each other, but are not disposed on the same straight line.

FIG. 88 is an explanatory view for illustrating a positional relationship between the respective cutting edges 632, 634, and 650 before and after mounting the inner needle 600 onto the overtube 300. FIG. 89 is an external perspective view of each of the cutting edges 632, 634, and 650 in the inner needle mounted state. FIG. 90 is a front view of each of the cutting edges 632, 634, and 650 in the inner needle mounted state seen from a distal end side thereof.

As shown with the reference sign 88A of FIG. 88, in a case where the inner needle 600 is mounted onto the overtube 300, the long needle part 602 of the inner needle 600 is inserted into the treatment tool insertion passage 308 from the second proximal end opening 314 of the overtube 300. Then, through the treatment tool insertion passage 308, the distal end part 606 of the long needle part 602 is positioned at a position protruding from the second distal end opening 316.

In contrast, the short needle part 610 of the inner needle 600 is inserted into the endoscope insertion passage 306 from the first proximal end opening 310 of the overtube 300. Then, through the endoscope insertion passage 306, the distal end part 614 of the short needle part 610 is positioned at a position protruding from the first distal end opening 312.

In this case, the endoscope insertion passage 306 and the treatment tool insertion passage 308 are disposed to obliquely intersect each other. In addition, since the short needle part 610 is formed of a resin material, compared to the long needle part 602 of which the shaft part 604 is formed of stainless steel, the short needle part 610 is deformable in a case of being inserted into the endoscope insertion passage 306. For this reason, the cutting edge 650 of the short needle part 610 moves relatively in parallel with the cutting edges 632 and 634 of the long needle part 602 in the plane perpendicular to the longitudinal axes 300a and 600a.

For this reason, as shown with the reference sign 88B of FIG. 88, and FIGS. 89 and 90, in a case where the pair of cutting edges 632 and 634 of the long needle part 602 and the cutting edge 650 of the short needle part 610 each are projected on the plane perpendicular to the longitudinal axes 300a and 600a in the inner needle mounted state, each of the cutting edges 632, 634, and 650 is disposed on the same straight line (refer to a straight line L3 of FIG. 90).

As illustrated in FIGS. 89 and 90, in the inner needle mounted state, the distal end of the shaft part 604 of the long needle part 602 is disposed at a position that substantially matches the opening surface of the second distal end opening 316, and the distal end part 606 formed of the needle tip 630 and cutting edges 632 and 634 is disposed to protrude from the opening surface of the second distal end opening 316 to the distal end side thereof. In this case, the cutting edges 632 and 634 each have a length component orthogonal to the longitudinal axis 300a of the overtube 300.

In addition, the cutting edge 650 of the short needle part 610 is disposed at a position that goes along the same plane with the cutting edges 632 and 634 of the long needle part 602, and is disposed on a distal end portion of the overtube 300 so as to protrude in a thin plate shape at a position that goes along the plane parallel to the longitudinal axis 300a (600a), the plane passing a position of the central axis of the long needle part 602 and a position of the central axis of the short needle part 610.

In addition, in the inner needle mounted state, the distal end surface 614S of the distal end part 614 of the short needle part 610 is disposed along the opening surface of the first distal end opening 312, and the distal end part 614 of the cutting edge 650 of the short needle part 610 is disposed to protrude from the opening surface of the first distal end opening 312 to the distal end side thereof. In this case, the cutting edge 650 has a length component orthogonal to the longitudinal axis 300a of the overtube 300 as the cutting edges 632 and 634 of the long needle part 602 do.

Disposing the distal end surface 614S of the distal end part 614 along the opening surface of the first distal end opening 312 includes not only a case where the distal end surface 614S and the opening surface of the first distal end opening 312 are parallel to and flush with each other, but also a case where the distal end surface 614S is disposed at a position closer to the proximal end side thereof or the distal end side thereof than the opening surface of the first distal end opening 312 is and a case where the distal end surface 614S and the opening surface of the first distal end opening 312 are substantially parallel (practically parallel) to each other.

According to the configuration of the overtube 300 and the configuration of the inner needle 600, which are described above, distal end portions of the overtube 300 and the inner needle 600 in the inner needle mounted state have a tapered shape (conical shape) as a whole by the distal end surface 304 (distal end cap part 360) of the overtube 300, the needle tip 630 (inclined surface 630S) of the distal end part 606 of the long needle part 602, and the distal end surface 614S of the distal end part 614 of the short needle part 610.

In addition, in a case where the distal end portion of the overtube 300 is projected onto a plane perpendicular to the longitudinal axis 300a, that is, in a case where the distal end portion of the overtube 300 is seen from the front, that is, from the distal end side thereof, the cutting edges 632 and 634 of the distal end part 606 of the long needle part 602 and the distal end part 614 of the cutting edge 650 of the short needle part 610 are disposed at positions that go along the same straight line as in FIG. 90.

Accordingly, the shapes of the distal end portions of the overtube 300 and the inner needle 600 in the inner needle mounted state are similar to a shape of a distal end portion of an overtube in a state where an inner needle having one needle part is mounted on the overtube having one insertion passage. For that reason, with respect to the amount of inserting force required in a case of puncturing a body wall with the overtube 300 and a penetration force required in a case where the overtube 300 passes through the body wall, an effect of having two insertion passages of the overtube 300 can be made small, a necessary amount of inserting force and a necessary penetration force can be made small, and puncturing can be made easy for the overtube 300.

In addition, an insertion load in a case of puncturing the body wall with the overtube 300 can be reduced without impairing a tearing task with respect to the body wall by linearly disposing each of the cutting edges 632, 634, and 650.

Insofar as the cutting edge 650 (first cutting edge) formed on the distal end part 614 of the short needle part 610 are disposed along the same straight line as the cutting edges 632 and 634 formed on the distal end part 606 of the long needle part 602 in a case of being projected on the plane perpendicular to the longitudinal axis 300a, a form thereof is not particularly limited. A form in which the cutting edge 650 is configured by a plurality of edges arranged in series along the same straight line, or a form in which the plurality of edges disposed in juxtaposition with a direction parallel to the same straight line are disposed along the same straight line as the cutting edges 632 and 634 may be adopted. That is, disposing along the same straight line herein includes not only a case where the first cutting edge and the second cutting edge are on the same straight line, but also a case where the first cutting edge and the second cutting edge are not on the same straight line but are parallel to each other and a case where the first cutting edge and the second cutting edge are not on the same straight line and not parallel to each other but are substantially parallel (practically parallel) to each other.

[Configuration of Sheathing Tube]

FIG. 91 is a side view of the sheathing tube 500. FIG. 92 is an exploded perspective view of the sheathing tube 500, in which the sheathing tube 500 is seen from a proximal end side thereof. FIG. 93 is an external perspective view of important parts of the sheathing tube 500 seen from a distal end side thereof. FIG. 94 is an exploded perspective view of the important parts of the sheathing tube 500.

As illustrated in FIGS. 91 to 94, the sheathing tube 500 has an insertion hole 532 passing through along a longitudinal axis 500a thereof, the insertion hole 532 allowing the overtube body 320 of the overtube 300 to be inserted (refer to FIGS. 4 and 5) therein. In a state where the sheathing tube 500 is sheathed to the overtube 300, the longitudinal axis 500a of the sheathing tube 500 is coaxial with the longitudinal axis 300a of the overtube 300. In addition, a relationship of forward, backward, right, left, up, and down of the sheathing tube 500 follows the relationship of forward, backward, right, left, up, and down of the overtube 300 in a state where the overtube 300 is mounted on the sheathing tube 500 as in FIG. 4.

The sheathing tube 500 comprises a sheathing tube body 501, a seal member 545, a cover member 546, a connection valve 556, an air supply tube 557, a joint 558, and a stopcock 559.

The reference sign 95A of FIG. 95 indicates a front view of the sheathing tube body 501 seen from a distal end side thereof, the reference sign 95B indicates a side view of the sheathing tube body 501, and the reference sign 95C indicates a rear view of the sheathing tube body 501 seen from a proximal end side thereof. The reference sign 96A of FIG. 96 indicates a rear view of the sheathing tube body 501 seen from the proximal end side thereof, and the reference sign 96B indicates a cross-sectional view of the sheathing tube body 501 shown with the reference sign 96A, which is taken along line "96"-"96".

As illustrated from FIGS. 91 to 96, the sheathing tube body 501 is formed of, for example, a resin material (polycarbonate or the like) in a substantially tubular shape extending in the forward-backward direction with the longitudinal axis 500a as a central axis, and has the insertion hole 532 that passes through the sheathing tube body 501 along the longitudinal axis 500a.

The insertion hole 532 has a diameter that is large enough for the overtube body 320 to be movable forward and backward in the forward-backward direction and to be insertable rotatably in the direction around the axis with the longitudinal axis 300a as reference. In a case where the overtube body 320 is inserted from the proximal end side thereof into the insertion hole 532 and is moved forward, the overtube body 320 is led out from a distal end side of the insertion hole 532. Accordingly, the sheathing tube 500 is sheathed (fitted) to an outer peripheral surface of the overtube body 320 (refer to FIG. 1 and the like), and a desired position of the overtube body 320 is fixed to the sheathing tube 500. A length of the sheathing tube body 501 in an axial direction of the longitudinal axis 500a is shorter than a length of the overtube body 320 in the axial direction of the longitudinal axis 300a, and the sheathing tube body 501 falls within a range of the overtube body 320 in the axial direction.

The sheathing tube body 501 has a substantially cylindrical sheathing tube insertion part 540 on the distal end side along the longitudinal axis 500a and a proximal end part 542 of which a proximal end side thereof is linked to a proximal end of the sheathing tube insertion part 540. The sheathing tube insertion part 540 is a portion that is inserted into the body wall together with the overtube body 320 inserted in the insertion hole 532 and is insertable into a hole (port) in the body wall and the body cavity. In addition, the sheathing tube insertion part 540 has a distal end opening part 532A on a distal end side thereof. The overtube body 320 inserted in the insertion hole 532 is led out from the distal end opening part 532A. An inner peripheral surface of the sheathing tube insertion part 540 has almost the same diameter as the overtube body 320, and the inner peripheral surface forms a part of the insertion hole 532.

Therefore, in a state where the overtube body 320 is inserted in the insertion hole 532 of the sheathing tube body 501, an inner peripheral surface of the sheathing tube body 501 is disposed to be in contact with or to approach the outer peripheral surface of the overtube body 320 substantially without a gap, and an outer peripheral surface of the sheathing tube insertion part 540 is disposed at a close position along the outer peripheral surface of the overtube body 320. Contact substantially without a gap herein means that a pneumoperitoneum gas, which is supplied from a pneumoperitoneum gas introduction port 542B to be described below into the sheathing tube insertion part 540, can be introduced into the body cavity from the distal end opening part 532A. In this case, an air supply groove or the like which leads the pneumoperitoneum gas to the distal end opening part 532A may be formed in an inner wall surface of the insertion hole 532.

A restricting part that has a shape restricting the unintended fluctuation of the sheathing tube body 501 with respect to the body wall is formed in the outer peripheral surface of the sheathing tube insertion part 540. In the outer peripheral surface, four vertical grooves 504 that restrict rotation of the sheathing tube body 501 with respect to the body wall in a direction around an axis with the longitudinal axis 500a as reference and multiple horizontal grooves 520 that restrict forward and backward movement of the sheathing tube body 501 with respect to the body wall in the axial direction of the longitudinal axis 500a are formed as one specific form of the restricting part in the outer peripheral surface.

Each of the vertical grooves 504 corresponds to a rotation restricting part according to the embodiment of the present invention. Each of the vertical grooves 504 is linearly formed in the outer peripheral surface of the sheathing tube insertion part 540 along the direction of the longitudinal axis 500a. In the embodiment, the four vertical grooves 504 are formed every 90 degrees in the outer peripheral surface in the direction around the axis with the longitudinal axis 500a as reference (rotation direction with the longitudinal axis 500a as a center). In a case where the overtube 300 to which the sheathing tube body 501 is fitted is inserted in the body wall, a part of the body wall enters each of the vertical grooves 504. Therefore, resistance occurs with respect to rotation of the overtube 300 around an axis (rotation in the rotation direction with the longitudinal axes 300a and 500a as a center), and thus the unintended rotation of the overtube 300 around the axis is prevented by the vertical grooves 504. Although the number of vertical grooves 504 is four in the embodiment, the number may be other than four.

Each of the horizontal grooves 520 corresponds to a movement restricting part according to the embodiment of the present invention. Each of the horizontal grooves 520 is linearly formed in a cyclic shape in the outer peripheral surface of the sheathing tube insertion part 540 along a direction around an axis with the longitudinal axis 500a as a center. The multiple horizontal grooves 520 are regularly formed in the direction of the longitudinal axis 500a.

FIG. 97 is a schematic view of the sheathing tube body 501 (sheathing tube 500) inserted in the body wall. As illustrated in FIG. 97, each of the horizontal grooves 520 is formed of a side surface 522 and a tapered surface 524. The side surface 522 restricts backward movement of the sheathing tube body 501 (that is, the overtube 300) with respect to the body wall. In addition, the tapered surface 524 restricts forward movement of the sheathing tube body 501 (that is, the overtube 300) with respect to the body wall.

A tilt angle of the side surface 522 (tilt angle with respect to a radial direction perpendicular to the longitudinal axis 500a) is formed to be smaller than a tilt angle of the tapered surface 524. For example, the side surface 522 is formed to be parallel to the radial direction perpendicular to the longitudinal axis 500a. In other words, a normal direction of the side surface 522 is formed to be parallel to the longitudinal axis 500a. Without being limited thereto, the tilt angle of the side surface 522 may be, for example, in a range of 0 degree to 30 degrees, both inclusive, preferably 0 degree to 15 degrees, both inclusive, forward or backward with respect to the radial direction.

In contrast, the tilt angle of the tapered surface 524 may be larger than the tilt angle of the side surface 522, and may be, for example, in a range of 45 degrees inclusive to 90 degrees exclusive, preferably a range of 60 degrees inclusive to 90 degrees exclusive, backward in the radial direction perpendicular to the longitudinal axis 500a.

In a case where the overtube 300 to which the sheathing tube body 501 is fitted is inserted in the body wall, a part of the body wall enters each of the horizontal grooves 520. Therefore, resistance occurs with respect to forward and backward movement of the overtube 300 in the axial direction, and thus the unintended forward and backward movement of the overtube 300 in the axial direction is prevented by the horizontal grooves 520.

In addition, in a case of moving the overtube 300 forward (forward and backward movement) with respect to the body wall, such movement is restricted by the tapered surface 524 of each of the horizontal grooves 520. At this time, since the tilt angle of the tapered surface 524 is large as described above, a large resistance force is not received compared to a case of moving the overtube 300 backward (forward and backward movement). Therefore, when inserting the overtube 300 to which the sheathing tube body 501 is fitted into the body wall, a defect that it is difficult for the sheathing tube body 501 to perform insertion operation does not occur, and also a defect that the horizontal grooves 520 crush body wall tissue does not occur.

The form of the rotation restricting part and the form of the movement restricting part, which are formed in the outer peripheral surface of the sheathing tube insertion part 540 of the sheathing tube body 501 and are described above, are merely examples, and other forms may be adopted. For example, instead of the vertical grooves 504 and the horizontal grooves 520, protrusion parts having the same functions respectively may be formed in the outer peripheral surface. In addition, instead of regularly forming along the outer peripheral surface of the sheathing tube insertion part 540 in the circumferential direction, the vertical grooves 504 and the horizontal grooves 520 may be formed irregularly, or may be formed spirally in the outer peripheral surface.

Referring back to FIGS. 92, 95, and 96, a proximal end opening part 532B into which the overtube body 320 is introduced is provided on the proximal end side of the proximal end part 542 of the sheathing tube body 501, and the proximal end opening part 532B has an outer diameter larger than the sheathing tube insertion part 540. Accordingly, the proximal end part 542 is not inserted into a hole in the body wall into which the sheathing tube insertion part 540 is inserted, and is disposed outside the body. Therefore, even in a case where restriction of forward movement of the overtube 300, to which the sheathing tube body 501 is fitted as described above, with respect to the body wall is weak compared to the backward movement, it is possible to reliably prevent the unintended forward movement of the overtube 300 with respect to the body wall as well by adjusting a fixing position of the sheathing tube body 501 with respect to the overtube 300 (overtube body 320) and using the proximal end part 542 at a position abutted against the body wall.

On a proximal end surface side of the proximal end part 542, a substantially cyclic fitting groove 542A is formed along an opening peripheral edge of the proximal end opening part 532B (insertion hole 532). The seal member 545 is fitted to the fitting groove 542A.

In addition, as illustrated from FIGS. 94 to 96, in the proximal end part 542, the pneumoperitoneum gas introduction port 542B that communicates with the insertion hole 532 therein is provided from an outer peripheral surface. Accordingly, a pneumoperitoneum gas can be supplied from the pneumoperitoneum gas introduction port 542B into the insertion hole 532. The connection valve 556 to be described below is connected to an end part of the pneumoperitoneum gas introduction port 542B, which is open on the outer peripheral surface of the proximal end part 542.

The reference sign 98A of FIG. 98 indicates a rear view of the seal member 545 seen from a proximal end side thereof, and the reference sign 98B indicates a cross-sectional view of the seal member 545 shown with the reference sign 98A, which is taken along line "98"-"98".

As illustrated in FIG. 98 and FIGS. 92 and 94, which are described above, the seal member 545 is formed of, for example, silicon rubber in a substantially a cyclic shape, and is fitted to the fitting groove 542A of the proximal end part 542. In the seal member 545, an overtube insertion hole 545A is formed at a position facing the proximal end opening part 532B.

The overtube insertion hole 545A is formed to have a diameter smaller than a diameter of the overtube body 320 of the overtube 300. For this reason, a wall surface of the overtube insertion hole 545A is closely attached with respect to the outer peripheral surface of the overtube body 320, which is inserted through the overtube insertion hole 545A from the proximal end opening part 532B and is inserted in the insertion hole 532, without a substantial gap. Accordingly, a pneumoperitoneum gas introduced in the insertion hole 532 from the pneumoperitoneum gas introduction port 542B is prevented from leaking from a proximal end opening part 532B side, and is introduced into the body cavity from the distal end opening part 532A. In addition, since the wall surface of the overtube insertion hole 545A is brought into pressure contact with the outer peripheral surface of the overtube body 320 by an elastic force, each of the rotation of the overtube body 320 in the circumferential direction and the movement thereof in the forward-backward direction is restricted by a force of the pressure contact. It is possible to adjust positions of the overtube body 320 in the circumferential direction and the forward-backward direction.

The reference sign 99A of FIG. 99 indicates a rear view of the cover member 546 seen from a proximal end side thereof, the reference sign 99B indicates a front view of the cover member 546 seen from a distal end side thereof, and the reference sign 99C indicates a cross-sectional view of the cover member 546 shown with the reference sign 99B, which is taken along line "99"-"99".

As illustrated in FIG. 99 and FIGS. 91 to 94, which are described above, the cover member 546 is a lid body formed of, for example, a resin material (polycarbonate or the like). After the seal member 545 is fitted to the fitting groove 542A of the proximal end part 542, the cover member 546 is attached to the proximal end part 542 in a state of covering an opening part of the proximal end part 542 on the proximal end side. In the cover member 546, an overtube insertion hole 546A is formed at a position facing the proximal end opening part 532B via the overtube insertion hole 545A. Accordingly, the overtube body 320 can be inserted into the insertion hole 532 from the overtube insertion hole 546A of the cover member 546 via the overtube insertion hole 545A of the seal member 545.

The reference sign 100(A) and the reference sign 100(B) of FIG. 100 indicate side views of the connection valve 556 seen from directions different from each other, and the reference sign 100(C) is a cross-sectional view of the connection valve 556 shown with the reference sign 100(B), which is taken along line "C"-"C".

As illustrated in FIG. 100 and FIGS. 92 to 96, which are described above, the connection valve 556 is formed of, for example, a resin material (polycarbonate or the like), and one end side thereof is connected to the pneumoperitoneum gas introduction port 542B of the proximal end part 542. In addition, the other end side of the connection valve 556 is connected to the air supply tube 557. An air supply passage 556A that communicates with the insertion hole 532 via the pneumoperitoneum gas introduction port 542B is formed in the connection valve 556. Accordingly, the connection valve 556 can supply a pneumoperitoneum gas supplied from the air supply tube 557 into the insertion hole 532 via the pneumoperitoneum gas introduction port 542B.

Referring back to FIGS. 91 and 92, the connection valve 556 is connected to one end side of the air supply tube 557, and the stopcock 559 is connected to the other end side of the air supply tube 557 via the joint 558. Since known techniques are adopted for the air supply tube 557 and the joint 558, specific description thereof will be omitted. In addition, the stopcock 559 is connected to the air supply device (not illustrated) via an air supply tube (not illustrated).

The stopcock 559 has an air supply passage 559A that communicates with the air supply device (not illustrated) and the air supply tube 557, and opens and closes the air supply passage 559A. The stopcock 559 opens the air supply passage 559A in a posture parallel to the air supply passage 559A, and closes the air supply passage 559A in a posture perpendicular to the air supply passage 559A.

By the stopcock 559 opening the air supply passage 559A, a pneumoperitoneum gas supplied from the air supply device (not illustrated) is supplied into the insertion hole 532 through the joint 558, the air supply tube 557, the connection valve 556, and the pneumoperitoneum gas introduction port 542B. The pneumoperitoneum gas supplied in the insertion hole 532 is introduced into the body cavity from the distal end opening part 532A through a gap between the inner wall surface of the insertion hole 532 and the overtube body 320, and the body cavity is filled with the pneumoperitoneum gas.

By configuring the sheathing tube 500 with an outer tube which is provided on the body wall and an inner tube which is rotatably held inside the outer tube and into which the overtube 300 is inserted, the inner tube and the overtube 300 may be made rotatable with respect to the outer tube in a direction around an axis with the longitudinal axes 300a and 500a integrally as a central axis.

[Syringe]

The reference sign 101(A) of FIG. 101 indicates a side view of the syringe 700 before suction of the cleaning liquid RW, and the reference sign 101(B) indicates a side view of the syringe 700 after suction of the cleaning liquid RW. As illustrated in FIG. 101 and FIG. 1, which is described above, the syringe 700 comprises a cylinder part 700A and a piston part 700B, in addition to the nozzle 704 and the stopcock 705 which are described above. In a case of sucking or ejecting the cleaning liquid RW by the syringe 700, an operator pulls or pushes the piston part 700B with respect to the cylinder part 700A in a state where the nozzle 704 is opened by the stopcock 705. Accordingly, the cleaning liquid RW is sucked or ejected from the nozzle 704 of the syringe 700.

The nozzle 704 is connected to the liquid feeding connector 357 (refer to FIG. 13) of the overtube 300 via the tube 701 described above. Accordingly, by an operator pushing or pulling the piston part 700B with respect to the cylinder part 700A in a state where the cleaning liquid RW is stored in the cylinder part 700A, the cleaning liquid RW can be supplied to the overtube 300 or the cleaning liquid RW can be sucked from the overtube 300. As a result, as illustrated in FIG. 68 described above, it is possible to eject the cleaning liquid RW from the cleaning liquid supply and discharge port 367A to the observation window 116 of the endoscope insertion part 102, and to suck the ejected cleaning liquid RW by means of the cleaning liquid supply and discharge port 367A.

The syringe 700 is not limited to having the shape illustrated in FIG. 101, and the syringe 700 having various types of known shapes can be used.

APPENDIX

Hereinafter, a using method and precautions of the surgical system 10 of the configuration will be described.

After taking each of the overtube 300, the sheathing tube 500, the inner needle 600, the syringe 700, and the tube 701 out from the storage case 800 in a sterile environment, the assembly of each taken out instrument starts. After initially mounting the inner needle 600 on the overtube 300, the overtube 300 on which the inner needle 600 is mounted is mounted onto the sheathing tube 500.

In addition, after sucking the cleaning liquid RW into the syringe 700, the stopcock 705 of the syringe 700 is closed.

In addition, one end of the tube 701 is connected to the overtube 300, and the syringe 700 is connected to the other end of the tube 701.

In addition, the endoscope insertion part 102 of the endoscope 100, which has a diameter of 3.8 mm, is inserted into the long needle part 602 from the proximal end opening 623A of the inner needle 600, allowing a state in front of the distal end part 606 of the long needle part 602 to be observed.

Next, the patient's body wall is incised to form a hole into which the overtube 300 or the like is insertable. In this case, caution needs to be exercised such that incision does not become insufficient or incision does not become excessive. Then, the overtube 300 or the like is inserted into the body cavity while being rotated by 30° to 90° from the hole formed in the body wall. In this case, a force is lightly and continuously applied to the head 620 of the inner needle 600. Before the overtube 300 or the like passes through the body wall and is inserted into the body cavity, a thickness of the body wall is checked. In addition, it is necessary to pay attention to an insertion amount of the overtube 300 or the like into the body cavity.

After insertion of the overtube 300 and the sheathing tube 500 into the body wall is completed and the inner needle 600 is removed from the overtube 300, the air supply device (not illustrated) is connected to the stopcock 559 of the sheathing tube 500. Next, the stopcock 559 is opened, and the body cavity is filled with a pneumoperitoneum gas. Since the stopcock 559 of the sheathing tube 500, which is taken out from the storage case 800 is closed in an initial state, it is necessary to perform opening operation of the stopcock 559.

The endoscope 100 is inserted into the endoscope insertion passage 306 from the first proximal end opening 310 of the overtube 300, and is coupled to the endoscope coupling part 420. In this case, it is necessary to pay attention to the fact that the insertion of the endoscope 100 into the endoscope insertion passage 306 is continued until the grip part 102A of the endoscope 100 abuts against the overtube 300. In addition, it is necessary to pay attention to the fact that the treatment tool 200 is removed first in a case of removing the endoscope 100 from the overtube 300.

Next, the treatment tool 200 is inserted into the treatment tool insertion passage 308 from the second proximal end opening 314 of the overtube 300, and is coupled to the treatment tool coupling part 422. Accordingly, the endoscope 100 and the treatment tool 200 can be interlocked with each other and can be moved forward and backward via the slider 400. In this case, it is necessary to pay attention to the fact that the endoscope 100 and the treatment tool 200, which correspond to the overtube 300, are used.

In a case where it is necessary to clean the observation window 116 of the endoscope 100, an operator moves the endoscope insertion part 102 backward, and moves the rear restriction end 408 of the coupling ring 402 to a position where the rear restriction end abuts against the proximal end cap part 340. Accordingly, the distal end of the endoscope insertion part 102 is moved to a position corresponding to the cleaning liquid supply and discharge port 367A. Then, after opening the stopcock 705 of the syringe 700, the observation window 116 can be cleaned with the cleaning liquid RW which is ejected and sucked from the cleaning liquid supply and discharge port 367A by pushing and pulling the piston part 700B.

Clean processing of the observation window 116 is performed a plurality of times as necessary. In addition, the syringe 700 or the like is cleaned with a sterilized physiological saline solution as necessary. Before removing the syringe 700 from the tube 701, it is necessary to pay attention to the fact the stopcock 705 is closed.

In a case where treatment by the treatment tool 200 or the like is completed, the endoscope 100 is removed from the overtube 300 after removing the treatment tool 200 from the overtube 300 first. Then, after closing the stopcock 559, the overtube 300 and the sheathing tube 500 are removed from the body wall, and an incised part of the body wall is suitably sutured. It is necessary to pay attention to the fact that the overtube 300 is not removed from the sheathing tube 500 before removing the overtube 300 and the sheathing tube 500 from the body wall. In addition, the suture of the incised part of the body wall is left to the discretion of an operator. In addition, it is necessary to pay attention to the fact that each instrument used in treatment needs to be suitably discarded.

Details (instructions for use) of the using method and precautions of the surgical system 10 will be described below with reference to illustration from FIGS. 102 to 109. Names and reference signs used in the embodiment are shown in parentheses.

[Instructions for Use]

1. Device components are taken out from a package tray (storage case 800) in aseptic operation. The device components are taken out from the package tray to an aseptic field while exercising caution that the device is not damaged.

2. The device is assembled before use through procedures below while carefully examining for damage to the device.

3. An inner trocar (overtube 300) in the package, an optical obturator (inner needle 600), an outer sheath sleeve (sheathing tube 500), and other accessories are not assembled into the device. Assembly is performed in accordance with the procedures below.

i. As shown with the reference sign 1102A and the reference sign 1102B of FIG. 102, the optical obturator is inserted into the inner trocar until an optical obturator proximal end housing (head 620) is mounted onto an inner trocar housing.

ii. As shown with the reference sign 1103A and the reference sign 1103B of FIG. 103, the inner trocar is inserted into the outer sheath sleeve until the inner trocar reaches the innermost part of the outer sheath sleeve.

iii. As shown with the reference sign 1103C and the reference sign 1103D of FIG. 103, a lens cleaning syringe (syringe 700) is filled with a sterile physiological saline solution, and a stopper (stopcock 559) is closed.

iv. As shown with the reference sign 1103E of FIG. 103, a clip is removed from a lens cleaning tube (tube 701) in a coiled state, one end of the lens cleaning tube is attached to the lens cleaning syringe, and the other end of the tube is attached to an inner trocar tube connecting part (liquid feeding connector 357).

v. As shown with the reference sign 1104A of FIG. 104, a compatible low-profile video laparoscope (endoscope 100) having a diameter of 3.8 mm is inserted into an insertion port of the optical obturator (refer to the reference sign 1104B of FIG. 104), and whether a distal end of the obturator can be observed is checked.

In a case where an interlock trocar (overtube 300) is inserted together into the compatible low-profile video laparoscope having a diameter of 3.8 mm, procedures below are performed.

4. One part is incised in normal surgical procedures such that the interlock trocar can be introduced.

Warning:

In a case where skin incision is insufficient, a penetration force increases, and thus there is a possibility that the operability for a clinical doctor aggravates in a case of entering from an incised part.

In a case where incision is excessively large, there is a possibility that the device becomes unstable at the incised part during the operation.

5. As shown with the reference sign 1104C of FIG. 104, the assembled interlock trocar is introduced from the skin incised part through rotational motion at 30 degrees to 90 degrees. A downward control pressure is lightly and continuously applied to an obturator housing.

Warning:

A patient's abdominal wall thickness increases accessibility to a peritoneal cavity or a penetration force in some cases. To check the patient's abdominal wall thickness before the initial access to the peritoneal cavity.

Not to move the interlock trocar forward further and to penetrate the peritoneal cavity after the device has completely entered the peritoneal cavity.

In a case where the device is continued to be inserted immediately before a timing of this moment, there is a possibility of causing damage to a structure inside an abdominal cavity.

6. Once the outer sheath sleeve is positioned at a suitable position in the abdominal cavity, the laparoscope is removed first. After then, a lock releasing button is pressed, and the optical obturator is removed from the inner trocar housing with the assembled interlock trocar remaining at that position. In a case where the obturator is pulled out, an inner seal of the inner trocar closes automatically. Even in a case where there are no instruments in the sleeve, a state of pneumoperitoneum is maintained by an airtight system.

7. As shown with the reference sign 1105A of FIG. 105, to supply air, an air supply tube is attached to a luer lock connector (liquid feeding connector 357) of the outer sheath sleeve, and the stopper is opened by making the tube parallel thereto as shown with the reference sign 1105B and the reference sign 1105C of FIG. 105.

Caution:

The stopper of the outer sheath sleeve is packaged at a closed position. To open the stopper before air supply (refer to the reference sign 1106A of FIG. 106). When an outer sheath sleeve tube and a lever of the stopper are parallel to each other, the stopper is at an open position (refer to the reference sign 1106B of FIG. 106).

In a case of suitably operating the compatible low-profile video laparoscope having a diameter of 3.8 mm and a treatment tool (treatment tool 200) having a diameter of 5 mm in the interlock trocar, procedures below are performed.

8. As shown with the reference sign 1106C of FIG. 106, the compatible low-profile video laparoscope having a diameter of 3.8 mm is inserted into the pipe line (first proximal end opening 310, endoscope insertion passage 306, and first distal end opening 312) (refer to the reference sign 1106D of FIG. 106) of the inner trocar on which "scope" is written. Until a shoulder of the laparoscope comes into contact with a proximal end housing of the inner trocar, the laparoscope is moved forward into the inner trocar.

Caution:

To check whether the laparoscope has been sufficiently inserted in the trocar until the shoulder of the laparoscope comes into contact with the proximal end housing of the inner trocar. In a case where this is neglected, direct alignment with the treatment tool becomes lost. To remove the treatment tool first in a case where it is necessary to remove the laparoscope from the trocar. In a case where this is neglected, there is a possibility that the inside of the abdominal cavity becomes damaged.

9. As shown with the reference sign 1107A of FIG. 107, the treatment tool having a standard 5 mm diameter is inserted into the pipe line (second proximal end opening 314, treatment tool insertion passage 308, and second distal end opening 316) (refer to the reference sign 1107B of FIG. 107) of the inner trocar on which "5 mm instrument" is written, and a relative working distal end distance between the treatment tool and the laparoscope is adjusted such that a structure inside the abdominal cavity and a distal end of the treatment tool are seen clearly.

Note:

After positioning is completed, the treatment tool and the laparoscope are coupled to each other and move together in a case where the treatment tool moves beyond 25 mm.

To adjust a distance between the treatment tool and a laparoscope distal end, the treatment tool may be simply moved forward or moved backward.

In a case where the treatment tool is removed, the laparoscope moves backward to a lens cleaning position in the trocar.

Warning:

To use the compatible laparoscope and the treatment tool having a diameter of 5 mm together. In a case where this is neglected, an image in a direct alignment relationship and the control of the treatment tool are lost.

To exercise caution such that careless damage to an interlock trocar mechanism and a seal, which have a possibility of losing the operability of the treatment tool and a state of pneumoperitoneum, is prevented in a case of introducing or removing the treatment tool via the "5 mm instrument" pipe line of the inner trocar.

To particularly exercise caution such that airtightness is not lost or the trocar mechanism does not become damaged in a case of inserting a low-invasive surgical instrument having a sharp or inclined end part.

Not to allow a suture tool or a suture thread and a suture needle pass the interlock trocar in a case of using a low-invasion instrument. There is a possibility that the interlock trocar mechanism becomes damaged.

10. In a case where lens cleaning is necessary during the operation, procedures below are performed.

i. As shown with the reference sign 1108A of FIG. 108, the treatment tool and the laparoscope are pulled by the hand until the distal end of the laparoscope stops at a position of the trocar distal end (refer to the reference sign 1108B of FIG. 108).

ii. By moving a syringe projector forward and backward until the visibility of the laparoscope becomes clear as shown with the reference sign 1108E of FIG. 108 after checking that the stopper of the syringe is opened (refer to the reference sign 1108C and the reference sign 1108D of FIG. 108), cleaning is performed from a distal end of the interlock trocar with a physiological saline solution, and the remaining physiological saline solution is sucked.

iv. Cleaning is repeated as necessary such that optimal visibility is maintained during the operation.

v. The stopper is closed, and the lens cleaning syringe is filled with a sterile physiological saline solution as necessary.

Warning:

Not to remove the lens cleaning syringe from the lens cleaning tube without closing the stopper first. In a case where this is neglected, airtightness is lost.

11. In a case where an operation is completed, from the inner trocar, i) the treatment tool is carefully removed (refer to the reference sign 1109A of FIG. 109), and ii) the laparoscope is removed (refer to the reference sign 1109B of FIG. 109). An air supply stopper is closed. After then, the entire interlock trocar is removed from the incised part (refer to the reference sign 1109C of FIG. 109), and iii) incision in the abdomen is suitably closed.

Caution:

Never to remove the inner trocar from the outer sheath sleeve after assembly. In a case the inner trocar is removed, a state of pneumoperitoneum is suddenly lost.

To always examine the hemostasis of a part that has gone through the operation after removing the interlock trocar from the abdominal cavity. In a case where bleeding is not stopped, it is necessary to use a suitable technique to stop bleeding.

Whether or not to close the incised part is left to the discretion of a clinical doctor. To reduce a possibility of an incisional hernia and living body infection, a fascia thereunder may be closed through suture.

There is a possibility that an instrument or a device that comes into contact with a body fluid requires special discarding processing for preventing biological contamination.

EXPLANATION OF REFERENCES

10: surgical system
100: endoscope
102: endoscope insertion part
102A: grip part
103: connecting part
104: cord part
108: processor device
110: light source device
112: monitor
114: distal end surface
116: observation window 200: treatment tool
202: treatment tool insertion part
204: operating part
206: treatment part
300: overtube
300a: longitudinal axis
302: proximal end surface
304: distal end surface
306: endoscope insertion passage
306a: endoscope insertion axis
308: treatment tool insertion passage
308a: treatment tool insertion axis
310: first proximal end opening
312: first distal end opening
314: second proximal end opening
316: second distal end opening
318: connector for cleaning
320: overtube body
322: long tubular body
322A: tapered portion
324: partition wall member
326: endoscope guide groove
328: treatment tool guide groove
329: attaching pin
330: tube attaching groove
340: proximal end cap part
341: pin attachment hole
342: endoscope guide hole
344: treatment tool guide groove
345: liquid feeding tube attachment hole
346: treatment tool guide hole
347: liquid feeding passage
349: liquid feeding passage
349A: distal end part
350: flange
350A: insertion hole
350B: chamfer
350C: engagement hole
351: connector
351A: long tubular body insertion part
351B: connector head
352: duckbill seal
352A: endoscope inserting part
352B: treatment tool inserting part
352C: notch
353: upper seal
353A: endoscope inserting part
353B: treatment tool inserting part
353C: notch
354: cover member
354A: bottom surface part
354B: side surface part
354C: fitting hole
354D: engaged part
355: strain relief
356: liquid feeding tube
357: liquid feeding connector
358: engagement claw
360: distal end cap part
360A: tapered part
360B: long tubular body insertion part
362: first through hole
364: second through hole
365: attachment hole
366: pin attachment hole
367: liquid passage
367A: cleaning liquid supply and discharge port
400: slider
402: coupling ring
404: ring part
404A: first engaging part
406: arm part
407: attaching part
408: rear restriction end
408A: opening
410: front restriction end
410A: opening
412: engagement hole
420: endoscope coupling part
422: treatment tool coupling part
424: liquid feeding tube
426: cap connecting part
426A: through hole
426B: pin attachment hole
430: endoscope fixing tool
431: guide bush
431A: chamfer
432: holding frame
432A: flat part
434: endoscope seal member
436: protrusion
450: treatment tool fixing tool
452: holding frame
454: treatment tool seal member
454A: treatment tool insertion passage
454B: chamfer
454D: holding surface
500: sheathing tube
500a: longitudinal axis
501: sheathing tube body
504: vertical groove
520: horizontal groove
522: side surface
524: tapered surface
532: insertion hole
532A: distal end opening part
532B: proximal end opening part
540: sheathing tube insertion part
542: proximal end part
542A: fitting groove
542B: pneumoperitoneum gas introduction port
545: seal member
545A: overtube insertion hole
546: cover member
546A: overtube insertion hole
556: connection valve
556A: air supply passage
557: air supply tube
558: joint
559: stopcock
559A: air supply passage
600: inner needle
600a: longitudinal axis
602: long needle part
604: shaft part
606: distal end part
610: short needle part
612: shaft part
614: distal end part
614S: distal end surface
620: head
622: head body
622A: non-through hole
622B: bottom part 622C: through groove
622D: lock lever attaching part
623: head cover
623A: proximal end opening
624: lock lever
624A: locking claw
625: seal member
625A: insertion hole
630: needle tip
630S: inclined surface
632: cutting edge
634: cutting edge
650: cutting edge
661: long needle part insertion hole
662: short needle part insertion hole
664: cover member attachment hole
700: syringe
700A: cylinder part
700B: piston part
701: tube
704: nozzle
705: stopcock
800: storage case
801: case body
803A: individual storage part
803B: individual storage part
803C: individual storage part
803D: individual storage part
803E: individual storage part
805: engagement claw
RW: cleaning liquid
S1: slit
S2: slit

What is claimed is:

1. A method of operating removing from a body cavity, a surgical system including an endoscope, a treatment tool, an overtube configured to guide an insertion part of the endoscope and an insertion part of the treatment tool into the body cavity, and a sheathing tube configured to cover an outer circumference of the overtube and to be inserted into the body cavity through an incision formed on a body wall, the method comprising:

a first step of removing the treatment tool from the sheathing tube inserted into the body cavity through the body wall in a state where the sheathing tube is covering the outer circumference of the overtube into which the insertion part of the endoscope and the insertion part of the treatment tool are inserted, while keeping the sheathing tube covering the outer circumference of the overtube;

a second step of, after performing the first step, removing the endoscope from the overtube while keeping the sheathing tube covering the outer circumference of the overtube; and a third step of, after performing the second step, removing the sheathing tube from the body wall while keeping the sheathing tube covering the outer circumference of the overtube.

2. The method according to claim 1, wherein
before performing the first step, a proximal end of the sheathing tube is connected to an air supply device which supplies a pneumoperitoneum gas into the body cavity, via an air supply passage, and
the third step is performed with the air supply passage closed.

3. The method according to claim 2, comprising
a fourth step of, before performing the third step, closing the air supply passage using a stopper which is provided in the surgical system and is configured to open and close the air supply passage.

4. The method according to claim 1, wherein
a space between the sheathing tube and the overtube is airtightly sealed, and
the first step and the second step are performed in a state where pneumoperitoneum is maintained.

5. The method according to claim 1, comprising
a fifth step of, after performing the third step, closing the incision.

6. The method according to claim 1, comprising
a sixth step of, after performing the third step, closing a fascia under the incision.

7. The method according to claim 1, comprising
a seventh step of, after performing the third step, leaving the incision unclosed.

* * * * *